US010612006B2

(12) United States Patent
Fukui et al.

(10) Patent No.: US 10,612,006 B2
(45) Date of Patent: Apr. 7, 2020

(54) METHOD FOR PRODUCING ALDEHYDE

(71) Applicant: AJINOMOTO CO., INC., Tokyo (JP)

(72) Inventors: Keita Fukui, Kanagawa (JP); Keiko Danjo, Kanagawa (JP); Junko Ito, Kanagawa (JP); Miku Toyazaki, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/951,496

(22) Filed: Apr. 12, 2018

(65) Prior Publication Data

US 2018/0230441 A1 Aug. 16, 2018

Related U.S. Application Data

(63) Continuation of application No. PCT/JP2016/081970, filed on Oct. 27, 2016.

(30) Foreign Application Priority Data

Oct. 27, 2015 (RU) .............................. 2015146077

(51) Int. Cl.
*C12N 9/04* (2006.01)
*C12Q 1/04* (2006.01)
*C12P 7/24* (2006.01)

(52) U.S. Cl.
CPC .............. *C12N 9/0006* (2013.01); *C12P 7/24* (2013.01); *C12Q 1/04* (2013.01); *C12Y 101/01001* (2013.01)

(58) Field of Classification Search
CPC ..... C12Q 1/04; C12P 7/24; C12Y 101/01001; C12N 9/0006
See application file for complete search history.

(56) References Cited

U.S. PATENT DOCUMENTS

| 9,080,189 | B2 | 7/2015 | Fukui et al. |
| 9,487,806 | B2 | 11/2016 | Toyazaki et al. |
| 9,822,385 | B2 | 11/2017 | Hara et al. |
| 2016/0130618 | A1 | 5/2016 | Hara et al. |
| 2017/0121743 | A1 | 5/2017 | Hirano et al. |
| 2017/0298397 | A1 | 10/2017 | Hara et al. |

FOREIGN PATENT DOCUMENTS

| EP | 2957629 A1 | 12/2015 |
| WO | WO2012/125688 A2 | 9/2012 |
| WO | WO2012/125688 A3 | 9/2012 |
| WO | WO2015/009558 A1 | 1/2015 |

OTHER PUBLICATIONS

Kisselev L., Polypeptide release factors in prokaryotes and eukaryotes: same function, different structure. Structure, 2002, vol. 10: 8-9. (Year: 2002).*
McShan et al., Heurstic search for metaboilc engineering: de novo synthesis of vanillin. Computers and Chem. Eng., 2005, vol. 29: 499-507. (Year: 2005).*
Wishart et al., A single mutation converts a novel phosphotyrosine binding domain into a dual-specificity phosphatase. J. Biol. Chem., 1995, vol. 270(45): (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Arndt, A., et al., "The Alcohol Dehydrogenase Gene adhA in Corynebacterium glutamicum Is Subject to Carbon Catabolite Repression," J. Bacteriol. 2007;189(20):7408-7416.
Database EMBL [Online], Jan. 22, 2015, retrieved from EBI accession No. EMBLCDS: AJE66399.
Database UniProt [Online], Nov. 28, 2012, retrieved from EBI accession No. UNIPROT: K0EY54, Database accession No. K0EY54.
Database UniProt [Online], Feb. 22, 2012, retrieved from EBI accession No. UNIPROT: H0QVY8, Database accession No. H0QVY8.
Database USPTO Proteins [Online], May 14, 2004, retrieved from EBI accession No. USPOP:AAT14391, Database accession No. AAT14391.
Database EPO Proteins [Online]. Oct. 14, 2009, retrieved from EBI accession No. EPOP:HC017185, Database accession No. HC017185.
Kunjapur, A. M., et al., "Synthesis and Accumulation of Aromatic Aldehydes in an Engineered Strain of Escherichia coli," J. Am. Chem. Soc. 2014;136:11644-11654.
Database USPTO Proteins [Online], Apr. 14, 2008, retrieved from EBI accession No. USPOP:ACC06449, Database accession No. ACC06449.
Database USPTO Proteins [Online], Aug. 18, 2008, retrieved from EBI accession No. USPOP:ACH05409, Database accession No. ACH05409.
Kaur, B., et al., "Biotechnological and Molecular Approaches for Vanillin Production: a Review," Appl. Biochem. Biotechnol. 2013;169:1353-1372.
Zaldivar, J., et al., "Effect of Selected Aldehydes on the Growth and Fermentation of Ethanologenic Escherichia coli," Biotechnol. Bioeng. 1999;65(1):24-33.
Shen, Y., et al., "High vanillin tolerance of an evolved Saccharomyces cerevisiae strain owing to its enhanced vanillin reduction and antioxidative capacity," J. Ind. Microbiol. Biotechnol. 2014;41:1637-1645.
Nguyen, T. T. M., et al., "Importance of glucose-6-phosphate dehydrogenase (G6PDH) for vanillin tolerance in Saccharomyces cerevisiae," J. Biosci. Bioeng. 2014;118(3):263-269.

(Continued)

*Primary Examiner* — Ganapathirama Raghu
(74) *Attorney, Agent, or Firm* — Cermak Nakajima & McGowan LLP; Shelly Guest Cermak

(57) ABSTRACT

A method is provided for producing an objective substance, for example, an aromatic aldehyde such as vanillin. The objective substance is produced from a carbon source or a precursor of the objective substance by using a coryneform bacterium that is able to produce the objective substance, wherein bacterium has been modified so that the activity of alcohol dehydrogenase is reduced.

24 Claims, 5 Drawing Sheets
Specification includes a Sequence Listing.

(56) References Cited

OTHER PUBLICATIONS

Hansen, E. H., et al., "De Novo Biosynthesis of Vanillin in Fission Yeast (*Schizosaccharomyces pombe*) and Baker's Yeast (*Saccharomyces cerevisiae*)," Appl. Environmen. Microbiol. 2009;75(9):2765-2774.

Venkitasubramanian, P., et al., "Aldehyde oxidoreductase as a biocatalyst: Reductions of vanillic acid," Enzyme and Microbial Technology 2008;42:130-137.

Brochado, A. R., et al., "Improved vanillin production in baker's yeast through in silico design," Microbial Cell Factories 2010;9(84):1-15.

Ma, X.-K., et al., "Effect of bioconversion conditions on vanillin production by *Amycolatopsis* sp. ATCC 39116 through an analysis of competing by-product formation," Bioprocess. Biosyst. Eng. 2014;37:891-899.

International Search Report for PCT Patent App. No. PCT/JP2016/081970 (dated Jul. 5, 2017).

Written Opinion for PCT Patent App. No. PCT/JP2016/081970 (dated Jul. 5, 2017).

U.S. Appl. No. 15/787,861, Hara et al., filed Oct. 19, 2017.
U.S. Appl. No. 62/509,320, Roche et al., filed May 22, 2017.
U.S. Appl. No. 62/509,326, Fukui et al., filed May 22, 2017.
U.S. Appl. No. 62/509,337, Roche et al., filed May 22, 2017.
U.S. Appl. No. 62/591,910, Mijts et al., filed Nov. 29, 2017.

\* cited by examiner

SEQUENCE LISTING

```
<160> NUMBER OF SEQ ID NOS: 102

<210> SEQ ID NO 1
<211> LENGTH: 68
<212> TYPE: DNA
<213> ORGANISM: Artificial Sequence
<220> FEATURE:
<223> OTHER INFORMATION: primer

<400> SEQUENCE: 1
caggcagatc gttctctgcc ctcatattgg cccagcaaag ggagcaagta tctagacgct    60
caagttag                                                             68

<210> SEQ ID NO 2
<211> LENGTH: 76
<212> TYPE: DNA
<213> ORGANISM: Artificial Sequence
<220> FEATURE:
<223> OTHER INFORMATION: primer

<400> SEQUENCE: 2
cttaagtctg gacgaaatgc ccgaaaacga agtttgagg cgtaaaaagc agatcttgaa    60
gcctgctttt ttatac                                                    76

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
agaaataggc aagacattgg                                                20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggattagcca tacgttcctc                                                20
```

-continued

<210> SEQ ID NO 5
<211> LENGTH: 51
<212> TYPE: DNA
<213> ORGANISM: Artificial Sequence
<220> FEATURE:
<223> OTHER INFORMATION: primer

<400> SEQUENCE: 5
ccatgattac gaattccccc tgttgacaat taatcatcgg ctcgtataat g    51

<210> SEQ ID NO 6
<211> LENGTH: 38
<212> TYPE: DNA
<213> ORGANISM: Artificial Sequence
<220> FEATURE:
<223> OTHER INFORMATION: primer

<400> SEQUENCE: 6
cgaccatatt cgagatcctg tgtgaaattg ttatccgc    38

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
tctcgaatat ggtcgatatg    20

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
atgcctgcag gtcgaccgca tatccggttg tcagg    35

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
ccaagcttgc atgccagatc gtttagatcc gaagg    35

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tgtatgtcct cctggacttc    20

<210> SEQ ID NO 11
<211> LENGTH: 35
<212> TYPE: DNA
<213> ORGANISM: Artificial Sequence
<220> FEATURE:

<223> OTHER INFORMATION: primer

<400> SEQUENCE: 11
ccaggaggac atacaatggc aactgacagc aggag                35

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
gtatgtcctc ctttataaca gacctaaatg acg                  33

<210> SEQ ID NO 13
<211> LENGTH: 36
<212> TYPE: DNA
<213> ORGANISM: Artificial Sequence
<220> FEATURE:
<223> OTHER INFORMATION: primer

<400> SEQUENCE: 13
aaaggaggac atacaatggt cgatatgaaa actacg               36

<210> SEQ ID NO 14
<211> LENGTH: 35
<212> TYPE: DNA
<213> ORGANISM: Artificial Sequence
<220> FEATURE:
<223> OTHER INFORMATION: primer

<400> SEQUENCE: 14
cggtacccgg ggatcccgca tatccggttg tcagg                35

<210> SEQ ID NO 15
<211> LENGTH: 35
<212> TYPE: DNA
<213> ORGANISM: Artificial Sequence
<220> FEATURE:
<223> OTHER INFORMATION: primer

<400> SEQUENCE: 15
cggtacccgg ggatccttac ttccgcgtat ccaac                35

<210> SEQ ID NO 16
<211> LENGTH: 41
<212> TYPE: DNA
<213> ORGANISM: Artificial Sequence
<220> FEATURE:
<223> OTHER INFORMATION: primer

<400> SEQUENCE: 16
ctaggaatcg cggccggtga actcctaaag aactatataa c          41

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ggccgcgatt cctagcatgc                                 20

```
<210> SEQ ID NO 18
<211> LENGTH: 35
<212> TYPE: DNA
<213> ORGANISM: Artificial Sequence
<220> FEATURE:
<223> OTHER INFORMATION: primer

<400> SEQUENCE: 18
ccaagcttgc atgccagtca tcatcaacgg tgccg                          35

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
atctccgcag aagacgtact g                                         21

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tccgatcatg tatgacctcc                                           20

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21
cggtacccgg ggatcggcat agtgcttcca acgctc                         36

<210> SEQ ID NO 22
<211> LENGTH: 36
<212> TYPE: DNA
<213> ORGANISM: Artificial Sequence
<220> FEATURE:
<223> OTHER INFORMATION: primer

<400> SEQUENCE: 22
tagctccact caagattcct cgatattacc tacagg                         36

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
tcttgagtgg agctagggcc                                           20

<210> SEQ ID NO 24
<211> LENGTH: 37
<212> TYPE: DNA
<213> ORGANISM: Artificial Sequence
<220> FEATURE:
<223> OTHER INFORMATION: primer
```

<400> SEQUENCE: 24
ccaagcttgc atgcccatat agagcccagg agctctc                         37

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
cgccgcaaag tccaaataga aag                                        23

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
ggattcttcc tgaactcagc                                            20

<210> SEQ ID NO 27
<211> LENGTH: 36
<212> TYPE: DNA
<213> ORGANISM: Artificial Sequence
<220> FEATURE:
<223> OTHER INFORMATION: primer

<400> SEQUENCE: 27
cggtacccgg ggatcgggct cgtcctgaaa ttgcac                          36

<210> SEQ ID NO 28
<211> LENGTH: 35
<212> TYPE: DNA
<213> ORGANISM: Artificial Sequence
<220> FEATURE:
<223> OTHER INFORMATION: primer

<400> SEQUENCE: 28
tccgtcgtga gccatgttgt gcccacgaga ctacc                           35

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
atggctcacg acggattgcg                                            20

<210> SEQ ID NO 30
<211> LENGTH: 36
<212> TYPE: DNA
<213> ORGANISM: Artificial Sequence
<220> FEATURE:
<223> OTHER INFORMATION: primer

<400> SEQUENCE: 30
ccaagcttgc atgcccggtt gcagccttca taaacg                          36

<210> SEQ ID NO 31
<211> LENGTH: 21

```
<212> TYPE: DNA
<213> ORGANISM: Artificial Sequence
<220> FEATURE:
<223> OTHER INFORMATION: primer

<400> SEQUENCE: 31
agaccaatga gtacccaacc g                                            21

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
tcagcgtctg gctcagctac                                              20

<210> SEQ ID NO 33
<211> LENGTH: 36
<212> TYPE: DNA
<213> ORGANISM: Artificial Sequence
<220> FEATURE:
<223> OTHER INFORMATION: primer

<400> SEQUENCE: 33
cggtacccgg ggatcaaccc cagctcaaat aacacc                            36

<210> SEQ ID NO 34
<211> LENGTH: 37
<212> TYPE: DNA
<213> ORGANISM: Artificial Sequence
<220> FEATURE:
<223> OTHER INFORMATION: primer

<400> SEQUENCE: 34
tttcaacaca atccgtcctt ctcgcttgga ttacttg                           37

<210> SEQ ID NO 35
<211> LENGTH: 23
<212> TYPE: DNA
<213> ORGANISM: Artificial Sequence
<220> FEATURE:
<223> OTHER INFORMATION: primer

<400> SEQUENCE: 35
cggattgtgt tgaaattgct ctg                                          23

<210> SEQ ID NO 36
<211> LENGTH: 35
<212> TYPE: DNA
<213> ORGANISM: Artificial Sequence
<220> FEATURE:
<223> OTHER INFORMATION: primer

<400> SEQUENCE: 36
ccaagcttgc atgcctcacc acgggaatct tcagg                             35

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
```

```
ccggactggg gtgtgttttg                                                  20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
cccggaaaat acggtatagc                                                  20

<210> SEQ ID NO 39
<211> LENGTH: 47
<212> TYPE: DNA
<213> ORGANISM: Artificial Sequence
<220> FEATURE:
<223> OTHER INFORMATION: primer

<400> SEQUENCE: 39
ccaagcttgc atgccaggag gattataatg cgcctgcgtg tctcgag                    47

<210> SEQ ID NO 40
<211> LENGTH: 34
<212> TYPE: DNA
<213> ORGANISM: Artificial Sequence
<220> FEATURE:
<223> OTHER INFORMATION: primer

<400> SEQUENCE: 40
cggtacccgg ggatccaact acgcggcgac gtac                                  34

<210> SEQ ID NO 41
<211> LENGTH: 2304
<212> TYPE: DNA
<213> ORGANISM: Homo sapiens

<400> SEQUENCE: 41
cggcctgcgt ccgccaccgg aagcgccctc ctaatccccg cagcgccacc gccattgccg      60
ccatcgtcgt ggggcttctg ggcagctag gctgcccgc cgcgctgcct gcgccggacc       120
ggggcgggtc cagtcccggg cgggccgtcg cgggagagaa ataacatctg ctttgctgcc    180
gagctcagag gagacccag accccctccg cagccagagg gctggagcct gctcagaggt    240
gctttgaaga tgccggaggc cccgcctctg ctgttggcag ctgtgttgct gggcctggtg    300
ctgctggtgg tgctgctgct gcttctgagg cactggggct ggggcctgtg ccttatcggc    360
tggaacgagt tcatcctgca gcccatccac aacctgctca tgggtgacac caaggagcag    420
cgcatcctga ccacgtgct gcagcatgcg gagcccggga acgcacagag cgtgctggag     480
gccattgaca cctactgcga gcagaaggag tgggccatga acgtgggcga caagaaaggc    540
aagatcgtgg acgccgtgat tcaggagcac cagccctccg tgctgctgga gctgggggcc    600
tactgtggct actcagctgt gcgcatggcc cgcctgctgt caccagggc gaggctcatc    660 accatcgaga tcaacccga ctgtgccgcc atcacccagc ggatggtgga tttcgctggc    720
gtgaaggaca ggtcaccct tgtggttgga gcgtccagg acatcatccc ccagctgaag    780
aagaagtatg atgtggacac actggacatg gtcttcctcg accactggaa ggaccggtac    840
ctgccggaca cgcttctctt ggaggaatgt ggcctgctgc ggaaggggac agtgctactg    900
gctgacaacg tgatctgccc aggtgcgcca gacttcctag cacacgtgcg cgggagcagc    960
tgctttgagt gcacacacta ccaatcgttc ctggaataca gggaggtggt ggacggcctg    1020
```

```
gagaaggcca tctacaaggg cccaggcagc gaagcagggc cctgactgcc ccccggccc      1080 ccctctcggg ctctctcacc cagcctggta ctgaaggtgc cagacgtgct cctgctgacc     1140
ttctgcggct ccgggctgtg tcctaaatgc aaagcacacc tcggccgagg cctgcgccct    1200
gacatgctaa cctctctgaa ctgcaacact ggattgttct tttttaagac tcaatcatga     1260
cttctttact aacactggct agctatatta tcttatatac taatatcatg ttttaaaaat    1320
ataaaataga aattaagaat ctaaatattt agatataact cgacttagta catccttctc    1380
aactgccatt ccctgctgc ccttgacttg ggcaccaaac attcaaagct ccccttgacg     1440
gacgctaacg ctaagggcgg ggcccctagc tggctgggtt ctgggtggca cgcctggccc   1500
actggcctcc cagccacagt ggtgcagagg tcagccctcc tgcagctagg ccaggggcac   1560
ctgttagccc catggggacg actgccggcc tgggaaacga agaggagtca gccagcattc    1620
acacctttct gaccaagcag gcgctgggga caggtggacc ccgcagcagc accagcccct   1680
ctgggcccca tgtggcacag agtggaagca tctccttccc tactcccac tgggccttgc    1740 ttacagaaga ggcaatggct cagaccagct cccgcatccc tgtagttgcc tccctggccc    1800
atgagtgagg atgcagtgct ggtttctgcc cacctcacacc tagagctgtc ccatctcct    1860 ccaaggggtc agactgctag ccacctcaga ggctccaagg gcccagttcc caggcccagg   1920
acaggaatca accctgtgct agctgagttc acctgcaccg agaccagccc ctagccaaga   1980
ttctactcct gggctcaagg cctggctagc ccccagccag cccactccta tggatagaca   2040
gaccagtgag cccaagtgga caagtttggg gccacccagg accagaaac agagcctctg    2100 caggacacag cagatgggca cctgggacca cctccaccca gggccctgcc ccagacgcgc   2160
agaggcccga cacaagggag aagccagcca cttgtgccag acctgagtgg cagaaagcaa   2220
aaagttcctt tgctgcttta attttaaat tttcttacaa aaatttaggt gtttaccaat    2280
agtcttattt tggcttattt ttaa                                           2304
```

<210> SEQ ID NO 42
<211> LENGTH: 2262
<212> TYPE: DNA
<213> ORGANISM: Homo sapiens

<400> SEQUENCE: 42

```
ctcccacggg aggagcaaga acacagaaca gagggggcaa gacagctcca ccaggagtca     60
ggagtgaatc ccctctggga acgaggcact aggaagaaga acttccagcc caggagaaat   120
aacatctgct ttgctgccga gctcaggaga accccagac ccctcccgca gccagagggc    180
tggagcctgc tcagaggtgc tttgaagatg ccggaggccc cgcctctgct gttggcagct   240
gtgttgctgg gcctggtgct gctggtggtg ctgctgctgc ttctgaggca ctggggctgg   300
ggcctgtgcc ttatcggctg gaacgagttc atcctgcagc ccatccacaa cctgctcatg   360
ggtgacacca aggagcagcg catcctgaac acgtgctgc agcatgcgga gcccgggaac   420
gcacagagcg tgctggaggc cattgacacc tactgcgagc agaaggagtg ggccatgaac   480
gtgggcgaca agaaaggcaa gatcgtggac gccgtgattc aggagcacca gccctccgtg    540
ctgctggagc tgggggccta ctgtggctac tcagctgtgc gcatggcccg cctgctgtca   600
ccaggggcga ggctcatcac catcgagatc aaccccgact gtgccgccat cacccagcgg   660
atggtggatt tcgctggcgt gaaggacaag gtcaccttg tggttggagc gtcccaggac   720
atcatccccc agctgaagaa gaagtatgat gtggacacac tggacatggt cttcctcgac    780
```

```
cactggaagg accggtacct gccggacacg cttctcttgg aggaatgtgg cctgctgcgg      840
aaggggacag tgctactggc tgacaacgtg atctgcccag gtgcgccaga cttcctagca      900
cacgtgcgcg ggagcagctg ctttgagtgc acacactacc aatcgttcct ggaatacagg      960
gaggtggtgg acggcctgga gaaggccatc tacaagggcc caggcagcga agcagggccc     1020
tgactgcccc cccggccccc ctctcgggct ctctcaccca gcctggtact gaaggtgcca     1080
gacgtgctcc tgctgacctt ctgcggctcc gggctgtgtc ctaaatgcaa agcacacctc     1140
ggccgaggcc tgcgccctga catgctaacc tctctgaact gcaacactgg attgttcttt     1200
tttaagactc aatcatgact tctttactaa cactggctag ctatattatc ttatatacta     1260
atatcatgtt ttaaaaatat aaaatagaaa ttaagaatct aaatatttag atataactcg     1320
acttagtaca tccttctcaa ctgccattcc cctgctgccc ttgacttggg caccaaacat     1380
tcaaagctcc ccttgacgga cgctaacgct aagggcgggg cccctagctg gctgggttct     1440
gggtggcacg cctggcccac tggcctccca gccacagtgg tgcagaggtc agccctcctg     1500
cagctaggcc aggggcacct gttagcccca tggggacgac tgccggcctg ggaaacgaag     1560
aggagtcagc cagcattcac acctttctga ccaagcaggc gctggggaca ggtggacccc     1620
gcagcagcac cagcccctct gggccccatg tggcacagag tggaagcatc tccttcccta     1680
ctccccactg ggccttgctt acagaagagg caatggctca gaccagctcc cgcatccctg     1740
tagttgcctc cctggcccat gagtgaggat gcagtgctgg tttctgccca cctacaccta     1800
gagctgtccc catctcctcc aaggggtcag actgctagcc acctcagagg ctccaagggc     1860
ccagttccca ggcccaggac aggaatcaac cctgtgctag ctgagttcac ctgcaccgag     1920
accagcccct agccaagatt ctactcctgg gctcaaggcc tggctagccc ccagccagcc     1980
cactcctatg gatagacaga ccagtgagcc caagtggaca gtttggggc cacccaggga      2040 ccagaaacag agcctctgca ggacacagca gatgggcacc tgggaccacc tccacccagg     2100
gccctgcccc agacgcgcag aggccccgaca caagggagaa gccagccact tgtgccagac     2160
ctgagtggca gaaagcaaaa agttcctttg ctgcttaat ttttaaattt tcttacaaaa      2220
atttaggtgt ttaccaatag tcttattttg gcttattttt aa                        2262
```

<210> SEQ ID NO 43
<211> LENGTH: 2279
<212> TYPE: DNA
<213> ORGANISM: Homo sapiens

<400> SEQUENCE: 43

```
tggagataac acggatcgct gtgtacactg tgtgctccgg ttgttgcatc cgagggttga       60
tcggatggtg gttcccatcc agatccaagt cctggcccct gatcacagag aaacacagct      120
ggacattaaa gtgaaataac atctgctttg ctgccgagct cagaggagac cccagacccc      180
tcccgcagcc agagggctgg agcctgctca gaggtgcttt gaagatgccg gaggccccgc      240
ctctgctgtt ggcagctgtg ttgctgggcc tggtgctgct gtggtgctg ctgctgcttc       300 tgaggcactg gggctggggc ctgtgcctta tcggctggaa cgagttcatc ctgcagccca      360
tccacaacct gctcatgggt gacaccaagg agcagcgcat cctgaaccac gtgctgcagc      420
atgcggagcc cgggaacgca cagagcgtgc tggaggccat tgacacctac tgcgagcaga      480
aggagtgggc catgaacgtg ggcgacaaga aaggcaagat cgtggacgcc gtgattcagg      540
agcaccagcc ctccgtgctg ctggagctgg ggcctactg tggctactca gctgtgcgca      600
tggcccgcct gctgtcacca ggggcgaggc tcatcaccat cgagatcaac cccgactgtg      660
```

```
ccgccatcac ccagcggatg gtggatttcg ctggcgtgaa ggacaaggtc acccttgtgg      720
ttggagcgtc ccaggacatc atcccccagc tgaagaagaa gtatgatgtg acacactgg       780 acatggtctt cctcgaccac tggaaggacc ggtacctgcc ggacacgctt ctcttggagg      840
aatgtggcct gctgcggaag gggacagtgc tactggctga acgtgatc tgcccaggtg        900 cgccagactt cctagcacac gtgcgcggga gcagctgctt tgagtgcaca cactaccaat     960
cgttcctgga atacagggag gtggtggacg gcctggagaa ggccatctac aagggcccag    1020
gcagcgaagc agggccctga ctgccccccc ggccccctc tcgggctctc tcacccagcc     1080
tggtactgaa ggtgccagac gtgctcctgc tgaccttctg cggctccggg ctgtgtccta    1140
aatgcaaagc acacctcggc cgaggcctgc gccctgacat gctaacctct ctgaactgca    1200
acactggatt gttcttttttt aagactcaat catgacttct ttactaacac tggctagcta   1260
tattatctta tatactaata tcatgtttta aaaatataaa atagaaatta gaatctaaa     1320 tatttagata taactcgact tagtacatcc ttctcaactg ccattcccct gctgcccttg    1380
acttgggcac caaacattca aagctcccct tgacggacgc taacgctaag ggcggggccc   1440
ctagctggct gggttctggg tggcacgcct ggcccactgg cctcccagcc acagtggtgc    1500
agaggtcagc cctcctgcag ctaggccagg ggcacctgtt agccccatgg ggacgactgc   1560
cggcctggga aacgaagagg agtcagccag cattcacacc tttctgacca agcaggcgct   1620
ggggacaggt ggaccccgca gcagcaccag cccctctggg ccccatgtgg cacagagtgg   1680
aagcatctcc ttccctactc cccactgggc cttgcttaca gaagaggcaa tggctcagac    1740
cagctcccgc atccctgtag ttgcctccct ggcccatgag tgaggatgca gtgctggttt    1800
ctgcccacct acacctagag ctgtccccat ctcctccaag gggtcagact gctagccacc   1860
tcagaggctc caagggccca gttcccaggc ccaggacagg aatcaaccct gtgctagctg    1920
agttcacctg caccgagacc agccctagc caagattcta ctcctgggct caaggcctgg    1980
ctagccccca gccagcccac tcctatggat agacagacca gtgagcccaa gtggacaagt    2040
ttggggccac ccagggacca gaaacagagc ctctgcagga cacagcagat gggcacctgg    2100
gaccacctcc acccagggcc ctgccccaga cgcgcagagg cccgacacaa gggagaagcc    2160
agccacttgt gccagacctg agtggcagaa agcaaaaagt tcctttgctg ctttaatttt    2220 taaatttct tacaaaaatt taggtgttta ccaatagtct tattttggct tatttttaa      2279
```

<210> SEQ ID NO 44
<211> LENGTH: 2035
<212> TYPE: DNA
<213> ORGANISM: Homo sapiens

<400> SEQUENCE: 44

```
gctgttggca gctgtgttgc tgggcctggt gctgctggtg gtgctgctgc tgcttctgag       60
gcactggggc tggggcctgt gccttatcgg ctggaacgag ttcatcctgc agcccatcca      120
caacctgctc atgggtgaca ccaaggagca gcgcatcctg aaccacgtgc tgcagcatgc      180
ggagcccggg aacgcacaga gcgtgctgga ggccattgac acctactgcg agcagaagga      240
gtgggccatg aacgtgggcg acaagaaagg caagatcgtg gacgccgtga ttcaggagca      300
ccagccctcc gtgctgctgg agctgggggc ctactgtggc tactcagctg tgcgcatggc      360
ccgcctgctg tcaccagggg cgaggctcat caccatcgat atcaacccg actgtgccgc      420 catcacccag cggatggtgg atttcgctgg cgtgaaggac aaggtcaccc ttgtggttgg      480
```

```
agcgtcccag gacatcatcc cccagctgaa gaagaagtat gatgtggaca cactggacat   540
ggtcttcctc gaccactgga aggaccggta cctgccggac acgcttctct tggaggaatg   600
tggcctgctg cggaagggga cagtgctact ggctgacaac gtgatctgcc caggtgcgcc   660
agacttccta gcacacgtgc gcgggagcag ctgctttgag tgcacacact accaatcgtt   720
cctggaatac agggaggtgg tggacggcct ggagaaggcc atctacaagg gcccaggcag   780
cgaagcaggg ccctgactgc cccccggcc cccctctcgg gctctctcac ccagcctggt   840
actgaaggtg ccagacgtgc tcctgctgac cttctgcggc tccggctgt gtcctaaatg   900
caaagcacac ctcggccgag gcctgcgccc tgacatgcta acctctctga actgcaacac   960
tggattgttc tttttaaga ctcaatcatg acttctttac taacactggc tagctatatt  1020
atcttatata ctaatatcat gttttaaaaa tataaaatag aaattaagaa tctaaatatt  1080
tagatataac tcgacttagt acatccttct caactgccat tcccctgctg cccttgactt  1140
gggcaccaaa cattcaaagc tcccccttgac ggacgctaac gctaagggcg gggcccctag  1200
ctggctgggt tctgggtggc acgcctgcc cactggcctc ccagccacag tggtgcagag  1260
gtcagccctc ctgcagctag gccaggggca cctgttagcc ccatggggac gactgccggc  1320
ctgggaaacg aagaggagtc agccagcatt cacacctttc tgaccaagca ggcgctgggg  1380
acaggtggac cccgcagcag caccagcccc tctgggcccc atgtggcaca gagtggaagc  1440
atctccttcc ctactcccca ctgggccttg cttacagaag aggcaatggc tcagaccagc  1500
tcccgcatcc ctgtagttgc ctccctggcc catgagtgag gatgcagtgc tggtttctgc  1560
ccacctacac ctagagctgt ccccatctcc tccaagggt cagactgcta gccacctcag  1620
aggctccaag ggcccagttc ccaggcccag acaggaatc aaccctgtgc tagctgagtt  1680
cacctgcacc gagaccagcc cctagccaag attctactcc tgggctcaag gcctggctag  1740
cccccagcca gcccactcct atggatagac agaccagtga gcccaagtgg acaagtttgg  1800
ggccacccag ggaccagaaa cagagcctct gcaggacaca gcagatgggc acctgggacc  1860
acctccaccc agggccctgc cccagacgcg cagaggcccg acacaaggga gaagccagcc  1920
acttgtgcca gacctgagtg gcagaaagca aaaagttcct ttgctgcttt aatttttaaa  1980
ttttcttaca aaaatttagg tgtttaccaa tagtcttatt ttggcttatt tttaa        2035

<210> SEQ ID NO 45
<211> LENGTH: 271
<212> TYPE: PRT
<213> ORGANISM: Homo sapiens

<400> SEQUENCE: 45

Met Pro Glu Ala Pro Leu Leu Ala Ala Val Leu Leu Gly Leu
1               5                   10                  15

Val Leu Leu Val Val Leu Leu Leu Leu Arg His Trp Gly Trp Gly
                20                  25                  30

Leu Cys Leu Ile Gly Trp Asn Glu Phe Ile Leu Gln Pro Ile His Asn
            35                  40                  45

Leu Leu Met Gly Asp Thr Lys Glu Gln Arg Ile Leu Asn His Val Leu
        50                  55                  60

Gln His Ala Glu Pro Gly Asn Ala Gln Ser Val Leu Glu Ala Ile Asp
    65                  70                  75                  80

Thr Tyr Cys Glu Gln Lys Glu Trp Ala Met Asn Val Gly Asp Lys Lys
                85                  90                  95

Gly Lys Ile Val Asp Ala Val Ile Gln Glu His Gln Pro Ser Val Leu
```

```
                100                 105                 110
Leu Glu Leu Gly Ala Tyr Cys Gly Tyr Ser Ala Val Arg Met Ala Arg
            115                 120                 125

Leu Leu Ser Pro Gly Ala Arg Leu Ile Thr Ile Glu Ile Asn Pro Asp
        130                 135                 140

Cys Ala Ala Ile Thr Gln Arg Met Val Asp Phe Ala Gly Val Lys Asp
145                 150                 155                 160

Lys Val Thr Leu Val Val Gly Ala Ser Gln Asp Ile Ile Pro Gln Leu
                165                 170                 175

Lys Lys Lys Tyr Asp Val Asp Thr Leu Asp Met Val Phe Leu Asp His
            180                 185                 190

Trp Lys Asp Arg Tyr Leu Pro Asp Thr Leu Leu Glu Glu Cys Gly
        195                 200                 205

Leu Leu Arg Lys Gly Thr Val Leu Leu Ala Asp Asn Val Ile Cys Pro
        210                 215                 220

Gly Ala Pro Asp Phe Leu Ala His Val Arg Gly Ser Ser Cys Phe Glu
225                 230                 235                 240

Cys Thr His Tyr Gln Ser Phe Leu Glu Tyr Arg Glu Val Val Asp Gly
                245                 250                 255

Leu Glu Lys Ala Ile Tyr Lys Gly Pro Gly Ser Glu Ala Gly Pro
            260                 265                 270

<210> SEQ ID NO 46
<211> LENGTH: 221
<212> TYPE: PRT
<213> ORGANISM: Homo sapiens

<400> SEQUENCE: 46

Met Gly Asp Thr Lys Glu Gln Arg Ile Leu Asn His Val Leu Gln His
1               5                   10                  15

Ala Glu Pro Gly Asn Ala Gln Ser Val Leu Glu Ala Ile Asp Thr Tyr
                20                  25                  30

Cys Glu Gln Lys Glu Trp Ala Met Asn Val Gly Asp Lys Lys Gly Lys
            35                  40                  45

Ile Val Asp Ala Val Ile Gln Glu His Gln Pro Ser Val Leu Leu Glu
        50                  55                  60

Leu Gly Ala Tyr Cys Gly Tyr Ser Ala Val Arg Met Ala Arg Leu Leu
65                  70                  75                  80

Ser Pro Gly Ala Arg Leu Ile Thr Ile Glu Ile Asn Pro Asp Cys Ala
                85                  90                  95

Ala Ile Thr Gln Arg Met Val Asp Phe Ala Gly Val Lys Asp Lys Val
            100                 105                 110

Thr Leu Val Val Gly Ala Ser Gln Asp Ile Ile Pro Gln Leu Lys Lys
        115                 120                 125

Lys Tyr Asp Val Asp Thr Leu Asp Met Val Phe Leu Asp His Trp Lys
    130                 135                 140

Asp Arg Tyr Leu Pro Asp Thr Leu Leu Leu Glu Cys Gly Leu Leu
145                 150                 155                 160

Arg Lys Gly Thr Val Leu Leu Ala Asp Asn Val Ile Cys Pro Gly Ala
                165                 170                 175

Pro Asp Phe Leu Ala His Val Arg Gly Ser Ser Cys Phe Glu Cys Thr
            180                 185                 190

His Tyr Gln Ser Phe Leu Glu Tyr Arg Glu Val Val Asp Gly Leu Glu
        195                 200                 205
```

Lys Ala Ile Tyr Lys Gly Pro Gly Ser Glu Ala Gly Pro
    210             215                 220

<210> SEQ ID NO 47
<211> LENGTH: 3501
<212> TYPE: DNA
<213> ORGANISM: Nocardia brasiliensis

<400> SEQUENCE: 47

| | | | | | |
|---|---|---|---|---|---|
| atggcgactg | attcgcgaag | cgatcggcta | cggcgtcgaa | ttgcacagtt | gttcgccgag | 60 |
| gacgagcagg | tgaaagccgc | ggtgccggac | caggaggtgg | tcgaggcgat | ccgggcgccc | 120 |
| ggcctgcgcc | tggcacagat | catgccacc | gtgatggagc | gctatgcgga | ccgccccgcg | 180 |
| gtgggacagc | gggcgagcga | gccggtcacc | gagagcggtc | gcaccacctt | ccggctgctc | 240 |
| ccggaattcg | agaccctgac | ctaccgcgag | ctgtgggcgc | gcgtccgcgc | ggtgccgcc | 300 |
| gcgtggcacg | agatgccga | aggcctttg | cgggccgggg | atttcgttgc | tctgctgggt | 360 |
| ttcgccggca | tcgattacgg | caccctcgat | ctcgcgaaca | tccatctcgg | cctcgtcacg | 420 |
| gtgccgctgc | aatccggcgc | cacggccccg | caactcgccg | cgatcctggc | cgagaccacg | 480 |
| ccccgggtgc | tggccgcgac | acccgaccat | ctcgatatcg | ccgtcgaatt | gctgaccggg | 540 |
| ggagcctcgc | cggaacggct | ggtggtattc | gactaccgcc | ccgcggacga | cgatcaccgg | 600 |
| gcggcgctcg | agtccgcgcg | cagacggttg | agcgacgcgg | gcagtgcggt | ggtggtcgag | 660 |
| acgctcgacg | cggtccgcgc | ccgcggcagc | gaattgccgg | ccgcgccgct | gttcgttccc | 720 |
| gccgcggacg | aggacccgct | ggctctgctc | atctacacct | ccggcagcac | cggcacgcct | 780 |
| aagggcgcca | tgtacaccga | aagactgaac | cgcacgacgt | ggctgagcgg | ggcgaaaggc | 840 |
| gtcggcctca | cgctcggcta | catgccgatg | agtcatattg | ccgggcgggc | ctcgttcgcc | 900 |
| ggtgtgctgg | cccgcggcgg | cacggtctac | ttcaccgccc | gcagcgatat | gtcgacgctg | 960 |
| ttcgaagatc | tggccctggt | gcggccgacc | gagatgttct | tcgtcccgcg | cgtgtgcgac | 1020 |
| atgatcttcc | agcgctatca | ggccgaactg | tcgcggcgcg | cgcccgccgc | ggccgcgagc | 1080 |
| ccggaactcg | agcaggaact | gaagaccgaa | ctgcgcttgt | ccgcggtcgg | ggaccgctta | 1140 |
| ctcggggcga | tcgcgggcag | cgcgccgctg | tcggccgaga | tgcgggagtt | catggagtcg | 1200 |
| ctgctggatc | tggaactgca | cgacggctac | ggctcgaccg | aggcgggtat | cggcgtactg | 1260 |
| caagacaata | tcgtccagcg | tccgccggtc | atcgattaca | agctcgtcga | cgtgccggaa | 1320 |
| ttgggctact | ccggacgga | ccagccgcat | ccccgcggtg | agttgctgtt | gaaaaccgaa | 1380 |
| gggatgattc | cgggctactt | ccggcggccc | gaggtgaccg | cggagatctt | cgacgaggac | 1440 |
| ggtttctaca | ggaccggtga | catcgtcgcc | gaactcgaac | cggatcggct | gatctacctg | 1500 |
| gaccgccgca | acaatgtgct | gaaactggcc | cagggcgagt | tcgtcacggt | cgcccatctg | 1560 |
| gaagcggtgt | tcgcgaccag | tccgctgatc | cggcagatct | acatctacgg | caacagcgag | 1620 |
| cgctcgttcc | tgctggcggt | gatcgtgccc | accgcggacg | cgctggccga | cggtgtcacc | 1680 |
| gacgcgctga | acacggcgct | gaccgaatcc | ttgcgacagc | tcgcgaaaga | agccgggctg | 1740 |
| caatcctatg | agctgccgcg | cgagttcctg | gtcgaaaccg | aaccgttcac | cgtcgagaac | 1800 |
| ggtctgctct | ccggtatcgc | gaaactgttg | cggcccaagc | tcaaggagca | ctacggcgag | 1860 |
| cgactcgagc | agctgtaccg | cgatatcgag | gcgaaccgca | acgacgagct | gatcgagctg | 1920 |
| cggcgcaccg | cggccgagct | gccggtgctc | gaaaccgtca | cgcgggctgc | acgttcgatg | 1980 |
| ctcggactgg | ccgcgtcgga | gttgcggccg | gacgcgcatt | tcaccgatct | cggcggtgat | 2040 |

-continued

```
tcactgtccg cgctgtcgtt ttcgaccctg ctgcaggaca tgctcgaggt cgaggtcccg    2100
gtcggtgtca tcgtgagccc cgccaactcg ctcgccgatc tggcgaaata catcgaggcc    2160
gaacggcatt cggggggtgcg gcggccgagc ctgatctcgg tgcacggtcc cggcaccgag    2220
atccgtgccg ccgatctcac cctggacaag ttcatcgacg agcgcaccct cgctgccgcg    2280
aaagcggttc cggccgcgcc ggcccaggcg cagaccgtcc tgctcaccgg ggcgaacggc    2340
tatctcggcc gcttcctgtg cctggaatgg ctgcagcgac tggaccagac cggcggcacg    2400
ctggtctgca tcgtgcgcgg taccgacgcg gccgccgcgc ggaagcgcct ggatgcggtg    2460
ttcgacagcg gtgatccgga gctgctcgac cactaccgga agctggccgc cgagcacctc    2520
gaggtgctcg cgggcgatat cggcgacccg aatctcggcc tggacgaagc gacttggcag    2580
cggctcgccg cgaccgtcga cctgatcgtg caccccgccg ccctcgtcaa ccatgtgctg    2640
ccgtacagcc agctgttcgg gccgaatgtg gtcggcaccg ccgagatcat ccggctggcc    2700
atcaccgagc gccgtaagcc cgtgacgtac ctgtcgacgg tcgcggtggc cgcacaggtc    2760
gatcccgccg gcttcgacga ggagcgcgat atccgggaga tgagcgcggt gcgctccatc    2820
gacgccgggt acgcgaacgg ttacggcaac agcaagtggg ccggcgaggt gctgctgcgc    2880
gaggcccatg atctgtgcgg gctgccggtc gccgtgttcc gctcggacat gatcctggcg    2940
cacagcaaat acgtcggtca gctcaacgtc cccgatgtgt tcacccggct catcctgagc    3000
ctggcgctca ccggcatcgc accgtattcg ttctacggga cggacagcgc cgggcagcgc    3060
aggcgggccc actacgacgg tctgcccgcc gatttcgtcg ccgaggcgat caccaccctc    3120
ggcgcgcgag ccgagtcggg gttccatacc tacgacgtgt ggaacccgta cgacgacggc    3180
atctcgctgg acgaattcgt cgactggctc ggcgatttcg gcgtgccgat ccagcggatc    3240
gacgactacg acgaatggtt ccggcgtttc gagaccgcga tccgcgcgct gcccgaaaag    3300
cagcgcgatg cttcgctgct accgctgctg gacgcacacc ggcggccact gcgcgcggtg    3360
cgcggttcgc tgttgcccgc caagaacttc caggcggcgg tgcagtccgc gcggatcggc    3420
cccgatcagg acatcccgca tctttccccg cagttgatcg acaagtacgt caccgacctg    3480
cgccacctcg gcctgctctg a                                               3501
```

<210> SEQ ID NO 48
<211> LENGTH: 1166
<212> TYPE: PRT
<213> ORGANISM: Nocardia brasiliensis

<400> SEQUENCE: 48

```
Met Ala Thr Asp Ser Arg Ser Asp Arg Leu Arg Arg Ile Ala Gln
1               5                   10                  15

Leu Phe Ala Glu Asp Glu Gln Val Lys Ala Ala Val Pro Asp Gln Glu
            20                  25                  30

Val Val Glu Ala Ile Arg Ala Pro Gly Leu Arg Leu Ala Gln Ile Met
        35                  40                  45

Ala Thr Val Met Glu Arg Tyr Ala Asp Arg Pro Ala Val Gly Gln Arg
    50                  55                  60

Ala Ser Glu Pro Val Thr Glu Ser Gly Arg Thr Thr Phe Arg Leu Leu
65                  70                  75                  80

Pro Glu Phe Glu Thr Leu Thr Tyr Arg Glu Leu Trp Ala Arg Val Arg
                85                  90                  95

Ala Val Ala Ala Ala Trp His Gly Asp Ala Glu Arg Pro Leu Arg Ala
            100                 105                 110
```

```
Gly Asp Phe Val Ala Leu Leu Gly Phe Ala Gly Ile Asp Tyr Gly Thr
            115                 120                 125

Leu Asp Leu Ala Asn Ile His Leu Gly Leu Val Thr Val Pro Leu Gln
130                 135                 140

Ser Gly Ala Thr Ala Pro Gln Leu Ala Ala Ile Leu Ala Glu Thr Thr
145                 150                 155                 160

Pro Arg Val Leu Ala Ala Thr Pro Asp His Leu Asp Ile Ala Val Glu
                165                 170                 175

Leu Leu Thr Gly Gly Ala Ser Pro Glu Arg Leu Val Val Phe Asp Tyr
            180                 185                 190

Arg Pro Ala Asp Asp Asp His Arg Ala Ala Leu Glu Ser Ala Arg Arg
        195                 200                 205

Arg Leu Ser Asp Ala Gly Ser Ala Val Val Glu Thr Leu Asp Ala
    210                 215                 220

Val Arg Ala Arg Gly Ser Glu Leu Pro Ala Ala Pro Leu Phe Val Pro
225                 230                 235                 240

Ala Ala Asp Glu Asp Pro Leu Ala Leu Leu Ile Tyr Thr Ser Gly Ser
                245                 250                 255

Thr Gly Thr Pro Lys Gly Ala Met Tyr Thr Glu Arg Leu Asn Arg Thr
            260                 265                 270

Thr Trp Leu Ser Gly Ala Lys Gly Val Gly Leu Thr Leu Gly Tyr Met
        275                 280                 285

Pro Met Ser His Ile Ala Gly Arg Ala Ser Phe Ala Gly Val Leu Ala
    290                 295                 300

Arg Gly Gly Thr Val Tyr Phe Thr Ala Arg Ser Asp Met Ser Thr Leu
305                 310                 315                 320

Phe Glu Asp Leu Ala Leu Val Arg Pro Thr Glu Met Phe Phe Val Pro
                325                 330                 335

Arg Val Cys Asp Met Ile Phe Gln Arg Tyr Gln Ala Glu Leu Ser Arg
            340                 345                 350

Arg Ala Pro Ala Ala Ala Ser Pro Glu Leu Glu Gln Glu Leu Lys
        355                 360                 365

Thr Glu Leu Arg Leu Ser Ala Val Gly Asp Arg Leu Leu Gly Ala Ile
    370                 375                 380

Ala Gly Ser Ala Pro Leu Ser Ala Glu Met Arg Glu Phe Met Glu Ser
385                 390                 395                 400

Leu Leu Asp Leu Glu Leu His Asp Gly Tyr Gly Ser Thr Glu Ala Gly
                405                 410                 415

Ile Gly Val Leu Gln Asp Asn Ile Val Gln Arg Pro Val Ile Asp
            420                 425                 430

Tyr Lys Leu Val Asp Val Pro Glu Leu Gly Tyr Phe Arg Thr Asp Gln
        435                 440                 445

Pro His Pro Arg Gly Glu Leu Leu Lys Thr Gly Met Ile Pro
    450                 455                 460

Gly Tyr Phe Arg Arg Pro Glu Val Thr Ala Glu Ile Phe Asp Glu Asp
465                 470                 475                 480

Gly Phe Tyr Arg Thr Gly Asp Ile Val Ala Glu Leu Glu Pro Asp Arg
                485                 490                 495

Leu Ile Tyr Leu Asp Arg Arg Asn Asn Val Leu Lys Leu Ala Gln Gly
            500                 505                 510

Glu Phe Val Thr Val Ala His Leu Glu Ala Val Phe Ala Thr Ser Pro
        515                 520                 525

Leu Ile Arg Gln Ile Tyr Ile Tyr Gly Asn Ser Glu Arg Ser Phe Leu
```

-continued

```
            530                 535                 540
Leu Ala Val Ile Val Pro Thr Ala Asp Ala Leu Ala Asp Gly Val Thr
545                 550                 555                 560

Asp Ala Leu Asn Thr Ala Leu Thr Glu Ser Leu Arg Gln Leu Ala Lys
                565                 570                 575

Glu Ala Gly Leu Gln Ser Tyr Glu Leu Pro Arg Glu Phe Leu Val Glu
                580                 585                 590

Thr Glu Pro Phe Thr Val Glu Asn Gly Leu Leu Ser Gly Ile Ala Lys
                595                 600                 605

Leu Leu Arg Pro Lys Leu Lys Glu His Tyr Gly Glu Arg Leu Glu Gln
            610                 615                 620

Leu Tyr Arg Asp Ile Glu Ala Asn Arg Asn Asp Glu Leu Ile Glu Leu
625                 630                 635                 640

Arg Arg Thr Ala Ala Glu Leu Pro Val Leu Glu Thr Val Thr Arg Ala
                645                 650                 655

Ala Arg Ser Met Leu Gly Leu Ala Ala Ser Glu Leu Arg Pro Asp Ala
                660                 665                 670

His Phe Thr Asp Leu Gly Gly Asp Ser Leu Ser Ala Leu Ser Phe Ser
                675                 680                 685

Thr Leu Leu Gln Asp Met Leu Glu Val Glu Val Pro Val Gly Val Ile
            690                 695                 700

Val Ser Pro Ala Asn Ser Leu Ala Asp Leu Ala Lys Tyr Ile Glu Ala
705                 710                 715                 720

Glu Arg His Ser Gly Val Arg Arg Pro Ser Leu Ile Ser Val His Gly
                725                 730                 735

Pro Gly Thr Glu Ile Arg Ala Ala Asp Leu Thr Leu Asp Lys Phe Ile
                740                 745                 750

Asp Glu Arg Thr Leu Ala Ala Ala Lys Ala Val Pro Ala Ala Pro Ala
            755                 760                 765

Gln Ala Gln Thr Val Leu Leu Thr Gly Ala Asn Gly Tyr Leu Gly Arg
            770                 775                 780

Phe Leu Cys Leu Glu Trp Leu Gln Arg Leu Asp Gln Thr Gly Gly Thr
785                 790                 795                 800

Leu Val Cys Ile Val Arg Gly Thr Asp Ala Ala Ala Arg Lys Arg
                805                 810                 815

Leu Asp Ala Val Phe Asp Ser Gly Asp Pro Glu Leu Leu Asp His Tyr
            820                 825                 830

Arg Lys Leu Ala Ala Glu His Leu Glu Val Leu Ala Gly Asp Ile Gly
            835                 840                 845

Asp Pro Asn Leu Gly Leu Asp Glu Ala Thr Trp Gln Arg Leu Ala Ala
850                 855                 860

Thr Val Asp Leu Ile Val His Pro Ala Ala Leu Val Asn His Val Leu
865                 870                 875                 880

Pro Tyr Ser Gln Leu Phe Gly Pro Asn Val Val Gly Thr Ala Glu Ile
                885                 890                 895

Ile Arg Leu Ala Ile Thr Glu Arg Arg Lys Pro Val Thr Tyr Leu Ser
                900                 905                 910

Thr Val Ala Val Ala Ala Gln Val Asp Pro Ala Gly Phe Asp Glu Glu
            915                 920                 925

Arg Asp Ile Arg Glu Met Ser Ala Val Arg Ser Ile Asp Ala Gly Tyr
            930                 935                 940

Ala Asn Gly Tyr Gly Asn Ser Lys Trp Ala Gly Glu Val Leu Leu Arg
945                 950                 955                 960
```

Glu Ala His Asp Leu Cys Gly Leu Pro Val Ala Val Phe Arg Ser Asp
            965                 970                 975

Met Ile Leu Ala His Ser Lys Tyr Val Gly Gln Leu Asn Val Pro Asp
            980                 985                 990

Val Phe Thr Arg Leu Ile Leu Ser  Leu Ala Leu Thr Gly  Ile Ala Pro
            995                 1000                1005

Tyr Ser  Phe Tyr Gly Thr Asp  Ser Ala Gly Gln Arg  Arg Arg Ala
    1010                 1015                1020

His Tyr  Asp Gly Leu Pro Ala  Asp Phe Val Ala Glu  Ala Ile Thr
    1025                 1030                1035

Thr Leu  Gly Ala Arg Ala Glu  Ser Gly Phe His Thr  Tyr Asp Val
    1040                 1045                1050

Trp Asn  Pro Tyr Asp Asp Gly  Ile Ser Leu Asp Glu  Phe Val Asp
    1055                 1060                1065

Trp Leu  Gly Asp Phe Gly Val  Pro Ile Gln Arg Ile  Asp Asp Tyr
    1070                 1075                1080

Asp Glu  Trp Phe Arg Arg Phe  Glu Thr Ala Ile Arg  Ala Leu Pro
    1085                 1090                1095

Glu Lys  Gln Arg Asp Ala Ser  Leu Leu Pro Leu Leu  Asp Ala His
    1100                 1105                1110

Arg Arg  Pro Leu Arg Ala Val  Arg Gly Ser Leu Leu  Pro Ala Lys
    1115                 1120                1125

Asn Phe  Gln Ala Ala Val Gln  Ser Ala Arg Ile Gly  Pro Asp Gln
    1130                 1135                1140

Asp Ile  Pro His Leu Ser Pro  Gln Leu Ile Asp Lys  Tyr Val Thr
    1145                 1150                1155

Asp Leu  Arg His Leu Gly Leu  Leu
    1160                 1165

<210> SEQ ID NO 49
<211> LENGTH: 621
<212> TYPE: DNA
<213> ORGANISM: Escherichia coli

<400> SEQUENCE: 49
atgaaaacta cgcatacctc cctcccsttt gccggacata cgctgcattt tgttgagttc      60
gatccggcga atttttgtga gcaggattta ctctggctgc cgcactacgc acaactgcaa     120
cacgctggac gtaaacgtaa aacagagcat ttagccggac ggatcgctgc tgtttatgct     180
ttgcgggaat atggctataa atgtgtgccc gcaatcggcg agctacgcca acctgtctgg     240
cctgcggagg tatacggcag tattagccac tgtgggacta cggcattagc cgtggtatct     300
cgtcaaccga ttggcattga tatagaagaa attttttctg tacaaaccgc aagagaattg     360
acagacaaca ttattacacc agcggaacac gagcgactcg cagactgcgg tttagccttt     420
tctctggcgc tgacactggc attttccgcc aaagagagcg catttaaggc aagtgagatc     480
caaactgatg caggttttct ggactatcag ataattagct ggaataaaca gcaggtcatc     540
attcatcgtg agaatgagat gtttgctgtg cactggcaga taaagaaaaa gatagtcata     600
acgctgtgcc aacacgatta a                                               621

<210> SEQ ID NO 50
<211> LENGTH: 206
<212> TYPE: PRT
<213> ORGANISM: Escherichia coli

<400> SEQUENCE: 50

Met Lys Thr Thr His Thr Ser Leu Pro Phe Ala Gly His Thr Leu His
1               5                   10                  15

Phe Val Glu Phe Asp Pro Ala Asn Phe Cys Glu Gln Asp Leu Leu Trp
            20                  25                  30

Leu Pro His Tyr Ala Gln Leu Gln His Ala Gly Arg Lys Arg Lys Thr
        35                  40                  45

Glu His Leu Ala Gly Arg Ile Ala Ala Val Tyr Ala Leu Arg Glu Tyr
    50                  55                  60

Gly Tyr Lys Cys Val Pro Ala Ile Gly Glu Leu Arg Gln Pro Val Trp
65                  70                  75                  80

Pro Ala Glu Val Tyr Gly Ser Ile Ser His Cys Gly Thr Thr Ala Leu
                85                  90                  95

Ala Val Val Ser Arg Gln Pro Ile Gly Ile Asp Ile Glu Glu Ile Phe
            100                 105                 110

Ser Val Gln Thr Ala Arg Glu Leu Thr Asp Asn Ile Ile Thr Pro Ala
        115                 120                 125

Glu His Glu Arg Leu Ala Asp Cys Gly Leu Ala Phe Ser Leu Ala Leu
    130                 135                 140

Thr Leu Ala Phe Ser Ala Lys Glu Ser Ala Phe Lys Ala Ser Glu Ile
145                 150                 155                 160

Gln Thr Asp Ala Gly Phe Leu Asp Tyr Gln Ile Ile Ser Trp Asn Lys
                165                 170                 175

Gln Gln Val Ile Ile His Arg Glu Asn Glu Met Phe Ala Val His Trp
            180                 185                 190

Gln Ile Lys Glu Lys Ile Val Ile Thr Leu Cys Gln His Asp
        195                 200                 205

<210> SEQ ID NO 51
<211> LENGTH: 654
<212> TYPE: DNA
<213> ORGANISM: Corynebacterium glutamicum

<400> SEQUENCE: 51
atgctggatg agtctttgtt tccaaattcg gcaaagtttt ctttcattaa aactggcgat     60
gctgttaatt tagaccattt ccatcagttg catccgttgg aaaaggcact ggtagcgcac    120
tcggttgata ttagaaaagc agagtttgga gatgccaggt ggtgtgcaca tcaggcactc    180
caagctttgg gacgagatag cggtgatccc attttgcgtg gggaacgagg aatgccattg    240
tggccttctt cggtgtctgg ttcattgacc cacactgacg gattccgagc tgctgttgtg    300
gcgccacgat tgttggtgcg ttctatggga ttggatgccg aacctgcgga gccgttgccc    360
aaggatgttt tgggttcaat cgctcgggtg ggggagattc ctcaacttaa gcgcttggag    420
gaacaaggtg tgcactgcgc ggatcgcctg ctgttttgtg ccaaggaagc aacatacaaa    480
gcgtggttcc gctgacgca taggtggctt ggttttgaac aagctgagat cgacttgcgt    540
gatgatggca cttttgtgtc ctatttgctg gttcgaccaa ctccagtgcc gtttatttca    600
ggtaaatggg tactgcgtga tggttatgtc atagctgcga ctgcagtgac ttga          654

<210> SEQ ID NO 52
<211> LENGTH: 217
<212> TYPE: PRT
<213> ORGANISM: Corynebacterium glutamicum

<400> SEQUENCE: 52

```
Met Leu Asp Glu Ser Leu Phe Pro Asn Ser Ala Lys Phe Ser Phe Ile
1               5                   10                  15

Lys Thr Gly Asp Ala Val Asn Leu Asp His Phe His Gln Leu His Pro
            20                  25                  30

Leu Glu Lys Ala Leu Val Ala His Ser Val Asp Ile Arg Lys Ala Glu
            35                  40                  45

Phe Gly Asp Ala Arg Trp Cys Ala His Gln Ala Leu Gln Ala Leu Gly
        50                  55                  60

Arg Asp Ser Gly Asp Pro Ile Leu Arg Gly Arg Gly Met Pro Leu
65                  70                  75                  80

Trp Pro Ser Ser Val Ser Gly Ser Leu Thr His Thr Asp Gly Phe Arg
                85                  90                  95

Ala Ala Val Val Ala Pro Arg Leu Leu Val Arg Ser Met Gly Leu Asp
                100                 105                 110

Ala Glu Pro Ala Glu Pro Leu Pro Lys Asp Val Leu Gly Ser Ile Ala
            115                 120                 125

Arg Val Gly Glu Ile Pro Gln Leu Lys Arg Leu Glu Glu Gln Gly Val
    130                 135                 140

His Cys Ala Asp Arg Leu Leu Phe Cys Ala Lys Glu Ala Thr Tyr Lys
145                 150                 155                 160

Ala Trp Phe Pro Leu Thr His Arg Trp Leu Gly Phe Glu Gln Ala Glu
                165                 170                 175

Ile Asp Leu Arg Asp Asp Gly Thr Phe Val Ser Tyr Leu Leu Val Arg
                180                 185                 190

Pro Thr Pro Val Pro Phe Ile Ser Gly Lys Trp Val Leu Arg Asp Gly
            195                 200                 205

Tyr Val Ile Ala Ala Thr Ala Val Thr
            210                 215

<210> SEQ ID NO 53
<211> LENGTH: 1428
<212> TYPE: DNA
<213> ORGANISM: Corynebacterium glutamicum

<400> SEQUENCE: 53
atgcgcctgc gtgtctcgag tagtctcctc cccttcctcg tcccaacct cgaccattac      60 ggtcgccctc tcctaaagga gcctggcatg gatatccgcc aaacaattaa cgacacagca    120
atgtcgagat atcagtggtt cattgtattt atcgcagtgc tgctcaacgc actggacggc    180
tttgatgtcc tcgccatgtc ttttactgcg aatgcagtga ccgaagaatt tggactgagt    240
ggcagccagc ttggtgtgct gctgagttcc gcgctgttcg gcatgaccgc tggatctttg    300
ctgttcggtc cgatcggtga ccgtttcggc cgtaagaatg ccctgatgat cgcgctgctg    360
ttcaacgtgg tgggattggt attgtccgcc accgcgcagt ccgcaggcca gttgggcgtg    420
tggcgtttga tcactggtat cggcatcggc ggaatcctcg cctgcatcac agtggtgatc    480
agtgagttct ccaacaacaa aaaccgcggc atggccatgt ccatctacgc tgctggttac    540
ggcatcggcg cgtccttggg cggattcggc gcagcgcagc tcatcccaac atttggatgg    600
cgctccgtgt tcgcagccgg tgcgatcgca actggtatcg ccaccatcgc tactttcttc    660
ttcctgccag aatccgttga ttggctgagc actcgccgcc ctgcgggcgc tcgcgacaag    720
atcaattaca ttgcgcgccc cctgggcaaa gtcggtacct tgagcttcc aggcgaacaa    780 agcttgtcga cgaaaaaagc cggtctccaa tcgtatgcag tgctcgttaa caaagagaac    840
cgtggaacca gcatcaagct gtgggttgcg ttcggcatcg tgatgttcgg cttctacttc    900
```

-continued

```
gccaacactt ggaccccgaa gctgctcgtg gaaaccggaa tgtcagaaca gcagggcatc    960
atcggtggtt tgatgttgtc catgggtgga gcattcggtt ccctgctcta cggtttcctc   1020
accaccaagt tcagctcccg aaacacactg atgaccttca tggtgctgtc cggcctgacg   1080
ctgatcctgt tcatttcctc cacctctgtt ccatccatcg cgtttgccag cggcgttgtc   1140
gtgggcatgc tgatcaatgg ttgtgtggct ggtctgtaca ccctgtcccc acagctgtac   1200
tccgctgaag tacgcaccac tggtgtgggc gctgcgattg gtatgggtcg tgtcggtgcg   1260
atttccgcgc cactgctggt gggtagcctg ctggattctg ctggtccccc aacgcagctg   1320
tatgttggtg tggcagtgat tgttattgcc ggtgcaaccg cattgattgg gatgcgcact   1380
caggcagtag ccgtcgaaaa gcagcctgaa gccctagcga ccaaatag               1428
```

<210> SEQ ID NO 54
<211> LENGTH: 475
<212> TYPE: PRT
<213> ORGANISM: Corynebacterium glutamicum

<400> SEQUENCE: 54

```
Met Arg Leu Arg Val Ser Ser Leu Leu Pro Phe Leu Val Pro Asn
1               5                   10                  15

Leu Asp His Tyr Gly Arg Pro Leu Leu Lys Glu Pro Gly Met Asp Ile
            20                  25                  30

Arg Gln Thr Ile Asn Asp Thr Ala Met Ser Arg Tyr Gln Trp Phe Ile
        35                  40                  45

Val Phe Ile Ala Val Leu Leu Asn Ala Leu Asp Gly Phe Asp Val Leu
    50                  55                  60

Ala Met Ser Phe Thr Ala Asn Ala Val Thr Glu Glu Phe Gly Leu Ser
65                  70                  75                  80

Gly Ser Gln Leu Gly Val Leu Ser Ser Ala Leu Phe Gly Met Thr
            85                  90                  95

Ala Gly Ser Leu Leu Phe Gly Pro Ile Gly Asp Arg Phe Gly Arg Lys
        100                 105                 110

Asn Ala Leu Met Ile Ala Leu Leu Phe Asn Val Val Gly Leu Val Leu
    115                 120                 125

Ser Ala Thr Ala Gln Ser Ala Gly Gln Leu Gly Val Trp Arg Leu Ile
130                 135                 140

Thr Gly Ile Gly Ile Gly Ile Leu Ala Cys Ile Thr Val Val Ile
145                 150                 155                 160

Ser Glu Phe Ser Asn Asn Lys Asn Arg Gly Met Ala Met Ser Ile Tyr
            165                 170                 175

Ala Ala Gly Tyr Gly Ile Gly Ala Ser Leu Gly Gly Phe Gly Ala Ala
        180                 185                 190

Gln Leu Ile Pro Thr Phe Gly Trp Arg Ser Val Phe Ala Ala Gly Ala
    195                 200                 205

Ile Ala Thr Gly Ile Ala Thr Ile Ala Thr Phe Phe Phe Leu Pro Glu
    210                 215                 220

Ser Val Asp Trp Leu Ser Thr Arg Arg Pro Ala Gly Ala Arg Asp Lys
225                 230                 235                 240

Ile Asn Tyr Ile Ala Arg Arg Leu Gly Lys Val Gly Thr Phe Glu Leu
            245                 250                 255

Pro Gly Glu Gln Ser Leu Ser Thr Lys Lys Ala Gly Leu Gln Ser Tyr
        260                 265                 270

Ala Val Leu Val Asn Lys Glu Asn Arg Gly Thr Ser Ile Lys Leu Trp
```

```
                275                 280                 285
Val Ala Phe Gly Ile Val Met Phe Gly Phe Tyr Phe Ala Asn Thr Trp
        290                 295                 300
Thr Pro Lys Leu Leu Val Glu Thr Gly Met Ser Glu Gln Gln Gly Ile
305                 310                 315                 320
Ile Gly Gly Leu Met Leu Ser Met Gly Gly Ala Phe Gly Ser Leu Leu
                325                 330                 335
Tyr Gly Phe Leu Thr Thr Lys Phe Ser Ser Arg Asn Thr Leu Met Thr
        340                 345                 350
Phe Met Val Leu Ser Gly Leu Thr Leu Ile Leu Phe Ile Ser Ser Thr
        355                 360                 365
Ser Val Pro Ser Ile Ala Phe Ala Ser Gly Val Val Gly Met Leu
    370                 375                 380
Ile Asn Gly Cys Val Ala Gly Leu Tyr Thr Leu Ser Pro Gln Leu Tyr
385                 390                 395                 400
Ser Ala Glu Val Arg Thr Thr Gly Val Gly Ala Ala Ile Gly Met Gly
                405                 410                 415
Arg Val Gly Ala Ile Ser Ala Pro Leu Leu Val Gly Ser Leu Leu Asp
            420                 425                 430
Ser Gly Trp Ser Pro Thr Gln Leu Tyr Val Gly Val Ala Val Ile Val
            435                 440                 445
Ile Ala Gly Ala Thr Ala Leu Ile Gly Met Arg Thr Gln Ala Val Ala
    450                 455                 460
Val Glu Lys Gln Pro Glu Ala Leu Ala Thr Lys
465                 470                 475

<210> SEQ ID NO 55
<211> LENGTH: 1296
<212> TYPE: DNA
<213> ORGANISM: Corynebacterium glutamicum

<400> SEQUENCE: 55
gtgtcaacga ccaccccaac ccgcgcaacc aaaagtgtcg gaacagttct cgcactcctg      60
tggttcgcaa ttgtcctcga cggctttgac ctagtcgtcc tgggcgcaac aatcccgtcc     120
atgctggagg atcccgcgtg ggatctcact gctggacagg ccacacagat tccaccatc     180
ggcctcgtcg gcatgaccat cggcgcactg accattggtt tcttaactga ccgtctgggt     240
cgacgccgcg tcatgctgtt ctctgtggca gtgttttctg tattcaccct cctgctggca     300
ttcaccacca acgtccagct cttcagcctg tggcgtttcc tcgcaggtgt tggccttggt     360
ggagcactcc ccaccgcaat tgccatggtg accgagtttc gccccggcac caaagcgggc     420
tctgcatcaa ctaccttgat gaccggatac cacgtcgggg cagtagcaac cgcttttcctt     480
ggtctcttcc ttatcgacgg ctttggttgg cactccatgt tcatcgcagg cgctgtgcca     540
ggactactcc tgctgccact gctgtatttc ttccttccag aatccccgca gtacctcaaa     600
atctccggca agttggatga ggcgcaggca gttgcagcat cttatggact ttccctggat     660
gatgatcttg atcgcgaaca cgaagaagaa cttggcgagt cctcctcact ttcctccctg     720
ttcaagccct cgttccgccg caacaccctg gcgatttggg gcacctcatt catgggactc     780
ctcctggtct acggcctgaa cacatggctg ccacaaatca tgcgccaagc agactacgac     840
atgggtaact ccctgggctt cctcatggtt cttaacatcg gcgcagtgat cggccttat      900
attgcagggc gaattgccga taagaactcc cctcgcaaaa cagcactcgt atggttcgtg     960
ttctctgcat ttttcctcgc actacttgct gtccggatgc cactgatcgg tctgtatggc    1020
```

-continued

```
atcgtgctgc tcaccggcat ctttgtgttc agctcccagg tactcatcta cgccttcgtt    1080
ggtgagaatc accctgccaa gatgcgtgca actgccatgg gattctccgc aggaattggt    1140
cgcctcggcg cgatctcggg tccgttgctg gcggcctgc ttgtcagtgc caaccttgct     1200
tacccatggg gcttcttcgc cttcgctggc gttggactgc tgggcgcgct gattttctcc    1260
gcatcgaaga ctctgaggca tcgcgagaac gcttag                              1296
```

<210> SEQ ID NO 56
<211> LENGTH: 431
<212> TYPE: PRT
<213> ORGANISM: Corynebacterium glutamicum

<400> SEQUENCE: 56

```
Met Ser Thr Thr Thr Pro Thr Arg Ala Thr Lys Ser Val Gly Thr Val
1               5                   10                  15

Leu Ala Leu Leu Trp Phe Ala Ile Val Leu Asp Gly Phe Asp Leu Val
            20                  25                  30

Val Leu Gly Ala Thr Ile Pro Ser Met Leu Glu Asp Pro Ala Trp Asp
        35                  40                  45

Leu Thr Ala Gly Gln Ala Thr Gln Ile Ser Thr Ile Gly Leu Val Gly
    50                  55                  60

Met Thr Ile Gly Ala Leu Thr Ile Gly Phe Leu Thr Asp Arg Leu Gly
65                  70                  75                  80

Arg Arg Arg Val Met Leu Phe Ser Val Ala Val Phe Ser Val Phe Thr
                85                  90                  95

Leu Leu Leu Ala Phe Thr Thr Asn Val Gln Leu Phe Ser Leu Trp Arg
            100                 105                 110

Phe Leu Ala Gly Val Gly Leu Gly Gly Ala Leu Pro Thr Ala Ile Ala
        115                 120                 125

Met Val Thr Glu Phe Arg Pro Gly Thr Lys Ala Gly Ser Ala Ser Thr
    130                 135                 140

Thr Leu Met Thr Gly Tyr His Val Gly Ala Val Ala Thr Ala Phe Leu
145                 150                 155                 160

Gly Leu Phe Leu Ile Asp Gly Phe Gly Trp His Ser Met Phe Ile Ala
                165                 170                 175

Gly Ala Val Pro Gly Leu Leu Leu Leu Pro Leu Leu Tyr Phe Phe Leu
            180                 185                 190

Pro Glu Ser Pro Gln Tyr Leu Lys Ile Ser Gly Lys Leu Asp Glu Ala
        195                 200                 205

Gln Ala Val Ala Ala Ser Tyr Gly Leu Ser Leu Asp Asp Leu Asp
    210                 215                 220

Arg Glu His Glu Glu Leu Gly Glu Ser Ser Ser Leu Ser Ser Leu
225                 230                 235                 240

Phe Lys Pro Ser Phe Arg Arg Asn Thr Leu Ala Ile Trp Gly Thr Ser
                245                 250                 255

Phe Met Gly Leu Leu Val Tyr Gly Leu Asn Thr Trp Leu Pro Gln
            260                 265                 270

Ile Met Arg Gln Ala Asp Tyr Asp Met Gly Asn Ser Leu Gly Phe Leu
        275                 280                 285

Met Val Leu Asn Ile Gly Ala Val Ile Gly Leu Tyr Ile Ala Gly Arg
    290                 295                 300

Ile Ala Asp Lys Asn Ser Pro Arg Lys Thr Ala Leu Val Trp Phe Val
305                 310                 315                 320
```

Phe Ser Ala Phe Phe Leu Ala Leu Leu Ala Val Arg Met Pro Leu Ile
              325                 330                 335

Gly Leu Tyr Gly Ile Val Leu Leu Thr Gly Ile Phe Val Phe Ser Ser
            340                 345                 350

Gln Val Leu Ile Tyr Ala Phe Val Gly Glu Asn His Pro Ala Lys Met
        355                 360                 365

Arg Ala Thr Ala Met Gly Phe Ser Ala Gly Ile Gly Arg Leu Gly Ala
    370                 375                 380

Ile Ser Gly Pro Leu Leu Gly Gly Leu Leu Val Ser Ala Asn Leu Ala
385                 390                 395                 400

Tyr Pro Trp Gly Phe Phe Ala Phe Ala Gly Val Gly Leu Leu Gly Ala
                405                 410                 415

Leu Ile Phe Ser Ala Ser Lys Thr Leu Arg His Arg Glu Asn Ala
            420                 425                 430

<210> SEQ ID NO 57
<211> LENGTH: 1131
<212> TYPE: DNA
<213> ORGANISM: Corynebacterium glutamicum

<400> SEQUENCE: 57
atgacactgt ccgaacgcaa gctcaccacc accgccaaga ttcttcccca cccactcaac     60
gcctggtacg tcgccgcttg ggattatgaa gtcacatcta aaaagcccat ggccaggaca    120
atcgccaaca aaccactcgc tttgtaccgc accaaagatg gccgagccgt tgcccttgca    180
gacgcctgct ggcaccgcct cgcaccgcta tccaagggaa aactcgtggg cacagacgga    240
atccaatgcc cttatcacgg cttggagtac aactccgcgg gccgctgcat gaaaatgccc    300
gcgcaggaaa ccctcaaccc gtcagcagcc gtcaactcct accccgtggt ggaagcccac    360
cgctttgtgt gggtgtggct gggcgatccc acattggcag atcccaccca gtacccgat    420 atgcaccaga tgagccaccc cgaatgggca ggcgatggac gcaccatctc cgctgactgc    480
aactaccaat tagtgctgga caacttgatg gacctcaccc acgaagaatt cgtgcactcc    540
tccagcatcg ccaagacgaa acttagtgaa tcagagttcg tggtcaccca cactgaagat    600
tccgtgacgg tcacccgctg gatgcatgac atagatgcac caccgttttg caaaagaac    660 atgaatgata gttcccagg atttgaaggc aaggtggatc gttggcagat catccactac    720
tactaccctt ccaccatctg cattgatgtt ggtgtagcaa aggctggaac cggcgcgcag    780
gaaggcgacc gcagccaggg cgttaatggg tatgtaatga acaccattac cccagattca    840
gatcgttcct ctcattactt ctgggcattc atgcgcaact accgcctgga agccaaacc    900 atcaccaccc agctgcgcga cggtgtatcc ggtgtattca agaagacga agacatgctg    960 accgctcagc aagatgccat cgacgccaac accgactatg agtttacag cctcaacatt   1020 gatgccggtg gcatgtgggt gcgccgaatc ctcgaggaag cactctccaa ggaaggccga   1080
ctggatatcc ccaccacatt cccccgcgca acaccgaagc cggaggcata a             1131

<210> SEQ ID NO 58
<211> LENGTH: 376
<212> TYPE: PRT
<213> ORGANISM: Corynebacterium glutamicum

<400> SEQUENCE: 58

Met Thr Leu Ser Glu Arg Lys Leu Thr Thr Thr Ala Lys Ile Leu Pro
1               5                   10                  15

His Pro Leu Asn Ala Trp Tyr Val Ala Ala Trp Asp Tyr Glu Val Thr

```
                    20                  25                  30
Ser Lys Lys Pro Met Ala Arg Thr Ile Ala Asn Lys Pro Leu Ala Leu
             35                  40                  45

Tyr Arg Thr Lys Asp Gly Arg Ala Val Ala Leu Ala Asp Ala Cys Trp
 50                  55                  60

His Arg Leu Ala Pro Leu Ser Lys Gly Lys Leu Val Gly Thr Asp Gly
 65                  70                  75                  80

Ile Gln Cys Pro Tyr His Gly Leu Glu Tyr Asn Ser Ala Gly Arg Cys
                 85                  90                  95

Met Lys Met Pro Ala Gln Glu Thr Leu Asn Pro Ser Ala Ala Val Asn
            100                 105                 110

Ser Tyr Pro Val Val Glu Ala His Arg Phe Val Trp Val Trp Leu Gly
            115                 120                 125

Asp Pro Thr Leu Ala Asp Pro Thr Gln Val Pro Asp Met His Gln Met
            130                 135                 140

Ser His Pro Glu Trp Ala Gly Asp Gly Arg Thr Ile Ser Ala Asp Cys
145                 150                 155                 160

Asn Tyr Gln Leu Val Leu Asp Asn Leu Met Asp Leu Thr His Glu Glu
                165                 170                 175

Phe Val His Ser Ser Ile Gly Gln Asp Glu Leu Ser Glu Ser Glu
            180                 185                 190

Phe Val Val Thr His Thr Glu Asp Ser Val Thr Val Thr Arg Trp Met
            195                 200                 205

His Asp Ile Asp Ala Pro Pro Phe Trp Gln Lys Asn Met Asn Asp Lys
            210                 215                 220

Phe Pro Gly Phe Glu Gly Lys Val Asp Arg Trp Gln Ile Ile His Tyr
225                 230                 235                 240

Tyr Tyr Pro Ser Thr Ile Cys Ile Asp Val Gly Val Ala Lys Ala Gly
                245                 250                 255

Thr Gly Ala Gln Glu Gly Asp Arg Ser Gln Gly Val Asn Gly Tyr Val
            260                 265                 270

Met Asn Thr Ile Thr Pro Asp Ser Asp Arg Ser Ser His Tyr Phe Trp
            275                 280                 285

Ala Phe Met Arg Asn Tyr Arg Leu Glu Ser Gln Thr Ile Thr Thr Gln
            290                 295                 300

Leu Arg Asp Gly Val Ser Gly Val Phe Lys Glu Asp Glu Asp Met Leu
305                 310                 315                 320

Thr Ala Gln Gln Asp Ala Ile Asp Ala Asn Thr Asp Tyr Glu Phe Tyr
                325                 330                 335

Ser Leu Asn Ile Asp Ala Gly Gly Met Trp Val Arg Arg Ile Leu Glu
            340                 345                 350

Glu Ala Leu Ser Lys Glu Gly Arg Leu Asp Ile Pro Thr Thr Phe Pro
            355                 360                 365

Arg Ala Thr Pro Lys Pro Glu Ala
            370                 375

<210> SEQ ID NO 59
<211> LENGTH: 978
<212> TYPE: DNA
<213> ORGANISM: Corynebacterium glutamicum

<400> SEQUENCE: 59
atgaactcgc aatggcaaga tgcacatgtt gtttccagcg aaatcatcgc tgcagacatt      60
cgacgaatag aactatcccc gaaatttgcg attccagtaa aacccggcga acatctcaag     120
```

```
atcatggtgc ccctaaaaac tggacaggaa aagagatcgt actccatcgt tgacgctcgt      180
cacgacggtt cgactctcgc cctgagcgta ctcaaaacca gaaactcccg tggaggatct      240
gagttcatgc atacgcttcg agctggagac acagttactg tctccaggcc gtctcaggat      300
tttcctctcc gcgtgggtgc gcctgagtat gtacttgttg ccggcggaat tggaatcaca      360
gcgatccgtt caatggcatc tttattaaag aaattgggag caaactaccg cattcatttc      420
gcagcacgca gccttgatgc catggcttac aaagatgagc tcgtggcaga cacggcgac       480 aagctgcacc tgcatctaga ttctgaaggc accaccatcg atgtcccagc attgatcgaa      540
accttaaacc cccacactga gctttatatg tgcggcccca tccgcttgat ggatgccatc      600
cggcgcgcat ggaacacccg cggacttgac cccaccaatc tgcgtttcga acgtttgga       660 aacagtggat ggtctccccc agaggttttc cacatccaag taccagagct ggggcttcac      720
gccacagtca acaaggatga agcatgctg gaggctttgc aaaaggctgg ggcgaatatg       780
atgtttgatt gtcgaaaagg cgaatgtggt ttgtgccagg ttcgcgttct agaagtcgat      840
ggccaggttg atcaccgcga tgtgttcttc tctgatcgtc aaaaagaatc cgacgcaaag      900
gcatgcgcct gcgtgtctcg agtagtctcc tccccttcct cgtccccaac ctcgaccatt      960
acggtcgccc tctcctaa                                                   978

<210> SEQ ID NO 60
<211> LENGTH: 325
<212> TYPE: PRT
<213> ORGANISM: Corynebacterium glutamicum

<400> SEQUENCE: 60

Met Asn Ser Gln Trp Gln Asp Ala His Val Val Ser Ser Glu Ile Ile
1               5                   10                  15

Ala Ala Asp Ile Arg Arg Ile Glu Leu Ser Pro Lys Phe Ala Ile Pro
            20                  25                  30

Val Lys Pro Gly Glu His Leu Lys Ile Met Val Pro Leu Lys Thr Gly
        35                  40                  45

Gln Glu Lys Arg Ser Tyr Ser Ile Val Asp Ala Arg His Asp Gly Ser
    50                  55                  60

Thr Leu Ala Leu Ser Val Leu Lys Thr Arg Asn Ser Arg Gly Gly Ser
65                  70                  75                  80

Glu Phe Met His Thr Leu Arg Ala Gly Asp Thr Val Thr Val Ser Arg
                85                  90                  95

Pro Ser Gln Asp Phe Pro Leu Arg Val Gly Ala Pro Glu Tyr Val Leu
            100                 105                 110

Val Ala Gly Gly Ile Gly Ile Thr Ala Ile Arg Ser Met Ala Ser Leu
        115                 120                 125

Leu Lys Lys Leu Gly Ala Asn Tyr Arg Ile His Phe Ala Ala Arg Ser
    130                 135                 140

Leu Asp Ala Met Ala Tyr Lys Asp Glu Leu Val Ala Glu His Gly Asp
145                 150                 155                 160

Lys Leu His Leu His Leu Asp Ser Glu Gly Thr Thr Ile Asp Val Pro
                165                 170                 175

Ala Leu Ile Glu Thr Leu Asn Pro His Thr Glu Leu Tyr Met Cys Gly
            180                 185                 190

Pro Ile Arg Leu Met Asp Ala Ile Arg Arg Ala Trp Asn Thr Arg Gly
        195                 200                 205

Leu Asp Pro Thr Asn Leu Arg Phe Glu Thr Phe Gly Asn Ser Gly Trp
```

```
                   210                 215                 220

Phe Ser Pro Glu Val Phe His Ile Gln Val Pro Glu Leu Gly Leu His
225                 230                 235                 240

Ala Thr Val Asn Lys Asp Glu Ser Met Leu Glu Ala Leu Gln Lys Ala
                245                 250                 255

Gly Ala Asn Met Met Phe Asp Cys Arg Lys Gly Glu Cys Gly Leu Cys
                260                 265                 270

Gln Val Arg Val Leu Glu Val Asp Gly Gln Val Asp His Arg Asp Val
            275                 280                 285

Phe Phe Ser Asp Arg Gln Lys Glu Ser Asp Ala Lys Ala Cys Ala Cys
        290                 295                 300

Val Ser Arg Val Val Ser Ser Pro Ser Ser Pro Thr Ser Thr Ile
305                 310                 315                 320

Thr Val Ala Leu Ser
            325

<210> SEQ ID NO 61
<211> LENGTH: 615
<212> TYPE: DNA
<213> ORGANISM: Corynebacterium glutamicum

<400> SEQUENCE: 61
atgattgata cagggaagaa cggcgagttc cgctacgagc agtcgaatat catcgatcag     60
aacgaagccg agttcggcat cactccttca cagaccgtgg gcccttacgt ccacatcggt    120 ttgaccttg aaggtgcgga gcatctcgtg gagccaggtt cggaaggcgc ggtgtccttt     180
actgtttccg caactgatgg caacggcgac cccatcgcgg atgccatgtt tgaactgtgg    240
caggccgatc cagagggcat ccacaactct gatttggatc caaaccgcac agcaccagca    300
accgcagatg gcttccgcgg gcttggtcgc gcgatggcaa acgcgcaggg tgaggcaacg    360
ttcaccactt tggttccggg agcattcgca gatgaggcac cacacttcaa ggttggtgtg    420
ttcgcccgtg gcatgctgga gcgtctgtac actcgcgcat acctgccaga cgccgatttg    480
agcaccgacc cagttttggc tgtggtccca gctgatcgac gtgacctcct ggtggctcaa    540
aagaccgatg atggattccg cttcgacatc actgtccagg ctgaagacaa tgaaacccca    600
ttttttggac tctaa                                                    615

<210> SEQ ID NO 62
<211> LENGTH: 204
<212> TYPE: PRT
<213> ORGANISM: Corynebacterium glutamicum

<400> SEQUENCE: 62

Met Ile Asp Thr Gly Lys Asn Gly Glu Phe Arg Tyr Glu Gln Ser Asn
1               5                   10                  15

Ile Ile Asp Gln Asn Glu Ala Glu Phe Gly Ile Thr Pro Ser Gln Thr
            20                  25                  30

Val Gly Pro Tyr Val His Ile Gly Leu Thr Leu Glu Gly Ala Glu His
        35                  40                  45

Leu Val Glu Pro Gly Ser Glu Gly Ala Val Ser Phe Thr Val Ser Ala
    50                  55                  60

Thr Asp Gly Asn Gly Asp Pro Ile Ala Asp Ala Met Phe Glu Leu Trp
65                  70                  75                  80

Gln Ala Asp Pro Glu Gly Ile His Asn Ser Asp Leu Asp Pro Asn Arg
                85                  90                  95
```

```
Thr Ala Pro Ala Thr Ala Asp Gly Phe Arg Gly Leu Gly Arg Ala Met
                100                 105                 110

Ala Asn Ala Gln Gly Glu Ala Thr Phe Thr Thr Leu Val Pro Gly Ala
            115                 120                 125

Phe Ala Asp Glu Ala Pro His Phe Lys Val Gly Val Phe Ala Arg Gly
130                 135                 140

Met Leu Glu Arg Leu Tyr Thr Arg Ala Tyr Leu Pro Asp Ala Asp Leu
145                 150                 155                 160

Ser Thr Asp Pro Val Leu Ala Val Val Pro Ala Asp Arg Arg Asp Leu
                165                 170                 175

Leu Val Ala Gln Lys Thr Asp Asp Gly Phe Arg Phe Asp Ile Thr Val
            180                 185                 190

Gln Ala Glu Asp Asn Glu Thr Pro Phe Phe Gly Leu
            195                 200

<210> SEQ ID NO 63
<211> LENGTH: 693
<212> TYPE: DNA
<213> ORGANISM: Corynebacterium glutamicum

<400> SEQUENCE: 63
atggacatcc cacacttcgc cccgacggga ggcgaatact ccccactgca cttcccggag      60
taccggacca ccatcaagcg caacccaagc aacgatctca tcatggttcc tagtcgcctc     120
ggcgagtcca cgggacctgt cttcggcgac cgcgacttgg gagacatcga caacgacatg     180
accaaggtga acgtggcga ggctatcggc cagcgcatct tcgttcacgg ccgtgtcctc      240
ggtttcgatg gcaagccagt tccgcacacc ttggtcgagg cgtggcaggc aaacgccgca     300
ggccgttacc gccacaagaa tgactcctgg ccagcgccac tggatccaca cttcaacggt     360
gttgcacgta ctctcaccga caaggacggc cagtaccact tctggaccgt tatgccaggt     420 aattacccctt ggggtaacca ccacaacgca tggcgcccgg cgcacattca cttctcgctc    480
tatggtcgtc agtttacgga gcgtctggtc acccagatgt acttcccgaa cgatccattg     540
ttcttccagg atccgatcta caacgcggtg ccaaagggtg cacgtgagcg catgatcgca     600
acgttcgact atgacgagac ccgtgaaaac ttcgcgcttg ttacaagttt cgacatcgtc     660
cttcgtggcc gcaacgccac cccatttgag taa                                  693

<210> SEQ ID NO 64
<211> LENGTH: 230
<212> TYPE: PRT
<213> ORGANISM: Corynebacterium glutamicum

<400> SEQUENCE: 64

Met Asp Ile Pro His Phe Ala Pro Thr Gly Gly Glu Tyr Ser Pro Leu
1               5                   10                  15

His Phe Pro Glu Tyr Arg Thr Thr Ile Lys Arg Asn Pro Ser Asn Asp
                20                  25                  30

Leu Ile Met Val Pro Ser Arg Leu Gly Glu Ser Thr Gly Pro Val Phe
            35                  40                  45

Gly Asp Arg Asp Leu Gly Asp Ile Asp Asn Asp Met Thr Lys Val Asn
50                  55                  60

Gly Gly Glu Ala Ile Gly Gln Arg Ile Phe Val His Gly Arg Val Leu
65                  70                  75                  80

Gly Phe Asp Gly Lys Pro Val Pro His Thr Leu Val Glu Ala Trp Gln
                85                  90                  95
```

```
Ala Asn Ala Ala Gly Arg Tyr Arg His Lys Asn Asp Ser Trp Pro Ala
            100                 105                 110

Pro Leu Asp Pro His Phe Asn Gly Val Ala Arg Thr Leu Thr Asp Lys
        115                 120                 125

Asp Gly Gln Tyr His Phe Trp Thr Val Met Pro Gly Asn Tyr Pro Trp
    130                 135                 140

Gly Asn His His Asn Ala Trp Arg Pro Ala His Ile His Phe Ser Leu
145                 150                 155                 160

Tyr Gly Arg Gln Phe Thr Glu Arg Leu Val Thr Gln Met Tyr Phe Pro
                165                 170                 175

Asn Asp Pro Leu Phe Phe Gln Asp Pro Ile Tyr Asn Ala Val Pro Lys
            180                 185                 190

Gly Ala Arg Glu Arg Met Ile Ala Thr Phe Asp Tyr Asp Glu Thr Arg
        195                 200                 205

Glu Asn Phe Ala Leu Gly Tyr Lys Phe Asp Ile Val Leu Arg Gly Arg
    210                 215                 220

Asn Ala Thr Pro Phe Glu
225                 230

<210> SEQ ID NO 65
<211> LENGTH: 1062
<212> TYPE: DNA
<213> ORGANISM: Corynebacterium glutamicum

<400> SEQUENCE: 65
atgagcatcc aagtaaaagc actccagaaa accggccccg aagcaccttt cgaggtcaaa      60
atcattgagc gtcgtgagcc tcgcgctgac gacgtagtta tcgacatcaa agctgccggc     120
atctgccaca gcgatatcca caccatccgc aacgaatggg gcgaggcaca cttcccgctc     180
accgtcggcc acgaaatcgc aggcgttgtc tctgcggttg ctccgatgt aaccaagtgg      240 aaagtcggcg accgcgttgg cgtcggctgc ctagttaact cctgcggcga atgtgaacag     300
tgtgtcgcgg gatttgaaaa caactgcctt cgcggaaacg tcggaaccta caactccgac     360
gacgtcgacg caccatcac gcaaggtggc tacgccgaaa aggtagtggt caacgaacgt     420
ttcctctgca gcatcccaga ggaactcgac ttcgatgtcg cagcaccact gctgtgcgca     480
ggcatcacca cctactcccc gatcgctcgc tggaacgtta agaaggcga caaagtagca     540 gtcatgggcc tcggcgggct cggccacatg ggtgtccaaa tcgccgcagc caagggcgct     600
gacgttaccg ttctgtcccg ttccctgcgc aaggctgaac ttgccaagga actcggcgca     660
gctcgcacgc ttgcgacttc tgatgaggat ttcttcaccg aacacgccgg tgaattcgac     720
ttcatcctca acaccattag cgcatccatc ccagtcgaca agtacctgag ccttctcaag     780
ccacacggtg tcatggctgt tgtcggtctg ccaccagaga agcagccact gagcttcggt     840
gcgctcatcg gcggcggaaa agtcctcacc ggatccaaca ttggcggcat ccctgaaacc     900
caggaaatgc tcgacttctg tgcaaaacac ggcctcggcg cgatgatcga actgtcggc      960 gtcaacgatg ttgatgcagc ctacgaccgc gttgttgccg gcgacgttca gttccgcgtt    1020
gtcattgata ctgcttcgtt tgcagaggta gaggcggttt ag                       1062

<210> SEQ ID NO 66
<211> LENGTH: 353
<212> TYPE: PRT
<213> ORGANISM: Corynebacterium glutamicum

<400> SEQUENCE: 66
```

```
Met Ser Ile Gln Val Lys Ala Leu Gln Lys Thr Gly Pro Glu Ala Pro
1               5                   10                  15

Phe Glu Val Lys Ile Ile Glu Arg Arg Glu Pro Arg Ala Asp Asp Val
                20                  25                  30

Val Ile Asp Ile Lys Ala Ala Gly Ile Cys His Ser Asp Ile His Thr
            35                  40                  45

Ile Arg Asn Glu Trp Gly Ala His Phe Pro Leu Thr Val Gly His
        50                  55                  60

Glu Ile Ala Gly Val Val Ser Ala Val Gly Ser Asp Val Thr Lys Trp
65                  70                  75                  80

Lys Val Gly Asp Arg Val Gly Val Gly Cys Leu Val Asn Ser Cys Gly
                85                  90                  95

Glu Cys Glu Gln Cys Val Ala Gly Phe Glu Asn Asn Cys Leu Arg Gly
                100                 105                 110

Asn Val Gly Thr Tyr Asn Ser Asp Val Asp Gly Thr Ile Thr Gln
            115                 120                 125

Gly Gly Tyr Ala Glu Lys Val Val Val Asn Glu Arg Phe Leu Cys Ser
    130                 135                 140

Ile Pro Glu Glu Leu Asp Phe Asp Val Ala Ala Pro Leu Leu Cys Ala
145                 150                 155                 160

Gly Ile Thr Thr Tyr Ser Pro Ile Ala Arg Trp Asn Val Lys Glu Gly
                165                 170                 175

Asp Lys Val Ala Val Met Gly Leu Gly Gly Leu Gly His Met Gly Val
            180                 185                 190

Gln Ile Ala Ala Lys Gly Ala Asp Val Thr Val Leu Ser Arg Ser
    195                 200                 205

Leu Arg Lys Ala Glu Leu Ala Lys Glu Leu Gly Ala Ala Arg Thr Leu
    210                 215                 220

Ala Thr Ser Asp Glu Asp Phe Phe Thr Glu His Ala Gly Glu Phe Asp
225                 230                 235                 240

Phe Ile Leu Asn Thr Ile Ser Ala Ser Ile Pro Val Asp Lys Tyr Leu
                245                 250                 255

Ser Leu Leu Lys Pro His Gly Val Met Ala Val Val Gly Leu Pro Pro
                260                 265                 270

Glu Lys Gln Pro Leu Ser Phe Gly Ala Leu Ile Gly Gly Lys Val
    275                 280                 285

Leu Thr Gly Ser Asn Ile Gly Gly Ile Pro Glu Thr Gln Glu Met Leu
    290                 295                 300

Asp Phe Cys Ala Lys His Gly Leu Gly Ala Met Ile Glu Thr Val Gly
305                 310                 315                 320

Val Asn Asp Val Asp Ala Ala Tyr Asp Arg Val Val Ala Gly Asp Val
            325                 330                 335

Gln Phe Arg Val Val Ile Asp Thr Ala Ser Phe Ala Glu Val Glu Ala
                340                 345                 350

Val
```

<210> SEQ ID NO 67
<211> LENGTH: 1113
<212> TYPE: DNA
<213> ORGANISM: Corynebacterium glutamicum

<400> SEQUENCE: 67
gtgtccatga gcactgtcgt gcctggaatt gtcgccctgt ccaaggggc accggtagaa     60 aaagtaaacg ttgttgtccc tgatccaggt gctaacgatg tcatcgtcaa gattcaggcc    120

```
tgcggtgtgt gccacaccga cttggcctac cgcgatggcg atatttcaga tgagttccct      180
tacctcctcg gccacgaggc agcaggtatt gttgaggagg taggcgagtc cgtcacccac      240
gttgaggtcg gcgatttcgt catcttgaac tggcgtgcag tgtgcggcga gtgccgtgca      300
tgtaagaagg gcgagccaaa gtactgcttt aacacccaca acgcatctaa gaagatgacc      360
ctggaagacg gcaccgagct gtccccagca ctgggtattg gcgcgttctt ggaaaagacc      420
ctggtccacg aaggccagtg caccaaggtt aaccctgagg aagatccagc agcagctggc      480
cttctgggtt gcggcatcat ggcaggtctt ggtgctgcgg taaacaccgg tgatattaag      540
cgcggcgagt ccgtggcagt cttcggcctt ggtggcgtgg gcatggcagc tattgctggc      600
gccaagattg ctggtgcatc gaagattatt gctgttgata tcgatgagaa gaagttggag      660
tgggcgaagg aattcggcgc aacccacacc attaattcct ctggtcttgg tggcgagggt      720
gatgcctctg aggtcgtggc aaaggttcgt gagctcactg atggtttcgg tactgacgtc      780
tccatcgatg cggtaggcat catgccgacc tggcagcagg cgttttactc ccgtgatcat      840
gcaggccgca tggtgatggt gggcgttcca aacctgacgt ctcgcgtaga tgttcctgcg      900 attgatttt acggtcgcgg tggctctgtg cgccctgcat ggtacggcga ctgcctgcct       960
gagcgtgatt tcccaactta tgtggatctg cacctgcagg tcgtttccc gctggataag       1020 tttgtttctg agcgtattgg tcttgatgat gttgaagagg ctttcaacac catgaaggct      1080
ggcgacgtgc tgcgttctgt ggtggagatc taa                                  1113
```

<210> SEQ ID NO 68
<211> LENGTH: 370
<212> TYPE: PRT
<213> ORGANISM: Corynebacterium glutamicum

<400> SEQUENCE: 68

```
Met Ser Met Ser Thr Val Val Pro Gly Ile Val Ala Leu Ser Lys Gly
1               5                   10                  15

Ala Pro Val Glu Lys Val Asn Val Val Pro Asp Pro Gly Ala Asn
            20                  25                  30

Asp Val Ile Val Lys Ile Gln Ala Cys Gly Val Cys His Thr Asp Leu
        35                  40                  45

Ala Tyr Arg Asp Gly Asp Ile Ser Asp Glu Phe Pro Tyr Leu Leu Gly
    50                  55                  60

His Glu Ala Ala Gly Ile Val Glu Glu Val Gly Glu Ser Val Thr His
65                  70                  75                  80

Val Glu Val Gly Asp Phe Val Ile Leu Asn Trp Arg Ala Val Cys Gly
                85                  90                  95

Glu Cys Arg Ala Cys Lys Lys Gly Glu Pro Lys Tyr Cys Phe Asn Thr
            100                 105                 110

His Asn Ala Ser Lys Lys Met Thr Leu Glu Asp Gly Thr Glu Leu Ser
        115                 120                 125

Pro Ala Leu Gly Ile Gly Ala Phe Leu Glu Lys Thr Leu Val His Glu
    130                 135                 140

Gly Gln Cys Thr Lys Val Asn Pro Glu Glu Asp Pro Ala Ala Ala Gly
145                 150                 155                 160

Leu Leu Gly Cys Gly Ile Met Ala Gly Leu Gly Ala Ala Val Asn Thr
                165                 170                 175

Gly Asp Ile Lys Arg Gly Glu Ser Val Ala Val Phe Gly Leu Gly Gly
            180                 185                 190
```

```
Val Gly Met Ala Ala Ile Ala Gly Ala Lys Ile Ala Gly Ala Ser Lys
        195                 200                 205
Ile Ile Ala Val Asp Ile Asp Glu Lys Lys Leu Glu Trp Ala Lys Glu
    210                 215                 220
Phe Gly Ala Thr His Thr Ile Asn Ser Ser Gly Leu Gly Gly Glu Gly
225                 230                 235                 240
Asp Ala Ser Glu Val Val Ala Lys Val Arg Glu Leu Thr Asp Gly Phe
                245                 250                 255
Gly Thr Asp Val Ser Ile Asp Ala Val Gly Ile Met Pro Thr Trp Gln
                260                 265                 270
Gln Ala Phe Tyr Ser Arg Asp His Ala Gly Arg Met Val Met Val Gly
            275                 280                 285
Val Pro Asn Leu Thr Ser Arg Val Asp Val Pro Ala Ile Asp Phe Tyr
        290                 295                 300
Gly Arg Gly Gly Ser Val Arg Pro Ala Trp Tyr Gly Asp Cys Leu Pro
305                 310                 315                 320
Glu Arg Asp Phe Pro Thr Tyr Val Asp Leu His Leu Gln Gly Arg Phe
                325                 330                 335
Pro Leu Asp Lys Phe Val Ser Glu Arg Ile Gly Leu Asp Asp Val Glu
            340                 345                 350
Glu Ala Phe Asn Thr Met Lys Ala Gly Asp Val Leu Arg Ser Val Val
        355                 360                 365
Glu Ile
    370

<210> SEQ ID NO 69
<211> LENGTH: 1047
<212> TYPE: DNA
<213> ORGANISM: Corynebacterium glutamicum

<400> SEQUENCE: 69
gtgagtttta tgaccactgc tgcacccccaa gaatttaccg ctgctgttgt tgaaaaattc      60
ggtcatgacg tgaccgtgaa ggatattgac cttccaaagc cagggccaca ccaggcattg     120
gtgaaggtac tcacctccgg catctgccac accgacctcc acgccttgga gggcgattgg     180
ccagtaaagc cggaaccacc attcgtacca ggacacgaag gtgtaggtga agttgttgag     240
ctcggaccag gtgaacacga tgtgaaggtc ggcgatattg tcggcaatgc gtggctctgg     300
tcagcgtgcg gcacctgcga atactgcatc acaggcaggg aaactcagtg taacgaagct     360
gagtacggtg gctacaccca aaatggatcc ttcggccagt acatgctggt ggatacccga     420
tacgccgctc gcatcccaga cggcgtggac tacctcgaag cagcgccaat tctgtgtgca     480
ggcgtgactg tctacaaggc actcaaagtc tctgaaaccc gcccgggcca attcatggtg     540
atctccggtg tcggcggact tggccacatc gcagtccaat acgcagcggc gatgggcatg     600
cgtgtcattg cggtagatat tgccgaggac aagctggaac ttgcccgtaa gcacggtgcg     660
gaatttaccg tgaatgcgcg taatgaagat ccaggcgaag ctgtacagaa gtacaccaac     720
ggtggcgcac acggcgtgct tgtgactgca gttcacgagg cagcattcgg ccaggcactg     780
gatatggctc gacgtgcagg aacaattgtg ttcaacggtc tgccaccggg agagttccca     840
gcatccgtgt tcaacatcgt attcaagggc ctgaccatcc gtggatccct cgtgggaacc     900
cgccaagact tggccgaagc gctcgatttc tttgcacgcg gactaatcaa gccaaccgtg     960
agtgagtgct ccctcgatga ggtcaatgga gttcttgacc gcatgcgaaa cggcaagatc    1020
gatggtcgtg tggcgattcg tttctaa                                        1047
```

<210> SEQ ID NO 70
<211> LENGTH: 348
<212> TYPE: PRT
<213> ORGANISM: Corynebacterium glutamicum

<400> SEQUENCE: 70

Met Ser Phe Met Thr Thr Ala Ala Pro Gln Glu Phe Thr Ala Ala Val
1               5                   10                  15

Val Glu Lys Phe Gly His Asp Val Thr Val Lys Asp Ile Asp Leu Pro
            20                  25                  30

Lys Pro Gly Pro His Gln Ala Leu Val Lys Val Leu Thr Ser Gly Ile
        35                  40                  45

Cys His Thr Asp Leu His Ala Leu Glu Gly Asp Trp Pro Val Lys Pro
    50                  55                  60

Glu Pro Pro Phe Val Pro Gly His Glu Gly Val Gly Glu Val Val Glu
65                  70                  75                  80

Leu Gly Pro Gly Glu His Asp Val Lys Val Gly Asp Ile Val Gly Asn
                85                  90                  95

Ala Trp Leu Trp Ser Ala Cys Gly Thr Cys Glu Tyr Cys Ile Thr Gly
            100                 105                 110

Arg Glu Thr Gln Cys Asn Glu Ala Glu Tyr Gly Gly Tyr Thr Gln Asn
        115                 120                 125

Gly Ser Phe Gly Gln Tyr Met Leu Val Asp Thr Arg Tyr Ala Ala Arg
    130                 135                 140

Ile Pro Asp Gly Val Asp Tyr Leu Glu Ala Ala Pro Ile Leu Cys Ala
145                 150                 155                 160

Gly Val Thr Val Tyr Lys Ala Leu Lys Val Ser Glu Thr Arg Pro Gly
                165                 170                 175

Gln Phe Met Val Ile Ser Gly Val Gly Gly Leu Gly His Ile Ala Val
            180                 185                 190

Gln Tyr Ala Ala Ala Met Gly Met Arg Val Ile Ala Val Asp Ile Ala
        195                 200                 205

Glu Asp Lys Leu Glu Leu Ala Arg Lys His Gly Ala Glu Phe Thr Val
    210                 215                 220

Asn Ala Arg Asn Glu Asp Pro Gly Glu Ala Val Gln Lys Tyr Thr Asn
225                 230                 235                 240

Gly Gly Ala His Gly Val Leu Val Thr Ala Val His Glu Ala Ala Phe
                245                 250                 255

Gly Gln Ala Leu Asp Met Ala Arg Arg Ala Gly Thr Ile Val Phe Asn
            260                 265                 270

Gly Leu Pro Pro Gly Glu Phe Pro Ala Ser Val Phe Asn Ile Val Phe
        275                 280                 285

Lys Gly Leu Thr Ile Arg Gly Ser Leu Val Gly Thr Arg Gln Asp Leu
    290                 295                 300

Ala Glu Ala Leu Asp Phe Phe Ala Arg Gly Leu Ile Lys Pro Thr Val
305                 310                 315                 320

Ser Glu Cys Ser Leu Asp Glu Val Asn Gly Val Leu Asp Arg Met Arg
                325                 330                 335

Asn Gly Lys Ile Asp Gly Arg Val Ala Ile Arg Phe
            340                 345

<210> SEQ ID NO 71
<211> LENGTH: 1020
<212> TYPE: DNA

<213> ORGANISM: Corynebacterium glutamicum

<400> SEQUENCE: 71

```
atgcccaaat acattgccat gcaggtatcc gaatccggtg caccgttagc cgcgaatctc    60
gtgcaacctg ctccgttgaa atcgagggaa gtccgcgtgg aaatcgctgc tagtggtgtg   120
tgccatgcag atattggcac ggcagcagca tcggggaagc acactgtttt cctgttacc   180
cctggtcatg agattgcagg aaccatcgcg gaaattggtg aaaacgtatc tcggtggacg   240
gttggtgatc gcgttgcaat cggttggttt ggtggcaatt gcggtgactg cgcttttgt   300
cgtgcaggtg atcctgtgca ttgcagagag cggaagattc ctggcgtttc ttatgcgggt   360
ggttgggcac agaatattgt tgttccagcg gaggctcttg ctgcgattcc agatggcatg   420
gacttttacg aggccgcccc gatgggctgc gcaggtgtga caacattcaa tgcgttgcga   480
aacctgaagc tggatcccgg tgcggctgtc gcggtctttg gaatcggcgg tttagtgcgc   540
ctagctattc agtttgctgc gaaaatgggt tatcgaacca tcaccatcgc ccgcggttta   600
gagcgtgagg agctagctag caacttggc gccaaccact acatcgatag caatgatctg   660
caccctggcc aggcgttatt tgaacttggc ggggctgact tgatcttgtc tactgcgtcc   720
accacgagc ctctttcgga gttgtctacc ggtctttcta ttggcgggca gctaaccatt   780
atcggagttg atgggggaga tatcaccgtt tcggcagccc aattgatgat gaaccgtcag   840
atcatcacag gtcacctcac tggaagtgcg aatgacacgg aacagactat gaaatttgct   900
catctccatg gcgtgaaacc gcttattgaa cggatgcctc tcgatcaagc caacgaggct   960
attgcacgta tttcagctgg taaaccacgt ttccgtattg tcttggagcc gaattcataa  1020
```

<210> SEQ ID NO 72
<211> LENGTH: 339
<212> TYPE: PRT
<213> ORGANISM: Corynebacterium glutamicum

<400> SEQUENCE: 72

```
Met Pro Lys Tyr Ile Ala Met Gln Val Ser Glu Ser Gly Ala Pro Leu
1               5                   10                  15

Ala Ala Asn Leu Val Gln Pro Ala Pro Leu Lys Ser Arg Glu Val Arg
            20                  25                  30

Val Glu Ile Ala Ala Ser Gly Val Cys His Ala Asp Ile Gly Thr Ala
        35                  40                  45

Ala Ala Ser Gly Lys His Thr Val Phe Pro Val Thr Pro Gly His Glu
    50                  55                  60

Ile Ala Gly Thr Ile Ala Glu Ile Gly Glu Asn Val Ser Arg Trp Thr
65                  70                  75                  80

Val Gly Asp Arg Val Ala Ile Gly Trp Phe Gly Gly Asn Cys Gly Asp
                85                  90                  95

Cys Ala Phe Cys Arg Ala Gly Asp Pro Val His Cys Arg Glu Arg Lys
            100                 105                 110

Ile Pro Gly Val Ser Tyr Ala Gly Gly Trp Ala Gln Asn Ile Val Val
        115                 120                 125

Pro Ala Glu Ala Leu Ala Ala Ile Pro Asp Gly Met Asp Phe Tyr Glu
    130                 135                 140

Ala Ala Pro Met Gly Cys Ala Gly Val Thr Thr Phe Asn Ala Leu Arg
145                 150                 155                 160

Asn Leu Lys Leu Asp Pro Gly Ala Ala Val Ala Val Phe Gly Ile Gly
                165                 170                 175
```

Gly Leu Val Arg Leu Ala Ile Gln Phe Ala Ala Lys Met Gly Tyr Arg
            180                 185                 190

Thr Ile Thr Ile Ala Arg Gly Leu Glu Arg Glu Leu Ala Arg Gln
        195                 200                 205

Leu Gly Ala Asn His Tyr Ile Asp Ser Asn Asp Leu His Pro Gly Gln
    210                 215                 220

Ala Leu Phe Glu Leu Gly Gly Ala Asp Leu Ile Leu Ser Thr Ala Ser
225                 230                 235                 240

Thr Thr Glu Pro Leu Ser Glu Leu Ser Thr Gly Leu Ser Ile Gly Gly
                245                 250                 255

Gln Leu Thr Ile Ile Gly Val Asp Gly Gly Asp Ile Thr Val Ser Ala
            260                 265                 270

Ala Gln Leu Met Met Asn Arg Gln Ile Ile Thr Gly His Leu Thr Gly
        275                 280                 285

Ser Ala Asn Asp Thr Glu Gln Thr Met Lys Phe Ala His Leu His Gly
    290                 295                 300

Val Lys Pro Leu Ile Glu Arg Met Pro Leu Asp Gln Ala Asn Glu Ala
305                 310                 315                 320

Ile Ala Arg Ile Ser Ala Gly Lys Pro Arg Phe Arg Ile Val Leu Glu
                325                 330                 335

Pro Asn Ser

<210> SEQ ID NO 73
<211> LENGTH: 879
<212> TYPE: DNA
<213> ORGANISM: Corynebacterium glutamicum

<400> SEQUENCE: 73

```
atgcaaaccc ttgctgctat tgttcgtgcc acgaagcaac cttttgagat caccaccatt      60
gatctggatg caccacgacc agatgaagtt caaatccgtg ttattgctgc cggagtgcgc     120
cacactgacg caattgttcg tgatcagatt tacccaactt ttcttcccgc agttttcggc     180
cacgaaggcg ccggagtagt tgtcgccgtg ggttctgcag tcacctcggt gaaaccagat     240
gacaaggtag tgctgggatt caactcttgt ggccagtgct tgaagtgttt gggcggtaag     300
cctgcgtact gtgagaaatt ctatgaccgc aacttcgcat gcacccgcga tgccgggcac     360
actactttgt ttacccgtgc aacaaaagag caggcagagg ccatcatcga cacccttgat     420
gatgttttct acgatgcgga tgcgggtttc ctggcatacc agcaactcc cccagaggct     480
tcggagtaa gcgtgttggt tgtcgcggct ggtacctctg atctccccca agcaaaggaa     540
gcactacaca ctgcctccta cttggggcgc tccacctcac tgattgttga ttttggagtg     600
gctggcatcc accgcctgct ttcatacgaa gaagaactcc gcgctgcggg cgtgctcatc     660
gttgccgctg aatggatgg tgcgctaccc ggagttgtcg caggcttagt gtccgcacct     720
gtcgtcgcac tgccaacctc cgtgggatac ggcgcaggtg ctggaggaat cgcaccacctt     780
ctgaccatgc ttaacgcctg cgcgccggga gttgagtgg tcaacattga taacggctat     840
ggagcaggac acctggctgc gcagattgcg gcgaggtaa                            879
```

<210> SEQ ID NO 74
<211> LENGTH: 292
<212> TYPE: PRT
<213> ORGANISM: Corynebacterium glutamicum

<400> SEQUENCE: 74

Met Gln Thr Leu Ala Ala Ile Val Arg Ala Thr Lys Gln Pro Phe Glu

```
  1               5                   10                  15
Ile Thr Thr Ile Asp Leu Asp Ala Pro Arg Pro Asp Glu Val Gln Ile
               20                  25                  30
Arg Val Ile Ala Ala Gly Val Arg His Thr Asp Ala Ile Val Arg Asp
               35                  40                  45
Gln Ile Tyr Pro Thr Phe Leu Pro Ala Val Phe Gly His Glu Gly Ala
               50                  55                  60
Gly Val Val Ala Val Gly Ser Ala Val Thr Ser Val Lys Pro Asp
 65                 70                  75                  80
Asp Lys Val Val Leu Gly Phe Asn Ser Cys Gly Gln Cys Leu Lys Cys
                   85                  90                  95
Leu Gly Gly Lys Pro Ala Tyr Cys Glu Lys Phe Tyr Asp Arg Asn Phe
                  100                 105                 110
Ala Cys Thr Arg Asp Ala Gly His Thr Thr Leu Phe Thr Arg Ala Thr
                  115                 120                 125
Lys Glu Gln Ala Glu Ala Ile Ile Asp Thr Leu Asp Asp Val Phe Tyr
                  130                 135                 140
Asp Ala Asp Ala Gly Phe Leu Ala Tyr Pro Ala Thr Pro Pro Glu Ala
145                 150                 155                 160
Ser Gly Val Ser Val Leu Val Ala Gly Thr Ser Asp Leu Pro
                   165                 170                 175
Gln Ala Lys Glu Ala Leu His Thr Ala Ser Tyr Leu Gly Arg Ser Thr
                   180                 185                 190
Ser Leu Ile Val Asp Phe Gly Val Ala Gly Ile His Arg Leu Leu Ser
                   195                 200                 205
Tyr Glu Glu Glu Leu Arg Ala Ala Gly Val Leu Ile Val Ala Ala Gly
                   210                 215                 220
Met Asp Gly Ala Leu Pro Gly Val Val Ala Gly Leu Val Ser Ala Pro
225                 230                 235                 240
Val Val Ala Leu Pro Thr Ser Val Gly Tyr Gly Ala Gly Ala Gly Gly
                   245                 250                 255
Ile Ala Pro Leu Leu Thr Met Leu Asn Ala Cys Ala Pro Gly Val Gly
                   260                 265                 270
Val Val Asn Ile Asp Asn Gly Tyr Gly Ala Gly His Leu Ala Ala Gln
                   275                 280                 285
Ile Ala Ala Arg
     290

<210> SEQ ID NO 75
<211> LENGTH: 3453
<212> TYPE: DNA
<213> ORGANISM: Nocardia brasiliensis

<400> SEQUENCE: 75
ttgttcgccg aggacgagca ggtgaaagcc gcggtgccgg accaggaggt ggtcgaggcg      60
atccgggcgc ccggcctgcg cctggcacag atcatggcca ccgtgatgga gcgctatgcg    120
gaccgccccg cggtgggaca gcgggcgagc gagccggtca ccgagagcgg tcgcaccacc    180
ttccggctgc tcccggaatt cgagaccctg acctaccgcg agctgtgggc gcgcgtccgc    240
gcggtggccg ccgcgtggca cggagatgcc gaaaggcctt gcgggccgg ggatttcgtt     300 gctctgctgg gtttcgccgg catcgattac ggcaccctcg atctcgcgaa catccatctc    360
ggcctcgtca cggtgccgct gcaatccggc gccacggccc cgcaactcgc cgcgatcctg    420
gccgagacca cgccccgggt gctggccgcg acacccgacc atctcgatat cgccgtcgaa    480
```

```
ttgctgaccg ggggagcctc gccggaacgg ctggtggtat tcgactaccg ccccgcggac      540
gacgatcacc gggcggcgct cgagtccgcg cgcagacggt tgagcgacgc gggcagtgcg      600
gtggtggtcg agacgctcga cgcggtccgc gcccgcggca gcgaattgcc ggccgcgccg      660
ctgttcgttc ccgccgcgga cgaggacccg ctggctctgc tcatctacac ctccggcagc      720
accggcacgc ctaagggcgc catgtacacc gaaagactga accgcacgac gtggctgagc      780
ggggcgaaag gcgtcggcct cacgctcggc tacatgccga tgagtcatat tgccgggcgg      840
gcctcgttcg ccggtgtgct ggcccgcggc ggcacggtct acttcaccgc ccgcagcgat      900
atgtcgacgc tgttcgaaga tctggccctg gtgcggccga ccgagatgtt cttcgtcccg      960
cgcgtgtgcg acatgatctt ccagcgctat caggccgaac tgtcgcggcg cgcgcccgcc     1020
gcggccgcga gcccggaact cgagcaggaa ctgaagaccg aactgcgctt gtccgcggtc     1080
ggggaccgct tactcggggc gatcgcgggc agcgcgccgc tgtcggccga gatgcgggag     1140
ttcatggagt cgctgctgga tctggaactg cacgacggct acggctcgac cgaggcgggt     1200
atcggcgtac tgcaagacaa tatcgtccag cgtccgccgg tcatcgatta caagctcgtc     1260
gacgtgccga aattgggcta cttccggacg gaccagccgc atccccgcgg tgagttgctg     1320
ttgaaaaccg aagggatgat tccgggctac ttccggcggc ccgaggtgac cgcggagatc     1380
ttcgacgagg acggtttcta caggaccggt gacatcgtcg ccgaactcga accggatcgg     1440
ctgatctacc tggaccgccg caacaatgtg ctgaaactgg cccagggcga gttcgtcacg     1500
gtcgcccatc tggaagcggt gttcgcgacc agtccgctga tccggcagat ctacatctac     1560
ggcaacagcg agcgctcgtt cctgctggcg gtgatcgtgc ccaccgcgga cgcgctggcc     1620
gacggtgtca ccgacgcgct gaacacggcg ctgaccgaat ccttgcgaca gctcgcgaaa     1680
gaagccgggc tgcaatccta tgagctgccg cgcgagttcc tggtcgaaac cgaaccgttc     1740
accgtcgaga acgtctgctc tccggtatc gcgaaactgt tgcggcccaa gctcaaggag     1800
cactacggcg agcgactcga gcagctgtac cgcgatatcg aggcgaaccg caacgacgag     1860
ctgatcgagc tgcggcgcac cgcggccgag ctgccggtgc tcgaaaccgt cacgcgggct     1920
gcacgttcga tgctcggact ggccgcgtcg gagttgcggc cggacgcgca tttcaccgat     1980
ctcggcggtg attcactgtc cgcgctgtcg ttttcgaccc tgctgcagga catgctcgag     2040
gtcgaggtcc cggtcggtgt catcgtgagc cccgccaact cgctcgccga tctggcgaaa     2100
tacatcgagg ccgaacggca ttcggggggtg cggcggccga gcctgatctc ggtgcacggt     2160
cccggcaccg agatcgtgcg cgccgatctc accctggaca agttcatcga cgagcgcacc     2220
ctcgctgccg cgaaagcggt tccggccgcg ccggcccagg cgcagaccgt cctgctcacc     2280
ggggcgaacg gctatctcgg ccgcttcctg tgcctggaat ggctgcagcg actgaccag     2340 accggcggca cgctggtctg catcgtgcgc ggtaccgacg cggccgccgc gcggaagcgc     2400
ctggatgcgt tgttcgacag cggtgatccg gagctgctcg accactaccg gaagctggcc     2460
gccgagcacc tcgaggtgct cgcgggcgat atcggcgacc cgaatctcgg cctggacgaa     2520
gcgacttggc agcggctcgc cgcgaccgtc gacctgatcg tgcacccccgc cgccctcgtc     2580 aaccatgtgc tgccgtacag ccagctgttc gggccgaatg tggtcggcac cgccgagatc     2640
atccggctgg ccatcaccga gcgccgtaag cccgtgacgt acctgtcgac ggtcgcggtg     2700
gccgcacagg tcgatcccgc cggcttcgac gaggagcgcg atatccggga gatgagcgcg     2760
gtgcgctcca tcgacgccgg gtacgcgaac ggttacggca acagcaagtg ggccggcgag     2820
```

-continued

```
gtgctgctgc gcgaggccca tgatctgtgc gggctgccgg tcgccgtgtt ccgctcggac    2880
atgatcctgg cgcacagcaa atacgtcggt cagctcaacg tccccgatgt gttcacccgg    2940
ctcatcctga gcctggcgct caccggcatc gcaccgtatt cgttctacgg gacggacagc    3000
gccgggcagc gcaggcgggc ccactacgac ggtctgcccg ccgatttcgt cgccgaggcg    3060
atcaccaccc tcggcgcgcg agccgagtcg gggttccata cctacgacgt gtggaacccg    3120
tacgacgacg gcatctcgct ggacgaattc gtcgactggc tcggcgattt cggcgtgccg    3180
atccagcgga tcgacgacta cgacgaatgg ttccggcgtt tcgagaccgc gatccgcgcg    3240
ctgcccgaaa agcagcgcga tgcttcgctg ctaccgctgc tggacgcaca ccggcggcca    3300
ctgcgcgcgg tgcgcggttc gctgttgccc gccaagaact tccaggcggc ggtgcagtcc    3360
gcgcggatcg gccccgatca ggacatcccg catctttccc cgcagttgat cgacaagtac    3420
gtcaccgacc tgcgccacct cggcctgctc tga                                3453
```

<210> SEQ ID NO 76
<211> LENGTH: 1150
<212> TYPE: PRT
<213> ORGANISM: Nocardia brasiliensis

<400> SEQUENCE: 76

```
Met Phe Ala Glu Asp Glu Gln Val Lys Ala Val Pro Asp Gln Glu
1               5                   10                  15

Val Val Glu Ala Ile Arg Ala Pro Gly Leu Arg Leu Ala Gln Ile Met
            20                  25                  30

Ala Thr Val Met Glu Arg Tyr Ala Asp Arg Pro Ala Val Gly Gln Arg
        35                  40                  45

Ala Ser Glu Pro Val Thr Glu Ser Gly Arg Thr Thr Phe Arg Leu Leu
    50                  55                  60

Pro Glu Phe Glu Thr Leu Thr Tyr Arg Glu Leu Trp Ala Arg Val Arg
65                  70                  75                  80

Ala Val Ala Ala Ala Trp His Gly Asp Ala Glu Arg Pro Leu Arg Ala
                85                  90                  95

Gly Asp Phe Val Ala Leu Leu Gly Phe Ala Gly Ile Asp Tyr Gly Thr
            100                 105                 110

Leu Asp Leu Ala Asn Ile His Leu Gly Leu Val Thr Val Pro Leu Gln
        115                 120                 125

Ser Gly Ala Thr Ala Pro Gln Leu Ala Ala Ile Leu Ala Glu Thr Thr
    130                 135                 140

Pro Arg Val Leu Ala Ala Thr Pro Asp His Leu Asp Ile Ala Val Glu
145                 150                 155                 160

Leu Leu Thr Gly Gly Ala Ser Pro Glu Arg Leu Val Val Phe Asp Tyr
                165                 170                 175

Arg Pro Ala Asp Asp Asp His Arg Ala Ala Leu Glu Ser Ala Arg Arg
            180                 185                 190

Arg Leu Ser Asp Ala Gly Ser Ala Val Val Glu Thr Leu Asp Ala
        195                 200                 205

Val Arg Ala Arg Gly Ser Glu Leu Pro Ala Ala Pro Leu Phe Val Pro
    210                 215                 220

Ala Ala Asp Glu Asp Pro Leu Ala Leu Leu Ile Tyr Thr Ser Gly Ser
225                 230                 235                 240

Thr Gly Thr Pro Lys Gly Ala Met Tyr Thr Glu Arg Leu Asn Arg Thr
                245                 250                 255

Thr Trp Leu Ser Gly Ala Lys Gly Val Gly Leu Thr Leu Gly Tyr Met
```

```
                260                 265                 270
Pro Met Ser His Ile Ala Gly Arg Ala Ser Phe Ala Gly Val Leu Ala
            275                 280                 285
Arg Gly Gly Thr Val Tyr Phe Thr Ala Arg Ser Asp Met Ser Thr Leu
        290                 295                 300
Phe Glu Asp Leu Ala Leu Val Arg Pro Thr Glu Met Phe Phe Val Pro
305                 310                 315                 320
Arg Val Cys Asp Met Ile Phe Gln Arg Tyr Gln Ala Glu Leu Ser Arg
                325                 330                 335
Arg Ala Pro Ala Ala Ala Ser Pro Glu Leu Glu Gln Glu Leu Lys
            340                 345                 350
Thr Glu Leu Arg Leu Ser Ala Val Gly Asp Arg Leu Leu Gly Ala Ile
            355                 360                 365
Ala Gly Ser Ala Pro Leu Ser Ala Glu Met Arg Glu Phe Met Glu Ser
        370                 375                 380
Leu Leu Asp Leu Glu Leu His Asp Gly Tyr Gly Ser Thr Glu Ala Gly
385                 390                 395                 400
Ile Gly Val Leu Gln Asp Asn Ile Val Gln Arg Pro Pro Val Ile Asp
                405                 410                 415
Tyr Lys Leu Val Asp Val Pro Glu Leu Gly Tyr Phe Arg Thr Asp Gln
            420                 425                 430
Pro His Pro Arg Gly Glu Leu Leu Lys Thr Glu Gly Met Ile Pro
            435                 440                 445
Gly Tyr Phe Arg Arg Pro Glu Val Thr Ala Glu Ile Phe Asp Glu Asp
        450                 455                 460
Gly Phe Tyr Arg Thr Gly Asp Ile Val Ala Glu Leu Glu Pro Asp Arg
465                 470                 475                 480
Leu Ile Tyr Leu Asp Arg Arg Asn Asn Val Leu Lys Leu Ala Gln Gly
                485                 490                 495
Glu Phe Val Thr Val Ala His Leu Glu Ala Val Phe Ala Thr Ser Pro
            500                 505                 510
Leu Ile Arg Gln Ile Tyr Ile Tyr Gly Asn Ser Glu Arg Ser Phe Leu
            515                 520                 525
Leu Ala Val Ile Val Pro Thr Ala Asp Ala Leu Ala Asp Gly Val Thr
        530                 535                 540
Asp Ala Leu Asn Thr Ala Leu Thr Glu Ser Leu Arg Gln Leu Ala Lys
545                 550                 555                 560
Glu Ala Gly Leu Gln Ser Tyr Glu Leu Pro Arg Glu Phe Leu Val Glu
                565                 570                 575
Thr Glu Pro Phe Thr Val Glu Asn Gly Leu Leu Ser Gly Ile Ala Lys
            580                 585                 590
Leu Leu Arg Pro Lys Leu Lys Glu His Tyr Gly Glu Arg Leu Glu Gln
            595                 600                 605
Leu Tyr Arg Asp Ile Glu Ala Asn Arg Asn Asp Glu Leu Ile Glu Leu
        610                 615                 620
Arg Arg Thr Ala Ala Glu Leu Pro Val Leu Glu Thr Val Thr Arg Ala
625                 630                 635                 640
Ala Arg Ser Met Leu Gly Leu Ala Ala Ser Glu Leu Arg Pro Asp Ala
                645                 650                 655
His Phe Thr Asp Leu Gly Gly Asp Ser Leu Ser Ala Leu Ser Phe Ser
            660                 665                 670
Thr Leu Leu Gln Asp Met Leu Glu Val Glu Val Pro Val Gly Val Ile
            675                 680                 685
```

```
Val Ser Pro Ala Asn Ser Leu Ala Asp Leu Ala Lys Tyr Ile Glu Ala
    690             695             700

Glu Arg His Ser Gly Val Arg Pro Ser Leu Ile Ser Val His Gly
705             710             715             720

Pro Gly Thr Glu Ile Arg Ala Ala Asp Leu Thr Leu Asp Lys Phe Ile
                725             730             735

Asp Glu Arg Thr Leu Ala Ala Ala Lys Ala Val Pro Ala Ala Pro Ala
            740             745             750

Gln Ala Gln Thr Val Leu Leu Thr Gly Ala Asn Gly Tyr Leu Gly Arg
        755             760             765

Phe Leu Cys Leu Glu Trp Leu Gln Arg Leu Asp Gln Thr Gly Gly Thr
    770             775             780

Leu Val Cys Ile Val Arg Gly Thr Asp Ala Ala Ala Arg Lys Arg
785             790             795             800

Leu Asp Ala Val Phe Asp Ser Gly Asp Pro Glu Leu Leu Asp His Tyr
            805             810             815

Arg Lys Leu Ala Ala Glu His Leu Glu Val Leu Ala Gly Asp Ile Gly
        820             825             830

Asp Pro Asn Leu Gly Leu Asp Glu Ala Thr Trp Gln Arg Leu Ala Ala
        835             840             845

Thr Val Asp Leu Ile Val His Pro Ala Ala Leu Val Asn His Val Leu
850             855             860

Pro Tyr Ser Gln Leu Phe Gly Pro Asn Val Val Gly Thr Ala Glu Ile
865             870             875             880

Ile Arg Leu Ala Ile Thr Glu Arg Arg Lys Pro Val Thr Tyr Leu Ser
            885             890             895

Thr Val Ala Val Ala Ala Gln Val Asp Pro Ala Gly Phe Asp Glu Glu
            900             905             910

Arg Asp Ile Arg Glu Met Ser Ala Val Arg Ser Ile Asp Ala Gly Tyr
        915             920             925

Ala Asn Gly Tyr Gly Asn Ser Lys Trp Ala Gly Glu Val Leu Leu Arg
        930             935             940

Glu Ala His Asp Leu Cys Gly Leu Pro Val Ala Val Phe Arg Ser Asp
945             950             955             960

Met Ile Leu Ala His Ser Lys Tyr Val Gly Gln Leu Asn Val Pro Asp
            965             970             975

Val Phe Thr Arg Leu Ile Leu Ser Leu Ala Leu Thr Gly Ile Ala Pro
            980             985             990

Tyr Ser Phe Tyr Gly Thr Asp Ser Ala Gly Gln Arg Arg Arg Ala His
        995             1000            1005

Tyr Asp Gly Leu Pro Ala Asp Phe Val Ala Glu Ala Ile Thr Thr
    1010            1015            1020

Leu Gly Ala Arg Ala Glu Ser Gly Phe His Thr Tyr Asp Val Trp
    1025            1030            1035

Asn Pro Tyr Asp Asp Gly Ile Ser Leu Asp Glu Phe Val Asp Trp
    1040            1045            1050

Leu Gly Asp Phe Gly Val Pro Ile Gln Arg Ile Asp Asp Tyr Asp
    1055            1060            1065

Glu Trp Phe Arg Arg Phe Glu Thr Ala Ile Arg Ala Leu Pro Glu
    1070            1075            1080

Lys Gln Arg Asp Ala Ser Leu Leu Pro Leu Leu Asp Ala His Arg
    1085            1090            1095
```

```
Arg Pro  Leu Arg Ala Val Arg  Gly Ser Leu Leu Pro  Ala Lys Asn
    1100             1105              1110

Phe Gln  Ala Ala Val Gln Ser  Ala Arg Ile Gly Pro  Asp Gln Asp
    1115             1120              1125

Ile Pro  His Leu Ser Pro Gln  Leu Ile Asp Lys Tyr  Val Thr Asp
    1130             1135              1140

Leu Arg  His Leu Gly Leu Leu
    1145             1150

<210> SEQ ID NO 77
<211> LENGTH: 51
<212> TYPE: DNA
<213> ORGANISM: Nocardia brasiliensis

<400> SEQUENCE: 77
atggcgactg attcgcgaag cgatcggcta cggcgtcgaa ttgcacagtt g          51

<210> SEQ ID NO 78
<211> LENGTH: 17
<212> TYPE: PRT
<213> ORGANISM: Nocardia brasiliensis

<400> SEQUENCE: 78

Met Ala Thr Asp Ser Arg Ser Asp Arg Leu Arg Arg Arg Ile Ala Gln
1               5                   10                  15

Leu

<210> SEQ ID NO 79
<211> LENGTH: 3510
<212> TYPE: DNA
<213> ORGANISM: Artificial Sequence
<220> FEATURE:
<223> OTHER INFORMATION: Nucleotide sequence of the DNA-fragment
      comprising the codon-optimized fadD9 gene and restriction sites

<400> SEQUENCE: 79
catatggcaa ctgacagcag gagcgaccgt ctacgtaggc ggatagctca gctatttgca      60
gaagatgaac aggttaaggc agcagttccg gatcaggaag ttgttgaagc aattcgtgca     120
cctggtctgc gtctggctca gattatggca accgtgatgg aacgttacgc agatcgtcct     180
gcagttgggc agcgtgcaag cgaaccggtt accgaaagcg ggcgtaccac ctttcgtctg     240
ttaccggagt ttgaaaccct gacctatcgt gaactgtggg cacgtgtgcg tgcagttgca     300
gcagcatggc atggggacgc agagaggccc ttacgtgcag gagactttgt cgctctgctg     360
gggtttgcag gtattgacta tggtacctta gacttagcaa atattcacct gggtttagtt     420
accgttccgc tgcaaagcgg tgcaactgca ccgcaactgg cagcaattct ggcagaaacc     480 accccctcgtg ttctggcagc aactcctgat cacctggaca ttgcagtaga gctactgacc     540
ggaggggcaa gcccggagcg tctggttgtc tttgactatc gtcctgcaga tgatgaccat     600
cgtgcagcat tagaaagcgc acgtaggcgt ctaagcgatg caggttcggc agttgttgtt     660
gaaaccttag atgcagtccg tgcacgcggt agcgagctac cggcagcacc gctgtttgtc     720
cctgcagcag atgaagatcc gctggctctg ttaatttaca ccagcggtag caccgggacc     780
cccaaaggtg caatgtatac cgagaggctg aatcgtacta cgtggctgag cggtgcaaag     840
ggtgttggtt taaccttagg ttatatgccg atgtcgcaca tagcaggacg tgcatcattt     900
gcaggggttc tggcacgcgg tggtaccgtt tattttaccg cacgcagcga catgagcacc     960
ctgtttgagg acctggcact ggttcgtccg accgaaatgt ttttgttcc gcgtgtttgt    1020
```

```
gacatgattt ttcaacgtta ccaggcagag ctgagccggc gtgcacctgc agcagcagca    1080
agcccggagt tagaacagga gctgaaaacc gagctgcgtc taagcgcagt cggagatcgt    1140
ctattagggg caattgcagg tagcgcaccg ctgagcgcag aaatgcgtga atttatggaa    1200
agcctgctgg acctggagct gcatgacggt tatggtagca ccgaagcagg gattggtgtc    1260
ctgcaagata acattgttca gaggccgccg gttattgact ataaattagt tgatgttccg    1320
gagctaggtt attttcgtac ggatcagccg caccctcgtg gggaactact gctaaagacc    1380
gagggaatga taccgggtta ttttcgtcgt cctgaagtta ccgcagaaat ttttgacgaa    1440
gatgggtttt acaggaccgg ggatattgtt gcagagttag agccggaccg tctgatttac    1500
cttgatcgtc gtaataacgt tctgaagctg gcacagggtg aatttgttac cgttgcacac    1560
ctggaggcag ttttttgcaac ctcgccgctg attcgtcaga tttacattta cggtaatagc    1620
gaacgtagct ttctgctggc agttattgtt cctaccgcag atgcactggc agatggggtt    1680
accgatgcac tgaataccgc actgaccgag agcctaaggc agttagcaaa ggaggcagga    1740
ctgcaaagct acgaactgcc gcgtgaattt ctggttgaga ccgagccgtt taccgtagaa    1800
aatgggctgt taagcgggat tgcaaagctg ctacgtccta aattaaaaga acattacggt    1860
gaaaggttag aacagctgta tcgtgacatt gaggcaaatc gtaatgatga actgattgag    1920
ctgcgtcgta ccgcagcaga actgccggtt ttagagaccg taacccgtgc tgctaggagc    1980
atgttagggc tggcagcaag cgaactacgt ccggatgcac actttaccga cttaggtggg    2040
gactcgctga gcgcactgag cttcagcacc ctgctgcagg atatgttaga agttgaagtt    2100
ccggttgggg ttattgttag ccctgcaaat agcttagcag acctggcaaa gtatattgag    2160
gcagagcgtc acagcggagt tcgtcgtccg agcctgatta gcgttcatgg gcctggtacc    2220
gaaattaggg cagcagactt aaccctggat aaatttattg acgaacgtac cttagctgca    2280
gcaaaggcag tcccggcagc accggcacag gcacagaccg tactgttaac cggagcaaat    2340
ggttacctgg gtcgttttct gtgtctggag tggctgcaga ggctggatca gaccgggggg    2400
accctggttt gtattgttcg tgggaccgat gcagcagcag cacgcaaacg tctggacgca    2460 gttttttgaca gcggggaccc ggagctgtta gatcattacc gtaaactggc agcagaacat    2520
ttagaagttt tagcaggtga cattggtgat ccgaacttag gtctggatga ggcaacttgg    2580
cagcgtttag cagcaaccgt cgatctgatt gttcatcctg cagcattagt taatcacgtt    2640
ctgccgtata gccagctgtt tggaccgaac gttgttggta ccgcagaaat tattcgtctg    2700
gcaattaccg aacgtaggaa acctgttacc tatctgagca ccgttgcagt tgcagctcag    2760
gttgacccgg caggttttga cgaagaacgt gacattcgtg aaatgagcgc agttcgtagc    2820
attgacgcag gatatgcaaa tgggtatggt aatagcaaat gggcaggtga agttctgctg    2880
cgtgaagcac acgatctgtg tggactgccg gttgcagttt ttcgtagcga tatgattctg    2940
gcacatagca gtatgttgg gcagttaaat gttcctgacg tttttacccg tttaattctg    3000
agcctggcat taaccgggat tgctccgtac agcttttacg gaaccgatag cgcaggacag    3060
cgtaggcgtg cacattacga cgggctgcct gcagactttg ttgcagaagc aattaccacc    3120
ttaggtgcaa gggcagaaag cggatttcac acctatgatg tttggaatcc gtatgatgat    3180
ggtattagcc tggatgagtt tgttgattgg ttaggtgact tggtgttcc gattcagcgt    3240 attgacgact atgatgagtg gtttcgtagg tttgaaaccg caattcgtgc actgcctgag    3300
aaacagcgtg acgctagcct gctaccgctg ctggatgctc atcgtcgtcc cctgcgtgca    3360
```

```
gttcgtggga gcctgctacc tgcaaaaaat tttcaagcag cagttcagag cgcacgcatt    3420
ggtcctgacc aggatattcc gcacctaagc ccgcagctaa ttgacaaata tgttaccgat    3480
ctgcgtcatt taggtctgtt ataagagctc                                    3510

<210> SEQ ID NO 80
<211> LENGTH: 6557
<212> TYPE: DNA
<213> ORGANISM: Artificial Sequence
<220> FEATURE:
<223> OTHER INFORMATION: Nucleotide sequence of the pELAC vector

<400> SEQUENCE: 80
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg agacaataac cctgataaat gcttcaataa tattgaaaaa ggaagagtat     600
gagtattcaa catttccgtg tcgcccttat ccctttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca acatggggg atcatgtaa ctcgccttga    1080 tcgttgggaa ccggagctga tgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca ccccgtag aaaagatcaa    1620 aggatcttct tgagatcctt ttttttctgcg cgtaatctgc tgcttgcaaa caaaaaaacc    1680
accgctacca gcggtggttt gtttgccgga tcaagagcta ccaactcttt tccgaaggt    1740 aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
```

-continued

```
accggataag gcgcagcggt cgggctgaac ggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgaggag cttccagggg gaaacgcctg gtatctttat agtcctgtcg ggtttcgcca    2160
cctctgactt gagcgtcgat ttttgtgatg ctcgtcaggg gggcggagcc tatggaaaaa   2220
cgccagcaac gcggccttt tacggttcct ggccttttgc tggccttttg ctcacatgtt    2280
ctttcctgcg ttatccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg gtcgtgaagc gattcacaga tgtctgcctg ttcatccgcg tccagctcgt   2760
tgagtttctc cagaagcgtt aatgtctggc ttctgataaa gcgggccatg ttaagggcgg   2820
ttttttcctg tttggtcact gatgcctccg tgtaagggg atttctgttc atggggggtaa    2880
tgataccgat gaaacgagag aggatgctca cgatacgggt tactgatgat gaacatgccc   2940
ggttactgga acgttgtgag ggtaaacaac tggcggtatg gatgcggcgg gaccagagaa   3000
aaatcactca gggtcaatgc cagcgcttcg ttaatacaga tgtaggtgtt ccacagggta   3060
gccagcagca tcctgcgatg cagatccgga acataatggt gcagggcgct gacttccgcg   3120
tttccagact ttacgaaaca cggaaaccga agaccattca tgttgttgct caggtcgcag   3180
acgttttgca gcagcagtcg cttcacgttc gctcgcgtat cggtgattca ttctgctaac   3240
cagtaaggca accccgccag cctagccggg tcctcaacga caggagcacg atcatgcgca   3300
cccgtggggc cgccatgccg gcgataatgg cctgcttctc gccgaaacgt ttggtggcgg   3360
gaccagtgac gaaggcttga gcgagggcgt gcaagattcc gaataccgca agcgacaggc   3420
cgatcatcgt cgcgctccag cgaaagcggt cctcgccgaa aatgacccag agcgctgccg   3480
gcacctgtcc tacgagttgc atgataaaga agacagtcat aagtgcggcg acgatagtca   3540
tgccccgcgc ccaccggaag gagctgactg ggttgaaggc tctcaagggc atcggtcgag   3600
atcccggtgc ctaatgagtg agctaactta cattaattgc gttgcgctca ctgcccgctt   3660
tccagtcggg aaacctgtcg tgccagctgc attaatgaat cggccaacgc gcggggagag   3720
gcggtttgcg tattgggcgc cagggtggtt tttcttttca ccagtgagac gggcaacagc   3780
tgattgccct tcaccgcctg gccctgagag agttgcagca agcggtccac gctggtttgc   3840
cccagcagg gaaaatcctg tttgatggtg gttaacggcg ggatataaca tgagctgtct    3900
tcggtatcgt cgtatcccac taccgagata tccgcaccaa cgcgcagccc ggactcggta   3960
atggcgcgca ttgcgcccag cgccatctga tcgttggcaa ccagcatcgc agtgggaacg   4020
atgccctcat tcagcatttg catggtttgt tgaaaaccgg acatggcact ccagtcgcct   4080
tcccgttccg ctatcggctg aatttgattg cgagtgagat atttatgcca gccagccaga   4140
cgcagacgcg ccgagacaga acttaatggg cccgctaaca gcgcgatttg ctggtgaccc   4200
aatgcgacca gatgctccac gcccagtcgc gtaccgtctt catgggagaa aataatactg   4260
```

```
ttgatgggtg tctggtcaga gacatcaaga ataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620 tttcccgcg ttttcgcaga acgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccataccc acgccgaaac aagcgctcat    4980
gagcccgaag tggcgagccc gatcttcccc atcggtgatg tcgcgatat aggcgccagc    5040 aaccgcacct gtggcgccgg tgatgccggc cacgatgcgt ccggcgtaga ggatcgagat    5100
ctgcgggcag tgagcgcaac gcaattaatg tgagttagct cactcattag gcaccccagg    5160
ctttacactt tatgcttccg gctcgtataa tgtgtggaat tgtgagcgga taacaatttc    5220
acacaggatc tagatttaag aaggagatat acatatggcc gaagaaggta aactggtaat    5280
ctggattaac ggcgataaag gctataacgg tctcgctgaa gtcggtaaga aattcgagaa    5340
agataccgga attaaagtca ccgttgagca tccggataaa ctggaagaga aattcccaca    5400
ggttgcggca acaggcgatg gcctgacat tatcttctgg gcacacgacc gctttggtgg    5460
ctacgctcaa tctggcctgt tggctgaaat caccccggac aaagcgttcc aggacaagct    5520
gtatccgttt acctgggatg ccgtacgtta acggcaag ctgattgctt accgatcgc    5580 tgttgaagcg ttatcgctga tttataacaa agatctgctg ccgaacccgc caaaaaccctg    5640 ggaagagatc ccggcgctgg ataaagaact gaaagcgaaa ggtaagagcg cgctgatgtt    5700
caacctgcaa gaaccgtact tcacctggcc gctgattgct gctgacgggg ttatgcgtt    5760 caagtatgaa aacggcaagt acgacattaa agacgtgggc gtggataacg ctggcgcgaa    5820
agcgggtctg acctccttggg ttgacctgat taaaaacaaa cacatgaatg cagacaccga    5880
ttactccatc gcagaagctg cctttaataa aggcgaaaca gcgatgacca tcaacggccc    5940
gtgggcatgg tccaacatcg acaccagcaa agtgaattat ggtgtaacgg tactgccgac    6000
cttcaagggt caaccatcca aaccgttcgt tggcgtgctg agcgcaggta ttaacgccgc    6060
cagtccgaac aaaagagctgg caaaagagtt cctcgaaaac tatctgctga ctgatgaagg    6120
tctggaagcg gttaataaag acaaaccgct gggtgccgta gcgctgaagt cttacgagga    6180
agagttggcg aaagatccac gtattgccgc cactatggaa aacgcccaga aggtgaaat    6240 catgccgaac atcccgcaga tgtccgcttt ctggtatgcc gtgcgtactg cggtgatcaa    6300
cgccgccagc ggtcgtcaga ctgtcgatga agccctgaaa gacgcgcaga ctaaggatcc    6360
gaattcgagc tccgtcgaca agcttgcggc cgcactcgag caccaccacc accaccactg    6420
agatccggct gctaacaaag cccgaaagga agctgagttg gctgctgcca ccgctgagca    6480
ataactagca taacccttg gggcctctaa acgggtcttg aggggttttt tgctgaaagg    6540
aggaactata tccggat                                                  6557
```

```
<210> SEQ ID NO 81
<211> LENGTH: 17
<212> TYPE: DNA
<213> ORGANISM: Artificial Sequence
<220> FEATURE:
<223> OTHER INFORMATION: Primer P1

<400> SEQUENCE: 81
cgtggctggc ctggttc                                                  17

<210> SEQ ID NO 82
<211> LENGTH: 19
<212> TYPE: DNA
<213> ORGANISM: Artificial Sequence
<220> FEATURE:
<223> OTHER INFORMATION: Primer P5

<400> SEQUENCE: 82
cgtccccatg ccatgctgc                                                19

<210> SEQ ID NO 83
<211> LENGTH: 20
<212> TYPE: DNA
<213> ORGANISM: Artificial Sequence
<220> FEATURE:
<223> OTHER INFORMATION: Primer P4

<400> SEQUENCE: 83
cgctgttgag atccagttcg                                               20

<210> SEQ ID NO 84
<211> LENGTH: 19
<212> TYPE: DNA
<213> ORGANISM: Artificial Sequence
<220> FEATURE:
<223> OTHER INFORMATION: Primer P6

<400> SEQUENCE: 84
gcacattacg acgggctgc                                                19

<210> SEQ ID NO 85
<211> LENGTH: 1053
<212> TYPE: DNA
<213> ORGANISM: Escherichia coli

<400> SEQUENCE: 85
atgaattatc agaacgacga tttacgcatc aaagaaatca agagttact tcctcctgtc     60 gcattgctgg aaaaattccc cgctactgaa aatgccgcga atacggttgc ccatgcccga   120
aaagcgatcc ataagatcct gaaaggtaat gatgatcgcc tgttggttgt gattggccca   180
tgctcaattc atgatcctgt cgcggcaaaa gagtatgcca ctcgcttgct ggcgctgcgt   240
gaagagctga agatgagct ggaaatcgta atgcgcgtct attttgaaaa gccgcgtacc   300
acggtgggct ggaaagggct gattaacgat ccgcatatgg ataatagctt ccagatcaac   360
gacggtctgc gtatagcccg taaattgctg cttgatatta cgacagcgg tctgccagcg   420 gcaggtgagt ttctcgatat gatcacccca caatatctcg ctgacctgat gagctggggc   480
gcaattggcg cacgtaccac cgaatcgcag gtgcaccgcg aactggcatc agggctttct   540
tgtccggtcg gcttcaaaaa tggcaccgac ggtacgatta agtggctat cgatgccatt   600 aatgccgccg gtcgccgca ctgcttcctg tccgtaacga aatgggggca ttcggcgatt   660
gtgaatacca gcggtaacgg cgattgccat atcattctgc gcggcggtaa agagcctaac   720
```

| | | |
|---|---|---|
| tacagcgcga agcacgttgc tgaagtgaaa gaagggctga acaaagcagg cctgccagca | 780 | |
| caggtgatga tcgatttcag ccatgctaac tcgtccaaac aattcaaaaa gcagatggat | 840 | |
| gtttgtgctg acgtttgcca gcagattgcc ggtggcgaaa aggccattat tggcgtgatg | 900 | |
| gtggaaagcc atctggtgga aggcaatcag agcctcgaga gcggggagcc gctggcctac | 960 | |
| ggtaagagca tcaccgatgc ctgcatcggc tgggaagata ccgatgctct gttacgtcaa | 1020 | |
| ctggcgaatg cagtaaaagc gcgtcgcggg taa | 1053 | |

<210> SEQ ID NO 86
<211> LENGTH: 350
<212> TYPE: PRT
<213> ORGANISM: Escherichia coli

<400> SEQUENCE: 86

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
    50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
    130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
    210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
    290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
            325                 330                 335

Leu Leu Arg Gln Leu Ala Asn Ala Val Lys Ala Arg Gly
        340                 345                 350

<210> SEQ ID NO 87
<211> LENGTH: 1089
<212> TYPE: DNA
<213> ORGANISM: Escherichia coli

<400> SEQUENCE: 87

| | | | | | |
|---|---|---|---|---|---|
| atggagagga | ttgtcgttac | tctcggggaa | cgtagttacc | caattaccat | cgcatctggt | 60 |
| ttgtttaatg | aaccagcttc | attcttaccg | ctgaaatcgg | gcgagcaggt | catgttggtc | 120 |
| accaacgaaa | ccctggctcc | tctgtatctc | gataaggtcc | gcggcgtact | tgaacaggcg | 180 |
| ggtgttaacg | tcgatagcgt | tatcctccct | gacggcgagc | agtataaaag | cctggctgta | 240 |
| ctcgataccg | tctttacggc | gttgttacaa | aaaccgcatg | gtcgcgatac | tacgctggtg | 300 |
| gcgcttggcg | gcggcgtagt | gggcgatctg | accggcttcg | cggcggcgag | ttatcagcgc | 360 |
| ggtgtccgtt | tcattcaagt | cccgacgacg | ttactgtcgc | aggtcgattc | ctccgttggc | 420 |
| ggcaaaactg | cggtcaacca | tcccctcggt | aaaaacatga | ttggcgcgtt | ctaccaacct | 480 |
| gcttcagtgg | tggtggatct | cgactgtctg | aaaacgcttc | ccccgcgtga | gttagcgtcg | 540 |
| gggctggcag | aagtcatcaa | atacggcatt | attcttgacg | gtgcgttttt | taactggctg | 600 |
| gaagagaatc | tggatgcgtt | gttgcgtctg | acggtccgg | caatggcgta | ctgtattcgc | 660 |
| cgttgttgtg | aactgaaggc | agaagttgtc | gccgccgacg | agcgcgaaac | cgggttacgt | 720 |
| gcttactga | atctgggaca | cacctttggt | catgccattg | aagctgaaat | ggggtatggc | 780 |
| aattggttac | atggtgaagc | ggtcgctgcg | ggtatggtga | tggcggcgcg | gacgtcggaa | 840 |
| cgtctcgggc | agtttagttc | tgccgaaacg | cagcgtatta | taccctgct | caagcgggct | 900 |
| gggttaccgg | tcaatgggcc | gcgcgaaatg | tccgcgcagg | cgtatttacc | gcatatgctg | 960 |
| cgtgacaaga | aagtccttgc | gggagagatg | cgcttaattc | ttccgttggc | aattggtaag | 1020 |
| agtgaagttc | gcagcggcgt | ttcgcacgag | cttgttctta | cgccattgc | cgattgtcaa | 1080 |
| tcagcgtaa | | | | | | 1089 |

<210> SEQ ID NO 88
<211> LENGTH: 362
<212> TYPE: PRT
<213> ORGANISM: Escherichia coli

<400> SEQUENCE: 88

Met Glu Arg Ile Val Val Thr Leu Gly Glu Arg Ser Tyr Pro Ile Thr
1               5                   10                  15

Ile Ala Ser Gly Leu Phe Asn Glu Pro Ala Ser Phe Leu Pro Leu Lys
            20                  25                  30

Ser Gly Glu Gln Val Met Leu Val Thr Asn Glu Thr Leu Ala Pro Leu
        35                  40                  45

Tyr Leu Asp Lys Val Arg Gly Val Leu Glu Gln Ala Gly Val Asn Val
    50                  55                  60

Asp Ser Val Ile Leu Pro Asp Gly Glu Gln Tyr Lys Ser Leu Ala Val
65                  70                  75                  80

Leu Asp Thr Val Phe Thr Ala Leu Leu Gln Lys Pro His Gly Arg Asp
                85                  90                  95

Thr Thr Leu Val Ala Leu Gly Gly Gly Val Val Gly Asp Leu Thr Gly
            100                 105                 110

Phe Ala Ala Ala Ser Tyr Gln Arg Gly Val Arg Phe Ile Gln Val Pro
            115                 120                 125

Thr Thr Leu Leu Ser Gln Val Asp Ser Ser Val Gly Gly Lys Thr Ala
            130                 135                 140

Val Asn His Pro Leu Gly Lys Asn Met Ile Gly Ala Phe Tyr Gln Pro
145                 150                 155                 160

Ala Ser Val Val Asp Leu Asp Cys Leu Lys Thr Leu Pro Pro Arg
                165                 170                 175

Glu Leu Ala Ser Gly Leu Ala Glu Val Ile Lys Tyr Gly Ile Ile Leu
            180                 185                 190

Asp Gly Ala Phe Phe Asn Trp Leu Glu Glu Asn Leu Asp Ala Leu Leu
            195                 200                 205

Arg Leu Asp Gly Pro Ala Met Ala Tyr Cys Ile Arg Arg Cys Cys Glu
            210                 215                 220

Leu Lys Ala Glu Val Val Ala Ala Asp Glu Arg Glu Thr Gly Leu Arg
225                 230                 235                 240

Ala Leu Leu Asn Leu Gly His Thr Phe Gly His Ala Ile Glu Ala Glu
                245                 250                 255

Met Gly Tyr Gly Asn Trp Leu His Gly Glu Ala Val Ala Ala Gly Met
            260                 265                 270

Val Met Ala Ala Arg Thr Ser Glu Arg Leu Gly Gln Phe Ser Ser Ala
            275                 280                 285

Glu Thr Gln Arg Ile Ile Thr Leu Leu Lys Arg Ala Gly Leu Pro Val
            290                 295                 300

Asn Gly Pro Arg Glu Met Ser Ala Gln Ala Tyr Leu Pro His Met Leu
305                 310                 315                 320

Arg Asp Lys Lys Val Leu Ala Gly Glu Met Arg Leu Ile Leu Pro Leu
                325                 330                 335

Ala Ile Gly Lys Ser Glu Val Arg Ser Gly Val Ser His Glu Leu Val
            340                 345                 350

Leu Asn Ala Ile Ala Asp Cys Gln Ser Ala
            355                 360

<210> SEQ ID NO 89
<211> LENGTH: 759
<212> TYPE: DNA
<213> ORGANISM: Escherichia coli

<400> SEQUENCE: 89
atgaaaaccg taactgtaaa agatctcgtc attggtacgg gcgcacctaa aatcatcgtc    60
tcgctgatgg cgaaagatat cgccagcgtg aaatccgaag ctctcgccta tcgtgaagcg   120
gactttgata ttctggaatg gcgtgtggac cactatgccg acctctccaa tgtggagtct   180
gtcatggcgg cagcaaaaat tctccgtgag accatgccaa aaaaccgct gctgtttacc   240 ttccgcagtg ccaaagaagg cggcgagcag gcgatttcca ccgaggctta tattgcactc   300
aatcgtgcag ccatcgacag cggcctggtt gatatgatcg atctggagtt atttaccggt   360
gatgatcagg ttaaagaaac cgtcgcctac gcccacgcgc atgatgtgaa agtagtcatg   420
tccaaccatg acttccataa aacgccggaa gccgaagaaa tcattgcccg tctgcgcaaa   480
atgcaatcct cgacgccga tattcctaag attgcgctga tgccgcaaag taccagcgat   540
gtgctgacgt tgcttgccgc gaccctggag atgcaggagc agtatgccga tcgtccaatt   600

```
atcacgatgt cgatggcaaa aactggcgta atttctcgtc tggctggtga agtatttggc      660
tcggcggcaa cttttggtgc ggtaaaaaaa gcgtctgcgc cagggcaaat ctcggtaaat      720
gatttgcgca cggtattaac tattttacac caggcataa                            759
```

<210> SEQ ID NO 90
<211> LENGTH: 252
<212> TYPE: PRT
<213> ORGANISM: Escherichia coli

<400> SEQUENCE: 90

```
Met Lys Thr Val Thr Val Lys Asp Leu Val Ile Gly Thr Gly Ala Pro
1               5                   10                  15

Lys Ile Ile Val Ser Leu Met Ala Lys Asp Ile Ala Ser Val Lys Ser
            20                  25                  30

Glu Ala Leu Ala Tyr Arg Glu Ala Asp Phe Asp Ile Leu Glu Trp Arg
        35                  40                  45

Val Asp His Tyr Ala Asp Leu Ser Asn Val Glu Ser Val Met Ala Ala
    50                  55                  60

Ala Lys Ile Leu Arg Glu Thr Met Pro Glu Lys Pro Leu Leu Phe Thr
65                  70                  75                  80

Phe Arg Ser Ala Lys Glu Gly Gly Glu Gln Ala Ile Ser Thr Glu Ala
                85                  90                  95

Tyr Ile Ala Leu Asn Arg Ala Ala Ile Asp Ser Gly Leu Val Asp Met
            100                 105                 110

Ile Asp Leu Glu Leu Phe Thr Gly Asp Asp Gln Val Lys Glu Thr Val
        115                 120                 125

Ala Tyr Ala His Ala His Asp Val Lys Val Val Met Ser Asn His Asp
    130                 135                 140

Phe His Lys Thr Pro Glu Ala Glu Glu Ile Ile Ala Arg Leu Arg Lys
145                 150                 155                 160

Met Gln Ser Phe Asp Ala Asp Ile Pro Lys Ile Ala Leu Met Pro Gln
                165                 170                 175

Ser Thr Ser Asp Val Leu Thr Leu Leu Ala Ala Thr Leu Glu Met Gln
            180                 185                 190

Glu Gln Tyr Ala Asp Arg Pro Ile Ile Thr Met Ser Met Ala Lys Thr
        195                 200                 205

Gly Val Ile Ser Arg Leu Ala Gly Glu Val Phe Gly Ser Ala Ala Thr
    210                 215                 220

Phe Gly Ala Val Lys Lys Ala Ser Ala Pro Gly Gln Ile Ser Val Asn
225                 230                 235                 240

Asp Leu Arg Thr Val Leu Thr Ile Leu His Gln Ala
                245                 250
```

<210> SEQ ID NO 91
<211> LENGTH: 843
<212> TYPE: DNA
<213> ORGANISM: Bacillus thuringiensis

<400> SEQUENCE: 91

```
atgaaatatt cgctatgtac catttcattt cgtcatcaat taatttcatt tactgatatt       60
gttcaatttg catatgaaaa cggttttgaa ggaattgaat tatggggggac gcatgcacaa     120 aatttgtaca tgcaagaacg tgaaacgaca gaacgagaat tgaattttct aaaggataaa     180
aacttagaaa ttcgatgat aagtgattac ttagatatat cattatcagc agattttgaa      240
aaaacgatag agaaaagtga acaacttgta gtactagcta attggtttaa tacgaataaa     300
```

```
attcgcacgt tgctgggca aaaagggagc aaggacttct cggaacaaga gagaaaagag     360
tatgtgaagc gaatacgtaa gatttgtgat gtgtttgctc agaacaatat gtatgtgctg     420
ttagaaacac atcccaatac actaacggac acattgcctt ctactataga gttattagaa     480
gaagtaaacc atccgaattt aaaaataaat cttgattttc ttcatatatg ggagtctggc     540
gcagatccaa tagacagttt ccatcgatta aagccgtgga cactacatta ccattttaag     600
aatatatctt cagcggatta tttgcatgtg tttgaaccta ataatgtata tgctgcagca     660
ggaagtcgta taggtatggt tccgttattt gaaggtattg taaattatga tgagattatt     720
caggaagtga gaaatacgga tcttttttgct tccttagaat ggtttggaca taattcaaaa     780
gagatattaa agaagaaat gaaagtatta ataaatagaa aattagaagt agtaacttcg     840
taa                                                                  843
```

<210> SEQ ID NO 92
<211> LENGTH: 280
<212> TYPE: PRT
<213> ORGANISM: Bacillus thuringiensis

<400> SEQUENCE: 92

```
Met Lys Tyr Ser Leu Cys Thr Ile Ser Phe Arg His Gln Leu Ile Ser
1               5                   10                  15

Phe Thr Asp Ile Val Gln Phe Ala Tyr Glu Asn Gly Phe Glu Gly Ile
            20                  25                  30

Glu Leu Trp Gly Thr His Ala Gln Asn Leu Tyr Met Gln Glu Arg Glu
        35                  40                  45

Thr Thr Glu Arg Glu Leu Asn Phe Leu Lys Asp Lys Asn Leu Glu Ile
    50                  55                  60

Thr Met Ile Ser Asp Tyr Leu Asp Ile Ser Leu Ser Ala Asp Phe Glu
65                  70                  75                  80

Lys Thr Ile Glu Lys Ser Glu Gln Leu Val Val Leu Ala Asn Trp Phe
                85                  90                  95

Asn Thr Asn Lys Ile Arg Thr Phe Ala Gly Gln Lys Gly Ser Lys Asp
            100                 105                 110

Phe Ser Glu Gln Glu Arg Lys Glu Tyr Val Lys Arg Ile Arg Lys Ile
        115                 120                 125

Cys Asp Val Phe Ala Gln Asn Asn Met Tyr Val Leu Leu Glu Thr His
    130                 135                 140

Pro Asn Thr Leu Thr Asp Thr Leu Pro Ser Thr Ile Glu Leu Leu Glu
145                 150                 155                 160

Glu Val Asn His Pro Asn Leu Lys Ile Asn Leu Asp Phe Leu His Ile
                165                 170                 175

Trp Glu Ser Gly Ala Asp Pro Ile Asp Ser Phe His Arg Leu Lys Pro
            180                 185                 190

Trp Thr Leu His Tyr His Phe Lys Asn Ile Ser Ser Ala Asp Tyr Leu
        195                 200                 205

His Val Phe Glu Pro Asn Asn Val Tyr Ala Ala Ala Gly Ser Arg Ile
    210                 215                 220

Gly Met Val Pro Leu Phe Glu Gly Ile Val Asn Tyr Asp Glu Ile Ile
225                 230                 235                 240

Gln Glu Val Arg Asn Thr Asp Leu Phe Ala Ser Leu Glu Trp Phe Gly
                245                 250                 255

His Asn Ser Lys Glu Ile Leu Lys Glu Glu Met Lys Val Leu Ile Asn
            260                 265                 270
```

Arg Lys Leu Glu Val Val Thr Ser
            275                 280

<210> SEQ ID NO 93
<211> LENGTH: 1542
<212> TYPE: DNA
<213> ORGANISM: Escherichia coli

<400> SEQUENCE: 93

| | | | | | |
|---|---|---|---|---|---|
| atgcgtctgg | aagtcttttg | tgaagaccga | ctcggtctga | cccgcgaatt | actcgatcta | 60 |
| ctcgtgctaa | gaggcattga | tttacgcggt | attgagattg | atcccattgg | gcgaatctac | 120 |
| ctcaattttg | ctgaactgga | gtttgagagt | ttcagcagtc | tgatggccga | aatacgccgt | 180 |
| attgcgggtg | ttaccgatgt | gcgtactgtc | ccgtggatgc | cttccgaacg | tgagcatctg | 240 |
| gcgttgagcg | cgttactgga | ggcgttgcct | gaacctgtgc | tctctgtcga | tatgaaaagc | 300 |
| aaagtggata | tggcgaaccc | ggcgagctgt | cagcttttg | ggcaaaaatt | ggatcgcctg | 360 |
| cgcaaccata | ccgccgcaca | attgattaac | ggctttaatt | ttttacgttg | gctggaaagc | 420 |
| gaaccgcaag | attcgcataa | cgagcatgtc | gttattaatg | gcagaatttt | cctgatggag | 480 |
| attacgcctg | tttatcttca | ggatgaaaat | gatcaacacg | tcctgaccgg | tgcggtggtg | 540 |
| atgttgcgat | caacgattcg | tatgggccgc | cagttgcaaa | atgtcgccgc | ccaggacgtc | 600 |
| agcgccttca | gtcaaattgt | cgccgtcagc | ccgaaaatga | agcatgttgt | cgaacaggcg | 660 |
| cagaaactgg | cgatgctaag | cgcgccgctg | ctgattacgg | gtgacacagg | tacaggtaaa | 720 |
| gatctctttg | cctacgcctg | ccatcaggca | agccccagag | cgggcaaacc | ttacctggcg | 780 |
| ctgaactgtg | cgtctatacc | ggaagatgcg | gtcgagagtg | aactgtttgg | tcatgctccg | 840 |
| gaagggaaga | aaggattctt | tgagcaggcg | aacggtggtt | cggtgctgtt | ggatgaaata | 900 |
| ggggaaatgt | caccacggat | gcaggcgaaa | ttactgcgtt | tccttaatga | tggcacttc | 960 |
| cgtcgggttg | gcgaagacca | tgaggtgcat | gtcgatgtgc | gggtgatttg | cgctacgcag | 1020 |
| aagaatctgg | tcgaactggt | gcaaaaaggc | atgttccgtg | aagatctcta | ttatcgtctg | 1080 |
| aacgtgttga | cgctcaatct | gccgccgcta | cgtgactgtc | cgcaggacat | catgccgtta | 1140 |
| actgagctgt | tcgtcgcccg | ctttgccgac | gagcagggcg | tgccgcgtcc | gaaactggcc | 1200 |
| gctgacctga | atactgtact | tacgcgttat | gcgtggccgg | gaaatgtgcg | gcagttaaag | 1260 |
| aacgctatct | atcgcgcact | gacacaactg | gacggttatg | agctgcgtcc | acaggatatt | 1320 |
| ttgttgccgg | attatgacgc | cgcaacggta | gccgtgggcg | aagatgcgat | ggaaggttcg | 1380 |
| ctggacgaaa | tcaccagccg | ttttgaacgc | tcggtattaa | cccagcttta | tcgcaattat | 1440 |
| cccagcacgc | gcaaactggc | aaaacgtctc | ggcgtttcac | ataccgcgat | tgccaataag | 1500 |
| ttgcgggaat | atggtctgag | tcagaagaag | aacgaagagt | aa | | 1542 |

<210> SEQ ID NO 94
<211> LENGTH: 513
<212> TYPE: PRT
<213> ORGANISM: Escherichia coli

<400> SEQUENCE: 94

Met Arg Leu Glu Val Phe Cys Glu Asp Arg Leu Gly Leu Thr Arg Glu
 1               5                  10                  15

Leu Leu Asp Leu Leu Val Leu Arg Gly Ile Asp Leu Arg Gly Ile Glu
            20                  25                  30

Ile Asp Pro Ile Gly Arg Ile Tyr Leu Asn Phe Ala Glu Leu Glu Phe

```
                35                  40                  45
Glu Ser Phe Ser Ser Leu Met Ala Glu Ile Arg Arg Ile Ala Gly Val
 50                  55                  60

Thr Asp Val Arg Thr Val Pro Trp Met Pro Ser Glu Arg Glu His Leu
 65                  70                  75                  80

Ala Leu Ser Ala Leu Leu Glu Ala Leu Pro Glu Pro Val Leu Ser Val
                 85                  90                  95

Asp Met Lys Ser Lys Val Asp Met Ala Asn Pro Ala Ser Cys Gln Leu
                100                 105                 110

Phe Gly Gln Lys Leu Asp Arg Leu Arg Asn His Thr Ala Ala Gln Leu
            115                 120                 125

Ile Asn Gly Phe Asn Phe Leu Arg Trp Leu Glu Ser Glu Pro Gln Asp
            130                 135                 140

Ser His Asn Glu His Val Val Ile Asn Gly Gln Asn Phe Leu Met Glu
145                 150                 155                 160

Ile Thr Pro Val Tyr Leu Gln Asp Glu Asn Asp Gln His Val Leu Thr
                165                 170                 175

Gly Ala Val Met Leu Arg Ser Thr Ile Arg Met Gly Arg Gln Leu
                180                 185                 190

Gln Asn Val Ala Ala Gln Asp Val Ser Ala Phe Ser Gln Ile Val Ala
            195                 200                 205

Val Ser Pro Lys Met Lys His Val Val Glu Gln Ala Gln Lys Leu Ala
210                 215                 220

Met Leu Ser Ala Pro Leu Leu Ile Thr Gly Asp Thr Gly Thr Gly Lys
225                 230                 235                 240

Asp Leu Phe Ala Tyr Ala Cys His Gln Ala Ser Pro Arg Ala Gly Lys
                245                 250                 255

Pro Tyr Leu Ala Leu Asn Cys Ala Ser Ile Pro Glu Asp Ala Val Glu
                260                 265                 270

Ser Glu Leu Phe Gly His Ala Pro Glu Gly Lys Lys Gly Phe Phe Glu
            275                 280                 285

Gln Ala Asn Gly Gly Ser Val Leu Leu Asp Glu Ile Gly Glu Met Ser
290                 295                 300

Pro Arg Met Gln Ala Lys Leu Leu Arg Phe Leu Asn Asp Gly Thr Phe
305                 310                 315                 320

Arg Arg Val Gly Glu Asp His Glu Val His Val Asp Val Arg Val Ile
                325                 330                 335

Cys Ala Thr Gln Lys Asn Leu Val Glu Leu Val Gln Lys Gly Met Phe
                340                 345                 350

Arg Glu Asp Leu Tyr Tyr Arg Leu Asn Val Leu Thr Leu Asn Leu Pro
            355                 360                 365

Pro Leu Arg Asp Cys Pro Gln Asp Ile Met Pro Leu Thr Glu Leu Phe
            370                 375                 380

Val Ala Arg Phe Ala Asp Glu Gln Gly Val Pro Arg Pro Lys Leu Ala
385                 390                 395                 400

Ala Asp Leu Asn Thr Val Leu Thr Arg Tyr Ala Trp Pro Gly Asn Val
                405                 410                 415

Arg Gln Leu Lys Asn Ala Ile Tyr Arg Ala Leu Thr Gln Leu Asp Gly
            420                 425                 430

Tyr Glu Leu Arg Pro Gln Asp Ile Leu Leu Pro Asp Tyr Asp Ala Ala
            435                 440                 445

Thr Val Ala Val Gly Glu Asp Ala Met Glu Gly Ser Leu Asp Glu Ile
450                 455                 460
```

Thr Ser Arg Phe Glu Arg Ser Val Leu Thr Gln Leu Tyr Arg Asn Tyr
465                 470                 475                 480

Pro Ser Thr Arg Lys Leu Ala Lys Arg Leu Gly Val Ser His Thr Ala
            485                 490                 495

Ile Ala Asn Lys Leu Arg Glu Tyr Gly Leu Ser Gln Lys Lys Asn Glu
        500                 505                 510

Glu

<210> SEQ ID NO 95
<211> LENGTH: 666
<212> TYPE: DNA
<213> ORGANISM: Niastella koreensis

<400> SEQUENCE: 95
atgaataatc aaattttga atccgttgac cattatatca gcgatttact gggttacgaa      60
gacgatgcat tgcttgccgc caccaattca ttagccgaag caggcatgcc tgccatcagc     120
gtatcaccca accagggcaa gtttctgcaa ttactggccc aattgtgcca ggcaaaaaat    180
atcctggagc tgggcacact ggcaggctac agcaccattt ggatggcccg gccttaccc    240 aaaaacggcc ggctcatcac ccttgaatat gaccccaaac atgcggccgt tgcacaaaaa    300
aatatcgacc gggccggcct tacttcacaa gtacagatca gaaccggtaa agcaattgac    360
atattaccgc aattagtgga agaaggcgcc ggacctttg atatgatctt tatcgatgcc    420
gataaaccac cttacaccga atattttcaa tgggcgcttc ggttatcacg tcccggtaca    480
ctcatcgtgg ccgataatgt gatccgtgat ggcaaagtgc tggatgaaaa cagtacggag    540
cctgctgtac agggcgcaag acgtttcaat gccatgctgg cgccaatac cgccgttgac    600 gccaccattc ttcaaatggt aggtgtaaaa gaatacgatg aatggctttt ggccatagta    660
aaataa                                                                666

<210> SEQ ID NO 96
<211> LENGTH: 221
<212> TYPE: PRT
<213> ORGANISM: Niastella koreensis

<400> SEQUENCE: 96

Met Asn Asn Gln Ile Phe Glu Ser Val Asp His Tyr Ile Ser Asp Leu
1               5                   10                  15

Leu Gly Tyr Glu Asp Asp Ala Leu Leu Ala Ala Thr Asn Ser Leu Ala
            20                  25                  30

Glu Ala Gly Met Pro Ala Ile Ser Val Ser Pro Asn Gln Gly Lys Phe
        35                  40                  45

Leu Gln Leu Leu Ala Gln Leu Cys Gln Ala Lys Asn Ile Leu Glu Leu
    50                  55                  60

Gly Thr Leu Ala Gly Tyr Ser Thr Ile Trp Met Ala Arg Ala Leu Pro
65                  70                  75                  80

Lys Asn Gly Arg Leu Ile Thr Leu Glu Tyr Asp Pro Lys His Ala Ala
                85                  90                  95

Val Ala Gln Lys Asn Ile Asp Arg Ala Gly Leu Thr Ser Gln Val Gln
            100                 105                 110

Ile Arg Thr Gly Lys Ala Ile Asp Ile Leu Pro Gln Leu Val Glu Glu
        115                 120                 125

Gly Ala Gly Pro Phe Asp Met Ile Phe Ile Asp Ala Asp Lys Pro Pro
    130                 135                 140

```
Tyr Thr Glu Tyr Phe Gln Trp Ala Leu Arg Leu Ser Arg Pro Gly Thr
145                 150                 155                 160

Leu Ile Val Ala Asp Asn Val Ile Arg Asp Gly Lys Val Leu Asp Glu
                165                 170                 175

Asn Ser Thr Glu Pro Ala Val Gln Gly Ala Arg Arg Phe Asn Ala Met
            180                 185                 190

Leu Gly Ala Asn Thr Ala Val Asp Ala Thr Ile Leu Gln Met Val Gly
        195                 200                 205

Val Lys Glu Tyr Asp Gly Met Ala Leu Ala Ile Val Lys
    210                 215                 220
```

<210> SEQ ID NO 97
<211> LENGTH: 3387
<212> TYPE: DNA
<213> ORGANISM: Gordonia effusa

<400> SEQUENCE: 97

| | | | | | |
|---|---|---|---|---|---|
| atgtctgacc | agcccaacgc | gcttccgtct | gccatcgagc | cgctgaaccc | cgatcctcaa | 60 |
| gcgacagagc | agatctcgca | ctgtgcgacg | attgccgaac | ttgtccgggt | tctcgccgag | 120 |
| agctacggtg | atcgccccgc | gctgggttgg | cgaaacaata | gtgatccctc | gtcctggcat | 180 |
| tcgatgactt | accgagatct | cgctgagcgg | gcggattcca | tggcgcgact | tctccattcg | 240 |
| acacttggcg | tcgccgagaa | cgaccgggtg | gcgacggtgg | gcttcactag | cgcggagtac | 300 |
| accatcgcct | cgcttgccgt | cggcacgctc | ggcgcgatgg | aggtaccact | gcaaaacgcc | 360 |
| gggtccgtcg | acgtctgggc | cgcaatcctc | accgaaaccg | actgtgtgag | cgcggttgtc | 420 |
| gcggccgatc | aactgccttc | gatcgctcgg | ctggccgaat | cgggcaccta | caccggcctg | 480 |
| cgacatgtgc | tggtcttcga | catcggctcg | cgcgacggaa | ccacgctcga | tgacgcggca | 540 |
| cgacgactgg | tcgctgcggg | cacccaggtg | catctccgcc | agcccggcgc | cgagccgacg | 600 |
| acaccgccgg | ctccactgcc | ccagatcacg | gccaaccccg | accgcgtcgc | cctcctcatc | 660 |
| tacacctccg | gtagcaccgg | agcccccaaa | ggcgccatgt | acaccgaaac | cgcggtgacc | 720 |
| cggttattcc | aatcgggact | cagcggcttg | gggcgcgcca | ccgacggtca | cggctggatc | 780 |
| accctgaact | tcatgccgat | gagccacgtg | atgggacgca | gcactctgtg | caaaccctg  | 840 |
| ggaaatggtg | gcaccgcgta | cttcaccccg | cgcgccgacc | tcgccgagtt | gctcaccgac | 900 |
| ctcgcagcgg | tccagccgac | cgacctgcaa | ttcgtaccgc | gcatctggga | catgctgtac | 960 |
| caggagtacg | tccgcctcac | cgatcaggac | gtcagtgaac | aagacgccct | cacccgtatg | 1020 |
| cgcgaacact | atttcggtac | ccggactgcc | accgccatca | ccggttccgc | accgatctcc | 1080 |
| gatgaggttc | ggcgtttcgt | cgaagcgatg | ctgccggttc | cactcatcga | aggctatgga | 1140 |
| agtaccgagg | ccgccggcgt | ctccatcgac | ggccgcatcc | agcgaccgcc | ggtggtggat | 1200 |
| tacaagcttc | tcgacgttcc | tgaactcggc | tacctgagca | ccgatcggcc | gcacccgcgc | 1260 |
| ggcgaactgc | tcgtcaagac | cgaccatatc | ttccgcgggt | actacaaccg | tcccgacctc | 1320 |
| acctcatcgg | tcttcgacga | ccagggctac | taccggacgg | cgacatcgt  | cgccgagacc | 1380 |
| ggcccagacc | aaatcgagta | tgtcgaccgc | cggaacaacg | tgatgaagct | ttcgcagggt | 1440 |
| gagttcgtcg | cgatcgccca | catcgaggcg | gtactgacca | ccccgccgat | ccagcaactg | 1500 |
| tacgtctacg | gcaacagcgc | gcggccctat | ctgctcgcgg | tcgtcgtgcc | cacccccgag | 1560 |
| ttacgcgaac | gacacgccga | cgacaacgag | ctgcgacgag | aagtactgac | ggcactgcgc | 1620 |
| tctcatggcg | aacgtaatgg | ccttgcggcc | gtagagattc | cgcgcgatgt | gattgtcgaa | 1680 |

```
cgcacgccgt tcagcctgga gaacggtctt cttaccggca tccgaaaact cgcgcgccca   1740
caactcaaag agcgctacgg cgctcggctg gaggccctct acgccgagct ggccgatagc   1800
cgtatcacca ggctgcgcga cgtcaaagcc gttgccgcac aacgctcaac ggtgacaacg   1860
gtcatcgacg tggtcacagc gatactcgac ctcgccgacg gggaggtcac ggccgcggca   1920
catttcaccg acctcggcgg agattccctc accgccgtca cggtcgggaa cgaactccgc   1980
gacatcttcg acgccgaagt accggtcggc gtcttgacca gcccgtcatc gacgctggcc   2040
gacatagccg aacatatcga cgggcgacac agcgaggccc ggccaaccgc ggaatcggtc   2100
cacggcaccg gaaccaccct tcgggcagcg gacctcactc tcgacaaatt cctcgacgag   2160
gagaccttgc gcgctgcgtc cgacgtgacg tcggctgcga ccgacgtacg gaccgtattc   2220
atcaccggcg caaccggatt cctcggtcgc tatctgacac tcgactggtt gcgtcggatg   2280
gcaaaagtcg gcggcacggt gatctgcctc gttcgaggtg cggacgatga tgccgcccgg   2340
gcgcgcctag acgcggcatt cgactccagc gatctatggt cggagtacca gcgactggcc   2400
aaagaccacc ttcgggttct cgccggcgac aaggactcgg atcacctcgc gctcacccca   2460
gacgtatggg atgaattggc aaagtccgtc gacctcatca tcgatcccgc ggcgctggtc   2520
aaccatgtgt tgccatatcg agaactattc ggacccaacg tatctggcac tgctgagctg   2580
atcagactcg cggtgacgac cacccgtaag ccatacgtgt atatctcaac ggtcggtgta   2640
ggcgaccagg tcgcgccggg atctttcacc gaggaccccg acatccgcga gatgagctcg   2700
gtacgcgaga ttaacgacac ttacgccaac ggatatggca acagcaaatg ggccggcgaa   2760
gtattgctcg cgcaggcgca cgaacgattt gagttaccgg tcagcgtctt tcgctgcgac   2820
atgatcgtcg ccgatgatca caccatcggg cagctgaacc tacctgacat gttcacgcgg   2880
ctactgatga gcgtgctcgc caccggcttg caccttcgct ctttctatca actcgccacc   2940
gacggatcgg cacaggaggc ccacttcgat gctctgccgg tcgatttcct cgccgaagcg   3000
atcaacaccc tgtgggttaa ggacggagcc cgcaccttca acgcgatgaa cccgcacgcc   3060
gacggcatcg gattcgatca gtacattcgc tggctgatcg acagcggcga gcagatcagc   3120
cttgtagaca actatgacga ttggtatcgg cgattcggtg cggccctcgc cgatctgccg   3180
gaaaagcagc gacgcggatc gttgattccg ttgctgcaca actatgttca cccgatgacg   3240
ccgcacaatc gcggtatggc gtcggcggac cgattccacg acgcggtccg aaccgctggc   3300
gtcgggcagt cgtccgacat cccgcatatc acgccacaga tcatcgagaa ctacgcccgc   3360
agcctccgcg gtctcggggt gatctga                                      3387
```

<210> SEQ ID NO 98
<211> LENGTH: 1128
<212> TYPE: PRT
<213> ORGANISM: Gordonia effusa

<400> SEQUENCE: 98

```
Met Ser Asp Gln Pro Asn Ala Leu Pro Ser Ala Ile Glu Pro Leu Asn
1               5                   10                  15

Pro Asp Pro Gln Ala Thr Glu Gln Ile Ser His Cys Ala Thr Ile Ala
            20                  25                  30

Glu Leu Val Arg Val Leu Ala Glu Ser Tyr Gly Asp Arg Pro Ala Leu
        35                  40                  45

Gly Trp Arg Asn Asn Ser Asp Pro Ser Ser Trp His Ser Met Thr Tyr
    50                  55                  60

Arg Asp Leu Ala Glu Arg Ala Asp Ser Met Ala Arg Leu Leu His Ser
```

-continued

```
             65                  70                  75                  80
Thr Leu Gly Val Ala Glu Asn Asp Arg Val Ala Thr Val Gly Phe Thr
                 85                  90                  95
Ser Ala Glu Tyr Thr Ile Ala Ser Leu Ala Val Gly Thr Leu Gly Ala
                100                 105                 110
Met Glu Val Pro Leu Gln Asn Ala Gly Ser Val Asp Val Trp Ala Ala
                115                 120                 125
Ile Leu Thr Glu Thr Asp Cys Val Ser Ala Val Ala Ala Asp Gln
130                 135                 140
Leu Pro Ser Ile Ala Arg Leu Ala Glu Ser Gly Thr Tyr Thr Gly Leu
145                 150                 155                 160
Arg His Val Leu Val Phe Asp Ile Gly Ser Arg Asp Gly Thr Thr Leu
                165                 170                 175
Asp Asp Ala Ala Arg Arg Leu Val Ala Ala Gly Thr Gln Val His Leu
                180                 185                 190
Arg Gln Pro Gly Ala Glu Pro Thr Thr Pro Ala Pro Leu Pro Gln
        195                 200                 205
Ile Thr Ala Asn Pro Asp Arg Val Ala Leu Leu Ile Tyr Thr Ser Gly
210                 215                 220
Ser Thr Gly Ala Pro Lys Gly Ala Met Tyr Thr Glu Thr Ala Val Thr
225                 230                 235                 240
Arg Leu Phe Gln Ser Gly Leu Ser Gly Leu Gly Arg Ala Thr Asp Gly
                245                 250                 255
His Gly Trp Ile Thr Leu Asn Phe Met Pro Met Ser His Val Met Gly
                260                 265                 270
Arg Ser Thr Leu Trp Gln Thr Leu Gly Asn Gly Gly Thr Ala Tyr Phe
        275                 280                 285
Thr Pro Arg Ala Asp Leu Ala Glu Leu Leu Thr Asp Leu Ala Ala Val
        290                 295                 300
Gln Pro Thr Asp Leu Gln Phe Val Pro Arg Ile Trp Asp Met Leu Tyr
305                 310                 315                 320
Gln Glu Tyr Val Arg Leu Thr Asp Gln Asp Val Ser Glu Gln Asp Ala
                325                 330                 335
Leu Thr Arg Met Arg Glu His Tyr Phe Gly Thr Arg Thr Ala Thr Ala
                340                 345                 350
Ile Thr Gly Ser Ala Pro Ile Ser Asp Glu Val Arg Arg Phe Val Glu
        355                 360                 365
Ala Met Leu Pro Val Pro Leu Ile Glu Gly Tyr Gly Ser Thr Glu Ala
        370                 375                 380
Ala Gly Val Ser Ile Asp Gly Arg Ile Gln Arg Pro Pro Val Val Asp
385                 390                 395                 400
Tyr Lys Leu Leu Asp Val Pro Glu Leu Gly Tyr Leu Ser Thr Asp Arg
                405                 410                 415
Pro His Pro Arg Gly Glu Leu Leu Val Lys Thr Asp His Ile Phe Ala
                420                 425                 430
Gly Tyr Tyr Asn Arg Pro Asp Leu Thr Ser Ser Val Phe Asp Asp Gln
        435                 440                 445
Gly Tyr Tyr Arg Thr Gly Asp Ile Val Ala Glu Thr Gly Pro Asp Gln
        450                 455                 460
Ile Glu Tyr Val Asp Arg Arg Asn Asn Val Met Lys Leu Ser Gln Gly
465                 470                 475                 480
Glu Phe Val Ala Ile Ala His Ile Glu Ala Val Leu Thr Thr Pro Pro
                485                 490                 495
```

```
Ile Gln Gln Leu Tyr Val Tyr Gly Asn Ser Ala Arg Pro Tyr Leu Leu
            500                 505                 510

Ala Val Val Pro Thr Pro Glu Leu Arg Glu Arg His Ala Asp Asp
        515                 520                 525

Asn Glu Leu Arg Arg Glu Val Leu Thr Ala Leu Arg Ser His Gly Glu
    530                 535                 540

Arg Asn Gly Leu Ala Ala Val Glu Ile Pro Arg Asp Val Ile Val Glu
545                 550                 555                 560

Arg Thr Pro Phe Ser Leu Glu Asn Gly Leu Leu Thr Gly Ile Arg Lys
                565                 570                 575

Leu Ala Arg Pro Gln Leu Lys Glu Arg Tyr Gly Ala Arg Leu Glu Ala
            580                 585                 590

Leu Tyr Ala Glu Leu Ala Asp Ser Arg Ile Thr Arg Leu Arg Asp Val
        595                 600                 605

Lys Ala Val Ala Ala Gln Arg Ser Thr Val Thr Val Ile Asp Val
    610                 615                 620

Val Thr Ala Ile Leu Asp Leu Ala Asp Gly Glu Val Thr Ala Ala Ala
625                 630                 635                 640

His Phe Thr Asp Leu Gly Gly Asp Ser Leu Thr Ala Val Thr Val Gly
                645                 650                 655

Asn Glu Leu Arg Asp Ile Phe Asp Ala Glu Val Pro Val Gly Val Leu
            660                 665                 670

Thr Ser Pro Ser Ser Thr Leu Ala Asp Ile Ala Glu His Ile Asp Gly
        675                 680                 685

Arg His Ser Glu Ala Arg Pro Thr Ala Glu Ser Val His Gly Thr Gly
    690                 695                 700

Thr Thr Leu Arg Ala Ala Asp Leu Thr Leu Asp Lys Phe Leu Asp Glu
705                 710                 715                 720

Glu Thr Leu Arg Ala Ala Ser Asp Val Thr Ser Ala Ala Thr Asp Val
                725                 730                 735

Arg Thr Val Phe Ile Thr Gly Ala Thr Gly Phe Leu Gly Arg Tyr Leu
            740                 745                 750

Thr Leu Asp Trp Leu Arg Arg Met Ala Lys Val Gly Gly Thr Val Ile
        755                 760                 765

Cys Leu Val Arg Gly Ala Asp Asp Ala Ala Arg Ala Arg Leu Asp
    770                 775                 780

Ala Ala Phe Asp Ser Ser Asp Leu Trp Ser Glu Tyr Gln Arg Leu Ala
785                 790                 795                 800

Lys Asp His Leu Arg Val Leu Ala Gly Asp Lys Ser Asp His Leu
                805                 810                 815

Ala Leu Thr Pro Asp Val Trp Asp Glu Leu Ala Lys Ser Val Asp Leu
            820                 825                 830

Ile Ile Asp Pro Ala Ala Leu Val Asn His Val Leu Pro Tyr Arg Glu
        835                 840                 845

Leu Phe Gly Pro Asn Val Ser Gly Thr Ala Glu Leu Ile Arg Leu Ala
    850                 855                 860

Val Thr Thr Thr Arg Lys Pro Tyr Val Tyr Ile Ser Thr Val Gly Val
865                 870                 875                 880

Gly Asp Gln Val Ala Pro Gly Ser Phe Thr Glu Asp Pro Asp Ile Arg
                885                 890                 895

Glu Met Ser Ser Val Arg Glu Ile Asn Asp Thr Tyr Ala Asn Gly Tyr
            900                 905                 910
```

-continued

```
Gly Asn Ser Lys Trp Ala Gly Glu Val Leu Leu Ala Gln Ala His Glu
            915                 920                 925
Arg Phe Glu Leu Pro Val Ser Val Phe Arg Cys Asp Met Ile Val Ala
    930                 935                 940
Asp Asp His Thr Ile Gly Gln Leu Asn Leu Pro Asp Met Phe Thr Arg
945                 950                 955                 960
Leu Leu Met Ser Val Leu Ala Thr Gly Leu Ala Pro Arg Ser Phe Tyr
                965                 970                 975
Gln Leu Ala Thr Asp Gly Ser Ala Gln Ala His Phe Asp Ala Leu
            980                 985                 990
Pro Val Asp Phe Leu Ala Glu Ala  Ile Asn Thr Leu Trp  Val Lys Asp
        995                 1000                1005
Gly Ala  Arg Thr Phe Asn Ala  Met Asn Pro His Ala  Asp Gly Ile
     1010                1015                1020
Gly Phe Asp Gln Tyr Ile Arg  Trp Leu Ile Asp Ser  Gly Glu Gln
     1025                1030                1035
Ile Ser  Leu Val Asp Asn Tyr  Asp Asp Trp Tyr Arg  Arg Phe Gly
     1040                1045                1050
Ala Ala  Leu Ala Asp Leu Pro  Glu Lys Gln Arg Arg  Gly Ser Leu
     1055                1060                1065
Ile Pro  Leu Leu His Asn Tyr  Val His Pro Met Thr  Pro His Asn
     1070                1075                1080
Arg Gly  Met Ala Ser Ala Asp  Arg Phe His Asp Ala  Val Arg Thr
     1085                1090                1095
Ala Gly  Val Gly Gln Ser Ser  Asp Ile Pro His Ile  Thr Pro Gln
     1100                1105                1110
Ile Ile  Glu Asn Tyr Ala Arg  Ser Leu Arg Gly Leu  Gly Val Ile
     1115                1120                1125
```

<210> SEQ ID NO 99
<211> LENGTH: 4522
<212> TYPE: DNA
<213> ORGANISM: Artificial Sequence
<220> FEATURE:
<223> OTHER INFORMATION: Nucleotide sequence of DNA fragment containing
      ACAR gene of Gordonia effusa (codon-optimized) and entD gene of
      Escherichia coli

<400> SEQUENCE: 99

```
ccaagcttgc atgccagatc gtttagatcc gaaggaaaac gtcgaaaagc aatttgcttt      60
tcgacgcccc accccgcgcg ttttagcgtg tcagtagacg cgtagggtaa gtggggtagc     120
ggcttgttag atatcttgaa atcggctttc aacagcattg atttcgatgt atttagctgg     180
ccgtttgaga cgcgatgtcc acagggtagc tggtagtttg aaaatcaacg ccgttgccct     240
taggattcag taactggcac attttgtaat gcgctagatc tgtgtgccca gtcttccagg     300
ctgcttatca cagtgaaagc aaaaccaatt cgtggctgcg aaagtcgtag ccaccacgaa     360
gtccaggagg acatacaatg agcgatcagc cgaatgcact gccgagcgca attgaaccgc     420
tgaatccgga tccgcaggca accgagcaga ttagccattg tgcaaccatt gcagaactgg     480
ttcgtgttct ggcagaaagc tatggtgatc gtccggcact gggttggcgt aataatagcg     540
atccgagcag ctggcatagc atgacctatc gtgatctggc cgaacgtgca gatagcatgg     600
cacgtctgct gcatagcacc ctgggtgttg cagaaaatga tcgtgttgca accgttggtt     660
ttaccagcgc agaatatacc attgcaagcc tggcagttgg tacactgggt gcaatggaag     720
ttccgctgca gaatgcaggt agcgttgatg tttgggcagc aattctgacc gaaaccgatt     780
```

```
gtgttagcgc agttgttgca gcagatcagc tgccgagcat tgcccgtctg cggaaagcg      840
gcacctatac cggtctgcgt catgttctgg tttttgatat tggtagccgt gatggcacca     900
ccctggatga tgcagcacgt cgtctggttg ccgcaggcac ccaggttcat ctgcgtcagc     960
ctggtgcaga accgaccacc cctccggcac cgctgccgca gattaccgca aacccggatc    1020
gtgtggcact gctgatttat accagcggta gcacaggtgc accgaaaggt gcaatgtata    1080
ccgaaacagc agttacccgt ctgtttcaga gcggtctgag tggtctgggt cgtgcaaccg    1140
atggtcatgg ttggattacc ctgaacttta tgccgatgag ccatgttatg ggtcgtagta    1200
ccctgtggca gaccctgggt aatggtggca ccgcatattt tacaccgcgt gcagatctgg    1260
ctgaactgct gaccgatctg gcagccgttc agccgacgga tctgcagttt gttccgcgta    1320
tttgggatat gctgtatcaa gaatatgttc gtctgacaga tcaggatgtt agcgaacagg    1380
atgcactgac ccgtatgcgt gaacattatt tcggcacccg taccgcaacc gcaattaccg    1440
gtagcgcacc gattagtgat gaagttcgtc gttttgttga agcaatgctg ccggttccgc    1500
tgattgaagg ttatggtagc accgaagcag ccggtgttag cattgatggt cgtattcagc    1560
gtccgcctgt tgttgattat aaactgctgg atgtgccgga actgggttat ctgagcaccg    1620
atcgtccgca tccgcgtggt gagctgctgg ttaaaaccga tcatattttt gccggttatt    1680
acaatcgtcc ggatctgacc agcagcgttt ttgatgatca gggttattat cgtaccggtg    1740
atattgttgc cgaaaccggt ccggatcaga ttgaatatgt tgatcgtcgt aacaacgtga    1800
tgaaactgag ccagggtgaa tttgttgcaa ttgcccatat tgaagcagtt ctgaccaccc    1860
caccgattca gcagctgtat gtttatggta atagcgcacg tccgtatctg ctggccgttg    1920
ttgttccgac accggaactg cgtgaacgtc atgcagatga taatgaactg cgtcgtgaag    1980
ttctgacagc actgcgtagc catggtgaac gtaatggtct ggcagcagtt gaaattccgc    2040
gtgatgttat tgttgaacgt accccgtttt agcctggaaaa tggtctgctg acaggtattc    2100
gtaaactggc acgtccgcag ctgaaagaac gttatggtgc acgtctggaa gcactgtatg    2160
ccgaactggc cgatagccgt attacacgtc tgcgtgatgt gaaagcagtt gcagcccagc    2220
gtagcaccgt taccaccgtt attgatgttg ttaccgcaat tctggatctg gcggatggtg    2280
aagttaccgc agcagcacat tttacagatc tgggtggtga tagcctgacc gcagttaccg    2340
ttggtaacga actgcgcgat atttttgatg ccgaagttcc ggttggtgtg ctgaccagcc    2400
cgagcagtac cctggcagat attgcggaac atattgatgg ccgtcatagc gaagcacgtc    2460
cgaccgcaga aagcgttcat ggcaccggta caacccctgcg tgcagccgat ctgaccctgg    2520
ataaatttct ggatgaagaa acactgcgtg ccgcaagtga tgttaccagt gcagccaccg    2580
atgttcgtac cgtgtttatt accggtgcaa ccggttttct gggtcgctac ctgacactgg    2640
attggctgcg tcgtatggca aaagttggtg gtacagttat ttgtctggtg cgtggtgccg    2700
atgatgacga gcccgtgcg cgtctggatg cagcatttga tagcagcgat ctgtggtctg    2760
aatatcagcg tctggcaaaa gatcatctgc gcgtgctggc aggcgataaa gatagcgatc    2820
atctggcact gacaccggat gtgtgggatg aactggcaaa aagcgttgat ctgattattg    2880
atccggcagc actggttaat catgtactgc cgtatcgcga actgtttggt ccgaatgtta    2940
gcggcaccgc agaactgatc cgtctggcag ttaccaccac ccgtaaaccg tatgtgtata    3000
tttcaaccgt gggtgttggt gatcaggttg ctccgggtag ctttaccgaa gatcctgata    3060
ttcgtgaaat gagcagcgtg cgtgaaatca atgataccta tgcaaatggt tacggcaata    3120
```

| | |
|---|---|
| gcaaatgggc aggcgaagtt ctgctggcac aggcacatga acgttttgaa ctgccggtta | 3180 |
| gcgttttccg ttgtgatatg attgttgcgg atgatcatac cattggtcag ctgaatctgc | 3240 |
| cggatatgtt tactcgcctg ctgatgagcg ttctggcaac aggtctggca ccgcgtagct | 3300 |
| tttatcagct ggcgaccgat ggtagtgcac aagaggcaca ttttgatgcg ctgccggtgg | 3360 |
| atttcctggc cgaagcaatt aatacactgt gggttaaaga tggtgcccgt acctttaatg | 3420 |
| caatgaatcc gcatgccgat ggtattggtt ttgatcagta tattcgttgg ctgattgata | 3480 |
| gcggtgaaca aattagcctg gtggataatt atgatgattg gtatcgtcgc tttggtgccg | 3540 |
| cactggcgga tctgcctgaa aaacagcgtc gtggtagcct gattccgctg ctgcacaatt | 3600 |
| atgttcatcc gatgacaccg cataatcgtg gtatggcaag cgcagatcgt tttcatgatg | 3660 |
| cagttcgtac agcaggcgtt ggtcagagca gcgatattcc gcatattacc cctcagatta | 3720 |
| ttgaaaatta tgcacgtagc ctgcgtggcc tgggtgtgat ttaaaggagg acatacaatg | 3780 |
| gtcgatatga aaactacgca tacctccctc cctttgccg acatacgct gcattttgtt | 3840 |
| gagttcgatc cggcgaattt ttgtgagcag gatttactct ggctgccgca ctacgcacaa | 3900 |
| ctgcaacacg ctggacgtaa acgtaaaaca gagcatttag ccggacggat cgctgctgtt | 3960 |
| tatgctttgc gggaatatgg ctataaatgt gtgcccgcaa tcggcgagct acgccaacct | 4020 |
| gtctggcctg cggaggtata cggcagtatt agccactgtg ggactacggc attagccgtg | 4080 |
| gtatctcgtc aaccgattgg cattgatata aagaaatttt ttctgtaca aaccgcaaga | 4140 |
| gaattgacag acaacattat tacaccagcg gaacacgagc gactcgcaga ctgcggttta | 4200 |
| gcctttttctc tggcgctgac actggcattt tccgccaaag agagcgcatt taaggcaagt | 4260 |
| gagatccaaa ctgatgcagg ttttctggac tatcagataa ttagctggaa taaacagcag | 4320 |
| gtcatcattc atcgtgagaa tgagatgttt gctgtgcact ggcagataaa agaaaagata | 4380 |
| gtcataacgc tgtgccaaca cgattaattg acaacatctg gtacgattcg cccgcagcca | 4440 |
| tcactgacca cgggcgaaag tgtaaagcag gtgccttacc atcctgacct gacaaccgga | 4500 |
| tatgcgggat ccccgggtac cg | 4522 |

```
<210> SEQ ID NO 100
<211> LENGTH: 3387
<212> TYPE: DNA
<213> ORGANISM: Gordonia effusa

<400> SEQUENCE: 100
```

| | |
|---|---|
| atgagcgatc agccgaatgc actgccgagc gcaattgaac cgctgaatcc ggatccgcag | 60 |
| gcaaccgagc agattagcca ttgtgcaacc attgcagaac tggttcgtgt tctggcagaa | 120 |
| agctatggtg atcgtccggc actgggttgg cgtaataata gcgatccgag cagctggcat | 180 |
| agcatgaccct atcgtgatct ggccgaacgt gcagatagca tggcacgtct gctgcatagc | 240 |
| accctgggtg ttgcagaaaa tgatcgtgtt gcaaccgttg gttttaccag cgcagaatat | 300 |
| accattgcaa gcctggcagt tggtacactg ggtgcaatgg aagttccgct gcagaatgca | 360 |
| ggtagcgttg atgtttgggc agcaattctg accgaaaccg attgtgttag cgcagttgtt | 420 |
| gcagcagatc agctgccgag cattgccgt ctggcgaaa gcggcaccta ccggtctg | 480 |
| cgtcatgttc tggttttttga tattggtagc cgtgatggca ccaccctgga tgatgcagca | 540 |
| cgtcgtctgg ttgccgcagg cacccaggtt catctgcgtc agcctggtgc agaaccgacc | 600 |
| accccctccgg caccgctgcc gcagattacc gcaaacccgg atcgtgtggc actgctgatt | 660 |
| tataccagcg gtagcacagg tgcaccgaaa ggtgcaatgt ataccgaaac agcagttacc | 720 |

```
cgtctgtttc agagcggtct gagtggtctg ggtcgtgcaa ccgatggtca tggttggatt    780
accctgaact ttatgccgat gagccatgtt atgggtcgta gtaccctgtg cagaccctg    840
ggtaatggtg gcaccgcata ttttacaccg cgtgcagatc tggctgaact gctgaccgat    900
ctggcagccg ttcagccgac ggatctgcag tttgttccgc gtatttggga tatgctgtat    960
caagaatatg ttcgtctgac agatcaggat gttagcgaac aggatgcact gacccgtatg   1020
cgtgaacatt atttcggcac ccgtaccgca accgcaatta ccggtagcgc accgattagt   1080
gatgaagttc gtcgttttgt tgaagcaatg ctgccggttc cgctgattga aggttatggt   1140
agcaccgaag cagccggtgt tagcattgat ggtcgtattc agcgtccgcc tgttgttgat   1200
tataaactgc tggatgtgcc ggaactgggt tatctgagca ccgatcgtcc gcatccgcgt   1260
ggtgagctgc tggttaaaac cgatcatatt tttgccggtt attacaatcg tccggatctg   1320
accagcagcg ttttgatga tcagggttat tatcgtaccg gtgatattgt tgccgaaacc   1380
ggtccggatc agattgaata tgttgatcgt cgtaacaacg tgatgaaact gagccagggt   1440
gaatttgttg caattgccca tattgaagca gttctgacca ccccaccgat tcagcagctg   1500
tatgtttatg gtaatagcgc acgtccgtat ctgctggccg ttgttgttcc gacaccggaa   1560
ctgcgtgaac gtcatgcaga tgataatgaa ctgcgtcgtg aagttctgac agcactgcgt   1620
agccatggtg aacgtaatgg tctggcagca gttgaaattc gcgtgatgt tattgttgaa   1680
cgtacccgt ttagcctgga aaatggtctg ctgacaggta ttcgtaaact ggcacgtccg   1740
cagctgaaag aacgttatgg tgcacgtctg gaagcactgt atgccgaact ggccgatagc   1800
cgtattacac gtctgcgtga tgtgaaagca gttgcagccc agcgtagcac cgttaccacc   1860
gttattgatg ttgttaccgc aattctggat ctggcggatg tgaagttac cgcagcagca   1920
cattttacag atctgggtgg tgatagcctg accgcagtta ccgttggtaa cgaactgcgc   1980
gatattttg atgccgaagt tccggttggt gtgctgacca gcccgagcag taccctggca   2040
gatattgcgg aacatattga tggccgtcat agcgaagcac gtccgaccgc agaaagcgtt   2100
catggcaccg gtacaaccct gcgtgcagcc gatctgaccc tggataaatt tctggatgaa   2160
gaaacactgc gtgccgcaag tgatgttacc agtgcagcca ccgatgttcg taccgtgttt   2220
attaccggtg caaccggttt tctgggtcgc tacctgacac tggattggct gcgtcgtatg   2280
gcaaaagttg gtgtacagt tatttgtctg gtgcgtggtg ccgatgatga cgcagcccgt   2340
gcgcgtctgg atgcagcatt tgatagcagc gatctgtggt ctgaatatca gcgtctggca   2400
aaagatcatc tgcgcgtgct ggcaggcgat aaagatagcg atcatctggc actgacaccg   2460
gatgtgtggg atgaactggc aaaaagcgtt gatctgatta ttgatccggc agcactggtt   2520
aatcatgtac tgccgtatcg cgaactgttt ggtccgaatg ttagcggcac cgcagaactg   2580
atccgtctgg cagttaccac cacccgtaaa ccgtatgtgt atatttcaac cgtgggtgtt   2640
ggtgatcagg ttgctccggg tagctttacc gaagatcctg atattcgtga atgagcagc   2700
gtgcgtgaaa tcaatgatac ctatgcaaat ggttacggca atagcaaatg gcaggcgaa   2760
gttctgctgg cacaggcaca tgaacgtttt gaactgccgg ttagcgtttt tcgttgtgat   2820
atgattgttg cggatgatca taccattggt cagctgaatc tgccggatat gtttactcgc   2880
ctgctgatga gcgttctggc aacaggtctg gcaccgcgta gcttttatca gctggcgacc   2940
gatggtagtg cacaagaggc acatttgat gcgctgccgg tggatttcct ggccgaagca   3000
attaatacac tgtgggttaa agatggtgcc cgtacccttta atgcaatgaa tccgcatgcc   3060
```

```
gatggtattg gttttgatca gtatattcgt tggctgattg atagcggtga acaaattagc    3120
ctggtggata attatgatga ttggtatcgt cgctttggtg ccgcactggc ggatctgcct    3180
gaaaaacagc gtcgtggtag cctgattccg ctgctgcaca attatgttca tccgatgaca    3240
ccgcataatc gtggtatggc aagcgcagat cgttttcatg atgcagttcg tacagcaggc    3300
gttggtcaga gcagcgatat tccgcatatt accccctcaga ttattgaaaa ttatgcacgt    3360
agcctgcgtg cctgggtgt gatttaa                                          3387
```

<210> SEQ ID NO 101
<211> LENGTH: 819
<212> TYPE: DNA
<213> ORGANISM: Escherichia coli

<400> SEQUENCE: 101

```
atggaaacct atgctgtttt tggtaatccg atagcccaca gcaaatcgcc attcattcat      60
cagcaatttg ctcagcaact gaatattgaa catccctatg gcgcgtgtt ggcacccatc     120 aatgatttca tcaacacact gaacgctttc tttagtgctg gtggtaaagg tgcgaatgtg    180
acggtgcctt ttaaagaaga ggcttttgcc agagcggatg agcttactga cgggcagcg    240 ttggctggtg ctgttaatac cctcatgcgg ttagaagatg gacgcctgct gggtgacaat    300
accgatggtg taggcttgtt aagcgatctg gaacgtctgt cttttatccg ccctggttta    360
cgtattctgc ttatcggcgc tggtggagca tctcgcggcg tactactgcc actcctttcc    420
ctggactgtg cggtgacaat aactaatcgg acggtatccc gcgcggaaga gttggctaaa    480
ttgtttgcgc acactggcag tattcaggcg ttgagtatgg acgaactgga aggtcatgag    540
tttgatctca ttattaatgc aacatccagt ggcatcagtg gtgatattcc ggcgatcccg    600
tcatcgctca ttcatccagg catttattgc tatgacatgt tctatcagaa aggaaaaact    660 cctttctctgg catggtgtga gcagcgaggc tcaaagcgta atgctgatgg tttaggaatg    720
ctggtggcac aggcggctca tgcctttctt ctctggcacg tgttctgcc tgacgtagaa    780 ccagttataa agcaattgca ggaggaattg tccgcgtga                            819
```

<210> SEQ ID NO 102
<211> LENGTH: 272
<212> TYPE: PRT
<213> ORGANISM: Escherichia coli

<400> SEQUENCE: 102

```
Met Glu Thr Tyr Ala Val Phe Gly Asn Pro Ile Ala His Ser Lys Ser
1               5                   10                  15

Pro Phe Ile His Gln Gln Phe Ala Gln Gln Leu Asn Ile Glu His Pro
            20                  25                  30

Tyr Gly Arg Val Leu Ala Pro Ile Asn Asp Phe Ile Asn Thr Leu Asn
        35                  40                  45

Ala Phe Phe Ser Ala Gly Gly Lys Gly Ala Asn Val Thr Val Pro Phe
    50                  55                  60

Lys Glu Glu Ala Phe Ala Arg Ala Asp Glu Leu Thr Glu Arg Ala Ala
65                  70                  75                  80

Leu Ala Gly Ala Val Asn Thr Leu Met Arg Leu Glu Asp Gly Arg Leu
                85                  90                  95

Leu Gly Asp Asn Thr Asp Gly Val Gly Leu Leu Ser Asp Leu Glu Arg
            100                 105                 110

Leu Ser Phe Ile Arg Pro Gly Leu Arg Ile Leu Leu Ile Gly Ala Gly
        115                 120                 125
```

-continued

```
Gly Ala Ser Arg Gly Val Leu Leu Pro Leu Leu Ser Leu Asp Cys Ala
        130                 135                 140

Val Thr Ile Thr Asn Arg Thr Val Ser Arg Ala Glu Glu Leu Ala Lys
145                     150                 155                 160

Leu Phe Ala His Thr Gly Ser Ile Gln Ala Leu Ser Met Asp Glu Leu
                165                 170                 175

Glu Gly His Glu Phe Asp Leu Ile Ile Asn Ala Thr Ser Ser Gly Ile
            180                 185                 190

Ser Gly Asp Ile Pro Ala Ile Pro Ser Ser Leu Ile His Pro Gly Ile
        195                 200                 205

Tyr Cys Tyr Asp Met Phe Tyr Gln Lys Gly Lys Thr Pro Phe Leu Ala
    210                 215                 220

Trp Cys Glu Gln Arg Gly Ser Lys Arg Asn Ala Asp Gly Leu Gly Met
225                 230                 235                 240

Leu Val Ala Gln Ala Ala His Ala Phe Leu Leu Trp His Gly Val Leu
                245                 250                 255

Pro Asp Val Glu Pro Val Ile Lys Gln Leu Gln Glu Glu Leu Ser Ala
            260                 265                 270
```

METHOD FOR PRODUCING ALDEHYDE

This application is a Continuation of, and claims priority under 35 U.S.C. § 120 to International Application PCT/JP2016/081970, filed Oct. 27, 2016, and claims priority therethrough under 35 U.S.C. § 119 to Russian Patent Application No. 2015-146077, filed Oct. 27, 2015, both of which the entireties are incorporated by reference herein. Also, the Sequence Listing filed electronically herewith is hereby incorporated by reference (File name: 2018-04-12T_US-576_Seq_List; File size: 170 KB; Date recorded: Apr. 12, 2018).

BACKGROUND OF THE INVENTION

Field of the Invention

The present invention relates to a method for producing an objective substance, for example, an aldehyde such as vanillin, by using a bacterium.

Brief Description of the Related Art

Vanillin is the major ingredient that provides the smell of vanilla, and is used as an aromatic by being blended in foods, drinks, perfumes, and so forth. Vanillin is mainly produced by extraction from natural products or by chemical synthesis.

Vanillin has also been produced via bioengineering techniques, such as using eugenol, isoeugenol, ferulic acid, glucose, vanillic acid, coconut husk, or the like, as a raw material in methods with microorganisms (Kaur et al., Appl. Biochem. Biotechnol., (2013) 169(4):1353-72).

However, vanillin is an aldehyde, and thus is highly toxic to microorganisms (Zaldivar J. et al., Biotech. and Bioeng., (1999) 65:24-33). Therefore, the toxicity of vanillin is an important issue for vanillin production using microorganisms. It has been reported that the toxicity of vanillin can be alleviated by converting vanillin into vanillyl alcohol (Shen Y. et al., J. Ind. Microbiol. Biotechnol., (2014) 31:1637-1645; Nguyen T T. et al., J. Biosci. Bioeng., (2014) 118:263-269). In addition, methods for producing vanillin using microorganisms while alleviating the toxicity of vanillin, such as methods exemplified below, have been reported.

*E. coli* or the like has been reported to have an ability to accumulate vanillin in high amounts using the raw materials eugenol or isoeugenol (Kaur et al., Appl. Biochem. Biotechnol., (2013) 169(4):1353-72). These raw materials are poorly water-soluble, and therefore, vanillin can be produced from these raw materials using a double layer fermentation, and a solvent such as dimethylsulfoxide can be added to further improve productivity. In double layer fermentation, vanillin accumulates in the organic layer, keeping the vanillin concentration in the water layer low, and thereby the toxicity of vanillin can be alleviated, resulting in accumulation of large amounts of vanillin. However, double layer fermentation increases the purification cost, and further increases the cost because a fermentation tank made of materials resistant to organic solvents is required. In addition, double layer fermentation under aerobic conditions involves a risk of explosion due to static electricity or the like.

Methods using resins can result in production and accumulation of high amounts of vanillin while alleviating the toxicity of vanillin (Kaur et al., Appl. Biochem. Biotechnol., (2013) 169(4):1353-72). However, use of resins also raises the production cost.

An alcohol dehydrogenase enzyme has been reported to be involved in the conversion of vanillin into vanillyl alcohol, and that attenuating the activity of such an enzyme can improve vanillin production by *E. coli* and yeast (Kunjapur A M. et al., J. Am. Chem. Soc., (2014) 136:11644-11654; Hansen E H. et al., App. Env. Microbiol., (2009) 75:2765-2774). However, the amount of vanillin that is produced using this method is about 0.5 g/L for both *E. coli* and yeast (Kunjapur A M. et al., J. Am. Chem. Soc., (2014) 136:11644-11654; Hansen E H. et al., App. Env. Microbiol., (2009) 75:2765-2774). In addition, the amount of vanillin that accumulates in the water layer system using *E. coli* is about a maximum of 2.5 g/L without absorbing vanillin using resins or the like (Venkitasubramanian P. et al., Enzyme and Microbial Technology, (2008) 42:130-137). Also, the amount of vanillin that accumulates in the water layer when using *Saccharomyces cerevisiae* is about 0.5 g/L at the maximum (Kunjapur A M. et al., J. Am. Chem. Soc., (2014) 136:11644-11654; Brochado A R. et al., Microbial Cell Factories, (2010) 9:84). Thus, a problem due to aldehyde toxicity in industrial production of vanillin is strongly indicated.

In contrast, microorganisms such as actinomycetes or the like, such as Amycolatopsis sp. ATCC39116, have been reported to produce and accumulate vanillin in the water layer (Kaur et al., Appl. Biochem. Biotechnol., (2013) 169(4):1353-72; Ma et al., Bioprocess Biosyst. Eng., (2014) 37:891-899). However, actinomycetes require quite a long culture period, which raises the cost. In addition, gene recombination techniques have not been established for these actinomycetes, and hence, it is difficult to improve vanillin production through strain modification. Furthermore, because vanillin is used for foods, vanillin should be produced by GRAS (Generally Recognized As Safe) microorganisms, the safety of which is certificated. However, GRAS microorganisms that highly accumulate vanillin in the water layer system have not been previously reported.

SUMMARY OF THE INVENTION

Aspects of the present invention include to develop a novel technique that improves production of an objective substance, for example, an aldehyde such as vanillin, and thereby provide a method for efficiently producing the objective substance. Particularly, an aspect of the present invention is to provide a method for efficiently producing an objective substance such as vanillin without having to alleviate the toxicity of the objective substance, such as by using expensive double layer fermentation and resins.

A method is provided for screening microorganism strains suitable for production of an objective substance, for example, an aldehyde such as vanillin. Using this method, coryneform bacteria were found to have superior vanillin resistance as compared to other bacteria. The ability of a coryneform bacterium to produce an objective substance such as vanillin was found to be significantly improved by modifying the bacterium so that the activity of alcohol dehydrogenase is reduced.

It is an aspect of the present invention to provide a coryneform bacterium having an ability to produce an objective substance, wherein said bacterium has been modified so that the activity of alcohol dehydrogenase is reduced as compared with a non-modified bacterium, and wherein the objective substance is an aldehyde.

It is a further aspect of the present invention to provide the bacterium as described above, wherein the alcohol dehydrogenase is a protein encoded by a NCgl0324 gene and/or a NCgl2709 gene.

It is a further aspect of the present invention to provide the bacterium as described above, wherein at least the activity of the protein encoded by NCgl0324 gene is reduced.

It is a further aspect of the present invention to provide the bacterium as described above, wherein at least the activity of the protein encoded by NCgl2709 gene is reduced.

It is a further aspect of the present invention to provide the bacterium as described above, wherein the protein encoded by the NCgl0324 gene is selected from the group consisting of: (a) a protein comprising the amino acid sequence of SEQ ID NO: 66; (b) a protein comprising the amino acid sequence of SEQ ID NO: 66 but including substitution, deletion, insertion, and/or addition of 1 to 10 amino acid residues, and wherein said protein has alcohol dehydrogenase activity; (c) a protein comprising an amino acid sequence having an identity of 90% or higher to the amino acid sequence of SEQ ID NO: 66, and wherein said protein has alcohol dehydrogenase activity.

It is a further aspect of the present invention to provide the bacterium as described above, wherein the protein encoded by the NCgl2709 gene is selected from the group consisting of: (a) a protein comprising the amino acid sequence of SEQ ID NO: 70; (b) a protein comprising the amino acid sequence of SEQ ID NO: 70 but including substitution, deletion, insertion, and/or addition of 1 to 10 amino acid residues, and wherein said protein has alcohol dehydrogenase activity; (c) a protein comprising an amino acid sequence having an identity of 90% or higher to the amino acid sequence of SEQ ID NO: 70, and wherein said protein has alcohol dehydrogenase activity.

It is a further aspect of the present invention to provide the bacterium as described above, wherein said activity of the alcohol dehydrogenase is reduced by reducing the expression of a gene encoding the alcohol dehydrogenase, or by disrupting the gene.

It is a further aspect of the present invention to provide the bacterium as described above, which has been further modified so that the activity of an enzyme that is involved in the biosynthesis of the objective substance is increased as compared with a non-modified bacterium.

It is a further aspect of the present invention to provide the bacterium as described above, wherein the enzyme that is involved in the biosynthesis of the objective substance catalyzes the conversion from a precursor of the objective substance into the objective substance.

It is a further aspect of the present invention to provide the bacterium as described above, wherein the enzyme that is involved in the biosynthesis of the objective substance is selected from the group consisting of 3-deoxy-D-arabino-heptulosonic acid 7-phosphate synthase, 3-dehydroquinate synthase, 3-dehydroquinate dehydratase, 3-dehydroshikimate dehydratase, O-methyltransferase, aromatic carboxylic acid reductase, phenylalanine ammonia lyase, and combinations thereof.

It is a further aspect of the present invention to provide the bacterium as described above, wherein the aromatic carboxylic acid reductase is selected from the group consisting of: (a) a protein comprising the amino acid sequence of SEQ ID NO: 48, 76, or 98; (b) a protein comprising the amino acid sequence of SEQ ID NO: 48, 76, or 98 but including substitution, deletion, insertion, and/or addition of 1 to 10 amino acid residues, and wherein said protein has aromatic carboxylic acid reductase activity; (c) a protein comprising an amino acid sequence having an identity of 90% or higher to the amino acid sequence of SEQ ID NO: 48, 76, or 98, and wherein said protein has aromatic carboxylic acid reductase activity.

It is a further aspect of the present invention to provide the bacterium as described above, which has been further modified so that the activity of phosphopantetheinyl transferase is increased as compared with a non-modified bacterium.

It is a further aspect of the present invention to provide the bacterium as described above, wherein the phosphopantetheinyl transferase is a protein defined in (a), (b), or (c) mentioned below: (a) a protein comprising the amino acid sequence of SEQ ID NO: 50 or 52; (b) a protein comprising the amino acid sequence of SEQ ID NO: 50 or 52 but wherein said amino acid sequence includes substitution, deletion, insertion, and/or addition of 1 to 10 amino acid residues, and wherein said protein has phosphopantetheinyl transferase activity; (c) a protein comprising an amino acid sequence having an identity of 90% or higher to the amino acid sequence of SEQ ID NO: 50 or 52, and wherein said protein has phosphopantetheinyl transferase activity.

It is a further aspect of the present invention to provide the bacterium as described above, which has been further modified so that the activity of an uptake system of a substance other than the objective substance is increased as compared with a non-modified bacterium.

It is a further aspect of the present invention to provide the bacterium as described above, wherein the uptake system is a vanillic acid uptake system and/or a protocatechuic acid uptake system.

It is a further aspect of the present invention to provide the bacterium as described above, wherein the vanillic acid uptake system is a protein selected from the group consisting of: (a) a protein comprising the amino acid sequence of SEQ ID NO: 54; (b) a protein comprising the amino acid sequence of SEQ ID NO: 54 but including substitution, deletion, insertion, and/or addition of 1 to 10 amino acid residues, and wherein said protein has vanillic acid uptake activity; (c) a protein comprising an amino acid sequence having an identity of 90% or higher to the amino acid sequence of SEQ ID NO: 54, and wherein said protein has vanillic acid uptake activity.

It is a further aspect of the present invention to provide the bacterium as described above, which has been further modified so that the activity of an enzyme that is involved in the production of a substance other than the objective substance is reduced as compared with a non-modified bacterium.

It is a further aspect of the present invention to provide the bacterium as described above, wherein the enzyme that is involved in the production of a substance other than the objective substance is selected from the group consisting of vanillate demethylase, protocatechuate 3,4-dioxygenase, shikimate dehydrogenase, and combinations thereof.

It is a further aspect of the present invention to provide the bacterium as described above, wherein the vanillate demethylase is a protein selected from the group consisting of: (a) a protein comprising the amino acid sequence of SEQ ID NO: 58 or 60; (b) a protein comprising the amino acid sequence of SEQ ID NO: 58 or 60 but including substitution, deletion, insertion, and/or addition of 1 to 10 amino acid residues, and wherein said protein has vanillate demethylase activity; (c) a protein comprising an amino acid sequence having an identity of 90% or higher to the amino acid sequence of SEQ ID NO: 58 or 60, and wherein said protein has vanillate demethylase activity.

It is a further aspect of the present invention to provide the bacterium as described above, wherein the coryneform bacterium belongs to the genus *Corynebacterium*.

It is a further aspect of the present invention to provide the bacterium as described above, wherein the coryneform bacterium is *Corynebacterium glutamicum*.

It is a further aspect of the present invention to provide a method for producing an objective substance, the method comprising using the bacterium as described above, wherein the objective substance is an aldehyde.

It is a further aspect of the present invention to provide the method as described above, wherein said using comprises cultivating the bacterium in a culture medium or reaction mixture, wherein said culture medium or reaction mixture comprises a carbon source so that the objective substance is produced and accumulates in the culture medium or reaction mixture.

It is a further aspect of the present invention to provide the method as described above, wherein a precursor of the objective substance is converted into the objective substance.

It is a further aspect of the present invention to provide the method as described above, wherein said using comprises cultivating the bacterium in a culture medium or reaction mixture, wherein said culture medium or reaction mixture comprises the precursor so that the object substance is produced and accumulates in the culture medium or reaction mixture.

It is a further aspect of the present invention to provide the method as described above, wherein said precursor is converted into the objective substance by allowing cells of the bacterium to act on the precursor in a culture medium or reaction mixture so that the objective substance is produced and accumulates in the culture medium or reaction mixture.

It is a further aspect of the present invention to provide the method as described above, wherein the cells are present in a culture medium, collected from a culture medium, a processed product of a culture medium, or combinations thereof.

It is a further aspect of the present invention to provide the method as described above, wherein the precursor is selected from the group consisting of protocatechuic acid, vanillic acid, benzoic acid, L-phenylalanine, cinnamic acid, and combinations thereof.

It is a further aspect of the present invention to provide the method as described above, the method further comprising collecting the objective substance from a culture medium or reaction mixture comprising the bacterium.

It is a further aspect of the present invention to provide the method as described above, wherein the objective substance is an aromatic aldehyde.

It is a further aspect of the present invention to provide the method as described above, wherein the aldehyde is selected from the group consisting of vanillin, benzaldehyde, cinnamaldehyde, and combinations thereof.

It is a further aspect of the present invention to provide a method for screening an aldehyde-resistant strain, the method comprising: culturing a microorganism in a medium containing an aldehyde; and selecting an aldehyde-resistant strain.

It is a further aspect of the present invention to provide the method as described above, wherein the aldehyde is present in the medium at a concentration of 2 g/L or higher.

It is a further aspect of the present invention to provide the method as described above, wherein the microorganism has been modified so that the activity of alcohol dehydrogenase is reduced as compared with a non-modified microorganism.

It is a further aspect of the present invention to provide the method as described above, wherein the aldehyde is vanillin.

BRIEF DESCRIPTION OF THE FIGURES

In FIG. 5, the FKS0165, FKFC1, FKFC3, FKFC5, FKFC7, FKFC9, FKFC11, and FKFC14 strains are represented as none, ΔNCgl313, ΔNCgl2709, ΔNCgl324, ΔNCgl2709ΔNCgl324, ΔNCgl2709ΔNCgl313, ΔNCgl324ΔNCgl313, and ΔNCgl2709ΔNCgl324ΔNCgl313.

DETAILED DESCRIPTION OF THE PREFERRED EMBODIMENTS

<1> Bacterium of the Present Invention

Figure 1:
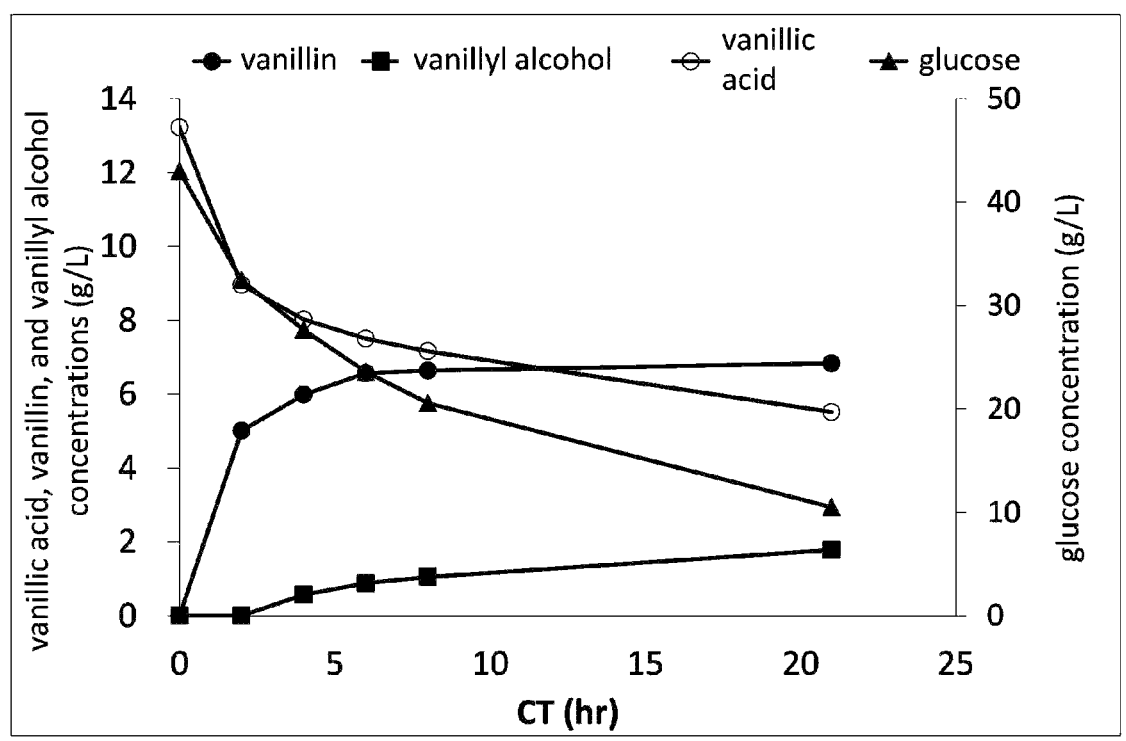
FIG. 1 shows results of vanillin production by *E. coli*.

The bacterium as described herein can be a coryneform bacterium that is able to produce an objective substance. This bacterium can be modified so that the activity of an alcohol dehydrogenase is reduced. The ability to produce an objective substance can also be referred to as an "objective substance-producing ability".

<1-1> Bacterium Having Objective Substance-Producing Ability

The phrase "bacterium having an objective substance-producing ability" can refer to a bacterium that is able to produce an objective substance.

The phrase "bacterium having an objective substance-producing ability" can refer to a bacterium that is able to produce an objective substance by fermentation, if the bacterium is used in a fermentation method. That is, the phrase "bacterium having an objective substance-producing ability" can refer to a bacterium that is able to an objective substance from a carbon source. Specifically, the phrase "bacterium having an objective substance-producing ability" can refer to a bacterium that is able to, upon being cultured in a culture medium, such as a culture medium containing a carbon source, produce and accumulate the objective substance in the culture medium to such a degree that the objective substance can be collected therefrom.

Also, the phrase "bacterium having an objective substance-producing ability" can refer to a bacterium that is able to produce an objective substance by bioconversion, if the bacterium is used in a bioconversion method. That is, the phrase "bacterium having an objective substance-producing ability" can refer to a bacterium that is able to produce an objective substance from a precursor of the objective substance. Specifically, the phrase "bacterium having an objective substance-producing ability" can refer to a bacterium that is able to, upon being cultured in a culture medium containing a precursor of the objective substance, produce and accumulate the objective substance in the culture medium to such a degree that the objective substance can be collected from the culture medium. Also, specifically, the phrase "bacterium having an objective substance-producing ability" can refer to a bacterium that is able to, upon being allowed to act on a precursor of an objective substance in a reaction mixture or culture medium, produce and accumulate the objective substance in the reaction mixture or culture medium to such a degree that the objective substance can be collected from the reaction mixture or culture medium.

The bacterium having an objective substance-producing ability can be a bacterium that is able to accumulate the objective substance in the culture medium or reaction mixture in an amount larger than that obtainable with a non-modified strain. The term "non-modified strain" can refer to a control strain that has not been modified so that the activity of alcohol dehydrogenase is reduced. Examples of the non-modified strain can include a wild-type strain or a parent strain, such as *Corynebacterium glutamicum* strains ATCC 13869 and ATCC 13032. The bacterium having an objective substance-producing ability can be a bacterium that is able to accumulate the objective substance in the culture medium or reaction mixture in an amount of, for example, 0.008 g/L or more, 0.05 g/L or more, 0.3 g/L or more, 0.5 g/L or more, 1.0 g/L or more, 3.0 g/L or more, 6.0 g/L or more, or 9.0 g/L or more.

The term "objective substance" can refer to an aldehyde. Examples of the aldehyde can include aromatic aldehydes. Examples of the aromatic aldehydes can include vanillin, benzaldehyde, and cinnamaldehyde. The bacterium as described herein may have an ability to produce only one kind of objective substance, or may have an ability to produce two or more kinds of objective substances. Also, the bacterium as described herein may have an ability to produce an objective substance from one kind of precursor of the objective substance or from two or more kinds of precursors of the objective substance.

Examples of the coryneform bacterium can include bacteria belonging to the genus *Corynebacterium, Brevibacterium, Microbacterium*, or the like.

Specific examples of such coryneform bacteria can include the following species.

*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes (Corynebacterium efficiens)*
*Corynebacterium herculis*
*Brevibacterium divaricatum (Corynebacterium glutamicum)*
*Brevibacterium flavum (Corynebacterium glutamicum)*
*Brevibacterium immariophilum*
*Brevibacterium lactofermentum (Corynebacterium glutamicum)*
*Brevibacterium roseum*
*Brevibacterium saccharolyticum*
*Brevibacterium thiogenitalis*
*Corynebacterium ammoniagenes (Corynebacterium stationis)*
*Brevibacterium album*
*Brevibacterium cerinum*
*Microbacterium ammoniaphilum*

Specific examples of the coryneform bacteria can include the following strains.

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium efficiens (Corynebacterium thermoaminogenes)* AJ12340 (FERM BP-1539)
*Corynebacterium herculis* ATCC 13868
*Brevibacterium divaricatum (Corynebacterium glutamicum)* ATCC 14020
*Brevibacterium flavum (Corynebacterium glutamicum)* ATCC 13826, ATCC 14067, AJ12418 (FERM BP-2205)
*Brevibacterium immariophilum* ATCC 14068
*Brevibacterium lactofermentum (Corynebacterium glutamicum)* ATCC 13869 (2256 strain)
*Brevibacterium roseum* ATCC 13825
*Brevibacterium saccharolyticum* ATCC 14066
*Brevibacterium thiogenitalis* ATCC 19240
*Corynebacterium ammoniagenes (Corynebacterium stationis)* ATCC 6871, ATCC 6872
*Brevibacterium album* ATCC 15111
*Brevibacterium cerinum* ATCC 15112
*Microbacterium ammoniaphilum* ATCC 15354

The coryneform bacteria can include bacteria that had previously been classified into the genus *Brevibacterium*, but have since been united into the genus *Corynebacterium* (Int. J. Syst. Bacteriol., 41, 255 (1991)). Moreover, *Corynebacterium stationis* can include bacteria that had previously been classified as *Corynebacterium ammoniagenes*, but is now re-classified into *Corynebacterium stationis* on the basis of nucleotide sequence analysis of 16S rRNA etc. (Int. J. Syst. Evol. Microbiol., 60, 874-879 (2010)).

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org). The registration numbers of the strains are listed in the catalogue of the American Type Culture Collection. These strains can also be obtained from, for example, the depositories at which the strains were deposited.

The bacterium as described herein may be a bacterium inherently having an objective substance-producing ability, or may be a bacterium modified so that it has an objective substance-producing ability. The bacterium having an objective substance-producing ability can be obtained by imparting an objective substance-producing ability to such a bacterium as described above, or enhancing an objective substance-producing ability of such a described as mentioned above.

Hereafter, specific examples of the method for imparting or enhancing an objective substance-producing ability will be described. Such modifications as exemplified below for imparting or enhancing an objective substance-producing ability may be independently used, or may be used in an appropriate combination.

The objective substance can be generated by the action of an enzyme that is involved in the biosynthesis of the objective substance. Such an enzyme can also be referred to as "objective substance biosynthesis enzyme". Therefore, the bacterium as described herein may have an objective substance biosynthesis enzyme. In other words, the bacterium as described herein may have a gene encoding an objective substance biosynthesis enzyme. Such a gene can also be referred to as an "objective substance biosynthesis"

gene". The bacterium as described herein may inherently have an objective substance biosynthesis gene, or may be a bacterium into which the objective substance biosynthesis gene has been introduced. The methods for introducing a gene will be described below.

Also, an objective substance-producing ability of a bacterium can be improved by increasing the activity of an objective substance biosynthesis enzyme. That is, examples of the method for imparting or enhancing an objective substance-producing ability can include a method of increasing the activity of an objective substance biosynthesis enzyme. That is, the bacterium as described herein can be modified so that the activity of an objective substance biosynthesis enzyme is increased. The activity of one kind of objective substance biosynthesis enzyme may be increased, or the activities of two or more kinds of objective substance biosynthesis enzymes may be increased. The method for increasing the activity of a protein (enzyme etc.) will be described below. The activity of a protein (enzyme etc.) can be increased by, for example, increasing the expression of a gene encoding the protein.

An objective substance can be generated from, for example, a carbon source and/or a precursor of the objective substance. Hence, examples of the objective substance biosynthesis enzyme can include, for example, enzymes that catalyze the conversion from the carbon source and/or the precursor into the objective substance. For example, 3-dehydroshikimic acid can be produced via a part of shikimate pathway, which can include steps catalyzed by 3-deoxy-D-arabino-heptulosonic acid 7-phosphate synthase (DAHP synthase), 3-dehydroquinate synthase, and/or 3-dehydroquinate dehydratase; 3-dehydroshikimic acid can be converted to protocatechuic acid by the action of 3-dehydroshikimate dehydratase (DHSD); protocatechuic acid can be converted to vanillic acid or protocatechualdehyde by the action of O-methyltransferase (OMT) or aromatic aldehyde oxidoreductase (aromatic carboxylic acid reductase; ACAR), respectively; and vanillic acid or protocatechualdehyde can be converted to vanillin by the action of ACAR or OMT, respectively. Also, benzaldehyde and cinnamaldehyde can be generated from, for example, benzoic acid and cinnamic acid, respectively, by the action of ACAR. That is, specific examples of the objective substance biosynthesis enzyme can include, for example, DAHP synthase, 3-dehydroquinate synthase, 3-dehydroquinate dehydratase, DHSD, OMT, and ACAR.

The term "3-deoxy-D-arabino-heptulosonic acid 7-phosphate synthase (DAHP synthase)" can refer to a protein that has the activity of catalyzing the reaction of converting D-erythrose 4-phosphate and phosphoenolpyruvic acid into 3-deoxy-D-arabino-heptulosonate 7-phosphate (DAHP) and phosphate (EC 2.5.1.54). The gene encoding DAHP synthase can also be referred to as a "DAHP synthase gene". Examples of DAHP synthase can include the AroF, AroG, and AroH proteins, which are encoded by the aroF, aroG, and aroH genes, respectively. Of these, AroG may function as the major DAHP synthase. The DAHP synthase, such as the AroF, AroG, and AroH proteins, can be derived from or native to various organisms, such as Enterobacteriaceae bacteria and coryneform bacteria. Specific examples of DAHP synthase can include the AroF, AroG, and AroH proteins of *E. coli*. The nucleotide sequence of the aroG gene of the *E. coli* K-12 MG1655 is shown as SEQ ID NO: 85, and the amino acid sequence of the AroG protein encoded by this gene is shown as SEQ ID NO: 86.

The DAHP synthase activity can be measured by, for example, incubating the enzyme with substrates (for example, D-erythrose 4-phosphate and phosphoenolpyruvic acid), and measuring the enzyme- and substrate-dependent generation of DAHP.

The term "3-dehydroquinate synthase" can refer to a protein that has the activity of catalyzing the reaction of dephosphorylating DAHP to generate 3-dehydroquinic acid (EC 4.2.3.4). The gene encoding 3-dehydroquinate synthase can also be referred to as "3-dehydroquinate synthase gene". Examples of 3-dehydroquinate synthase can include the AroB protein, which is encoded by the aroB gene. The 3-dehydroquinate synthase, such as the AroB protein, can be derived from or native to various organisms such as Enterobacteriaceae bacteria and coryneform bacteria. Specific examples of 3-dehydroquinate synthase can include the AroB protein of *E. coli*. The nucleotide sequence of the aroB gene of the *E. coli* K-12 MG1655 is shown as SEQ ID NO: 87, and the amino acid sequence of the AroB protein encoded by this gene is shown as SEQ ID NO: 88.

The 3-dehydroquinate synthase activity can be measured by, for example, incubating the enzyme with a substrate (for example, DAHP), and measuring the enzyme- and substrate-dependent generation of 3-dehydroquinic acid.

The term "3-dehydroquinate dehydratase" can refer to a protein that has the activity of catalyzing the reaction of dehydrating 3-dehydroquinic acid to generate 3-dehydroshikimic acid (EC 4.2.1.10). The gene encoding 3-dehydroquinate dehydratase can also be referred to as "3-dehydroquinate dehydratase gene". Examples of 3-dehydroquinate dehydratase can include AroD protein, which is encoded by aroD gene. The 3-dehydroquinate dehydratase, such as AroD protein, can be derived from or native to various organisms such as Enterobacteriaceae bacteria and coryneform bacteria. Specific examples of 3-dehydroquinate dehydratase can include the AroD protein of *E. coli*. The nucleotide sequence of the aroD gene of the *E. coli* K-12 MG1655 is shown as SEQ ID NO: 89, and the amino acid sequence of the AroD protein encoded by this gene is shown as SEQ ID NO: 90.

The 3-dehydroquinate dehydratase activity can be measured by, for example, incubating the enzyme with a substrate (for example, 3-dehydroquinic acid), and measuring the enzyme- and substrate-dependent generation of 3-dehydroshikimic acid.

The term "3-dehydroshikimate dehydratase (DHSD)" can refer to a protein that has the activity of catalyzing the reaction of dehydrating 3-dehydroshikimic acid to generate protocatechuic acid (EC 4.2.1.118). The gene encoding DHSD can also be referred to as a "DHSD gene". Examples of DHSD can include the AsbF protein, which is encoded by the asbF gene. DHSD, such as the AsbF protein, can be derived from or native to various organisms such as *Bacillus thuringiensis*, *Neurospora crassa*, or *Podospora pauciseta*. The nucleotide sequence of the asbF gene of *Bacillus thuringiensis* BMB171 is shown as SEQ ID NO: 91, and the amino acid sequence of the AsbF protein encoded by this gene is shown as SEQ ID NO: 92.

The DHSD activity can be measure by, for example, incubating the enzyme with a substrate (for example, 3-dehydroshikimic acid), and measuring the enzyme- and substrate-dependent generation of protocatechuic acid.

The expression of a gene encoding an enzyme of shikimate pathway, such as DAHP synthase, 3-dehydroquinate synthase, and 3-dehydroquinate dehydratase, is repressed by a tyrosine repressor TyrR, which is encoded by tyrR gene. Therefore, the activity of an enzyme of shikimate pathway can also be increased by reducing the activity of the tyrosine repressor TyrR. The nucleotide sequence of the tyrR gene of E. coli K-12 MG1655 is shown as SEQ ID NO: 93, and the amino acid sequence of the TyrR protein encoded by this gene is shown as SEQ ID NO: 94.

The term "O-methyltransferase (OMT)" can refer to a protein that has the activity of catalyzing the reaction of methylating protocatechuic acid and/or protocatechualdehyde in the presence of a methyl group donor to generate vanillic acid and/or vanillin (for example, methylation of hydroxyl group at the meta-position, EC 2.1.1.68 etc.). This activity can also be referred to as "OMT activity". A gene encoding OMT can also be referred to as an "OMT gene". OMT may generally use both protocatechuic acid and protocatechualdehyde as the substrate, but is not necessarily limited thereto. That is, OMT can be used that has the substrate specificity that is required depending on the type of the biosynthesis pathway via which the objective substance is produced in the method as described herein. For example, when vanillin is produced via conversion from protocatechuic acid into vanillic acid, OMT that uses at least protocatechuic acid can be used. Also, for example, when vanillin is produced via conversion from protocatechualdehyde into vanillin, OMT that uses at least protocatechualdehyde can be used. Examples of the methyl group donor can include S-adenosylmethionine (SAM). OMT can be derived from or native to various organisms, such as the OMT of *Homo sapiens* (Hs) (GenBank Accession No. NP_000745 and NP_009294), the OMT of *Arabidopsis thaliana* (GenBank Accession Nos. NP_200227 and NP_009294), the OMT of *Fragariaxananassa* (GenBank Accession No. AAF28353), and other various OMTs of mammals, plants, and microorganisms exemplified in WO2013/022881A1. Four kinds of transcript variants and two kinds of OMT isoforms are known for the OMT gene of *Homo sapiens*. The nucleotide sequences of these four transcript variants (transcript variant 1-4, GenBank Accession No. NM_000754.3, NM_001135161.1, NM_001135162.1, and NM_007310.2) are shown as SEQ ID NOS: 41 to 44, the amino acid sequence of the longer OMT isoform (MB-COMT, GenBank Accession No. NP_000745.1) is shown as SEQ ID NO: 45, and the amino acid sequence of the shorter OMT isoform (S-COMT, GenBank Accession No. NP_009294.1) is shown as SEQ ID NO: 46. SEQ ID NO: 46 is identical to SEQ ID NO: 45, except the N-terminal 50 amino acid residues are truncated in SEQ ID NO: 46. Examples of OMT further can include OMTs of Bacteroidetes bacteria (for example, bacteria belonging to the phylum Bacteroidetes). Examples of the Bacteroidetes bacteria can include bacteria belonging to the genus *Niastella, Terrimonas, Chitinophaga*, or the like (International Journal of Systematic and Evolutionary Microbiology (2007), 57, 1828-1833). Examples of the *Niastella* bacteria can include *Niastella koreensis*. The nucleotide sequence of the OMT gene of *Niastella koreensis* is shown as SEQ ID NO: 95, and the amino acid sequence of OMT encoded by this gene is shown as SEQ ID NO: 96.

OMT may also catalyze the reaction of methylating protocatechuic acid and/or protocatechualdehyde to generate isovanillic acid and/or isovanillin (for example, methylation of hydroxyl group at the para-position) as a side reaction. The chosen OMT can also selectively catalyze the methylation of hydroxyl group at the meta-position. The expression "selectively catalyze the methylation of hydroxyl group at the meta-position" can mean that the chosen OMT selectively generates vanillic acid from protocatechuic acid and/or that the chosen OMT selectively generates vanillin from protocatechualdehyde. The expression "selectively generating vanillic acid from protocatechuic acid" can mean that OMT generates vanillic acid in an amount of, for example, 3 times or more, 5 times or more, 10 times or more, 15 times or more, 20 times or more, 25 times or more, or 30 times or more of that of isovanillic acid in terms of molar ratio, when OMT is allowed to act on protocatechuic acid. Also, the expression "selectively generating vanillin from protocatechualdehyde" can mean that OMT generates vanillin in an amount of, for example, 3 times or more, 5 times or more, 10 times or more, 15 times or more, 20 times or more, 25 times or more, or 30 times or more of that of isovanillin in terms of molar ratio, when OMT is allowed to act on protocatechualdehyde. Examples of OMT that selectively catalyzes the methylation of hydroxyl group at the meta-position can include OMT having a "specific mutation" described herein.

OMT having the "specific mutation" can also be referred to as "mutant OMT". A gene encoding a mutant OMT can also be referred to as "mutant OMT gene".

OMT not having the "specific mutation" can also be referred to as a "wild-type OMT". A gene encoding a wild-type OMT can also be referred to as a "wild-type OMT gene". The term "wild-type" can be used to distinguish the "wild-type" OMT from the "mutant" OMT, and the "wild-type" OMT is not limited to natural or native substances, but can include any OMT not having the "specific mutation". Examples of wild-type OMT can include, for example, the OMTs exemplified above. In addition, all conservative variants of OMTs exemplified above can be considered as wild-type OMTs, provided that such conservative variants do not have the "specific mutation".

Examples of the "specific mutation" can include the mutations contained in the mutant OMTs described in WO2013/022881A1. That is, examples of the "specific mutation" can include the mutation that the leucine residue at position 198 of the wild-type OMT (L198) is replaced with an amino acid residue having a hydrophobic index (hydropathy index) lower than that of a leucine residue, and the mutation that the glutamate residue at position 199 of the wild-type OMT (E199) is replaced with an amino acid residue having either a neutral or positive side-chain charge at pH 7.4. The mutant OMT may have either one or both of these mutations.

Examples of the "amino acid residue having a hydrophobic index (hydropathy index) lower than that of a leucine residue" can include Ala, Arg, Asn, Asp, Cys, Glu, Gln, Gly, His, Lys, Met, Phe, Pro, Ser, Thr, Trp, and Tyr. The "amino acid residue having a hydrophobic index (hydropathy index) lower than that of leucine residue can include Ala, Arg, Asn, Asp, Glu, Gln, Gly, His, Lys, Met, Pro, Ser, Thr, Trp, and Tyr. Tyr is a particular example.

The "amino acid residue having either a neutral or positive side-chain charge at pH 7.4" can include Ala, Arg, Asn, Cys, Gln, Gly, His, Ile, Leu, Lys, Met, Phe, Pro, Ser, Thr, Trp, Tyr, and Val. Ala and Gln are particular examples.

The phrase "L198" and "E199" in an arbitrary wild-type OMT can refer to "an amino acid residue corresponding to the leucine residue at position 198 of the amino acid sequence shown as SEQ ID NO: 46" and "an amino acid residue corresponding to the glutamate residue at position 199 of the amino acid sequence shown as SEQ ID NO: 46", respectively. The positions of these amino acid residues represent the relative positions, and the absolute positions thereof may shift due to deletion, insertion, addition, and so forth of amino acid residue(s). For example, if one amino acid residue is deleted or inserted at a position on the N-terminus side of position X in the amino acid sequence shown as SEQ ID NO: 46, the amino acid residue originally at position X is relocated at position X−1 or X+1, however, it can still be regarded as the "amino acid residue corresponding to the amino acid residue at position X of the amino acid sequence shown as SEQ ID NO: 46". Furthermore, although "L198" and "E199" are usually a leucine residue and a glutamate residue, respectively, they may not be a leucine residue and a glutamate residue, respectively. That is, when "L198" and "E199" are not leucine residue and glutamate residue, respectively, the "specific mutation" can include a mutation that those amino acid residues each are replaced with any of the aforementioned amino acid residues.

In the amino acid sequence of an arbitrary OMT, the amino acid residue that is the amino acid residue corresponding to "L198" or "E199" can be determined by aligning the amino acid sequence of the arbitrary OMT and the amino acid sequence of SEQ ID NO: 46. The alignment can be performed by, for example, using known gene analysis software. Specific examples of such software can include DNASIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

A mutant OMT gene can be obtained by, for example, modifying a wild-type OMT gene so that OMT encoded thereby has the "specific mutation". The wild-type OMT gene to be modified can be obtained by, for example, cloning from an organism having the wild-type OMT gene, or chemical synthesis. Furthermore, a mutant OMT gene can also be obtained without using a wild-type OMT gene. For example, a mutant OMT gene may be directly obtained by chemical synthesis. The obtained mutant OMT gene may be further modified before use.

Genes can be modified by using a known method. For example, an objective mutation can be introduced into a target site of DNA by the site-specific mutagenesis method. Examples of the site-specific mutagenesis method can include a method using PCR (Higuchi, R., 61, in PCR Technology, Erlich, H. A. Eds., Stockton Press (1989); Carter P., Meth. In Enzymol., 154, 382 (1987)), and a method of using a phage (Kramer, W. and Frits, H. J., Meth. in Enzymol., 154, 350 (1987); Kunkel, T. A. et al., Meth. in Enzymol., 154, 367 (1987)).

The OMT activity can be measured by, for example, incubating the enzyme with a substrate (for example, protocatechuic acid or protocatechualdehyde) in the presence of SAM, and measuring the enzyme- and substrate-dependent generation of the corresponding product, for example, vanillic acid or vanillin (WO2013/022881A1). Furthermore, by measuring the generation of the corresponding by-product, for example, isovanillic acid or isovanillin, under the same conditions, and comparing the generation of the by-product with the generation of the product, it can be determined whether OMT selectively generates the product.

The term "aromatic aldehyde oxidoreductase (aromatic carboxylic acid reductase; ACAR)" can refer to a protein that has an activity of catalyzing the reaction of reducing an aromatic carboxylic acid in the presence of an electron donor and ATP to generate a corresponding aromatic aldehyde (EC 1.2.99.6 etc.). This activity can also be referred to as an "ACAR activity". A gene encoding ACAR can also be referred to as an "ACAR gene". An ACAR protein can be used that has a substrate specificity required by the specific biosynthesis pathway via which the objective substance is produced in the method as described herein. For example, when vanillin is produced via the conversion step from vanillic acid into vanillin, ACAR that uses at least vanillic acid can be used. Also, for example, when vanillin is produced via the conversion step from protocatechuic acid into protocatechualdehyde, ACAR that uses at least protocatechuic acid can be used. That is, specifically, the term "ACAR" can also refer to a protein that has an activity of catalyzing the reaction of reducing vanillic acid and/or protocatechuic acid in the presence of an electron donor and ATP to generate vanillin and/or protocatechualdehyde. ACAR may use both vanillic acid and protocatechuic acid as the substrate, but is not necessarily limited thereto. Also, when benzaldehyde is produced, ACAR that uses at least benzoic acid can be used. That is, specifically, the term "ACAR" can also refer to a protein that has an activity of catalyzing the reaction of reducing benzoic acid in the presence of an electron donor and ATP to generate benzaldehyde. Also, when cinnamaldehyde is produced, ACAR that uses at least cinnamic acid can be used. That is, specifically, the term "ACAR" can also refer to a protein that has an activity of catalyzing the reaction of reducing cinnamic acid in the presence of an electron donor and ATP to generate cinnamaldehyde. Examples of the electron donor can include NADH and NADPH.

Examples of ACAR can include ACARs of various microorganisms such as *Nocardia* sp. strain NRRL 5646, *Actinomyces* sp., *Clostridium thermoaceticum*, *Aspergillus niger*, *Corynespora melonis*, *Coriolus* sp., and *Neurospora* sp. (J. Biol. Chem., 2007, Vol. 282, No. 1, pp. 478-485). *Nocardia* sp. strain NRRL 5646 has been classified into *Nocardia iowensis*. Examples of ACAR further can include ACARs of other *Nocardia* bacteria such as *Nocardia brasiliensis* and *Nocardia vulneris*. The nucleotide sequence of the ACAR gene of *Nocardia brasiliensis* ATCC 700358 is shown as SEQ ID NO: 75, and the amino acid sequence of ACAR encoded by this gene is shown as SEQ ID NO: 76. In addition, the nucleotide sequence of an example of variant ACAR gene of *Nocardia brasiliensis* ATCC 700358 is shown as SEQ ID NO: 47, and the amino acid sequence of ACAR encoded by this gene is shown as SEQ ID NO: 48. Examples of ACAR further can include ACARs of *Gordonia* bacteria (for example, bacteria belonging to the genus *Gordonia*). Examples of the *Gordonia* bacteria can include *Gordonia effusa*. The nucleotide sequence of the ACAR gene of *Gordonia effusa* is shown as SEQ ID NO: 97, and the amino acid sequence of ACAR encoded by this gene is shown as SEQ ID NO: 98. In addition, the nucleotide sequence of an example of codon-optimized ACAR gene of *Gordonia effusa* is shown as SEQ ID NO: 100.

The ACAR activity can be measured by, for example, incubating the enzyme with a substrate (for example, vanillic acid or protocatechuic acid) in the presence of ATP and NADPH, and measuring the enzyme- and substrate-dependent oxidation of NADPH (modification of the method described in J. Biol. Chem., 2007, Vol. 282, No. 1, pp. 478-485).

ACAR can be made into an active enzyme by phosphopantetheinylation (J. Biol. Chem., 2007, Vol. 282, No. 1, pp. 478-485). Therefore, ACAR activity can also be increased by increasing the activity of an enzyme that catalyzes phosphopantetheinylation of a protein (also referred to as "phosphopantetheinylation enzyme"). That is, examples of the method for imparting or enhancing an objective substance-producing ability can include a method of increasing the activity of a phosphopantetheinylation enzyme. That is, the bacterium as described herein may have been modified so that the activity of a phosphopantetheinylation enzyme is increased. Examples of the phosphopantetheinylation enzyme can include phosphopantetheinyl transferase (PPT).

The term "phosphopantetheinyl transferase (PPT)" can refer to a protein that has an activity of catalyzing the reaction of phosphopantetheinylating ACAR in the presence of a phosphopantetheinyl group donor. This activity can also be referred to as "PPT activity". A gene encoding PPT can also be referred to as "PPT gene". Examples of the phosphopantetheinyl group donor can include coenzyme A (CoA). Examples of PPT can include EntD protein, which is encoded by entD gene. Examples of PPT such as EntD protein can include those of various organisms. Specific examples of PPT can include EntD protein of *E. coli*. The nucleotide sequence of the entD gene of the *E. coli* K-12 MG1655 is shown as SEQ ID NO: 49, and the amino acid sequence of the EntD protein encoded by this gene is shown as SEQ ID NO: 50. Specific examples of PPT also can include PPT of *Nocardia brasiliensis*, PPT of *Nocardia farcinica* IFM10152 (J. Biol. Chem., 2007, Vol. 282, No. 1, pp. 478-485), and PPT of *Corynebacterium glutamicum* (App. Env. Microbiol. 2009, Vol. 75, No. 9, pp. 2765-2774). The nucleotide sequence of the PPT gene of *C. glutamicum* ATCC 13032 is shown as SEQ ID NO: 51, and the amino acid sequence of PPT encoded by this gene is shown as SEQ ID NO: 52.

The PPT activity can be measured on the basis of, for example, enhancement of the ACAR activity observed when the enzyme is incubated with ACAR in the presence of CoA (J. Biol. Chem., 2007, Vol. 282, No. 1, pp. 478-485).

Also, as described above, benzaldehyde and cinnamaldehyde can be generated from, for example, benzoic acid and cinnamic acid, respectively. That is, examples of the objective substance biosynthesis enzyme also can include, for example, benzoic acid biosynthesis enzymes and cinnamic acid biosynthesis enzymes. Specifically, cinnamic acid can be generated from, for example, L-phenylalanine, by the action of phenylalanine ammonia lyase (PAL; EC 4.3.1.24). That is, examples of cinnamic acid biosynthesis enzymes can include, for example, L-phenylalanine biosynthesis enzymes and PAL. Examples of the L-phenylalanine biosynthesis enzymes can include common biosynthesis enzymes of aromatic amino acids, such as 3-deoxy-D-arabinoheptulosonate-7-phosphate synthase (aroF, aroG, aroH), 3-dehydroquinate synthase (aroB), 3-dehydroquinate dehydratase (aroD), shikimate dehydrogenase (aroF), shikimate kinase (aroK, aroL), 5-enolpyruvylshikimate-3-phosphate synthase (aroA), and chorismate synthase (aroC); as well as chorismate mutase (pheA), prephenate dehydratase (pheA), and tyrosine amino transferase (tyrB). Chorismate mutase and prephenate dehydratase may be encoded by pheA gene as a bifunctional enzyme.

Examples of the method for imparting or enhancing the ability to produce the objective substance also can include a method of increasing the activity of an uptake system of a substance other than the objective substance, such as a substance generated as an intermediate during production of the objective substance and a substance that functions as a precursor of the objective substance. That is, the bacterium as described herein may have been modified so that the activity of such an uptake system is increased. The term "uptake system of a substance" can refer to a protein having a function of incorporating the substance from the outside of a cell into the cell. This activity can also be referred to as "uptake activity of a substance". A gene encoding such an uptake system can also be referred to as "uptake system gene". Examples of such an uptake system can include a vanillic acid uptake system and a protocatechuic acid uptake system. Examples of the vanillic acid uptake system can include VanK protein, which is encoded by vanK gene (M. T. Chaudhry, et al., Microbiology, 2007, 153:857-865). The nucleotide sequence of the vanK gene (NCgl2302) of the *C. glutamicum* ATCC 13869 is shown as SEQ ID NO: 53, and the amino acid sequence of the VanK protein encoded by this gene is shown as SEQ ID NO: 54. Examples of the protocatechuic acid uptake system gene can include PcaK protein, which is encoded by pcaK gene (M. T. Chaudhry, et al., Microbiology, 2007, 153:857-865). The nucleotide sequence of the pcaK gene (NCgl1031) of the *C. glutamicum* ATCC 13869 is shown as SEQ ID NO: 55, and the amino acid sequence of the PcaK protein encoded by this gene is shown as SEQ ID NO: 56.

The uptake activity of a substance can be measured according to, for example, a known method (M. T. Chaudhry, et al., Microbiology, 2007. 153:857-865).

Examples of the method for imparting or enhancing the ability to produce the objective substance further can include a method of reducing the activity of an enzyme that is involved in the production of a substance other than the objective substance. Such a substance other than the objective substance can also be referred to as "byproduct". Such an enzyme can also be referred to as "byproduct generation enzyme". Examples of the byproduct generation enzyme can include, for example, enzymes that are involved in the utilization of an objective substance, and enzymes that catalyze a reaction branching away from the biosynthetic pathway of an objective substance to generate a substance other than the objective substance. The method for reducing the activity of a protein such as an enzyme etc. will be described herein. The activity of a protein such as an enzyme etc. can be reduced by, for example, disrupting a gene that encodes the protein. For example, it has been reported that, in coryneform bacteria, vanillin is metabolized in the order of vanillin→vanillic acid→protocatechuic acid, and utilized (Current Microbiology, 2005, Vol. 51, pp. 59-65). That is, specific examples of the byproduct generation enzyme can include an enzyme that catalyzes the conversion from vanillin into protocatechuic acid and enzymes that catalyze further metabolization of protocatechuic acid. Examples of such enzymes can include vanillate demethylase, protocatechuate 3,4-dioxygenase, and various enzymes that further decompose the reaction product of protocatechuate 3,4-dioxygenase to succinyl-CoA and acetyl-CoA (Appl. Microbiol. Biotechnol., 2012, Vol. 95, p 77-89). In addition, 3-dehydroshikimic acid, which is an intermediate of the biosynthetic pathway of vanillin, can also be converted into shikimic acid by the action of shikimate dehydrogenase. That is, specific examples of the byproduct generation enzyme for vanillin production also can include shikimate dehydrogenase.

The term "vanillate demethylase" can refer to a protein having an activity for catalyzing the reaction of demethylating vanillic acid to generate protocatechuic acid. This activity can also be referred to as "vanillate demethylase activity". A gene encoding vanillate demethylase can also be referred to as "vanillate demethylase gene". Examples of vanillate demethylase can include VanAB proteins, which are encoded by vanAB genes (Current Microbiology, 2005, Vol. 51, pp. 59-65). The vanA gene and vanB gene encode the subunit A and subunit B of vanillate demethylase, respectively. To reduce the vanillate demethylase activity, both the vanAB genes may be disrupted or the like, or only one of the two may be disrupted or the like. The nucleotide sequences of the vanAB genes of the *C. glutamicum* ATCC 13869 are shown as SEQ ID NOS: 57 and 59, and the amino acid sequences of the VanAB proteins encoded by these genes are shown as SEQ ID NOS: 58 and 60, respectively. The vanAB genes usually make up the vanABK operon together with the vanK gene. Therefore, in order to reduce the vanillate demethylase activity, the vanABK operon may be totally disrupted or the like (for example, deleted). In such a case, the vanK gene may be introduced to a host again. For example, when vanillic acid present outside cells is used, and the vanABK operon is totally disrupted or the like (for example, deleted), the vanK gene should be newly introduced.

The vanillate demethylase activity can be measured by, for example, incubating the enzyme with a substrate (for example, vanillic acid), and measuring the enzyme- and substrate-dependent generation of protocatechuic acid (J Bacteriol, 2001, Vol. 183, p 3276-3281).

The term "protocatechuate 3,4-dioxygenase" can refer to a protein having an activity for catalyzing the reaction of oxidizing protocatechuic acid to generate beta-carboxy-cis, cis-muconic acid. This activity can also be referred to as "protocatechuate 3,4-dioxygenase activity". A gene encoding protocatechuate 3,4-dioxygenase can also be referred to as "protocatechuate 3,4-dioxygenase gene". Examples of protocatechuate 3,4-dioxygenase can include PcaGH proteins, which are encoded by pcaGH genes (Appl. Microbiol. Biotechnol., 2012, Vol. 95, p 77-89). The pcaG gene and pcaH gene encode the alpha subunit and beta subunit of protocatechuate 3,4-dioxygenase, respectively. To reduce the protocatechuate 3,4-dioxygenase activity, both the pcaGH genes may be disrupted or the like, or only one of the two may be disrupted or the like. The nucleotide sequences of the pcaGH genes of the C. glutamicum ATCC 13032 are shown as SEQ ID NOS: 61 and 63, and the amino acid sequences of the PcaGH proteins encoded by these genes are shown as SEQ ID NOS: 62 and 64, respectively.

The protocatechuate 3,4-dioxygenase activity can be measured by, for example, incubating the enzyme with a substrate (for example, protocatechuic acid), and measuring the enzyme- and substrate-dependent oxygen consumption (Meth. Enz., 1970, Vol. 17A, p 526-529).

The term "shikimate dehydrogenase" can refer to a protein that has the activity of catalyzing the reaction of reducing 3-dehydroshikimic acid in the presence of an electron donor to generate shikimic acid (EC 1.1.1.25). This activity can also be referred to as "shikimate dehydrogenase activity". A gene encoding shikimate dehydrogenase can also be referred to as "shikimate dehydrogenase gene". Examples of the electron donor can include NADH and NADPH. Examples of shikimate dehydrogenase can include AroE protein, which is encoded by aroE gene. The nucleotide sequence of the aroE gene of the E. coli K-12 MG1655 is shown as SEQ ID NO: 101, and the amino acid sequence of the AroE protein encoded by this gene is shown as SEQ ID NO: 102.

The shikimate dehydrogenase activity can be measured by, for example, incubating the enzyme with a substrate (for example, 3-dehydroshikimic acid) in the presence of NADPH or NADH, and measuring the enzyme- and substrate-dependent oxidation of NADPH or NADH.

The protein to be modified can be appropriately chosen depending on the type of the biosynthesis pathway via which an objective substance is produced in the method as described herein and on the types and activities of the proteins inherent to the bacterium as described herein. For example, when vanillin is produced by the bioconversion method from protocatechuic acid, the activity or activities of one or more of OMT, ACAR, PPT, and/or the protocatechuic acid uptake system can be increased. Also, when vanillin is produced by the bioconversion method from protocatechualdehyde, the activity of OMT can be increased. Also, when vanillin is produced by the bioconversion method from vanillic acid, activity or activities of one or more kinds of ACAR, PPT, and/or the vanillic acid uptake system can be increased.

The genes and proteins used for breeding a bacterium having an objective substance-producing ability may have, for example, the above-exemplified or other known nucleotide sequences and amino acid sequences, respectively. Also, the genes and proteins used for breeding a bacterium having an objective substance-producing ability may be conservative variants of the genes and proteins exemplified above, such as genes and proteins having the above-exemplified or other known nucleotide sequences and amino acid sequences, respectively. Specifically, for example, the genes used for breeding a bacterium having an objective substance-producing ability may each be a gene encoding a protein having the amino acid sequence exemplified above or the amino acid sequence of a known protein, but that include substitution, deletion, insertion, or addition of one or several some amino acid residues at one or several positions, so long as their original function, for example, enzymatic activity, transporter activity, etc., is maintained. As for conservative variants of genes and proteins, the descriptions concerning conservative variants of the ADH gene and ADH described herein can be applied mutatis mutandis.

<1-2> Reduction of Alcohol Dehydrogenase Activity

The bacterium as described herein has been modified so that the activity of alcohol dehydrogenase (ADH) is reduced. Specifically, the bacterium as described herein has been modified so that the activity of ADH is reduced as compared with a non-modified bacterial strain. By modifying a coryneform bacterium so that the activity of ADH is reduced, an objective substance-producing ability of the bacterium can be improved, and therefore, the production of an objective substance by using the bacterium can be increased.

The bacterium as described herein can be obtained by modifying a coryneform bacterium having an objective substance-producing ability so that the activity of ADH thereof is reduced. The bacterium as described herein can also be obtained by modifying a coryneform bacterium so that the activity of ADH thereof is reduced, and then imparting an objective substance-producing ability to the bacterium or enhancing an objective substance-producing ability of the bacterium. In addition, the bacterium as described herein may be a bacterium that has acquired an objective substance-producing ability as a result of a modification for reducing the activity of ADH, or as a result of a combination of a modification for reducing the activity of ADH and other modification(s) for imparting or enhancing an objective substance-producing ability. The modifications for constructing the bacterium as described herein can be performed in an arbitrary order.

The term "alcohol dehydrogenase (ADH)" can refer to a protein that has an activity for catalyzing the reaction of reducing an aldehyde in the presence of an electron donor to generate an alcohol (EC 1.1.1.1, EC 1.1.1.2, EC 1.1.1.71, etc.). This activity can also be referred to as "ADH activity". A gene encoding ADH can also be referred to as "ADH gene". Examples of the aldehyde used as a substrate of ADH can include aldehydes exemplified as objective substances in the method as described herein, that is, aromatic aldehydes such as vanillin, benzaldehyde, and cinnamaldehyde. That is, examples of combinations of the aldehyde and alcohol referred to in the definition of "ADH activity" can include a combination of an aromatic aldehyde and the corresponding aromatic alcohol, such as the combination of vanillin and vanillyl alcohol, the combination of benzaldehyde and benzyl alcohol, and the combination of cinnamaldehyde and cinnamyl alcohol. ADH that uses an aromatic aldehyde, vanillin, benzaldehyde, or cinnamaldehyde can also be referred to as "aromatic alcohol dehydrogenase", "vanillyl alcohol dehydrogenase", "benzyl alcohol dehydrogenase", or "cinnamyl alcohol dehydrogenase", respectively. Furthermore, the ADH activity wherein an aromatic aldehyde, vanillin, benzaldehyde, or cinnamaldehyde is used as a substrate can also be referred to as "aromatic alcohol dehydrogenase activity", "vanillyl alcohol dehydrogenase activity", "benzyl alcohol dehydrogenase activity", or "cinnamyl alcohol dehydrogenase activity", respectively. ADH may use one kind of alcohol, or may use two or more kinds of alcohols. Examples of the electron donor can include NADH and NADPH.

The ADH activity can be measured by, for example, incubating the enzyme with a substrate (for example, an aldehyde such as vanillin) in the presence of NADPH or NADH, and measuring the enzyme- and substrate-dependent oxidation of NADPH or NADH. It is sufficient that the ADH activity is detected under at least one appropriate condition, that is, in the presence of an appropriate electron donor such as NADPH or NADH.

Examples of ADH can include NCgl0324 protein, NCgl0313 protein, NCgl2709 protein, NCgl0219 protein, and NCgl2382 protein, which are encoded by NCgl0324 gene, NCgl0313 gene, NCgl2709 gene, NCgl0219 gene, and NCgl2382 gene, respectively. The NCgl0324 gene, NCgl0313 gene, NCgl2709 gene, NCgl0219 gene, and NCgl2382 gene can be found in coryneform bacteria such as C. glutamicum. The nucleotide sequences of the NCgl0324 gene, NCgl0313 gene, and NCgl2709 gene of the C. glutamicum ATCC 13869 are shown as SEQ ID NOS: 65, 67, and 69, respectively, and the amino acid sequences of the proteins encoded by these genes are shown as SEQ ID NOS: 66, 68, and 70, respectively. The nucleotide sequences of the NCgl0219 gene and NCgl2382 gene of the C. glutamicum ATCC 13032 are shown as SEQ ID NOS: 71 and 73, respectively, and the amino acid sequences of the proteins encoded by these genes are shown as SEQ ID NOS: 72 and 74, respectively. That is, ADH gene may be, for example, a gene having the nucleotide sequence shown as SEQ ID NOS: 65, 67, 69, 71, or 73. Also, ADH may be, for example, a protein having the amino acid sequence shown as SEQ ID NOS: 66, 68, 70, 72, or 74. The expression "a gene or protein has a nucleotide or amino acid sequence" encompasses when a gene or protein includes the nucleotide or amino acid sequence, and when a gene or protein is only the nucleotide or amino acid sequence.

The activity of one kind of ADH may be reduced, or the activities of two or more kinds of ADHs may be reduced. For example, the activity or activities of one or more kinds of ADHs, such as the NCgl0324 protein, NCgl2709 protein, and/or NCgl0313 protein may be reduced. Also, at least the activity or activities of either one or both of NCgl0324 protein and NCgl2709 protein may be reduced. That is, for example, at least the activity of NCgl0324 protein may be reduced, and the activity of NCgl2709 protein may further be reduced. Alternatively, at least the activity of NCgl2709 protein may be reduced, and the activity of NCgl0324 protein may further be reduced. Combination of ADH and the objective substance is not particularly limited, so long as a reduction in the activity of ADH in a coryneform bacterium provides an increased production of the objective substance. For example, the activity of ADH that uses at least an aldehyde to be produced as an objective substance in the method as described herein may be reduced. That is, for example, the activity of an aromatic alcohol dehydrogenase such as vanillyl alcohol dehydrogenase, benzyl alcohol dehydrogenase, and cinnamyl alcohol dehydrogenase may be reduced for production of an aromatic aldehyde such as vanillin, benzaldehyde, and cinnamaldehyde, respectively. Specifically, for example, when vanillin is produced, the activity or activities of either one or both of NCgl0324 protein and NCgl0313 protein may be reduced, or at least the activity of NCgl0324 protein may be reduced. Also, specifically, when benzaldehyde is produced, the activity or activities of either one or both of NCgl0324 protein and NCgl2709 protein may be reduced. Also, specifically, when cinnamaldehyde is produced, the activity or activities of either one or both of NCgl0324 protein and NCgl2709 protein may be reduced. NCgl0324 protein may have all of the vanillyl alcohol dehydrogenase activity, benzyl alcohol dehydrogenase activity, and cinnamyl alcohol dehydrogenase activity. NCgl2709 protein may have both the benzyl alcohol dehydrogenase activity and cinnamyl alcohol dehydrogenase activity.

The ADH gene may be a variant of any of the ADH genes exemplified above (that is, NCgl0324 gene, NCgl0313 gene, NCgl2709 gene, NCgl0219 gene, and NCgl2382 gene), so long as the original function thereof is maintained. Similarly, ADH may be a variant of any of ADHs exemplified above, that is, NCgl0324 protein, NCgl0313 protein, NCgl2709 protein, NCgl0219 protein, and NCgl2382 protein, so long as the original function thereof is maintained. A variant that maintains the original function thereof may also be referred to as "conservative variant". Namely, the terms "NCgl0324 gene", "NCgl0313 gene", "NCgl2709 gene", "NCgl0219 gene", and "NCgl2382 gene" can include not only the NCgl0324 gene, NCgl0313 gene, NCgl2709 gene, NCgl0219 gene, and NCgl2382 gene exemplified above, respectively, but also can include respective conservative variants thereof. Similarly, the terms "NCgl0324 protein", "NCgl0313 protein", "NCgl2709 protein", "NCgl0219 protein", and "NCgl2382 protein" can include not only the NCgl0324 protein, NCgl0313 protein, NCgl2709 protein, NCgl0219 protein, and NCgl2382 protein exemplified above, respectively, but also can include respective conservative variants thereof. Examples of the conservative variants can include, for example, homologues and artificially modified versions of the ADH genes or ADHs exemplified above.

The expression "the original function is maintained" can mean that a variant of the gene or protein has a function, such as activity or property, corresponding to the function, such as activity or property, of the original gene or protein. The expression "the original function is maintained" relative to a gene can mean that a variant of the gene encodes a protein that maintains the original function. That is, the expression "the original function is maintained" when referring to an ADH gene can mean that the variant of the gene encodes ADH. The expression "the original function is maintained" relative to ADH can mean that the variant of the protein has the ADH activity.

Hereafter, examples of the conservative variants will be explained.

Homologues of an ADH gene or homologues of ADH can be easily obtained from public databases by, for example, BLAST search or FASTA search using any of the nucleotide sequences of the ADH genes exemplified above or any of the amino acid sequences of ADHs exemplified above as a query sequence. Furthermore, homologues of an ADH gene can be obtained by, for example, PCR using a chromosome of an organism such as coryneform bacteria as the template, and oligonucleotides prepared on the basis of any of the nucleotide sequences of the ADH genes exemplified above as primers.

The ADH gene may be a gene encoding a protein having any of the aforementioned amino acid sequences, for example, the amino acid sequences shown as SEQ ID NOS: 66, 68, 70, 72, and 74 for NCgl0324 protein, NCgl0313 protein, NCgl2709 protein, NCgl0219 protein, and NCgl2382 protein, respectively, including substitution, deletion, insertion, and/or addition of one or several amino acid residues at one or several positions, so long as the original function is maintained. For example, the encoded protein may have an extended or deleted N-terminus and/or C-terminus. Although the number meant by the term "one or several" used above may differ depending on the positions of amino acid residues in the three-dimensional structure of the protein or the types of amino acid residues, specifically, it is, for example, 1 to 50, 1 to 40, 1 to 30, 1 to 20, 1 to 10, 1 to 5, or 1 to 3.

The aforementioned substitution, deletion, insertion, and/or addition of one or several amino acid residues can be each a conservative mutation that allows for maintenance of the original function of the protein. Typical examples of the conservative mutation are conservative substitutions. The conservative substitution can be a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, or the like of amino acid residues as mentioned above can include a naturally occurring mutation due to an individual difference, or a difference of species of the organism from which the gene is derived or native to (mutant or variant).

Furthermore, the ADH gene may be a gene encoding a protein having an amino acid sequence showing a homology of, for example, 50% or more, 65% or more, 80% or more, 90% or more, 95% or more, 97% or more, or 99% or more, to the total amino acid sequence of any of the aforementioned amino acid sequences, so long as the original function is maintained. In addition, "homology" means "identity".

Furthermore, the ADH gene may be a gene, such as a DNA, that is able to hybridize under stringent conditions with a probe that can be prepared from any of the aforementioned nucleotide sequences, for example, the nucleotide sequences shown as SEQ ID NOS: 65, 67, 69, 71, and 73 for NCgl0324 gene, NCgl0313 gene, NCgl2709 gene, NCgl0219 gene, and NCgl2382 gene, such as a sequence complementary to the whole sequence or a partial sequence of any of the aforementioned nucleotide sequences, so long as the original function is maintained. The "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 50%, 65%, 80%, 90%, 95%, 97%, or 99% homologous, hybridize to each other, and DNAs less homologous than the above do not hybridize to each other, or conditions of washing of a typical Southern hybridization, for example, conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned genes as a template. As the probe, for example, a DNA fragment having a length of about 300 bp can be used. When a DNA fragment having a length of about 300 bp is used as the probe, in particular, the washing conditions of the hybridization may be, for example, 50° C., 2×SSC and 0.1% SDS.

Furthermore, since properties concerning degeneracy of codons changes depending on the host, the ADH gene can include substitution of respective equivalent codons for arbitrary codons. That is, the ADH gene may be a variant of any of the ADH genes exemplified above due to the degeneracy of the genetic code.

The percentage of the sequence identity between two sequences can be determined by, for example, using a mathematical algorithm. Non-limiting examples of such a mathematical algorithm can include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and a modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison, for example, alignment, for determining the sequence identity can be performed. The program can be appropriately executed by a computer. Examples of such a program can include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, a BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

The aforementioned descriptions concerning conservative variants of the genes and proteins can be applied mutatis mutandis to variants of arbitrary proteins such as objective substance biosynthesis enzymes and genes encoding them.

<1-3> Methods for Increasing Activity of Protein

Hereafter, the methods for increasing the activity of a protein will be described.

The expression "the activity of a protein is increased" can mean that the activity of the protein is increased as compared with a non-modified strain. Specifically, the expression "the activity of a protein is increased" can mean that the activity of the protein per cell is increased as compared with that of a non-modified strain. The term "non-modified strain" can refer to a control strain that has not been modified so that the activity of an objective protein is increased. Examples of the non-modified strain can include a wild-type strain and/or parent strain. Specific examples of the non-modified strain can include the respective strains of the species of bacteria which are going to be modified, for example, a strain of a coryneform bacterium. Specific examples of the non-modified strain also can include strains exemplified above in relation to the description of bacteria. That is, in an embodiment, the activity of a protein may be increased as compared with a strain of a coryneform bacterium, for example, a strain of the species which belongs to the coryneform bacterium as described herein. In another embodiment, the activity of a protein may also be increased as compared with *C. glutamicum* ATCC 13869. In another embodiment, the activity of a protein may also be increased as compared with *C. glutamicum* ATCC 13032. The phrase "the activity of a protein is increased" may also be expressed as "the activity of a protein is enhanced". More specifically, the expression "the activity of a protein is increased" can mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (for example, the amount of mRNA) encoding the protein, or the translation amount of the protein (for example, the amount of the protein). Furthermore, the phrase that "the activity of a protein is increased" can include not only when the activity of an objective protein is increased in a strain inherently having the activity of the objective protein, but also when the activity of an objective protein is imparted to a strain not inherently having the activity of the objective protein. Furthermore, so long as the activity of the protein is eventually increased, the activity of an objective protein inherent to a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased to, for example, 1.2 times or more, 1.5 times or more, 2 times or more, or 3 times or more of that of a non-modified strain. Furthermore, when the non-modified strain does not have the activity of the objective protein, it is sufficient that the protein is produced as a result of introduction of the gene encoding the protein, and for example, the protein may be produced to such an extent that the activity thereof can be measured.

The modification for increasing the activity of a protein can be attained by, for example, increasing the expression of a gene encoding the protein. The expression "the expression of a gene is increased" can mean that the expression of the gene is increased as compared with a non-modified strain such as a wild-type strain and parent strain. Specifically, the expression "the expression of a gene is increased" can mean that the expression amount of the gene per cell is increased as compared with that of a non-modified strain. More specifically, the expression "the expression of a gene is increased" may mean that the transcription amount of the gene, for example, the amount of mRNA, is increased, and/or the translation amount of the gene, for example, the amount of the protein expressed from the gene, is increased. The state that "the expression of a gene is increased" can also be referred to as "the expression of a gene is enhanced". The expression of a gene may be increased to, for example, 1.2 times or more, 1.5 times or more, 2 times or more, or 3 times or more of that of a non-modified strain. Furthermore, the phrase "the expression of a gene is increased" can include not only when the expression amount of an objective gene is increased in a strain that inherently expresses the objective gene, but also when the gene is introduced into a strain that does not inherently express the objective gene, and is expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination can include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Alternatively, homologous recombination may be performed by using an appropriate sequence on a chromosome such as a gene unnecessary for the production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in the chosen host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector can be a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in coryneform bacteria can include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVK9 described in WO2007/046389; pVS7 described in WO2013/069634; and pVC7 described in Japanese Patent Laid-open (Kokai) No. 9-070291.

When a gene is introduced, it is sufficient that the gene is able to be expressed by the chosen host. Specifically, it is sufficient that the gene is harbored by a host so that it is expressed under control of a promoter that is able to function in the host. The term "a promoter that is able to function in the host" can refer to a promoter that shows a promoter activity in the host. The promoter may be a promoter derived from the host, or a heterogenous promoter. The promoter may be the native promoter of the gene to be introduced, or a promoter of another gene. As the promoter, for example, such a stronger promoter as mentioned later may also be used.

A terminator for termination of gene transcription may be located downstream of the gene. The terminator is not particularly limited so long as it functions in a host. The terminator may be a terminator derived from the host, or a heterogenous terminator. The terminator may be the native terminator of the gene to be introduced, or a terminator of another gene.

Vectors, promoters, and terminators can be used that are available in various microorganisms are disclosed in detail in "Fundamental Microbiology Vol. 8, Genetic Engineering, KYORITSU SHUPPAN CO., LTD, 1987.

Furthermore, when two or more of genes are introduced, it is sufficient that the genes each are able to be expressed by the chosen host. For example, all the genes may be carried by a single expression vector or a chromosome. Furthermore, the genes may be separately carried by two or more expression vectors, or separately carried by a single or two or more expression vectors and a chromosome. An operon that includes two or more genes may also be introduced. The phrase "introducing two or more genes" can include, for example, introducing respective genes encoding two or more kinds of proteins such as enzymes, introducing respective genes encoding two or more subunits constituting a single protein complex such as enzyme complex, and a combination of these.

The gene to be introduced is not particularly limited so long as it encodes a protein that functions in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required. That is, a variant of a gene may be obtained by modifying the gene. A gene can be modified by a known technique. For example, an objective mutation can be introduced into an objective site of DNA by the site-specific mutation method. That is, the coding region of a gene can be modified by the site-specific mutation method so that a specific site of the encoded protein can include substitution, deletion, insertion, or addition of amino acid residues. Examples of the site-specific mutation method can include a method utilizing PCR (Higuchi, R., 61, in PCR Technology, Erlich, H. A. Eds., Stockton Press (1989); Carter, P., Meth. in Enzymol., 154, 382 (1987)), and a method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of a gene may be entirely synthesized.

In addition, when a protein functions as a complex having a plurality of subunits, some or all of the subunits may be modified, so long as the activity of the protein is eventually increased. That is, for example, when the activity of a protein is increased by increasing the expression of a gene, the expression of a part or all of the plurality of genes encoding the subunits may be enhanced. Enhancing the expression of all of the genes encoding the subunits is a particular example. Furthermore, the subunits constituting the complex may be derived from a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively can refer to sites that affect the expression of a gene. Examples of the expression control sequence can include, for example, a promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" can mean a promoter providing improved transcription of a gene compared with the inherent wild-type promoter of the gene. Examples of stronger promoters that function in coryneform bacteria can include, for example, the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, and cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Furthermore, as the stronger promoter, a highly-active existing promoter may also be obtained by using various reporter genes. For example, by making the −35 and −10 regions in a promoter region closer to the consensus sequence, the activity of the promoter can be enhanced (WO00/18935). Examples of highly active promoters can include various tac-like promoters (Katashkina J I et al., Russian Federation Patent Application No. 2006134574). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. A "stronger SD sequence" can mean a SD sequence that provides improved translation of mRNA compared with the inherent wild-type SD sequence of the gene. Examples of stronger SD sequences can include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying these regions.

The translation efficiency of a gene can also be improved by, for example, modifying codons. For example, the translation efficiency of the gene can be improved by replacing a rare codon present in the gene with a synonymous more frequently used codon. That is, the gene to be introduced may be modified, for example, so as to contain optimal codons according to the frequencies of codons observed in a host to be used. Codons can be replaced by, for example, the site-specific mutation method for introducing an objective mutation into an objective site of DNA. Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in any arbitrary combination.

Furthermore, the modification that increases the activity of a protein can also be attained by, for example, enhancing the specific activity of the enzyme. Enhancement of the specific activity also can include reduction or elimination of feedback inhibition. A protein having an enhanced specific activity can be obtained by, for example, searching various organisms. Furthermore, a highly-active protein may also be obtained by introducing a mutation into an existing protein. The mutation to be introduced may be, for example, substitution, deletion, insertion, or addition of one or several amino acid residues at one or several position of the protein. The mutation can be introduced by, for example, such a site-specific mutation method as mentioned above. The mutation may also be introduced by, for example, a mutagenesis treatment. Examples of the mutagenesis treatment can include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in any arbitrary combination with such methods for enhancing gene expression as mentioned above.

The method for the transformation is not particularly limited, and conventionally known methods can be used. Transformation of coryneform bacteria can be performed by using, for example, the protoplast method (Gene, 39, 281-286 (1985)), the electroporation method (Bio/Technology, 7, 1067-1070 (1989)), or the electric pulse method (Japanese Patent Laid-open (Kokai) No. 2-207791).

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA can include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may increase to, for example, 1.2 times or more, 1.5 times or more, 2 times or more, or 3 times or more of that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase to, for example, 1.2 times or more, 1.5 times or more, 2 times or more, or 3 times or more of that of a non-modified strain.

The aforementioned methods for increasing the activity of a protein can be applied to enhancement of the activities of arbitrary proteins such as an objective substance biosynthesis enzyme, phosphopantetheinylation enzyme, and uptake system of a substance, and enhancement of the expression of arbitrary genes such as genes encoding those arbitrary proteins.

<1-4> Method for Reducing Activity of Protein

Hereafter, the methods for reducing the activity of a protein such as ADH will be described.

The expression "the activity of a protein is reduced" can mean that the activity of the protein is reduced as compared with a non-modified strain. Specifically, the expression "the activity of a protein is reduced" can mean that the activity of the protein per cell is reduced as compared with that of a non-modified strain. The term "non-modified strain" can refer to a control strain that has not been modified so that the activity of an objective protein is reduced. Examples of the non-modified strain can include a wild-type strain and parent strain. Specific examples of the non-modified strain can include the respective strains of the species of bacteria which are going to be modified, for example, a strain of a coryneform bacterium. Specific examples of the non-modified strain also can include strains exemplified above in relation to the description of bacteria. That is, in an embodiment, the activity of a protein may be reduced as compared with a strain of a coryneform bacterium, for example, a strain of the species which belongs to the coryneform bacterium as described herein. In another embodiment, the activity of a protein may also be reduced as compared with *C. glutamicum* ATCC 13869. In another embodiment, the activity of a protein may also be reduced as compared with *C. glutamicum* ATCC 13032. The phrase "the activity of a protein is reduced" also can include when the activity of the protein has completely disappeared. More specifically, the expression "the activity of a protein is reduced" can mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (for example, the amount of mRNA) encoding the protein or the translation amount of the protein (for example, the amount of the protein). The phrase "the number of molecules of the protein per cell is reduced" also can include when the protein is completely eliminated. The phrase "the function of each molecule of the protein is reduced" also can include when the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The phrase "the expression of a gene is reduced" can mean that the expression of the gene is reduced as compared with a non-modified strain such as a wild-type strain and parent strain. Specifically, the expression "the expression of a gene is reduced" may mean that the expression of the gene per cell is reduced as compared with that of a non-modified strain. More specifically, the expression "the expression of a gene is reduced" may mean that the transcription amount of the gene (for example, the amount of mRNA) is reduced, and/or the translation amount of the gene (for example, the amount of the protein expressed from the gene) is reduced. The phrase "the expression of a gene is reduced" also can include when the gene is not expressed at all. The state that "the expression of a gene is reduced" can also be referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or both. The expression of a gene can be reduced by modifying an expression control sequence of the gene such as a promoter, the Shine-Dalgarno (SD) sequence (also referred to as ribosome-binding site (RBS)), and a spacer region between RBS and the start codon of the gene. When an expression control sequence is modified, one or more nucleotides, two or more nucleotides, or three or more nucleotides, of the expression control sequence are modified. For example, the transcription efficiency of a gene can be reduced by, for example, replacing the promoter of the gene on a chromosome with a weaker promoter. The term "weaker promoter" can mean a promoter providing attenuated transcription of a gene compared with the inherent wild-type promoter of the gene. Examples of weaker promoters can include, for example, inducible promoters. That is, an inducible promoter may function as a weaker promoter under a non-induced condition, such as in the absence of the corresponding inducer. Furthermore, a part or the entire expression control sequence may be deleted. The expression of a gene can also be reduced by, for example, manipulating a factor responsible for expression control. Examples of the factor responsible for expression control can include molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous less frequently used codon in a host. Furthermore, for example, the gene expression may be reduced due to disruption of a gene as described herein.

The modification for reducing the activity of a protein can also be attained by, for example, disrupting a gene encoding the protein. The expression "a gene is disrupted" can mean that a gene is modified so that a protein that can normally function is not produced. The phrase "a protein that normally functions is not produced" can include when the protein is not produced at all from the gene, and when the protein of which the function (such as activity or property) per molecule is reduced or eliminated is produced from the gene.

Disruption of a gene can be attained by, for example, deleting a part or the entire coding region of the gene on a chromosome. Furthermore, the entire gene including sequences upstream and downstream from the gene on a chromosome may be deleted. The deleted region may be any region, such as an N-terminus region, an internal region, or a C-terminus region, so long as the activity of the protein is reduced. Deletion of a longer region can usually more surely inactivate the gene. Furthermore, the reading frames of the sequences upstream and downstream from the deleted region should not be the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. The insertion site may be in any region of the gene, and insertion of a longer region can usually more surely inactivate the gene. The reading frames of the sequences upstream and downstream from the insertion site should not be the same. The other sequence is not particularly limited so long as a sequence that reduces or eliminates the activity of the encoded protein is chosen, and examples thereof can include, for example, a marker gene such as antibiotic resistance genes, and a gene useful for production of an objective substance.

Such modification of a gene on a chromosome as described above can be attained by, for example, preparing a gene modified so that it is unable to produce a normally functioning protein, and transforming a host with a recombinant DNA containing this gene to cause homologous recombination between the gene and the wild-type gene on the chromosome and thereby substituting the gene for the wild-type gene on the chromosome. In this procedure, if a marker gene selected according to the characteristics of the host such as auxotrophy is included in the recombinant DNA, the operation is easier. Examples of the modified gene can include a gene in which all or a part of the gene is deleted, gene including a missense mutation, gene including a nonsense mutation, gene including a frame shift mutation, and gene including insertion of a transposon or marker gene. The protein encoded by the this modified gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Reducing the activity of a protein can also be attained by, for example, a mutagenesis treatment. Examples of the mutagenesis treatment can include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex made up of a plurality of subunits, a part or all of the subunits may be modified, so long as the activity of the protein is eventually reduced. That is, for example, a part or all of the genes encoding the respective subunits may be disrupted or the like. Furthermore, when there is a plurality of isozymes of a protein, a part or all of the activities of the isozymes may be reduced, so long as the activity of the protein is eventually reduced. That is, for example, a part or all of the genes encoding the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that observed in a non-modified strain. Examples of the method for evaluating the amount of mRNA can include Northern hybridization, RT-PCR, and so forth (Molecular Cloning, Cold Spring Harbor Laboratory Press, Cold Spring Harbor (USA), 2001). The amount of mRNA can be reduced to, for example, 50% or less, 20% or less, 10% or less, 5% or less, or 0%, of that observed in a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein can be reduced to, for example, 50% or less, 20% or less, 10% or less, 5% or less, or 0%, of that observed in a non-modified strain.

Disruption of a gene can be confirmed by determining nucleotide sequence of a part or the entire gene, restriction enzyme map, full length, or the like of the gene depending on the means used for the disruption.

Such methods for reducing the activity of a protein as mentioned above can also be applied to, besides the reduction in the ADH activity, reduction in the activities of arbitrary proteins such as a byproduct generation enzyme, and reduction in the expression of arbitrary genes such as genes encoding such arbitrary proteins.

<2> Method of the Present Invention

The method as described herein is a method for producing an objective substance by using the bacterium as described herein.

<2-1> Fermentation Method

An objective substance can be produced by, for example, fermentation of the bacterium as described herein. That is, an embodiment of the method as described herein may be a method for producing an objective substance by fermentation of the bacterium as described herein. This embodiment can also be referred to as "fermentation method". Also, the step of producing an objective substance by fermentation of the bacterium as described herein can also be referred to as "fermentation step".

The fermentation step can be performed by cultivating the bacterium as described herein. Specifically, in the fermentation method, an objective substance can be produced from a carbon source. That is, the fermentation step may be, for example, a step of cultivating the bacterium as described herein in a culture medium, such as a culture medium containing a carbon source, to produce and accumulate the objective substance in the culture medium. That is, the fermentation method may be a method for producing an objective substance that includes the step of cultivating the bacterium as described herein in a culture medium, such as a culture medium containing a carbon source, to produce and accumulate the objective substance in the culture medium.

The culture medium to be used is not particularly limited, so long as the bacterium as described herein can proliferate in it and produce an objective substance. As the culture medium, for example, a typical culture medium used for culture of bacteria such as coryneform bacteria can be used. The culture medium may contain carbon source, nitrogen source, phosphate source, and sulfur source, as well as other medium components such as various organic components and inorganic components as required. The types and concentrations of the medium components can be appropriately determined according to various conditions such as the chosen bacterium.

The carbon source is not particularly limited, so long as the bacterium as described herein can utilize it and produce an objective substance. Specific examples of the carbon source can include, for example, saccharides such as glucose, fructose, sucrose, lactose, galactose, xylose, arabinose, blackstrap molasses, hydrolysates of starches, and hydrolysates of biomass; organic acids such as acetic acid, citric acid, succinic acid, and gluconic acid; alcohols such as ethanol, glycerol, and crude glycerol; and fatty acids. As the carbon source, plant-derived materials can be used. Examples of the plant can include, for example, corn, rice, wheat, soybean, sugarcane, beet, and cotton. Examples of the plant-derived materials can include, for example, organs such as root, stem, trunk, branch, leaf, flower, and seed, plant bodies including them, and decomposition products of these plant organs. The forms of the plant-derived materials at the time of use thereof are not particularly limited, and they can be used in any form such as unprocessed product, juice, ground product, and purified product. Pentoses such as xylose, hexoses such as glucose, or mixtures of them can be obtained from, for example, plant biomass, and used. Specifically, these saccharides can be obtained by subjecting a plant biomass to such a treatment as steam treatment, hydrolysis with concentrated acid, hydrolysis with diluted acid, hydrolysis with an enzyme such as cellulase, and alkaline treatment. Since hemicellulose is generally more easily hydrolyzed compared with cellulose, hemicellulose in a plant biomass may be hydrolyzed beforehand to liberate pentoses, and then cellulose may be hydrolyzed to generate hexoses. Furthermore, xylose may be supplied by conversion from hexoses by, for example, imparting a pathway for converting hexose such as glucose to xylose to the bacterium as described herein. As the carbon source, one kind of carbon source may be used, or two or more kinds of carbon sources may be used in combination.

The concentration of the carbon source in the medium is not particularly limited, so long as the bacterium as described herein can proliferate and produce an objective substance. The concentration of the carbon source in the medium may be as high as possible within such a range that production of the objective substance is not inhibited. Initial concentration of the carbon source in the medium may be, for example, usually 5 to 30% (w/v), or 10 to 20% (w/v). Furthermore, the carbon source may be additionally supplied to the medium as required. For example, the carbon source may be additionally supplied to the medium in proportion to a decrease or depletion of the carbon source accompanying progress of the fermentation. While the carbon source may be temporarily depleted so long as an objective substance can be eventually produced, the culture should be performed so that the carbon source is not depleted or the carbon source does not continue to be depleted.

Specific examples of the nitrogen source can include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas and aqueous ammonia used for pH adjustment may also be used as a nitrogen source. As the nitrogen source, one kind of nitrogen source may be used, or two or more kinds of nitrogen sources may be used in combination.

Specific examples of the phosphate source can include, for example, phosphate salts such as potassium dihydrogenphosphate and dipotassium hydrogenphosphate, and phosphoric acid polymers such as pyrophosphoric acid. As the phosphate source, one kind of phosphate source may be used, or two or more kinds of phosphate sources may be used in combination.

Specific examples of the sulfur source can include, for example, inorganic sulfur compounds such as sulfates, thiosulfates, and sulfites, and sulfur-containing amino acids such as cysteine, cystine, and glutathione. As the sulfur source, one kind of sulfur source may be used, or two or more kinds of sulfur sources may be used in combination.

Specific examples of other various organic and inorganic components can include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing these such as peptone, casamino acid, yeast extract, and soybean protein decomposition product. As the other various organic and inorganic components, one kind of component may be used, or two or more kinds of components may be used in combination.

Furthermore, when an auxotrophic mutant strain that requires a nutrient such as amino acids for growth thereof is used, such a required nutrient can be added to the culture medium. Furthermore, a component used for production of an objective substance may be supplemented to the medium. Specific examples of such a component can include, for example, methyl group donors such as SAM and precursors thereof such as methionine.

Culture conditions are not particularly limited, so long as the bacterium as described herein can proliferate, and an objective substance is produced. The culture can be performed with, for example, usual conditions used for culture of bacteria such as coryneform bacteria. The culture conditions may be appropriately determined according to various conditions such as the chosen bacterium.

The culture can be performed by using a liquid medium. At the time of the culture, for example, the bacterium as described herein cultured on a solid medium such as agar medium may be directly inoculated into a liquid medium, or the bacterium as described herein cultured in a liquid medium as seed culture may be inoculated into a liquid medium for main culture. That is, the culture may be performed separately as seed culture and main culture. In such a case, the culture conditions of the seed culture and the main culture may be or may not be the same. It is sufficient that an objective substance is produced at least during the main culture. The amount of the bacterium as described herein present in the culture medium at the time of the start of the culture is not particularly limited. For example, seed culture showing an OD660 of 4 to 100 may be added to a culture medium for main culture in an amount of 0.1 to 100 mass %, or 1 to 50 mass %, at the time of the start of the culture.

The culture can be performed as batch culture, fed-batch culture, continuous culture, or a combination of these. The culture medium used at the start of the culture can also be referred to as a "starting medium". The culture medium supplied to the culture system (e.g. fermentation tank) in the fed-batch culture or the continuous culture can also be referred to as a "feed medium". To supply a feed medium to the culture system in the fed-batch culture or the continuous culture can also be referred to as "feed". Furthermore, when the culture is performed separately as seed culture and main culture, the culture schemes of the seed culture and the main culture may be or may not be the same. For example, both the seed culture and the main culture may be performed as batch culture. Alternatively, for example, the seed culture may be performed as batch culture, and the main culture may be performed as fed-batch culture or continuous culture.

The various components such as the carbon source may be present in the starting medium, feed medium, or both. That is, the various components such as the carbon source may be added to the culture medium independently or in an arbitrary combination during the culture. These components may be added once or a plurality of times, or may be continuously added. The types of the components present in the starting medium may be or may not be the same as the components present in the feed medium. Furthermore, the concentrations of the components present in the starting medium may be or may not be the same as the concentrations of the components present in the feed medium. Furthermore, two or more kinds of feed media containing components of different types and/or different concentrations may be used. For example, when feeding is intermittently performed two or more times, the types and/or concentrations of components contained in the feed medium may be or may not be the same for each feeding.

The culture can be performed, for example, under aerobic conditions. The term "aerobic conditions" may refer to conditions where the dissolved oxygen concentration in the culture medium is 0.33 ppm or higher, or 1.5 ppm or higher. The oxygen concentration can be controlled to be, for example, 1 to 50%, or about 5%, of the saturated oxygen concentration. The culture can be performed, for example, with aeration or shaking. The pH of the culture medium may be, for example, 3 to 10, or 4.0 to 9.5. The pH of the culture medium can be adjusted during the culture as required. pH of the culture medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 45° C., or 25 to 37° C. The culture time may be, for example, 10 to 120 hours. The culture may be continued, for example, until the carbon source present in the culture medium is consumed, or until the activity of the bacterium as described herein is lost.

By cultivating the bacterium as described herein under such conditions as described above, an objective substance accumulates in the culture medium.

Production of an objective substance can be confirmed by known methods used for detection or identification of compounds. Examples of such methods can include, for example, HPLC, UPLC, LC/MS, GC/MS, and NMR. These methods may be independently used, or may be used in an appropriate combination. These methods can also be used for determining the concentrations of various components present in the culture medium.

The produced objective substance can be appropriately collected. That is, the fermentation method may further include a step of collecting the objective substance from the culture medium, (for example, a culture broth. The objective substance can be collected by known methods used for separation and purification of compounds. Examples of such methods can include, for example, ion-exchange resin method, membrane treatment, precipitation, distillation, and crystallization. The objective substance can also be collected by extraction with an organic solvent such as ethyl acetate or by steam distillation. These methods may be independently used, or may be used in an appropriate combination.

Furthermore, when an objective substance precipitates in the culture medium, it can be collected by, for example, centrifugation or filtration. The objective substance precipitated in the culture medium and the objective substance dissolved in the culture medium may be isolated together after the objective substance dissolved in the culture medium is crystallized.

The collected objective substance may contain, for example, bacterial cells, medium components, moisture, and by-product metabolites of the bacterium, in addition to the objective substance. Purity of the collected objective substance may be, for example, 30% (w/w) or higher, 50% (w/w) or higher, 70% (w/w) or higher, 80% (w/w) or higher, 90% (w/w) or higher, or 95% (w/w) or higher.

<2-2> Bioconversion Method

An objective substance can also be produced by, for example, bioconversion using the bacterium as described herein. That is, another embodiment of the method as described herein may be a method for producing an objective substance by bioconversion using the bacterium as described herein. This embodiment can also be referred to as "bioconversion method". Also, the step of producing an objective substance by bioconversion using the bacterium as described herein can also be referred to as "bioconversion step".

Specifically, in the bioconversion method, an objective substance can be produced from a precursor of the objective substance. More specifically, in the bioconversion method, an objective substance can be produced by converting a precursor of the objective substance into the objective substance by using the bacterium as described herein. That is, the bioconversion step may be a step of converting a precursor of an objective substance into the objective substance by using the bacterium as described herein.

A precursor of an objective substance can also be referred to simply as a "precursor". Examples of the precursor can include intermediates of the biosynthesis pathway of the object substance, such as those recited in relation to the descriptions of the objective substance biosynthesis enzymes. Specific examples of the precursor can include, for example, protocatechuic acid, protocatechualdehyde, vanillic acid, benzoic acid, L-phenylalanine, and cinnamic acid. Protocatechuic acid, protocatechualdehyde, and vanillic acid each may be used as a precursor for producing, for example, vanillin. Benzoic acid may be used as a precursor for producing, for example, benzaldehyde. L-phenylalanine and cinnamic acid each may be used as a precursor for producing, for example, cinnamaldehyde. As the precursor, one kind of precursor may be used, or two or more kinds of precursors may be used in combination. When the precursor is a compound that can form a salt, the precursor may be a free compound, a salt thereof, or a mixture thereof. That is, the term "precursor" can refer to a precursor in a free form, a salt thereof, or a mixture thereof, unless otherwise stated. Examples of the salt can include, for example, sulfate salt, hydrochloride salt, carbonate salt, ammonium salt, sodium salt, and potassium salt. As the salt of the precursor, one kind of salt may be used, or two or more kinds of salts may be used in combination.

As the precursor, a commercial product may be used, or one appropriately prepared and obtained may be used. That is, the bioconversion method may further include producing a precursor. The method for producing a precursor is not particularly limited, and for example, known methods can be used. A precursor can be produced by, for example, a chemical synthesis method, enzymatic method, bioconversion method, fermentation method, or a combination of these methods. That is, for example, a precursor of an objective substance can be produced from a pre-precursor using an enzyme that catalyzes the conversion of the pre-precursor into the precursor of the objective substance (also referred to as "precursor biosynthesis enzyme"). Furthermore, for example, a precursor of an objective substance can be produced from a carbon source or a pre-precursor by using a microorganism that is able to produce the precursor. The term "microorganism able to produce a precursor" can refer to a microorganism that is able to generate a precursor of an objective substance from a carbon source or a pre-precursor. For example, examples of the method for producing protocatechuic acid according to an enzymatic method or bioconversion method can include the method of converting para-cresol into protocatechuic acid using *Pseudomonas putida* KS-0180 (Japanese Patent Laid-open (Kokai) No. 7-75589), the method of converting para-hydroxybenzoic acid into protocatechuic acid using an NADH-dependent para-hydroxybenzoic acid hydroxylase (Japanese Patent Laid-open (Kokai) No. 5-244941), the method of producing protocatechuic acid by cultivating a transformant harboring a gene that is involved in the reaction of generating protocatechuic acid from terephthalic acid in a culture medium containing terephthalic acid (Japanese Patent Laid-open (Kokai) No. 2007-104942), and the method of producing protocatechuic acid from a precursor thereof by using a microorganism having protocatechuic acid-producing ability and having a reduced activity of protocatechuic acid 5-oxidase or being deficient in that activity (Japanese Patent Laid-open (Kokai) No. 2010-207094). Furthermore, examples of the method for producing protocatechuic acid by fermentation can include the method of producing protocatechuic acid by using a bacterium of the genus *Brevibacterium* and acetic acid as a carbon source (Japanese Patent Laid-open (Kokai) No. 50-89592), the method of producing protocatechuic acid by using a bacterium of the genus *Escherichia* or *Klebsiella* introduced with a gene encoding 3-dihydroshikimate dehydrogenase and glucose as a carbon source (U.S. Pat. No. 5,272,073). Furthermore, vanillic acid can be produced by using protocatechuic acid as a precursor according to an enzymatic method using OMT or a bioconversion method using a microorganism having OMT (J. Am. CHm. Soc., 1998, Vol. 120), or by using ferulic acid as a precursor according to a bioconversion method using *Pseudomonas* sp. AV10 (J. App. Microbiol., 2013, Vol. 116, p 903-910). Furthermore, protocatechualdehyde can be produced by using protocatechuic acid as a precursor according to an enzymatic method using ACAR or a bioconversion method using a microorganism having ACAR. The produced precursor can be used for the bioconversion method as it is, or after being subjected to an appropriate treatment such as concentration, dilution, drying, fractionation, extraction, and purification, as required. That is, as the precursor, for example, a product purified to a desired extent may be used, or a material containing a precursor may be used. The material containing a precursor is not particularly limited so long as the bacterium as described herein can use the precursor. Specific examples of the material containing a precursor can include a culture broth obtained by cultivating a microorganism that is able to produce the precursor, a culture supernatant separated from the culture broth, and processed products thereof such as concentrated products (such as concentrated liquid) thereof and dried products thereof.

In an embodiment, the bioconversion step can be performed by, for example, cultivating the bacterium as described herein. This embodiment can also be referred to as "first embodiment of the bioconversion method". That is, the bioconversion step may be, for example, a step of cultivating the bacterium as described herein in a culture medium containing a precursor of an objective substance to convert the precursor into the objective substance. The bioconversion step may be, specifically, a step of cultivating the bacterium as described herein in a culture medium containing a precursor of an objective substance to produce and accumulate the objective substance in the culture medium.

The culture medium to be used is not particularly limited, so long as the culture medium contains a precursor of an objective substance, and the bacterium as described herein can proliferate in it and produce the objective substance. Culture conditions are not particularly limited, so long as the bacterium as described herein can proliferate, and an objective substance is produced. The descriptions concerning the culture for the fermentation method, such as those describing the culture medium and culture conditions, can be applied mutatis mutandis to the culture in the first embodiment of the bioconversion method, except that the culture medium contains the precursor in this embodiment.

The precursor may be present in the culture medium over the entire period of the culture, or may be present in the culture medium during only a partial period of the culture. That is, the phrase "cultivating a bacterium in a culture medium containing a precursor" does not necessarily mean that the precursor is present in the culture medium over the entire period of the culture. For example, the precursor may be or may not be contained in the culture medium from the start of the culture. When the precursor is not present in the culture medium at the time of the start of the culture, the precursor is added to the culture medium after the start of the culture. Timing of the addition can be appropriately determined according to various conditions such as the length of the culture period. For example, after the bacterium as described herein has sufficiently grown, the precursor may be added to the culture medium. Furthermore, in any case, the precursor may be added to the culture medium as required. For example, the precursor may be added to the culture medium in proportion to the decrease or depletion of the precursor as the objective substance accumulates. Means for adding the precursor to the culture medium are not particularly limited. For example, the precursor can be added to the culture medium by feeding a feed medium containing the precursor to the culture medium. Furthermore, for example, the bacterium as described herein and a microorganism that is able to produce the precursor can be co-cultured so that the precursor accumulates in the culture medium, and thereby the precursor is added to the culture medium. These methods of adding a precursor may be independently used, or may be used in an appropriate combination. The concentration of the precursor in the culture medium is not particularly limited so long as the bacterium as described herein can use the precursor as a raw material of an objective substance. The concentration of the precursor in the culture medium, for example, may be 0.1 g/L or higher, 1 g/L or higher, 2 g/L or higher, 5 g/L or higher, 10 g/L or higher, or 15 g/L or higher; or may be 200 g/L or lower, 100 g/L or lower, 50 g/L or lower, or 20 g/L or lower, or may be within a range defined relative to the weight of the free compound. The precursor may be or may not be present in the culture medium at a concentration within the range exemplified above during the whole period of the culture. For example, the precursor may be present in the culture medium at a concentration within the range exemplified above at the time of the start of the culture, or it may be added to the culture medium so that a concentration within the range exemplified above is attained after the start of the culture. When the culture is performed separately as seed culture and main culture, it is sufficient that an objective substance is produced at least during the main culture. Hence, it is sufficient that the precursor is present in the culture medium at least during the main culture, for example, over the whole period of the main culture or during a partial period of the main culture, and that is, the precursor may be or may not be present in the culture medium during the seed culture. In such cases, terms regarding the culture, such as "culture period (period of culture)" and "start of culture", can be read as those regarding the main culture.

In another embodiment, the bioconversion step can also be performed by, for example, using cells of the bacterium as described herein. This embodiment can also be referred to as "second embodiment of the bioconversion method". That is, the conversion step may be, for example, a step of converting a precursor of an objective substance in a reaction mixture into the objective substance by using cells of the bacterium as described herein. The conversion step may be, specifically, a step of allowing cells of the bacterium as described herein to act on a precursor of an objective substance in a reaction mixture to generate and accumulate the objective substance in the reaction mixture. The bioconversion step performed by using such cells can also be referred to as "conversion reaction".

Cells of the bacterium as described herein can be obtained by cultivating the bacterium as described herein. The culture method for obtaining the cells is not particularly limited so long as the bacterium as described herein can proliferate. At the time of the culture for obtaining the cells, the precursor may be or may not be present in the culture medium. Also, at the time of the culture for obtaining the cells, an objective substance may be or may not be produced in the culture medium. The descriptions concerning the culture mentioned for the fermentation method, such as those concerning the culture medium and culture conditions, can be applied mutatis mutandis to the culture for obtaining the cells used for the second embodiment of the bioconversion method.

The cells may be used in the conversion reaction while present in the culture medium or culture broth, or after being collected from the culture medium or culture broth. The cells may also be used for the conversion reaction after being subjected to a treatment as required. That is, the cells can be present in a culture broth, be collected from the culture broth, or exist as a processed product thereof. Examples of the processed product can include products obtained by subjecting the cells, such as a culture broth containing the cells, or the cells collected from the culture broth, to a treatment. Cells in these forms may be independently used, or may be used in an appropriate combination.

The method for collecting the cells from the culture medium is not particularly limited, and for example, known methods can be used. Examples of such methods can include, for example, spontaneous precipitation, centrifugation, and filtration. A flocculant may also be used. These methods may be independently used, or may be used in an appropriate combination. The collected cells can be washed as required by using an appropriate medium. The collected cells can be re-suspended as required by using an appropriate medium. Examples of the medium usable for washing or suspending the cells can include, for example, aqueous media or aqueous solvents such as water and aqueous buffer.

Examples of the treatment of the cells can include, for example, dilution, condensation, immobilization on a carrier such as acrylamide and carrageenan, freezing and thawing treatment, and treatment for increasing permeability of cell membranes. Permeability of cell membranes can be increased by, for example, using a surfactant or organic solvent. These treatments may be independently used, or may be used in an appropriate combination.

The cells used for the conversion reaction are not particularly limited so long as the cells can produce the objective substance. The cells can maintain the metabolic activities thereof. The expression "the cells can maintain the metabolic activities thereof" can mean that the cells have an ability to utilize a carbon source to generate or regenerate a substance required for producing an objective substance. Examples of such substance can include, for example, ATP, electron donors such as NADH and NADPH, and methyl group donors such as SAM. The cells may have or may not have proliferation ability.

The conversion reaction can be carried out in an appropriate reaction mixture. Specifically, the conversion reaction can be carried out by allowing the cells and the precursor to coexist in an appropriate reaction mixture. The conversion reaction may be carried out by the batch method or may be carried out by the column method. In the case of the batch method, the conversion reaction can be carried out by, for example, mixing the cells of the bacterium as described herein and the precursor in a reaction mixture in a reaction vessel. The conversion reaction may be carried out statically, or may be carried out with stirring or shaking the reaction mixture. In the case of the column method, the conversion reaction can be carried out by, for example, passing a reaction mixture containing the precursor through a column filled with immobilized cells. Examples of the reaction mixture can include those based on an aqueous medium or aqueous solvent such as water and aqueous buffer.

The reaction mixture may contain components other than the precursor as required, in addition to the precursor. Examples of the components other than the precursor can include ATP, electron donors such as NADH and NADPH, methyl group donors such as SAM, metal ions, buffering agents, surfactants, organic solvents, carbon sources, phosphate sources, and other various medium components. That is, for example, a culture medium containing the precursor may also be used as a reaction mixture. That is, the descriptions concerning the culture medium mentioned for the first embodiment of the bioconversion method may also be applied mutatis mutandis to the reaction mixture in the second embodiment of the bioconversion method. The types and concentrations of the components contained in the reaction mixture may be determined according to various conditions such as the type of the precursor to be used and the form of the cells to be used.

Conditions of the conversion reaction, such as dissolved oxygen concentration, pH of the reaction mixture, reaction temperature, reaction time, concentrations of various components, etc., are not particularly limited so long as an objective substance is generated. The conversion reaction can be performed with, for example, typical conditions used for substance conversion using microbial cells such as resting cells. The conditions of the conversion reaction may be determined according to various conditions such as the chosen bacterium. The conversion reaction can be performed, for example, under aerobic conditions. The term "aerobic conditions" can refer to conditions wherein the dissolved oxygen concentration in the reaction mixture is 0.33 ppm or higher, or 1.5 ppm or higher. The oxygen concentration can be controlled to be, for example, 1 to 50%, or about 5%, of the saturated oxygen concentration. The pH of the reaction mixture may be, for example, usually 6.0 to 10.0, or 6.5 to 9.0. The reaction temperature may be, for example, usually 15 to 50° C., 15 to 45° C., or 20 to 40° C. The reaction time may be, for example, 5 minutes to 200 hours. In the case of the column method, the loading rate of the reaction mixture may be, for example, such a rate that the reaction time falls within the range of the reaction time exemplified above. Furthermore, the conversion reaction can also be performed with, for example, a culture condition, such as usual conditions used for culture of bacteria such as coryneform bacteria. During the conversion reaction, the cells may or may not proliferate. That is, the descriptions concerning the culture conditions mentioned for the first embodiment of the bioconversion method may also be applied mutatis mutandis to the conditions of the conversion reaction in the second embodiment of the bioconversion method, except that the cells may or may not proliferate in this embodiment. In such a case, the culture conditions for obtaining the cells and the conditions of the conversion reaction may be the same or different. The concentration of the precursor in the reaction mixture, for example, may be 0.1 g/L or higher, 1 g/L or higher, 2 g/L or higher, 5 g/L or higher, 10 g/L or higher, or 15 g/L or higher, or may be 200 g/L or lower, 100 g/L or lower, 50 g/L or lower, or 20 g/L or lower, or may be within a range defined with a combination thereof, in terms of the weight of the free compound. The density of the cells in the reaction mixture, for example, may be 1 or higher, or may be 300 or lower, or may be within a range defined with a combination thereof, in terms of the optical density (OD) at 600 nm.

During the conversion reaction, the cells, the precursor, and the other components may be additionally supplied to the reaction mixture independently or in any arbitrary combination thereof. For example, the precursor may be added to the culture medium in proportion to the decrease or depletion of the precursor that occurs as the objective substance accumulates. These components may be added once or a plurality of times, or may be continuously added.

Means for adding the various components such as the precursor to the reaction mixture are not particularly limited. These components each can be added to the reaction mixture by, for example, directly adding them to the reaction mixture. Furthermore, for example, the bacterium as described herein and a microorganism that is able to produce a precursor can be co-cultured so that the precursor accumulates in the reaction mixture, and thereby supply the precursor to the reaction mixture. Furthermore, for example, components such as ATP, electron donors, and methyl group donors each may be generated or regenerated in the reaction mixture, may be generated or regenerated in the cells of the bacterium as described herein, or may be generated or regenerated by a coupling reaction between different cells. For example, when cells of the bacterium as described herein maintain the metabolic activities thereof, they can generate or regenerate components such as ATP, electron donors, and methyl group donors within them by using a carbon source. In addition, examples of the method for generating or regenerating ATP can include, for example, the method of supplying ATP from a carbon source by using a *Corynebacterium* bacterium (Hori, H. et al., Appl. Microbiol. Biotechnol., 48(6):693-698 (1997)), the method of regenerating ATP by using yeast cells and glucose (Yamamoto, S et al., Biosci. Biotechnol. Biochem., 69(4):784-789 (2005)), the method of regenerating ATP using phosphoenolpyruvic acid and pyruvate kinase (C. Aug'e and Ch. Gautheron, Tetrahedron Lett., 29:789-790 (1988)), and the method of regenerating ATP by using polyphosphoric acid and polyphosphate kinase (Murata, K. et al., Agric. Biol. Chem., 52(6):1471-1477 (1988)).

Furthermore, the reaction conditions may be constant from the start to the end of the conversion reaction, or they may change during the conversion reaction. The expression "the reaction conditions change during the conversion reaction" can include not only when the reaction conditions are temporally changed, but also can include when the reaction conditions are spatially changed. The expression "the reaction conditions are spatially changed" can mean that, for example, when the conversion reaction is performed by the column method, the reaction conditions such as reaction temperature and cell density differ depending on position in the flow.

A culture medium, for example, culture broth, or reaction mixture containing an objective substance is obtained by carrying out the bioconversion step as described above. Confirmation of the production of the objective substance and collection of the objective substance can be carried out in the same manners as those for the fermentation method described above. That is, the bioconversion method may further include the step of collecting the objective substance from the culture medium, for example, culture broth or reaction mixture. The collected objective substance may contain, for example, bacterial cells, medium components, reaction mixture components, moisture, and by-product metabolites of the bacterium, in addition to the objective substance. Purity of the collected objective substance may be, for example, 30% (w/w) or higher, 50% (w/w) or higher, 70% (w/w) or higher, 80% (w/w) or higher, 90% (w/w) or higher, or 95% (w/w) or higher.

<3> Screening Method as Described Herein

The screening method as described herein is a method for screening an aldehyde-resistant strain that includes the steps of cultivating a microorganism in a culture medium containing an aldehyde and selecting an aldehyde-resistant strain.

The candidate microorganism for an aldehyde resistant strain is not particularly limited. Examples of the microorganism can include bacteria and yeast.

Examples of the bacteria can include bacteria belonging to the family Enterobacteriaceae and coryneform bacteria. Examples of bacteria belonging to the family Enterobacteriaceae can include bacteria belonging to the genus *Escherichia, Enterobacter, Pantoea, Klebsiella, Serratia, Envinia, Photorhabdus, Providencia, Salmonella, Morganella*, or the like. Examples of coryneform bacteria can include such coryneform bacteria as mentioned above.

Examples of the yeast can include yeast belonging to the genus *Saccharomyces, Candida, Pichia, Hansenula, Schizosaccharomyces*, or the like.

The candidate microorganism for an aldehyde-resistant strain may be a wild-type strain or may be a modified strain. Examples of the modified strain can include strains that have been modified so that the activity of alcohol dehydrogenase is reduced, and/or, the activity of a byproduct generation enzyme is reduced. In addition, the candidate microorganism for an aldehyde-resistant strain may be or may not be an isolated strain. For example, a sample containing a microorganism, such as soil samples and water samples obtained from nature can also be used. That is, the candidate "microorganism" for an aldehyde-resistant strain may be present in such samples.

The culture medium to be used is not particularly limited, so long as the culture medium contains an aldehyde, and the aldehyde-resistant strain can proliferate in it. As the medium, for example, a culture medium obtained by adding an aldehyde to a usual culture medium used for culture of microorganisms such as bacteria and yeast can be used. The types and concentrations of the medium components can be appropriately determined according to various conditions such as the chosen microorganism.

Examples of the aldehyde used for the screening can include aldehydes exemplified as objective substances in the method as described herein, that is, aromatic aldehydes such as vanillin, benzaldehyde, and cinnamaldehyde. As the aldehyde, one kind of aldehyde may be used, or two or more kinds of aldehydes may be used in combination.

As the aldehyde, a commercial product may be used, or one appropriately prepared and obtained may be used. The method for producing an aldehyde is not particularly limited, and for example, known methods can be used. An aldehyde can be produced by, for example, a chemical synthesis method, enzymatic method, bioconversion method, fermentation method, or a combination of these. An aldehyde can be produced by, for example, the method as described herein.

The concentration of the aldehyde in the culture medium is not particularly limited so long as aldehyde resistance can be evaluated. The concentration of the aldehyde in the culture medium, for example, may be 2 g/L or higher, 3 g/L or higher, 4 g/L or higher, 5 g/L or higher, or 6 g/L or higher; or may be 10 g/L or lower, or may be within a range defined with a combination thereof. The aldehyde may be present in the culture medium over the whole period of the culture, or may be present in the culture medium during only a partial period of the culture. That is, the phrase "cultivating a microorganism in a culture medium containing an aldehyde" does not necessarily mean that the aldehyde is present in the culture medium over the whole period of the culture. For example, the aldehyde may be present in the culture medium from the start of the culture, or may be added to the culture medium during the period when the microorganism is proliferating after the start of the culture. The aldehyde may be added to the culture medium during, for example, the exponential growth phase of the microorganism. The aldehyde may be or may not be present in the culture medium at a concentration within the range exemplified above over the whole period of the culture. For example, the aldehyde may be present in the culture medium at a concentration within the range exemplified above at the time of the start of the culture, or it may be added to the culture medium so that a concentration within the range exemplified above is attained after the start of the culture.

Culture conditions are not particularly limited, so long as an aldehyde-resistant strain can proliferate. The culture can be performed with, for example, usual conditions used for culture of microorganisms such as bacteria and yeast. The culture conditions may be appropriately determined according to various conditions such as the chosen microorganism.

The descriptions concerning the culture mentioned for the fermentation method, such as those concerning the culture medium and culture conditions, can be applied mutatis mutandis to the culture, such as the culture medium and culture conditions, in the screening method as described herein, except that the culture medium containing an aldehyde is used in the screening method.

An aldehyde-resistant strain can be selected on the basis of the culture result. That is, an aldehyde-resistant strain can be selected on the basis of the degree of growth of the microorganism during the period when the culture medium contains an aldehyde, for example, during the period after the start of the culture when an aldehyde is present in the culture medium from the start of the culture, or during the period after the aldehyde is added when the aldehyde is added to the culture medium after the start of the culture. For example, a microorganism can be identified as an aldehyde-resistant strain when the growth of the microorganism is observed during the period when the culture medium contains an aldehyde. Also, for example, a microorganism can be identified as an aldehyde-resistant strain when the growth of the microorganism is observed to a certain extent or higher during the period when the culture medium contains an aldehyde. The "certain extent" can be determined according to various conditions such as the type of the microorganism and the culture conditions. For example, a microorganism can be identified as an aldehyde-resistant strain when the amount of cells of the microorganism is increased to 1.5 times, 2 times, 5 times, 10 times, 100 times, or 1000 times during a period from the start of the culture or when an aldehyde is added to a certain time point. The increased amount of cells of the microorganism is measured as, for example, an increased value of OD600 nm of the culture medium. The "certain time point" can be determined according to various conditions such as the type of the microorganism and the culture conditions. For example, the "certain time point" can be 10 hr, 20 hr, or 30 hr after the start of the culture or after adding an aldehyde. Specifically, for example, a microorganism can be identified as an aldehyde-resistant strain when the microorganism is inoculated to a culture medium containing an aldehyde in an initial concentration of 2 g/L or higher so as to obtain an initial OD600 nm of 0.01 to 0.1, and the microorganism grows so as to obtain OD600 nm of 1 by 30 hr after the start of the culture.

EXAMPLES

Hereafter, the present invention will be more specifically explained with reference to examples. However, the present invention is not limited by these Examples.

Reference Example: Vanillin Production by *Escherichia coli*

In this reference example, a strain was constructed in which the yqhD gene was deleted in order to reduce the by-production of vanillyl alcohol, and in which aromatic carboxylic acid reductase (ACAR) gene and phosphopantetheinyl transferase (PPT) gene were amplified in order to enhance conversion of vanillic acid into vanillin. The parent strain or starting strain was *Escherichia coli* JM109, and vanillin production was performed with the constructed strain.

<1> Construction of *Escherichia coli* JM109ΔyqhD Strain

The yqhD gene encodes an NADP-dependent alcohol dehydrogenase that participates in the conversion of vanillin into vanillyl alcohol (J. Am. Chem. Soc., 136, 11644 (2014)). Therefore, in order to enhance the vanillin accumulation by blocking the conversion of vanillin into vanillyl alcohol, a yqhD gene-deficient strain of *Escherichia coli* JM109 was constructed. First, by PCR using the DNA fragment of pMW118-attL-Cm-attR (WO2005/010175) as the template, and the synthetic DNAs of SEQ ID NOS: 1 and 2 as the primers, a fragment for deleting the yqhD gene consisting of an upstream region of orf of the yqhD gene, attR$_\lambda$ sequence, chloramphenicol resistance gene, attL$_\lambda$ sequence, and downstream region of orf of the yqhD gene ligated in this order was obtained. The 50 residues of SEQ ID NO: 1 on the 5'-end side correspond to the upstream sequence of orf of the yqhD gene, and the remainder corresponds to the attR$_\lambda$ sequence. The 50 residues of SEQ ID NO: 2 on the 5'-end side correspond to the downstream sequence of orf of the yqhD gene, and the remainder corresponds to the attL$_\lambda$ sequence. Then, competent cells of *Escherichia coli* JM109 (Takara Bio) were transformed with the pKD46 plasmid (Proc. Natl. Acad. Sci. USA, 2000, vol. 97, No. 12, pp. 6640-6645), applied to the LB medium containing 100 μg/mL of ampicillin, and cultured overnight at 30° C. to obtain single colonies, and *E. coli* JM109/pKD46 strain was obtained as a transformant. The *E. coli* JM109/pKD46 strain was cultured in the LB medium containing 100 μg/mL of ampicillin and 50 mM arabinose, and the fragment for deleting the yqhD gene was introduced by the electric pulse method. The cells were applied to the LB agar medium containing 100 μg/mL of ampicillin and 25 μg/mL of chloramphenicol, and cultured at 30° C. PCR was performed by using a colony that appeared as the template and the synthetic DNAs of SEQ ID NOS: 3 and 4 as the primers, and *E. coli* JM109ΔyqhD::Cm$^R$/pKD46 strain, in which the yqhD gene was replaced with the chloramphenicol resistance gene, was obtained on the basis of the size of the amplified fragment. Furthermore, the *E. coli* JM109ΔyqhD::Cm$^R$/pKD46 strain was cultured at 42° C., and *E. coli* JM109ΔyqhD::Cm$^R$ strain, in which pKD46 was eliminated, was obtained on the basis of loss of ampicillin resistance. The *E. coli* JM109ΔyqhD::Cm$^R$ strain was cultured in the LB medium containing 25 μg/mL of chloramphenicol, and the pMW-int-xis plasmid (WO2007/037460, Japanese Patent Laid-open (Kokai) No. 2005-058827) was introduced by the electric pulse method. The cells were applied to the LB agar medium containing 100 μg/mL of ampicillin, and cultured at 30° C. to obtain colonies. A plurality of the obtained colonies were cultured again at 30° C. on the agar medium, and a colony that proliferated on the LB agar medium containing 100 μg/mL of ampicillin, but did not proliferate on the LB agar medium containing 100 μg/mL of ampicillin and 25 μg/mL of chloramphenicol was identified. The colonies were also cultured at 37° C. in parallel, and a colony that did not proliferate on the LB agar medium containing 100 μg/mL of ampicillin, but proliferated on the LB agar medium not containing ampicillin, of which susceptibility to chloramphenicol had been separately confirmed above, was selected to obtain a strain in which chloramphenicol resistance gene and pMX-int-xis were eliminated. The thus-obtained strain was designated as *E. coli* JM109ΔyqhD strain.

<2> Construction of Plasmid pEPlac-Car for Amplification of ACAR Gene

A plasmid pEPlac-car for amplification of ACAR gene of *Nocardia brasiliensis* ATCC 700358 was constructed by the following method.

The nucleotide sequence of the ACAR gene of *Nocardia brasiliensis* ATCC 700358 is shown as SEQ ID NO: 75, and the amino acid sequence of ACAR encoded by this gene is shown as SEQ ID NO: 76. The N-terminus Met residue of the amino acid sequence shown as SEQ ID NO: 76 was designed to be deleted, and then the N-terminus region of the thus-shortened amino acid sequence of ACAR was designed to be extended with the amino acid sequence (17 aa) shown as SEQ ID NO: 78, which is encoded by the nucleotide sequence shown as SEQ ID NO: 77, to thereby design a variant ACAR of *Nocardia brasiliensis* ATCC 700358 (SEQ ID NO: 48) and a variant ACAR gene encoding it (SEQ ID NO: 47). The amino acid sequence shown as SEQ ID NO: 78 100% identical to the amino acid sequence (17 aa) at the N-terminus region of an ACAR homologue from another strain of *Nocardia brasiliensis* (NCBI reference sequences: WP_042262686.1 and GI:754904305).

The variant ACAR gene having the nucleotide sequence shown as SEQ ID NO: 47 was codon-optimized for the expression in *E. coli* and introduced at the 3'- and 5'-ends with the nucleotide sequences having the NdeI and SacI restriction sites, respectively. Hereinafter, the codon-optimized variant ACAR gene is also referred to simply as "ACAR gene". The DNA-fragment that includes the ACAR gene flanked by NdeI and SacI were chemically synthesized using the service provided by ATG Service Gen (Russian Federation, Saint-Petersburg). The nucleotide sequence of the DNA-fragment that includes the ACAR gene flanked by NdeI and SacI is shown as SEQ ID NO: 79. The DNA-fragment was obtained from the gene-manufacturer as a part of a plasmid.

To express the ACAR gene in *E. coli* cells, the obtained DNA-fragment (SEQ ID NO: 79) was re-cloned at the NdeI and SacI restriction sites in the pELAC vector (SEQ ID NO: 80; Smirnov S. V. et al., *Appl. Microbiol. Biotechnol.*, 2010, 88(3):719-726). The pELAC vector was constructed by replacing BglII-XbaI-fragment of pET22b(+) (Novagen) with synthetic BglII-XbaI-fragment containing $P_{lacUV5}$ promoter. To insert DNA-fragment into pELAC, ligation reaction using T4 DNA ligase (Fermentas, Lithuania) was performed as recommended by the supplier. The ligation mixture was treated with ethanol, and the obtained precipitate was dissolved in water and introduced into *E. coli* TG1 cells using electroporation. The cells were applied onto LA-plates supplemented with ampicillin (Ap, 200 mg/L) (Sambrook J. and Russell D. W., Molecular Cloning: A Laboratory Manual (3rd ed.), Cold Spring Harbor Laboratory Press, 2001) and cultured overnight at 37° C. The obtained colonies were analyzed using PCR to select the required clones. The PCR conditions were as follows: initial denaturation for 5 min at 95° C.; then 30 cycles: 30 sec at 95° C., 30 sec at 54° C., 1 min at 72° C.; final elongation for 5 min at 72° C. That is, primer pairs P1 (SEQ ID NO: 81)/P5 (SEQ ID NO: 82) and P4 (SEQ ID NO: 83)/P6 (SEQ ID NO: 84) were used to select colonies containing the ACAR gene. The DNA-fragment (917 bp) was obtained when the vector-specific primer P1 and the reverse primer P5 for the 5'-end part of the ACAR gene were used. The DNA-fragment (1378 bp) was obtained when the vector-specific primer P4 and the primer P6 for the 3'-end part of the ACAR gene were used. A plasmid containing the ACAR gene was extracted from the selected colony, and was designated as pEPlac-car.

<3> Construction of Plasmid pMW218::Ptac10000-entD for Amplification of entD Gene The entD gene encodes PPT, which converts ACAR, which catalyzes the reaction of converting vanillic acid into vanillin, into an active type thereof by phosphopantetheinylation (J. Biol. Chem., 2007, Vol. 282, No. 1, pp. 478-485). Therefore, in order to improve ACAR activity, a plasmid pMW218::Ptac10000-entD for amplification of the entD gene was constructed by the following method.

PCR was performed by using a DNA fragment containing λattL-Kmr-λattR-Ptac (WO2008/090770A1) as the template, and the synthetic DNAs of SEQ ID NOS: 5 and 6 as the primers to obtain a PCR product containing the tac promoter region. Separately, PCR was also performed by using the genomic DNA of the E. coli MG1655 strain as the template, and the synthetic DNAs of SEQ ID NOS: 7 and 8 as the primer to obtain a PCR product containing orf of the entD gene. The sequences of SEQ ID NOS: 6 and 7 are partially complementary to each other. Then, the PCR product containing the tac promoter region and the PCR product containing orf of the entD gene were mixed in approximately equimolar amounts, and inserted into the pMW218 vector (Nippon Gene) treated with EcoRI and SalI by using In Fusion HD Cloning Kit (Clontech). With this DNA, competent cells of Escherichia coli JM109 (Takara Bio) were transformed, and the cells were applied to the LB medium containing 100 μM IPTG, 40 μg/mL of X-Gal, and 40 μg/mL of kanamycin, and cultured overnight. Then, white colonies that appeared were picked up, and separated into single colonies to obtain transformants. Plasmids were extracted from the obtained transformants, and one into which the target PCR product (PCR product containing orf of the entD gene ligated downstream from the tac promoter region) was inserted was designated as pMW218::Ptac10000-entD.

<4> Construction of E. coli JM109ΔyqhD/pMW218::Ptac10000-entD+pEPlac-Car Strain pMW218::Ptac10000-entD and pEPlac-car were introduced into the E. coli JM109ΔyqhD strain by the electric pulse method. The cells were applied to the LB agar medium containing 25 μg/ml of kanamycin and 100 μg/mL of ampicillin, and cultured at 37° C. The grown strain was purified on this agar medium, and designated as E. coli JM109ΔyqhD/pMW218::Ptac10000-entD+pEPlac-car strain.

<5> Vanillin Production by E. coli JM109ΔyqhD/pMW218::Ptac10000-entD+pEPlac-Car Strain The cells of the E. coli JM109ΔyqhD/pMW218::Ptac10000-entD+pEPlac-car strain obtained by the culture on the LB agar medium containing 25 μg/ml of kanamycin and 100 μg/mL of ampicillin were inoculated into 4 mL of the LB medium contained in a test tube, and cultured at 37° C. for about 16 hours with shaking as preculture. The whole volume of the obtained preculture broth was added to 200 ml of the LB medium in a Sakaguchi flask, culture was performed at 37° C. under an aerobic condition until OD at 600 nm became 0.5, then IPTG was added at 1 mM, and culture was further performed at 37° C. for 2 hours with shaking. Then, the obtained culture broth was centrifuged at 8000 rpm for 5 minutes, the supernatant was removed, and the cells were washed with sterilized physiological saline. After the washing, the whole amount of the cells were suspended in 5 ml of a vanillin production medium (16 g/L of vanillic acid, 40 g/L of glucose, 100 mM $Na_2HPO_4$-$12H_2O$, 100 mM TES buffer (adjusted to pH 6.6 with KOH), 60 g/L of $CaCO_3$ (sterilized with hot air at 180° C. for 3 hours, and then mixed)), and cultured at 30° C. for about 20 hours with shaking.

After the completion of the culture, the concentration of the residual glucose in the medium was analyzed with Biotech Analyzer AS-310 (Sakura SI). The amounts of vanillic acid and vanillin in the medium were also analyzed by using Ultra Performance Liquid Chromatography NEXERA X2 System (SHIMADZU) with the following conditions. The cell density (OD) was measured by using a spectrophotometer U-2900 (HITACHI).

Conditions of UPLC Analysis:
Column: KINETEX 2.6 μm XB-C18, 150×30 mm (Phenomenex)
Oven temperature: 40° C.
Mobile phase (A): 0.1% Trifluoroacetic acid
Mobile phase (B): 0.1% Trifluoroacetic acid/80% acetonitrile
Gradient program (time, A (%), B (%)): (0, 90, 10)→(3, 80, 20)
Flow rate: 1.5 ml/min The results are shown in FIG. 1. The E. coli JM109ΔyqhD/pMW218::Ptac10000-entD+pEPlac-car strain, which was deficient in the yqhD gene and in which the ACAR gene and entD gene were amplified, accumulated about 6.6 g/L of vanillin in about 8 hours. Thereafter, however, the accumulation amount of vanillin hardly increased, but the by-production amount of vanillyl alcohol increased.

Example 1: Screening for Vanillin-Resistant Strain

<1> Screening for Vanillin-Resistant Strain (Wild-Type Strain)

Figure 2:
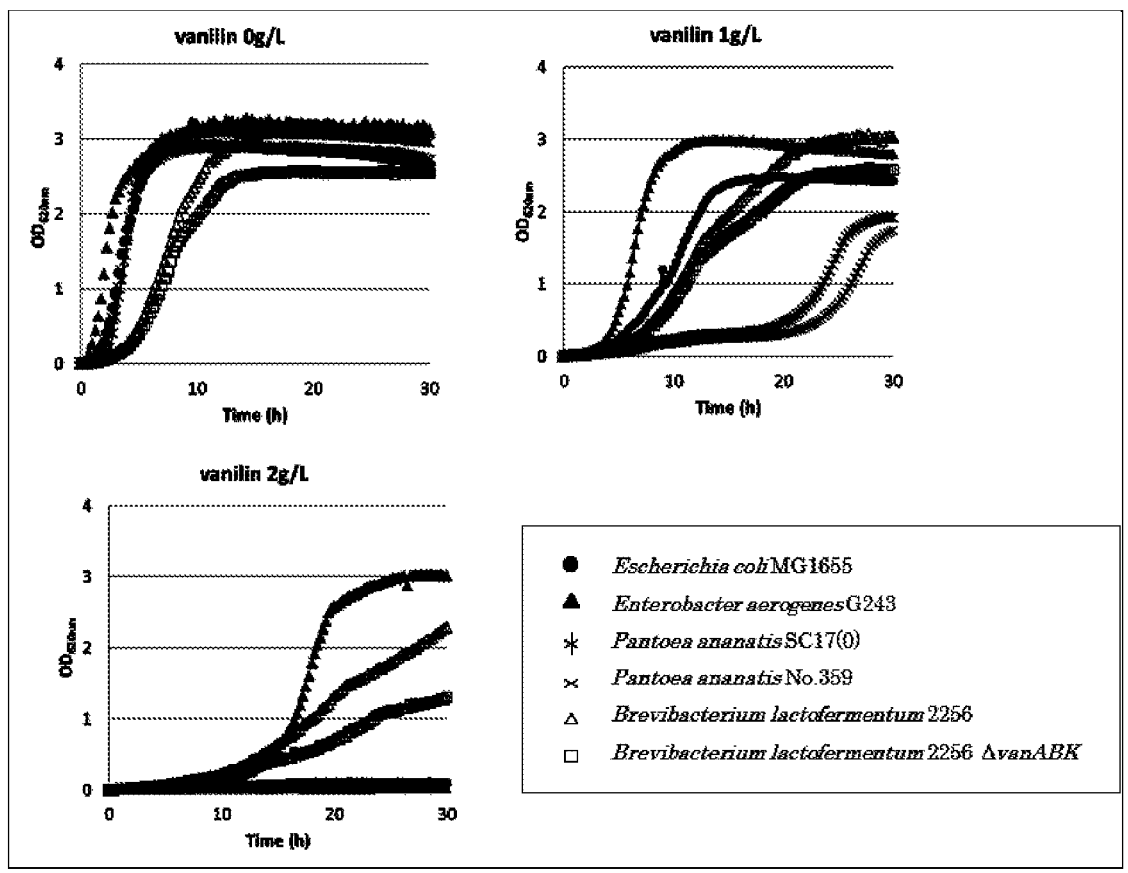
FIG. 2 shows results of an evaluation of vanillin resistance in bacteria.
Figure 3:
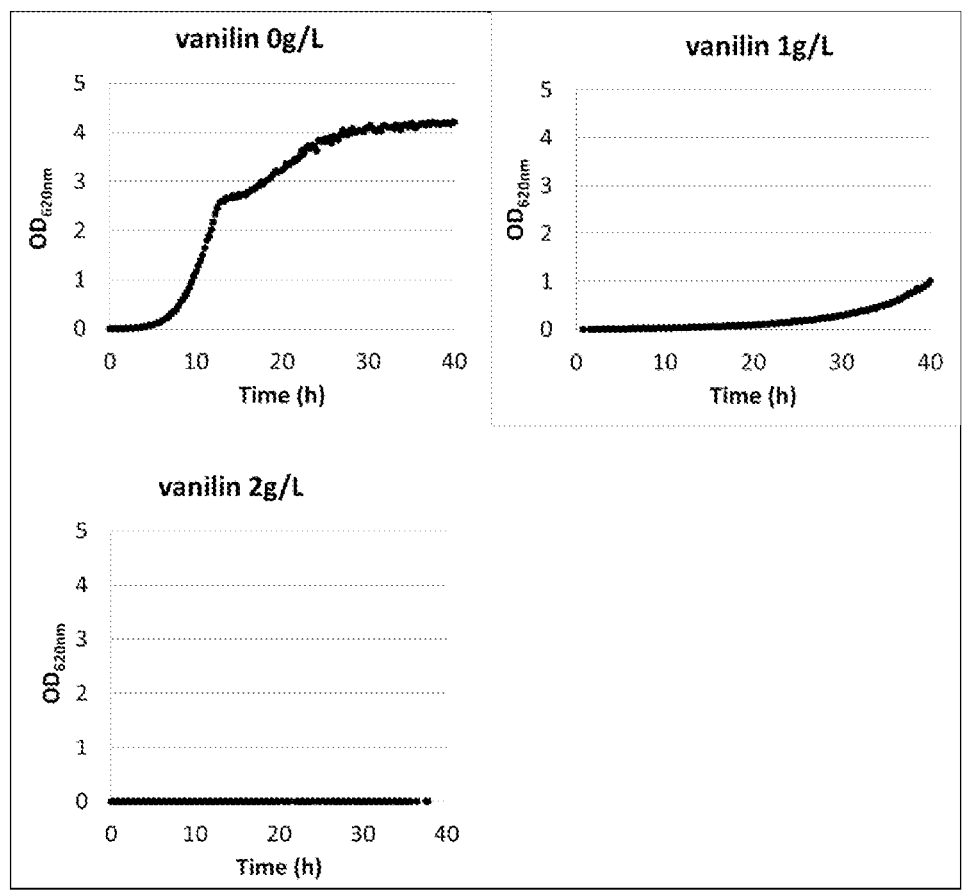
FIG. 3 shows results of an evaluation of vanillin resistance in *Saccharomyces cerevisiae* S228C strain.

In order to obtain improved vanillin accumulation amount as compared with that obtained with E. coli, screening for vanillin-resistant strains was performed. Specifically, by using the E. coli MG1655 strain as a control strain, vanillin resistance of Pantoea ananatis No. 359 strain (AJ13355 strain, FERM BP-6614), P. ananatis SC17(0) strain (VKPM B-9246), Enterobacter aerogenes G243 strain (AJ110637, FERM BP-10955), Corynebacterium glutamicum 2256 strain (ATCC 13869), C. glutamicum 2256ΔvanABK strain (mentioned later) obtained by deleting the vanillin utilization ability of the 2256 strain, and Saccharomyces cerevisiae S228C strain (ATCC 26108) was investigated. As the medium, there were used the LB medium for E. coli, P. ananatis, and E. aerogenes, CM2B medium (10 g/L of polypeptone, 10 g/L of yeast extract, 5 g/L of NaCl, 10 μg/L of biotin, pH 7.0 adjusted with KOH) for C. glutamicum, and YPD medium (10 g/L of yeast extract, 20 g/L of Bacto peptone, 20 g/L of glucose) for S. cerevisiae, all of which contained 0, 1, or 2 g/L of vanillin. Culture temperature was set at 30° C. (S. cerevisiae), 31.5° C. (C. glutamicum), 34° C. (E. aerogenes, P ananatis), or 37° C. (E. coli), and culture was performed under an aerobic condition. The results for the bacteria are shown in FIG. 2, and the results for S. cerevisiae are shown in FIG. 3. The P. ananatis SC17(0) strain and the S. cerevisiae S228C strain grew in the presence of 1 g/L of vanillin, but they did not grow at all in the presence of 2 g/L of vanillin. By contrast, it could be confirmed that the C. glutamicum 2256 strain and the E. aerogenes G243 strain could grow even in the presence of 2 g/L of vanillin. On the basis of the results mentioned above, the C. glutamicum 2256 strain and the E. aerogenes G243 strain were selected as strains showing vanillin resistance higher than that of E. coli.

<2> Screening for Vanillin-Resistant Strain, that is, a Strain Showing Reduced Vanillyl Alcohol by-Production Vanillin resistance of coryneform bacteria showing reduced vanillyl alcohol by-production was investigated. Specifically, by using the *E. coli* JM109ΔyqhD strain, that is, a strain showing reduced vanillyl alcohol by-production, and the *S. cerevisiae* S228C strain, that is, a wild-type strain, as a control strain, vanillin resistance of the *C. glutamicum* FKFC14 strain, described herein, which is a coryneform bacterium strain showing reduced vanillyl alcohol by-production, was investigated. There were used the LBGM9 medium (10 g/L of Bacto tryptone, 5 g/L of yeast extract, 10 g/L of NaCl, 6 g/L of Na$_2$HPO$_4$, 3 g/L of KH$_2$PO$_4$, 0.5 g/L of NaCl, 1 g/L of NH$_4$Cl, 5 g/L of glucose, 15 g/L of agar) for the *E. coli* JM109ΔyqhD strain, and CM2B medium containing 30 g/L of glucose for the *C. glutamicum* FKFC14 strain, and culture was performed until OD at 600 nm became about 2. Then, vanillin was added at a concentration of 0, 3, or 6 g/L, and growth was examined. As for the *S. cerevisiae* S228C strain, it was cultured by using the YPD medium of which glucose concentration was changed to 30 g/L until OD at 600 nm became about 2, glucose was supplemented to obtain a glucose concentration of 20 g/L, it was further cultured for 1 hour, then vanillin was added at a concentration of 0, 3, or 6 g/L, and growth was examined.

Figure 4:
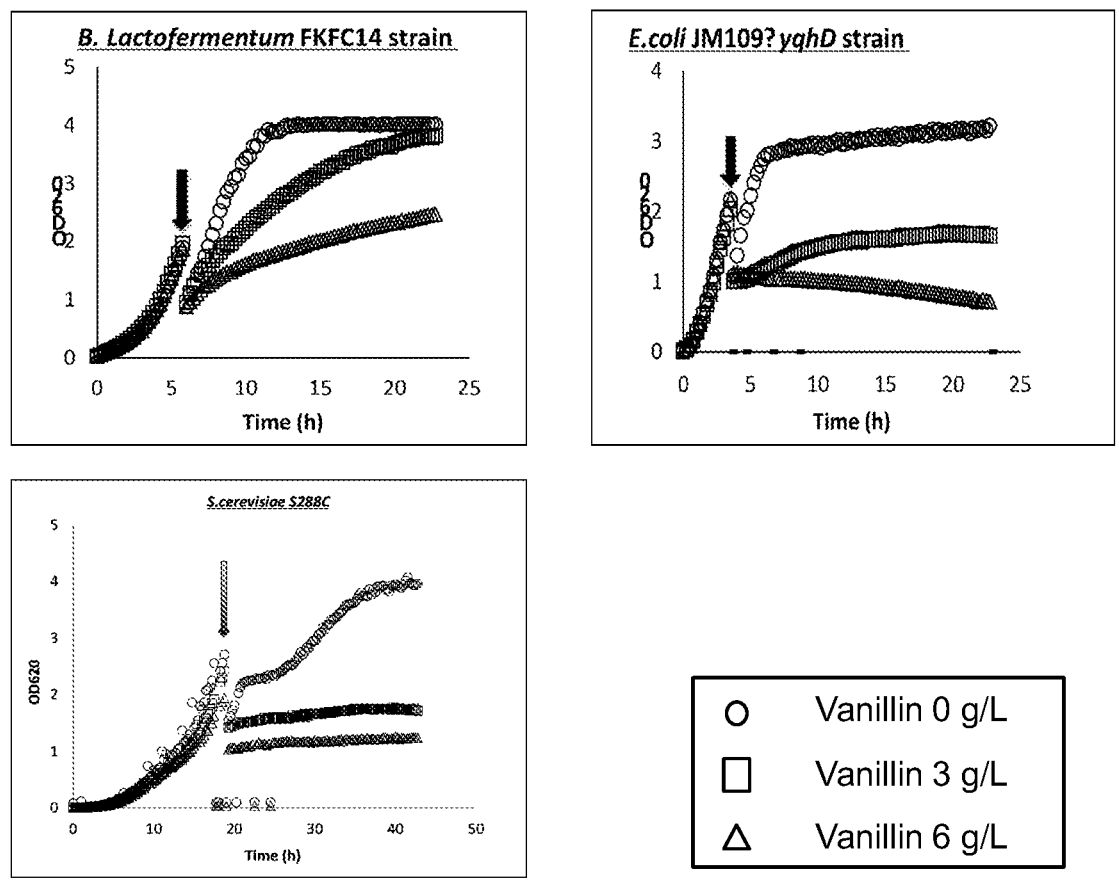
FIG. 4 shows results of an evaluation of vanillin resistance of a coryneform bacterium strain showing reduced vanillyl alcohol by-production.

The results are shown in FIG. 4. It was demonstrated that the *C. glutamicum* FKFC14 strain, which is a coryneform bacterium strain showing reduced vanillyl alcohol by-production, shows vanillin resistance higher than that of the *E. coli* JM109ΔyqhD strain, that is, a strain showing reduced vanillyl alcohol by-production, and the *S. cerevisiae* S228C strain, that is, a wild-type strain.

Example 2: Vanillin Production by *Corynebacterium glutamicum*

In this example, a strain in which ACAR gene and entD gene (PPT gene) were amplified was constructed from the *Corynebacterium glutamicum* 2256 strain (ATCC 13869) as the parent strain, and vanillin production was performed with the constructed strain.

<1> Construction of Plasmid pVK9::Ptuf-Car+entD for Amplification of ACAR Gene and entD Gene A plasmid pVK9::Ptuf-car+entD for expressing the ACAR gene derived from *Nocardia* brasdiensis and the entD gene derived from *E. coli* was constructed via the following procedure.

PCR was performed by using the genomic DNA of the *C. glutamicum* 2256 strain as the template and the synthetic DNAs of SEQ ID NOS: 9 and 10 as the primers to obtain a PCR product containing the promoter region and SD sequence of the elongation factor Tu gene. PCR was performed by using the pEPlac-car plasmid (Reference Example) as the template and the synthetic DNAs of SEQ ID NOS: 11 and 12 as the primers to obtain a PCR product containing orf of the ACAR gene. PCR was performed by using the genomic DNA of the *E. coli* MG1655 strain as the template and the synthetic DNAs of SEQ ID NOS: 13 and 14 as the primers to obtain a PCR product containing orf and the SD sequence of the entD gene. Then, these fragments were inserted into the pVK9 vector (WO2007/046389) treated with BamHI and PstI using In Fusion HD Cloning Kit (Clontech). pVK9 is a shuttle vector for coryneform bacteria and *E. coli*. By using this DNA, competent cells of *Escherichia coli* JM109 (Takara Shuzo) were transformed, and the cells were applied to the LB medium containing 100 μM IPTG, 40 μg/mL of X-Gal, and 25 μg/mL of kanamycin, and cultured overnight. Then, the white colonies that appeared were picked up, and separated into single colonies to obtain transformants. Plasmids were extracted from the obtained transformants, and one in which the target PCR product was inserted was designated as pVK9::Ptuf-car+entD. In pVK9::Ptuf-car+entD, the ACAR gene and the entD gene constitute an operon structure, and are expressed from the tuf promoter.

<2> Construction of *C. glutamicum* 2256/pVK9::Ptuf-Car+entD Strain pVK9::Ptuf-car+entD was introduced into the *C. glutamicum* 2256 strain (wild-type strain) by the electric pulse method. The cells were applied to the CM-Dex agar medium (5 g/L of glucose, 10 g/L of polypeptone, 10 g/L of yeast extract, 1 g/L of KH$_2$PO$_4$, 0.4 g/L of MgSO$_4$-7H$_2$O, 0.01 g/L of FeSO$_4$-7H$_2$O, 0.01 g/L of MnSO$_4$-4-5H$_2$O, 3 g/L of urea, 1.2 g/L of soybean hydrolysate, 10 μg/L of biotin, 15 g/L of agar, adjusted to pH 7.5 with NaOH) containing 25 μg/ml of kanamycin, and cultured at 31.5° C. A grown strain was purified on the same agar medium, and designated as 2256/pVK9::Ptuf-car+entD strain.

<3> Vanillin Production by *C. glutamicum* 2256/pVK9::Ptuf-Car+entD Strain

The cells of the *C. glutamicum* 2256/pVK9::Ptuf-car+entD strain obtained by the culture on the CM-Dex agar medium were inoculated into 4 mL of the CM-Dex medium (having the same composition as that of the CM-Dex agar medium except that it does not contain agar) containing 25 μg/ml of kanamycin, 2.5 g/L of fructose, 2 g/L of succinic acid, and 4 g/L of gluconic acid in a test tube, and cultured at 31.5° C. for about 16 hours with shaking as preculture. The whole volume of the obtained preculture broth was added to 200 ml of the CM-Dex medium containing 2.5 g/L of fructose, 2 g/L of succinic acid, and 4 g/L of gluconic acid in a Sakaguchi flask, culture was performed at 31.5° C. with shaking under an aerobic condition until OD at 600 nm became 1.5. Then, the obtained culture broth was centrifuged at 8000 rpm for 5 minutes, the supernatant was removed, and the cells were washed with sterilized physiological saline. After the washing, all of the cells were suspended in 5 ml of a vanillin production medium (16 g/L of vanillic acid, 70 g/L of glucose, 100 mM Na$_2$HPO$_4$-12H$_2$O, 100 mM TES buffer (adjusted to pH 6.6 with KOH), 60 g/L of CaCO$_3$ (sterilized with hot air at 180° C. for 3 hours and then mixed)), and cultured at 30° C. for 20 hours with shaking.

After the completion of the culture, the concentration of the residual glucose in the medium was analyzed with Biotech Analyzer AS-310 (Sakura SI). The amounts of vanillic acid and vanillin in the medium were also analyzed by using Ultra Performance Liquid Chromatography NEXERA X2 System (SHIMADZU) with the following conditions. The cell density (OD) was measured by using a spectrophotometer U-2900 (HITACHI).

Conditions of UPLC Analysis:
Column: KINETEX 2.6 μm XB-C18, 150×30 mm (Phenomenex)
Oven temperature: 40° C.
Mobile phase (A): 0.1% Trifluoroacetic acid
Mobile phase (B): 0.1% Trifluoroacetic acid/80% acetonitrile
Gradient program (time, A (%), B (%)): (0, 90, 10)→(3, 80, 20)
Flow rate: 1.5 ml/min The results are shown in Table 1. The 2256/pVK9::Ptuf-car+entD strain, which was obtained by amplifying the ACAR gene and entD gene in the wild-type strain used as the parent strain, did not generate vanillin at all, but accumulated 14.1 g/L of vanillyl alcohol. That is, it is suggested that all the generated vanillin was converted into vanillyl alcohol.

TABLE 1

Vanillin production by *C. glutamicum* 2256/pVK9::Ptuf-car + entD strain (±S.E.)

| Strain | Consumed glucose (g/L) | Consumed vanillic acid (g/L) | Generated vanillin (g/L) | Generated vanillyl alcohol (g/L) |
|---|---|---|---|---|
| 2256/pVK9::Ptuf-car + entD | 67.6 ± 10.6 | 15 ± 0.0 | 0.0 ± 0.0 | 14.1 ± 0.2 |

Example 3: Effect of Deletion of Alcohol Dehydrogenase Homologue Genes on Vanillin Production by *Corynebacterium glutamicum*

In this example, a strain deficient in alcohol dehydrogenase homologue genes was constructed from the *Corynebacterium glutamicum* 2256 strain (ATCC 13869) as a parent strain, and vanillin production was performed with the constructed strain.

<1> Construction of Strain Deficient in Vanillin Utilization Genes (FKS0165 Strain)

It has been reported that, in coryneform bacteria, vanillin is metabolized in the order of vanillin→vanillic acid→protocatechuic acid, and utilized (Current Microbiology, 2005, Vol. 51, pp. 59-65). The conversion reaction from vanillic acid to protocatechuic acid is catalyzed by vanillate demethylase. The vanA gene and vanB gene encode the subunit A and subunit B of vanillate demethylase, respectively. The vanK gene encodes the vanillic acid uptake system, and constitutes the vanABK operon together with the vanAB genes (M. T. Chaudhry, et al., Microbiology, 2007, 153:857-865). Therefore, a vanillin utilization ability-deficient strain (FKS0165 strain) was first constructed from the *C. glutamicum* 2256 strain by deleting the vanABK operon. The procedure is shown below.

<1-1> Construction of Plasmid pBS4SΔvanABK56 for Deletion of vanABK Genes

PCR was performed by using the genomic DNA of the *C. glutamicum* 2256 strain as the template, and the synthetic DNAs of SEQ ID NOS: 15 and 16 as the primers to obtain a PCR product containing an N-terminus side coding region of the vanA gene. Separately, PCR was also performed by using the genomic DNA of the *C. glutamicum* 2256 strain as the template, and the synthetic DNAs of SEQ ID NOS: 17 and 18 as the primers to obtain a PCR product containing a C-terminus side coding region of the vanK gene. The sequences of SEQ ID NOS: 16 and 17 are partially complementary to each other. Then, the PCR product containing the N-terminus side coding region of the vanA gene and the PCR product containing the C-terminus side coding region of the vanK gene were mixed in approximately equimolar amounts, and inserted into the pBS4S vector (WO2007/046389) treated with BamHI and PstI by using In Fusion HD Cloning Kit (Clontech). With this DNA, competent cells of *Escherichia coli* JM109 (Takara Bio) were transformed, and the cells were applied to the LB medium containing 100 μM IPTG, 40 μg/mL of X-Gal, and 40 μg/mL of kanamycin, and cultured overnight. Then, white colonies that appeared were picked up, and separated into single colonies to obtain transformants. Plasmids were extracted from the obtained transformants, and one into which the target PCR product was inserted was designated as pBS4SΔvanABK56.

<1-2> Construction of FKS0165 Strain pBS4SΔvanABK56 obtained above does not contain the region enabling autonomous replication of the plasmid in cells of coryneform bacteria. Therefore, if coryneform bacteria are transformed with this plasmid, a strain in which this plasmid is incorporated into the genome by homologous recombination appears as a transformant, although it occurs at an extremely low frequency. Therefore, pBS4SΔvanABK56 was introduced into the *C. glutamicum* 2256 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4SΔvanABK56 was incorporated into the genome by homologous recombination. This once-recombinant strain had both the wild-type vanABK genes, and the deficient type vanABK genes.

The once-recombinant strain was cultured overnight in the CM-Dex liquid medium, and the culture broth was applied to the S10 agar medium (100 g/L of sucrose, 10 g/L of polypeptone, 10 g/L of yeast extract, 1 g/L of $KH_2PO_4$, 0.4 g/L of $MgSO_4$-$7H_2O$, 0.01 g/L of $FeSO_4$-$7H_2O$, 0.01 g/L of $MnSO_4$-$4$-$5H_2O$, 3 g/L of urea, 1.2 g/L of soybean protein hydrolysate solution, 10 μg/L of biotin, 20 g/L of agar, adjusted to pH 7.5 with NaOH, and autoclaved at 120° C. for 20 minutes), and cultured at 31.5° C. Among the colonies that appeared, a strain that showed kanamycin susceptibility was purified on the CM-Dex agar medium. By preparing genomic DNA from the purified strain, and using it to perform PCR with the synthetic DNAs of SEQ ID NOS: 19 and 20 as the primers, deletion of the vanABK genes was confirmed, and the strain was designated as FKS0165 strain.

<2> Construction of Strain Deficient in Alcohol Dehydrogenase Homologue Genes (FKFC14 Strain)

Subsequently, by using the *Corynebacterium glutamicum* FKS0165 strain as a parent strain, there was constructed a strain FKFC14, which is deficient in alcohol dehydrogenase homologue genes, for example, NCgl0324 gene (adhC), NCgl0313 gene (adhE), and NCgl2709 gene (adhA), via the following procedure.

<2-1> Construction of FKFC5 Strain (FKS0165ΔNCgl0324 Strain)

<2-1-1> Construction of Plasmid pBS4SΔ2256adhC for Deletion of NCgl0324 Gene

PCR was performed by using the genomic DNA of the *C. glutamicum* 2256 strain as the template, and the synthetic DNAs of SEQ ID NOS: 21 and 22 as the primers to obtain a PCR product containing an N-terminus side coding region of the NCgl0324 gene. Separately, PCR was performed by using the genomic DNA of the *C. glutamicum* 2256 strain as the template, and the synthetic DNAs of SEQ ID NOS: 23 and 24 as the primers to obtain a PCR product containing a C-terminus side coding region of the NCgl0324 gene. The sequences of SEQ ID NOS: 22 and 23 are partially complementary to each other. Then, approximately equimolar amounts of the PCR product containing the N-terminus side coding region of the NCgl0324 gene and the PCR product containing the C-terminus side coding region of the NCgl0324 gene were mixed, and inserted into the pBS4S vector (WO2007/046389) treated with BamHI and PstI by using In Fusion HD Cloning Kit (Clontech). With this DNA, competent cells of *Escherichia coli* JM109 (Takara Bio) were transformed, and the cells were applied to the LB medium containing 100 μM IPTG, 40 μg/mL of X-Gal, and 40 µg/mL of kanamycin, and cultured overnight. Then, white colonies that appeared were picked up, and separated into single colonies to obtain transformants. Plasmids were extracted from the obtained transformants, and one in which the target PCR product was inserted was designated as pBS4SΔ2256adhC.

<2-1-2> Construction of FKFC5 Strain (FKS0165ΔNCgl0324 Strain)

Since pBS4SΔ2256adhC obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4S42256adhC was introduced into the C. glutamicum FKS0165 strain by the electric pulse method. The cells were applied to the CM-Dex agar medium containing 25 µg/mL of kanamycin, and cultured at 31.5° C. It was confirmed by PCR that the grown strain was a once-recombinant strain in which pBS4S42256adhC was incorporated into the genome by homologous recombination. This once-recombinant strain had both the wild-type NCgl0324 gene, and the deficient type NCgl0324 gene.

The once-recombinant strain was cultured overnight in the CM-Dex liquid medium, the culture medium was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 25 and 26 as the primers to confirm deletion of the NCgl0324 gene, and the strain was designated as FKFC5 strain.

<2-2> Construction of FKFC11 Strain (2256ΔvanABKΔNCgl0324ΔNCgl0313 Strain)

<2-2-1> Construction of Plasmid pBS4SΔ2256adhE for Deletion of NCgl0313 Gene

PCR was performed by using the genomic DNA of the C. glutamicum 2256 strain as the template, and the synthetic DNAs of SEQ ID NOS: 27 and 28 as the primers to obtain a PCR product containing an N-terminus side coding region of the NCgl0313 gene. Separately, PCR was performed by using the genomic DNA of the C. glutamicum 2256 strain as the template, and the synthetic DNAs of SEQ ID NOS: 29 and 30 as the primers to obtain a PCR product containing a C-terminus side coding region of the NCgl0313 gene. The sequences of SEQ ID NOS: 28 and 29 are partially complementary to each other. Then, approximately equimolar amounts of the PCR product containing the N-terminus side coding region of the NCgl0313 gene and the PCR product containing the C-terminus side coding region of the NCgl0313 gene were mixed, and inserted into the pBS4S vector (WO2007/046389) treated with BamHI and PstI by using In Fusion HD Cloning Kit (Clontech). With this DNA, competent cells of Escherichia coli JM109 (Takara Bio) were transformed, and the cells were applied to the LB medium containing 100 µM IPTG, 40 µg/mL of X-Gal, and 40 µg/mL of kanamycin, and cultured overnight. Then, white colonies that appeared were picked up, and separated into single colonies to obtain transformants. Plasmids were extracted from the obtained transformants, and one in which the target PCR product was inserted was designated as pBS4SΔ2256adhE.

<2-2-2> Construction of FKFC11 Strain (2256ΔvanABKΔNCgl0324ΔNCgl0313 Strain)

Since pBS4SΔ2256adhE obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256adhE was introduced into the C. glutamicum FKFC5 strain by the electric pulse method. The cells were applied to the CM-Dex agar medium containing 25 µg/mL of kanamycin, and cultured at 31.5° C. It was confirmed by PCR that the grown strain was a once-recombinant strain in which pBS4SΔ2256adhE was incorporated into the genome by homologous recombination. This once-recombinant strain had both the wild-type NCgl0313 gene, and the deficient type NCgl0313 gene.

The once-recombinant strain was cultured overnight in the CM-Dex liquid medium, the culture medium was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 31 and 32 as the primers to confirm deletion of the NCgl0313 gene, and the strain was designated as FKFC11 strain.

<2-3> Construction of FKFC14 Strain (2256ΔvanABKΔNCgl0324ΔNCgl0313ΔNCgl2709 Strain)

<2-3-1> Construction of Plasmid pBS4SΔ2256adhA for Deletion of NCgl2709 Gene

PCR was performed by using the genomic DNA of the C. glutamicum 2256 strain as the template, and the synthetic DNAs of SEQ ID NOS: 33 and 34 as the primers to obtain a PCR product containing an N-terminus side coding region of the NCgl2709 gene. Separately, PCR was performed by using the genomic DNA of the C. glutamicum 2256 strain as the template, and the synthetic DNAs of SEQ ID NOS: 35 and 36 as the primers to obtain a PCR product containing a C-terminus side coding region of the NCgl2709 gene. The sequences of SEQ ID NOS: 34 and 35 are partially complementary to each other. Then, approximately equimolar amounts of the PCR product containing the N-terminus side coding region of the NCgl2709 gene and the PCR product containing the C-terminus side coding region of the NCgl2709 gene were mixed, and inserted into the pBS4S vector treated with BamHI and PstI by using In Fusion HD Cloning Kit (Clontech). With this DNA, competent cells of Escherichia coli JM109 (Takara Bio) were transformed, and the cells were applied to the LB medium containing 100 µM IPTG, 40 µg/mL of X-Gal, and 40 µg/mL of kanamycin, and cultured overnight. Then, white colonies that appeared were picked up, and separated into single colonies to obtain transformants. Plasmids were extracted from the obtained transformants, and one in which the target PCR product was inserted was designated as pBS4S42256adhA.

<2-3-2> Construction of FKFC14 Strain (2256ΔvanABKΔNCgl0324ΔNCgl0313ΔNCgl2709 Strain)

Since pBS4S42256adhA obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4S42256adhA was introduced into the C. glutamicum FKFC11 strain by the electric pulse method. The cells were applied to the CM-Dex agar medium containing 25 µg/mL of kanamycin, and cultured at 31.5° C. It was confirmed by PCR that the grown strain was a once-recombinant strain in which pBS4S42256adhA was incorporated into the genome by homologous recombination. This once-recombinant strain had both the wild-type NCgl2709 gene, and the deficient type NCgl2709 gene.

The once-recombinant strain was cultured overnight in the CM-Dex liquid medium, the culture medium was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 37 and 38 as the primers to confirm deletion of the NCgl2709 gene, and the strain was designated as FKFC14 strain.

<3> Construction of Vanillin-Producing Strain

<3-1> Construction of Plasmid pVS7::Plac-vanK for Expression of vanK Gene

The vanK gene encodes a vanillic acid uptake system. Thus, in order to improve the uptake of vanillic acid, a plasmid pVS7::Plac-vanK for expression of vanK gene of the *C. glutamicum* 2256 strain was constructed via the following procedure. The nucleotide sequence of the vanK gene of the *C. glutamicum* 2256 strain and the amino acid sequence of the VanK protein encoded by this gene are shown as SEQ ID NOS: 53 and 54, respectively.

PCR was performed by using the genomic DNA of the *C. glutamicum* 2256 strain as the template, and the synthetic DNAs of SEQ ID NOS: 39 and 40 as the primers to obtain a PCR product containing an ORF and SD sequence of the vanK gene. Then, the PCR product was inserted into the pVS7 vector (WO2013/069634) treated with BamHI and PstI using In Fusion HD Cloning Kit (Clontech). The pVS7 vector is a shuttle vector for coryneform bacteria and *E. coli*. By using this DNA, competent cells of *Escherichia coli* JM109 (Takara Bio) were transformed, and the cells were applied to the LB medium containing 100 μM IPTG, 40 μg/mL of X-Gal, and 50 μg/mL of spectinomycin, and cultured overnight. Then, white colonies that appeared were picked up, and separated into single colonies to obtain transformants. Plasmids were extracted from the obtained transformants, and one into which the target PCR product was inserted was designated as pVS7::Plac-vanK. In pVS7::Plac-vanK, the cloned vanK gene is expressed from lac promoter derived from the pVS7 vector.

<3-2> Introduction of pVK9::Ptuf-Car+entD and pVS7::Plac-vanK pVS7::Plac-vanK, and pVK9 or pVK9::Ptuf-car+entD were introduced into the *C. glutamicum* FKFC14 strain by the electric pulse method. The cells were applied to the CM-Dex agar medium containing 25 μg/ml of kanamycin and 50 μg/mL of spectinomycin, and cultured at 31.5° C. The grown strains were purified on the same agar medium, and designated as FKFC14/pVS7::Plac-vanK+pVK9 strain, and FKFC14/pVS7::Plac-vanK+pVK9::Ptuf-car+entD strain, respectively.

<4> Effect of Deletion of NCgl2709, NCgl0324, and NCgl0313 Genes on Vanillin Production The cells of the FKFC14/pVS7::Plac-vanK+pVK9 strain, and the FKFC14/pVS7::Plac-vanK+pVK9::Ptuf-car+entD strain obtained by the culture on the CM-Dex agar medium were each inoculated into 4 mL of the CM-Dex medium containing 50 μg/mL of spectinomycin, 25 μg/ml of kanamycin, 2.5 g/L of fructose, 2 g/L of succinic acid, and 4 g/L of gluconic acid contained in a test tube, and cultured at 31.5° C. with shaking for about 16 hours as preculture. The whole volume of the obtained preculture broth was added to 200 ml of the CM-Dex medium containing 2.5 g/L of fructose, 2 g/L of succinic acid, and 4 g/L of gluconic acid contained in a Sakaguchi flask, culture was performed at 31.5° C. with shaking under an aerobic condition until OD at 600 nm became 0.625. Then, the obtained culture broth was centrifuged at 7000 rpm for 5 minutes, the supernatant was removed, and the cells were washed with sterilized physiological saline. Then, 1.5 ml of the sterilized physiological saline was added to the cells, and the cells were suspended in it. The whole volume of the suspension was mixed with 3.5 ml of a vanillin production medium (12 g/L of vanillic acid, 40 g/L of glucose, 100 mM $Na_2HPO_4$-$12H_2O$, 100 mM TES buffer (adjusted to pH 6.6 with KOH), 30 g/L of $CaCO_3$ (sterilized with hot air at 180° C. for 3 hours and then mixed), and culture was performed at 30° C. for about 20 hours with shaking.

After completion of the culture, the concentration of the residual glucose in the medium was analyzed with Biotech Analyzer AS-310 (Sakura SI). The amounts of vanillic acid and vanillin in the medium were also analyzed by using Ultra Performance Liquid Chromatography NEXERA X2 System (SHIMADZU) with the following conditions. The cell density (OD) was measured by using a spectrophotometer U-2900 (HITACHI).

Conditions of UPLC Analysis

Column: KINETEX 2.6 μm XB-C18, 150×30 mm (Phenomenex)

Oven temperature: 40° C.

Mobile phase (A): 0.1% Trifluoroacetic acid

Mobile phase (B): 0.1% Trifluoroacetic acid/80% acetonitrile

Gradient program (time, A (%), B (%)): (0, 90, 10)→(3, 80, 20)

Flow rate: 1.5 ml/min

The results are shown in Table 2. The FKFC14/pVS7::Plac-vanK+pVK9 strain as the control did not generate vanillin, but the FKFC14/pVS7::Plac-vanK+pVK9::Ptuf-car+entD strain, in which ACAR gene and entD gene were amplified, accumulated about 10 g/L of vanillin, which means that the vanillin accumulation amount was markedly improved compared with using *E. coli* as the host (Reference Example). Furthermore, by-production of vanillyl alcohol was not detected at all for either of the FKFC14/pVS7::Plac-vanK+pVK9 strain and the FKFC14/pVS7::Plac-vanK+pVK9::Ptuf-car+entD strain, which were deficient in the alcohol dehydrogenase homologue genes, NCgl2709 gene, NCgl0324 gene, and NCgl0313 gene. On the basis of the above results, it was revealed that (1) in coryneform bacteria, one or more of the NCgl2709 gene, NCgl0324 gene, and NCgl0313 gene encode an enzyme for conversion from vanillin to vanillyl alcohol, and deletion of these genes eliminates by-production of vanillyl alcohol, and (2) coryneform bacteria have a high vanillin-producing ability.

TABLE 2

Vanillin production by ADH-gene deficient strains of *C. glutamicum*

| Strain | Consumed glucose (g/L) | Consumed vanillic acid (g/L) | Generated vanillin (g/L) | Generated vanillyl alcohol (g/L) |
|---|---|---|---|---|
| FKFC14/ pVS7::Plac-vanK + pVK9 | 38 ± 0.00 | 0.20 ± 0.15 | 0.00 ± 0.00 | N.D.* |
| FKFC14/ pVS7::Plac-vanK + pVK9::Ptuf-car + entD | 34 ± 0.57 | 11 ± 0.13 | 9.6 ± 0.19 | N.D. |

N.D.: not detected

Example 4: Identification of Gene Involved in Vanillyl Alcohol Production

Then, in order to identify the gene involved in vanillyl alcohol production among NCgl0324, NCgl0313, and NCgl2709 genes, single-gene-deletion strains and double-gene-deletion strains were constructed.

<1> Construction of Strains Deficient in Alcohol Dehydrogenase Homologue Gene(s)

<1-1> Construction of FKFC1 Strain (2256ΔvanABKΔNCgl0313)

Since pBS4SΔ2256adhE obtained above (Example 3 <2-2-1>) does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256adhE was introduced into the *C. glutamicum* FKS0165 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4SΔ2256adhE was incorporated into the genome by homologous recombination. This once-recombinant strain had both the wild-type NCgl0313 gene, and the deficient type NCgl0313 gene.

The once-recombinant strain was cultured overnight in the CM-Dex liquid medium, the culture medium was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 31 and 32 as the primers to confirm deletion of the NCgl0313 gene, and the strain was designated as FKFC1 strain.

<1-2> Construction of FKFC3 Strain (2256ΔvanABKΔNCgl2709)

Since pBS4SΔ2256adhA obtained above (Example 3 <2-3-1>) does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256adhA was introduced into the *C. glutamicum* FKS0165 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4SΔ2256adhA was incorporated into the genome by homologous recombination. This once-recombinant strain had both the wild-type NCgl2709 gene, and the deficient type NCgl2709 gene.

The once-recombinant strain was cultured overnight in the CM-Dex liquid medium, the culture medium was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 37 and 38 as the primers to confirm deletion of the NCgl2709 gene, and the strain was designated as FKFC3 strain.

<1-3> Construction of FKFC7 Strain (2256ΔvanABKΔNCgl0324ΔNCgl2709)

Since pBS4SΔ2256adhA obtained above (Example 3 <2-3-1>) does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4S42256adhA was introduced into the *C. glutamicum* FKFC5 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4S42256adhA was incorporated into the genome by homologous recombination. This once-recombinant strain had both the wild-type NCgl2709 gene, and the deficient type NCgl2709 gene.

The once-recombinant strain was cultured overnight in the CM-Dex liquid medium, the culture medium was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 37 and 38 as the primers to confirm deletion of the NCgl2709 gene, and the strain was designated as FKFC7 strain.

<1-4> Construction of FKFC9 Strain (2256ΔvanABKΔNCgl2709ΔNCgl0313)

Since pBS4SΔ2256adhE obtained above (Example 3 <2-2-1>) does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256adhE was introduced into the *C. glutamicum* FKFC3 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4SΔ2256adhE was incorporated into the genome by homologous recombination. This once-recombinant strain had both the wild-type NCgl0313 gene, and the deficient type NCgl0313 gene.

The once-recombinant strain was cultured overnight in the CM-Dex liquid medium, the culture medium was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 31 and 32 as the primers to confirm deletion of the NCgl0313 gene, and the strain was designated as FKFC9 strain.

<2> Vanillyl Alcohol Production Experiment

The *C. glutamicum* FKS0165, FKFC1, FKFC3, FKFC5, FKFC7, FKFC9, FKFC11, and FKFC14 strains were each cultured in the presence of vanillin, and the generation amount of vanillyl alcohol was determined, to thereby identify the gene involved in vanillyl alcohol production.

The culture was performed using CM2B liquid medium containing 1 g/L of vanillin at 30° C. for about 24 hours.

After the completion of the culture, the amounts of vanillin and vanillyl alcohol in the medium were analyzed by using Ultra Performance Liquid Chromatography NEXERA X2 System (SHIMADZU) with the following conditions. The cell density (OD) was measured by using a spectrophotometer U-2900 (HITACHI).

Figure 5:
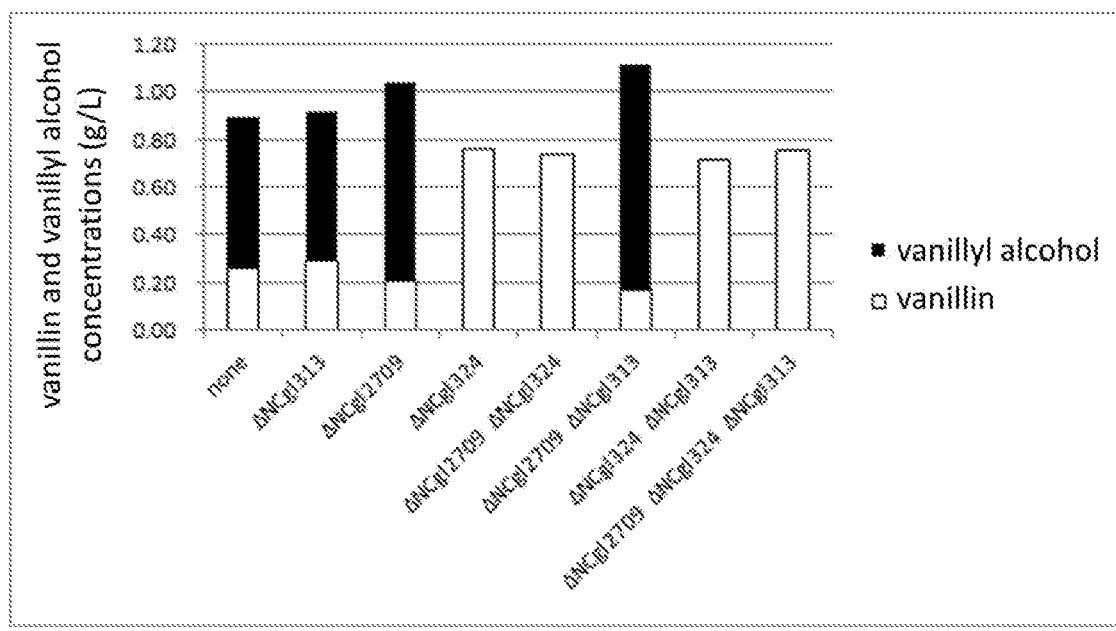
FIG. 5 shows results of an evaluation of vanillyl alcohol production from vanillin by coryneform bacterium strains deficient in alcohol dehydrogenase gene homologue(s).

Conditions of UPLC Analysis
Column: KINETEX 2.6 µm XB-C18, 150×30 mm (Phenomenex)
Oven temperature: 40° C.
Mobile phase (A): 0.1% Trifluoroacetic acid
Mobile phase (B): 0.1% Trifluoroacetic acid/80% acetonitrile
Gradient program (time, A (%), B (%)): (0, 90, 10)→(3, 80, 20)
Flow rate: 1.5 ml/min As a result, vanillyl alcohol was not detected at all only for NCgl0324-deficient strains (FIG. 5). From the result, it was revealed that NCgl0324 gene is involved in conversion from vanillin to vanillyl alcohol.

Example 5: Benzaldehyde Production and Cinnamaldehyde Production by ADH Gene-Deficient Strains of *Corynebacterium glutamicum*

In this example, benzaldehyde production and cinnamaldehyde production were performed with the ADH gene-deficient strains of *Corynebacterium glutamicum*.

<1> Construction of Aromatic Aldehyde-Producing Strains
<1-1> Construction of Plasmids for Co-Expression of ACAR and PPT Genes A plasmid pVK9::Ptuf*-Ge_ACAR-entD for co-expression of ACAR gene of *Gordonia effusa* (Ge_ACAR, codon-optimized) and PPT gene (entD) of *Escherichia coli* was constructed via the following procedure.

The pVK9 vector (WO2007/046389) was treated with BamHI and PstI, and inserted with a DNA fragment that includes an artificial operon consisting of Tuf* promoter, SD sequence, Ge_ACAR (codon-optimized), SD sequence, and *E. coli* entD gene in this order, to obtain the plasmid pVK9::Ptuf*-Ge_ACAR-entD. The nucleotide sequence of a part containing the inserted DNA fragment of this plasmid is shown as SEQ ID NO: 99, wherein the inserted DNA fragment corresponds to position 16-4517. Ge_ACAR (codon-optimized) has been codon-optimized for the codon usage of *E. coli*. The nucleotide sequence of Ge_ACAR (codon-optimized) is shown as SEQ ID NO: 100.

<1-2> Construction of Aromatic Aldehyde-Producing Strains

The plasmid pVK9::Ptuf*-Ge_ACAR-entD and the plasmid pVS7::Plac-vanK were introduced into the *C. glutamicum* FKS0165, FKFC1, FKFC3, FKFC5, FKFC7, FKFC9, FKFC11, and FKFC14 strains by the electric pulse method.

The cells were applied to the CM-Dex SGFC agar medium (2.5 g/L of glucose, 2.5 g/L of fructose, 10 g/L of polypeptone, 10 g/L of yeast extract, 1 g/L of $KH_2PO_4$, 0.4 g/L of $MgSO_4$-$7H_2O$, 0.01 g/L of $FeSO_4$-$7H_2O$, 0.01 g/L of $MnSO_4$-$4$-$5H_2O$, 2 g/L of disodium succinate hexahydrate, 4 g/L of sodium gluconate, 3 g/L of urea, 1.2 g/L of soybean hydrolysate, 10 µg/L of biotin, 15 g/L of agar, adjusted to pH 7.5 with NaOH) containing 25 µg/mL of kanamycin and 50 µg/mL of spectinomycin, and cultured at 31.5° C. The grown strains were purified on the same agar medium, and designated as FKS0165/pVK9::Ptuf*-Ge_ACAR-entD pVS7-vanK, FKFC1/pVK9::Ptuf*-Ge_ACAR-entD pVS7-vanK, FKFC3/pVK9::Ptuf*-Ge_ACAR-entD pVS7-vanK, FKFC5/pVK9::Ptuf*-Ge_ACAR-entD pVS7-vanK, FKFC7/pVK9::Ptuf*-Ge_ACAR-entD pVS7-vanK, FKFC9/pVK9::Ptuf*-Ge_ACAR-entD pVS7-vanK, FKFC11/pVK9::Ptuf*-Ge_ACAR-entD pVS7-vanK, and FKFC14/pVK9::Ptuf*-Ge_ACAR-entD pVS7-vanK, respectively. These strains were each inoculated into 4 mL of the CM-Dex SGFC medium (having the same composition as that of the CM-Dex SGFC agar medium except that it does not contain agar) containing 25 µg/mL of kanamycin and 50 µg/mL of spectinomycin, contained in a test tube, and cultured at 31.5° C. with shaking for about 16 hr. A 0.75 mL aliquot of the obtained culture broth was mixed with 0.75 mL of 40% glycerol aqueous solution to obtain a glycerol stock, and stored at −80° C.

<2> Comparison of Benzaldehyde Production Amount for ADH Gene-Deficient Strains of *Corynebacterium glutamicum*

A 20 µL aliquot of each of the glycerol stocks of the constructed aromatic aldehyde-producing strains was applied to the CM-Dex SGFC agar medium containing 25 µg/mL of kanamycin and 50 µg/mL of spectinomycin, and cultured at 31.5° C. for 20 hr as preculture. The obtained cells were suspended in sterilized physiological saline. The optical density (OD) of the cell suspension was measured, and the cell suspension was diluted with physiological saline to obtain an OD at 600 nm of 83. A 1.5 mL aliquot of the diluted cell suspension was inoculated into 3.5 mL of a benzaldehyde production medium (14.3 g/L of benzoic acid, 85.7 g/L of glucose, 10 g/L of polypeptone, 10 g/L of yeast extract, 1 g/L of $KH_2PO_4$, 0.4 g/L of $MgSO_4$-$7H_2O$, 0.01 g/L of $FeSO_4$-$7H_2O$, 0.01 g/L of $MnSO_4$-$4$-$5H_2O$, 3 g/L of urea, 1.2 g/L of soybean hydrolysate, 10 µg/L of biotin, adjusted to pH 7.4 with KOH, and then mixed with 8.6 g/L of $CaCO_3$ (sterilized with hot air at 180° C. for 3 hours)) containing 25 µg/mL of kanamycin and 50 µg/mL of spectinomycin contained in a test tube, and cultured at 30° C. with shaking for 4 hr.

At the start and completion of the culture, the concentration of glucose in the medium was analyzed with Biotech Analyzer AS-310 (Sakura SI). The concentrations of benzoic acid, benzaldehyde, and benzyl alcohol in the medium were also analyzed by using High Performance Liquid Chromatography GL7700 System (GL Science) with the following conditions.

Conditions of HPLC Analysis
Column: CAPCELL PAK C18 MG II 3 µm, 150×4.6 mm (SHISEIDO)
Oven temperature: 40° C.
Mobile phase (A): 10 mM $K_2HPO_4$/10 mM $KH_2PO_4$
Mobile phase (B): 100% acetonitrile
Gradient program (time, A (%), B (%)): (0, 98, 2)→(2, 98, 2)→(16, 50, 50)→(16.01, 98, 2)
Flow rate: 1 ml/min The results are shown in Table 3. An increased production amount of benzaldehyde was observed for the strains deficient in either of NCgl0324 and NCgl2709 genes, for example, FKFC3/pVK9::Ptuf*-Ge_ACAR-entD pVS7-vanK, FKFC5/pVK9::Ptuf*-Ge_ACAR-entD pVS7-vanK, FKFC9/pVK9::Ptuf*-Ge_ACAR-entD pVS7-vanK, and FKFC11/pVK9::Ptuf*-Ge_ACAR-entD pVS7-vanK, as compared with the control strain FKS0165/pVK9::Ptuf*-Ge_ACAR-entD pVS7-vanK. In addition, a further increased production amount of benzaldehyde and a reduced production amount of benzyl alcohol were observed for the strains deficient in both NCgl0324 and NCgl2709 genes, for example, FKFC7/pVK9::Ptuf*-Ge_ACAR-entD pVS7-vanK and FKFC14/pVK9::Ptuf*-Ge_ACAR-entD pVS7-vanK. From these results, it was revealed that NCgl0324 and NCgl2709 genes are involved in conversion from benzaldehyde to benzyl alcohol.

optical density (OD) of the cell suspension was measured, and the cell suspension was diluted with physiological saline to obtain an OD at 600 nm of 83. A 1.5 mL aliquot of the diluted cell suspension was inoculated into 3.5 mL of a cinnamaldehyde production medium (14.3 g/L of cinnamic acid, 85.7 g/L of glucose, 10 g/L of polypeptone, 10 g/L of yeast extract, 1 g/L of $KH_2PO_4$, 0.4 g/L of $MgSO_4$-$7H_2O$, 0.01 g/L of $FeSO_4$-$7H_2O$, 0.01 g/L of $MnSO_4$-$4$-$5H_2O$, 3 g/L of urea, 1.2 g/L of soybean hydrolysate, 10 µg/L of biotin, adjusted to pH 7.4 with KOH, and then mixed with 8.6 g/L of $CaCO_3$ (sterilized with hot air at 180° C. for 3 hours)) containing 25 µg/mL of kanamycin and 50 µg/mL of spectinomycin contained in a test tube, and statically incubated at the room temperature for 5 min.

After the completion of the incubation, the concentration of glucose in the medium was analyzed with Biotech Analyzer AS-310 (Sakura SI). The concentrations of cinnamic acid, cinnamaldehyde, and cinnamyl alcohol in the medium were also analyzed by using Ultra Performance Liquid Chromatography NEXERA X2 System (SHIMADZU) with the following conditions.

Conditions of UPLC Analysis
Column: KINETEX 2.6 µm Biphenyl, 100×3.0 mm (Phenomenex)
Oven temperature: 40° C.
Mobile phase (A): sodium phosphate buffer pH2.6 (10 mM $PO_4^{3-}$)
Mobile phase (B): methanol
Gradient program (time, A (%), B (%)): (0, 75, 25)→(8, 35, 65)
Flow rate: 1 ml/min The results are shown in Table 4. An increased production amount of cinnamaldehyde was observed for the strains deficient in either of NCgl0324 and NCgl2709 genes, for

TABLE 3

Benzaldehyde production by ADH-gene deficient strains of *C. glutamicum*

| Strain | Consumed glucose (g/L) | Consumed benzoic acid (g/L) | Generated benz-aldehyde (g/L) | Generated benzyl alcohol (g/L) |
|---|---|---|---|---|
| FKS0165/pVK9::Ptuf*-Ge_ACAR-entD pVS7-vanK | 7.70 ± 0.33 | 2.6 ± 0.00 | 0.18 ± 0.00 | 1.93 ± 0.05 |
| FKFC1/pVK9::Ptuf*-Ge_ACAR-entD pVS7-vanK | 6.01 ± 1.24 | 2.59 ± 0.15 | 0.16 ± 0.00 | 1.76 ± 0.01 |
| FKFC3/pVK9::Ptuf*-Ge_ACAR-entD pVS7-vanK | 7.47 ± 0.82 | 2.99 ± 0.52 | 0.34 ± 0.00 | 2.11 ± 0.06 |
| FKFC5/pVK9::Ptuf*-Ge_ACAR-entD pVS7-vanK | 7.64 ± 0.25 | 2.83 ± 0.05 | 0.32 ± 0.00 | 1.75 ± 0.03 |
| FKFC7/pVK9::Ptuf*-Ge_ACAR-entD pVS7-vanK | 6.36 ± 0.41 | 1.49 ± 0.30 | 0.95 ± 0.01 | 0.01 ± 0.00 |
| FKFC9/pVK9::Ptuf*-Ge_ACAR-entD pVS7-vanK | 7.88 ± 0.08 | 3.52 ± 0.03 | 0.34 ± 0.01 | 2.24 ± 0.08 |
| FKFC11/pVK9::Ptuf*-Ge_ACAR-entD pVS7-vanK | 8.28 ± 0.82 | 3.29 ± 0.05 | 0.41 ± 0.00 | 1.93 ± 0.02 |
| FKFC14/pVK9::Ptuf*-Ge_ACAR-entD pVS7-vanK | 6.65 ± 0.99 | 2.04 ± 0.23 | 1.1 ± 0.01 | 0.01 ± 0.00 |

<3> Comparison of Cinnamaldehyde Production Amount for ADH Gene-Deficient Strains of *Corynebacterium glutamicum*

A 20 µL aliquot of each of the glycerol stocks of the constructed aromatic aldehyde-producing strains was applied to the CM-Dex SGFC agar medium containing 25 µg/mL of kanamycin and 50 µg/mL of spectinomycin, and cultured at 31.5° C. for 20 hr as preculture. The obtained cells were suspended in sterilized physiological saline. The example, FKFC3/pVK9::Ptuf*-Ge_ACAR-entD pVS7-vanK, FKFC5/pVK9::Ptuf*-Ge_ACAR-entD pVS7-vanK, FKFC9/pVK9::Ptuf*-Ge_ACAR-entD pVS7-vanK, and FKFC11/pVK9::Ptuf*-Ge_ACAR-entD pVS7-vanK, as compared with the control strain FKS0165/pVK9::Ptuf*-Ge_ACAR-entD pVS7-vanK. In addition, a further increased production amount of cinnamaldehyde and a reduced production amount of cinnamyl alcohol were observed for the strains deficient in both NCgl0324 and NCgl2709 genes, for example, FKFC7/pVK9::Ptuf*-

Ge_ACAR-entD pVS7-vanK and FKFC14/pVK9::Ptuf*-Ge_ACAR-entD pVS7-vanK. From these results, it was revealed that NCgl0324 and NCgl2709 genes are involved in conversion from cinnamaldehyde to cinnamyl alcohol.

TABLE 4

Cinnamaldehyde production by ADH-gene deficient strains of *C. glutamicum*

| Strain | Residual glucose (g/L) | Residual cinnamic acid (g/L) | Generated cinnamaldehyde (mg/L) | Generated cinnamyl alcohol (mg/L) |
|---|---|---|---|---|
| FKS0165/pVK9::Ptuf*-Ge_ACAR-entD pVS7-vanK | 60.55 ± 0.00 | 8.52 ± 0.22 | 5.11 ± 0.32 | 41.11 ± 4.46 |
| FKFC1/pVK9::Ptuf*-Ge_ACAR-entD pVS7-vanK | 61.60 ± 1.48 | 8.61 ± 0.08 | 5.87 ± 0.27 | 42.04 ± 0.04 |
| FKFC3/pVK9::Ptuf*-Ge_ACAR-entD pVS7-vanK | 60.03 ± 0.25 | 8.49 ± 0.06 | 37.34 ± 0.62 | 8.48 ± 0.26 |
| FKFC5/pVK9::Ptuf*-Ge_ACAR-entD pVS7-vanK | 61.25 ± 0.99 | 8.71 ± 0.13 | 8.25 ± 0.26 | 52.32 ± 1.46 |
| FKFC7/pVK9::Ptuf*-Ge_ACAR-entD pVS7-vanK | 59.85 ± 0.49 | 8.92 ± 0.23 | 52.27 ± 0.8 | 3.80 ± 0.00 |
| FKFC9/pVK9::Ptuf*-Ge_ACAR-entD pVS7-vanK | 60.38 ± 0.74 | 8.99 ± 0.07 | 41.05 ± 0.35 | 9.38 ± 1.13 |
| FKFC11/pVK9::Ptuf*-Ge_ACAR-entD pVS7-vanK | 61.43 ± 0.25 | 8.50 ± 0.28 | 9.62 ± 0.46 | 59.97 ± 0.89 |
| FKFC14/pVK9::Ptuf*-Ge_ACAR-entD pVS7-vanK | 61.43 ± 1.24 | 8.37 ± 0.01 | 66.84 ± 0.76 | 3.63 ± 0.20 |

According to the present invention, an ability of coryneform bacteria for producing an objective substance, for example, an aromatic aldehyde such as vanillin, can be improved, and the objective substance can be efficiently produced. Particularly, according to the present invention, the objective substance may be efficiently produced without using means for alleviating the toxicity of the objective substance such as double layer fermentation and resins.

EXPLANATION OF SEQUENCE LISTING

SEQ ID NOS: 1 to 40: Primers
41 to 44: Nucleotide sequences of transcript variants 1 to 4 of OMT gene of *Homo sapiens*
45: Amino acid sequence of OMT isoform (MB-COMT) of *Homo sapiens*
46: Amino acid sequence of OMT isoform (S-COMT) of *Homo sapiens*
47: Nucleotide sequence of variant ACAR gene of *Nocardia brasiliensis*
48: Amino acid sequence of variant ACAR protein of *Nocardia brasiliensis*
49: Nucleotide sequence of entD gene of *Escherichia coli* MG1655
50: Amino acid sequence of EntD protein of *Escherichia coli* MG1655
51: Nucleotide sequence of PPT gene of *C. glutamicum* ATCC 13032
52: Amino acid sequence of PPT protein of *C. glutamicum* ATCC 13032
53: Nucleotide sequence of vanK gene of *C. glutamicum* ATCC 13869 (*C. glutamicum* 2256)
54: Amino acid sequence of VanK protein of *C. glutamicum* ATCC 13869 (*C. glutamicum* 2256)
55: Nucleotide sequence of pcaK gene of *C. glutamicum* ATCC 13869 (*C. glutamicum* 2256)
56: Amino acid sequence of PcaK protein of *C. glutamicum* ATCC 13869 (*C. glutamicum* 2256)
57: Nucleotide sequence of vanA gene of *C. glutamicum* ATCC 13869 (*C. glutamicum* 2256)
58: Amino acid sequence of VanA protein of *C. glutamicum* ATCC 13869 (*C. glutamicum* 2256)
59: Nucleotide sequence of vanB gene of *C. glutamicum* ATCC 13869 (*C. glutamicum* 2256)
60: Amino acid sequence of VanB protein of *C. glutamicum* ATCC 13869 (*C. glutamicum* 2256)
61: Nucleotide sequence of pcaG gene of *C. glutamicum* ATCC 13032
62: Amino acid sequence of PcaG protein of *C. glutamicum* ATCC 13032
63: Nucleotide sequence of pcaH gene of *C. glutamicum* ATCC 13032
64: Amino acid sequence of PcaH protein of *C. glutamicum* ATCC 13032
65: Nucleotide sequence of NCgl0324 gene of *C. glutamicum* ATCC 13869 (*C. glutamicum* 2256)
66: Amino acid sequence of NCgl0324 protein of *C. glutamicum* ATCC 13869 (*C. glutamicum* 2256)
67: Nucleotide sequence of NCgl0313 gene of *C. glutamicum* ATCC 13869 (*C. glutamicum* 2256)
68: Amino acid sequence of NCgl0313 protein of *C. glutamicum* ATCC 13869 (*C. glutamicum* 2256)
69: Nucleotide sequence of NCgl2709 gene of *C. glutamicum* ATCC 13869 (*C. glutamicum* 2256)
70: Amino acid sequence of NCgl2709 protein of *C. glutamicum* ATCC 13869 (*C. glutamicum* 2256)
71: Nucleotide sequence of NCgl0219 gene of *C. glutamicum* ATCC 13032
72: Amino acid sequence of NCgl0219 protein of *C. glutamicum* ATCC 13032
73: Nucleotide sequence of NCgl2382 gene of *C. glutamicum* ATCC 13032
74: Amino acid sequence of NCgl2382 protein of *C. glutamicum* ATCC 13032
75: Nucleotide sequence of ACAR gene of *Nocardia brasiliensis*
76: Amino acid sequence of ACAR protein of *Nocardia brasiliensis*
77: Nucleotide sequence of ACAR gene homologue of *Nocardia brasiliensis*, fragment
78: Amino acid sequence of ACAR homologue of *Nocardia brasiliensis*, fragment 79: Nucleotide sequence of codon-optimized variant ACAR gene of *Nocardia brasiliensis* flanked by NdeI and SacI
80: pELAC vector
81 to 84: primers
85: Nucleotide sequence of aroG gene of *Escherichia coli* MG1655
86: Amino acid sequence of AroG protein of *Escherichia coli* MG1655
87: Nucleotide sequence of aroB gene of *Escherichia coli* MG1655
88: Amino acid sequence of AroB protein of *Escherichia coli* MG1655
89: Nucleotide sequence of aroD gene of *Escherichia coli* MG1655
90: Amino acid sequence of AroD protein of *Escherichia coli* MG1655
91: Nucleotide sequence of asbF gene of *Bacillus thuringiensis* BMB171
92: Amino acid sequence of AsbF protein of *Bacillus thuringiensis* BMB171
93: Nucleotide sequence of tyrR gene of *Escherichia coli* MG1655
94: Amino acid sequence of TyrR protein of *Escherichia coli* MG1655
95: Nucleotide sequence of OMT gene of *Niastella koreensis*
96: Amino acid sequence of OMT of *Niastella koreensis*
97: Nucleotide sequence of ACAR gene of *Gordonia effusa*
98: Amino acid sequence of ACAR protein of *Gordonia effusa*
99: Nucleotide sequence of DNA fragment containing ACAR gene of *Gordonia effusa* (codon-optimized) and entD gene of *Escherichia coli*
100: Nucleotide sequence of ACAR gene of *Gordonia effusa* codon-optimized for codon usage of *E. coli*
101: Nucleotide sequence of aroE gene of *Escherichia coli* MG1655
102: Amino acid sequence of AroE protein of *Escherichia coli* MG1655

The invention claimed is:

1. A method for producing an objective substance, the method comprising using a coryneform bacterium having an ability to produce an objective substance,
wherein said bacterium has been modified so that the activity of alcohol dehydrogenase is reduced as compared with a non-modified bacterium,
wherein the objective substance is an aldehyde selected from the group consisting of vanillin, benzaldehyde, cinnamaldehyde, and combinations thereof,
wherein the alcohol dehydrogenase is a protein encoded by a NCgl0324 gene, and
wherein the protein encoded by the NCgl0324 gene is selected from the group consisting of:
(a) a protein comprising the amino acid sequence of SEQ ID NO: 66;
(b) a protein comprising the amino acid sequence of SEQ ID NO: 66 but including substitution, deletion, insertion, addition, or a combination thereof of 1 to 10 amino acid residues, and wherein said protein has alcohol dehydrogenase activity;
(c) a protein comprising an amino acid sequence having an identity of 90% or higher to the amino acid sequence of SEQ ID NO: 66, and wherein said protein has alcohol dehydrogenase activity; and
(d) combinations thereof.

2. The method according to claim 1, wherein the coryneform bacterium is *Corynebacterium glutamicum*.

3. The method according to claim 1, wherein the bacterium has been further modified so that the activity of a protein encoded by a NCgl2709 gene is reduced as compared with a non-modified bacterium, and wherein the protein encoded by the NCgl2709 gene is selected from the group consisting of:
(a) a protein comprising the amino acid sequence of SEQ ID NO: 70;
(b) a protein comprising the amino acid sequence of SEQ ID NO: 70 but including substitution, deletion, insertion, addition, or a combination thereof of 1 to 10 amino acid residues, and wherein said protein has alcohol dehydrogenase activity;
(c) a protein comprising an amino acid sequence having an identity of 90% or higher to the amino acid sequence of SEQ ID NO: 70, and wherein said protein has alcohol dehydrogenase activity.

4. The method according to claim 1, wherein said activity of the alcohol dehydrogenase is reduced by reducing the expression of a gene encoding the alcohol dehydrogenase, or by disrupting the gene.

5. The method according to claim 1, wherein the bacterium has been further modified so that the activity of an enzyme that is involved in the biosynthesis of the objective substance is increased as compared with a non-modified bacterium.

6. The method according to claim 5, wherein the enzyme that is involved in the biosynthesis of the objective substance catalyzes the conversion from a precursor of the objective substance into the objective substance.

7. The method according to claim 5, wherein the enzyme that is involved in the biosynthesis of the objective substance is selected from the group consisting of 3-deoxy-D-arabino-heptulosonic acid 7-phosphate synthase, 3-dehydroquinate synthase, 3-dehydroquinate dehydratase, 3-dehydroshikimate dehydratase, O-methyltransferase, aromatic carboxylic acid reductase, phenylalanine ammonia lyase, and combinations thereof.

8. The method according to claim 7, wherein the aromatic carboxylic acid reductase is selected from the group consisting of:
(a) a protein comprising the amino acid sequence of SEQ ID NO: 98;
(b) a protein comprising the amino acid sequence of SEQ ID NO: 98 but wherein said amino acid sequence can include substitution, deletion, insertion, addition, or a combination thereof of 1 to 10 amino acid residues, and wherein said protein has aromatic carboxylic acid reductase activity;
(c) a protein comprising an amino acid sequence having an identity of 90% or higher to the amino acid sequence of SEQ ID NO: 98, and wherein said protein has aromatic carboxylic acid reductase activity.

9. The method according to claim 1, wherein the bacterium has been further modified so that the activity of phosphopantetheinyl transferase is increased as compared with a non-modified bacterium.

10. The method according to claim 9, wherein the phosphopantetheinyl transferase is selected from the group consisting of:
   (a) a protein comprising the amino acid sequence of SEQ ID NO: 52;
   (b) a protein comprising the amino acid sequence of SEQ ID NO: 52 but wherein said amino acid sequence can include substitution, deletion, insertion, and/or addition of 1 to 10 amino acid residues, and wherein said protein has phosphopantetheinyl transferase activity;
   (c) a protein comprising an amino acid sequence having an identity of 90% or higher to the amino acid sequence of SEQ ID NO: 52, and wherein said protein has phosphopantetheinyl transferase activity.

11. The method according to claim 1, wherein the bacterium has been further modified so that the activity of an uptake system of a substance other than the objective substance is increased as compared with a non-modified bacterium, and wherein the uptake system has a function of incorporating the substance from the outside of the bacterium into the bacterium.

12. The method according to claim 11, wherein the uptake system is selected from the group consisting of a vanillic acid uptake system, a protocatechuic acid uptake system, and a combination thereof.

13. The method according to claim 12, wherein the vanillic acid uptake system is a protein selected from the group consisting of:
   (a) a protein comprising the amino acid sequence of SEQ ID NO: 54;
   (b) a protein comprising the amino acid sequence of SEQ ID NO: 54 but including substitution, deletion, insertion, addition, or combinations thereof of 1 to 10 amino acid residues, and wherein said protein has vanillic acid uptake activity;
   (c) a protein comprising an amino acid sequence having an identity of 90% or higher to the amino acid sequence of SEQ ID NO: 54, and wherein said protein has vanillic acid uptake activity.

14. The method according to claim 1, wherein the bacterium has been further modified so that the activity of an enzyme that is involved in the production of a substance other than the objective substance is reduced as compared with a non-modified bacterium.

15. The method according to claim 14, wherein the enzyme that is involved in the production of a substance other than the objective substance is selected from the group consisting of vanillate demethylase, protocatechuate 3,4-dioxygenase, shikimate dehydrogenase, and combinations thereof.

16. The method according to claim 15, wherein the vanillate demethylase is a protein selected from the group consisting of:
   (a) a protein comprising the amino acid sequence of SEQ ID NO: 58 or 60;
   (b) a protein comprising the amino acid sequence of SEQ ID NO: 58 or 60 but including substitution, deletion, insertion, addition, or combinations thereof of 1 to 10 amino acid residues, and wherein said protein has vanillate demethylase activity;
   (c) a protein comprising an amino acid sequence having an identity of 90% or higher to the amino acid sequence of SEQ ID NO: 58 or 60, and wherein said protein has vanillate demethylase activity.

17. The method according to claim 1, wherein the coryneform bacterium belongs to the genus *Corynebacterium*.

18. The method according to claim 1, wherein said using comprises cultivating the bacterium in a culture medium or reaction mixture, wherein said culture medium or reaction mixture comprises a carbon source so that the objective substance is produced and accumulates in the culture medium or reaction mixture.

19. The method according to claim 1, wherein a precursor of the objective substance is converted into the objective substance.

20. The method according to claim 19, wherein said using comprises cultivating the bacterium in a culture medium or reaction mixture, wherein said culture medium or reaction mixture comprises the precursor so that the objective substance is produced and accumulates in the culture medium or reaction mixture.

21. The method according to claim 19, wherein said precursor is converted into the objective substance by allowing cells of the bacterium to act on the precursor in a reaction mixture so that the objective substance is produced and accumulates in the reaction mixture.

22. The method according to claim 21, wherein the cells are present in a culture medium, collected from a culture medium, a processed product of a culture medium, or combinations thereof.

23. The method according to claim 19, wherein the precursor is selected from the group consisting of protocatechuic acid, vanillic acid, benzoic acid, L-phenylalanine, cinnamic acid and combinations thereof.

24. The method according to claim 1, the method further comprising collecting the objective substance from a culture medium or reaction mixture comprising the bacterium.

* * * * *